US006051424A

United States Patent [19]
Kato et al.

[11] Patent Number: 6,051,424
[45] Date of Patent: Apr. 18, 2000

[54] HUMAN CDNAS AND PROTEINS ENCODED THEREBY

[75] Inventors: Seishi Kato, Sagamihara, Japan; Suwan Oh, Taejeon, Rep. of Korea; Shingo Sekine; Namsoon Kim, both of Sagamihara, Japan; Takae Kato; Akiyo Iwahori, both of Tokyo, Japan

[73] Assignee: Sagami Chemical Research Center, Tokyo, Japan

[21] Appl. No.: 08/390,207

[22] Filed: Feb. 16, 1995

Related U.S. Application Data

[63] Continuation-in-part of application No. 08/379,441, filed as application No. PCT/JP93/01095, Aug. 4, 1993, abandoned.

[30] Foreign Application Priority Data

| Aug. 4, 1992 | [JP] | Japan | 4-208077 |
| Nov. 13, 1992 | [JP] | Japan | 4-327619 |
| Feb. 26, 1993 | [JP] | Japan | 5-61431 |

[51] Int. Cl.⁷ .......................... C12N 15/12; C12N 15/63; C07H 21/00
[52] U.S. Cl. ................. 435/320.1; 536/23.1; 536/23.5; 536/24.3
[58] Field of Search ................ 435/320.1; 536/23.1, 536/23.5, 24.3

[56] References Cited

U.S. PATENT DOCUMENTS

| 4,727,138 | 2/1988 | Goeddel et al. | 536/27 |
| 4,762,791 | 8/1988 | Goeddel et al. | 435/243 |
| 4,925,793 | 5/1990 | Goeddel et al. | 435/69.51 |
| 4,929,554 | 5/1990 | Goeddel et al. | 435/172.3 |
| 5,096,705 | 3/1992 | Goeddel et al. | 424/85.5 |

FOREIGN PATENT DOCUMENTS

| 1-35639 | 7/1989 | Japan . |
| 4-117292 | 4/1992 | Japan . |
| WO 94/03599 | 2/1994 | WIPO . |
| WO 9734013 | 9/1997 | WIPO . |

OTHER PUBLICATIONS

Robakis et al., "Molecular cloning and characterization of a cDNA encoding the cerebrovascular and the neuritic plaque amyloid peptides", Proc. Natl. Acad. Sci. USA 84: 4190–4194, Jun. 1987.

Oh et al., "Human cDNA encoding DnaJ protein homologue", Biochim. Biophys. Acta 1174: 114–116, Jul. 1993.

GenBank Acc. No. D13388, Oh et al., US National Library of Medicine, Bathesda, MD, Sep. 1993.

Aksoy et al., "Human liver nicotinamide N–methyltransferase", J. Biol. Chem. 269(20): 14835–14840, May 1994.

Gen Bank acc. No. L13452, Reinhart et al., US National Library of Medicine, Bathesda, MD, Jul. 1993.

Reinhart et al., "The structure of two murine class–mu glutathione transferase genes coordinately induced by butylated hydroxyanisole", Arch. Biochem. Biophys. 303(2): 383–393, Jun. 1993.

Imai et al., "Novel nuclear autoantigen with splicing factor motifs identified with antibody from hepatocellular carcinoma", J. Clin. Invest. 92: 2419–2426, Nov. 1993.

Shuttleworth et al., "p40 (MO15), a cdc–2–related protein kinase involved in negative regulation of meiotic maturation of Xenopus oocytes", EMBO J. 9(10): 3233–3240, Oct. 1990.

Wu et al., "Molecular cloning of the human CAK1 gene encoding a cyclin–dependent kinase–activating kinase", Oncogene 9(7): 2089–2096, Jul. 1994.

Burke et al., "Characterization of a polyubiquitin gene from Arabidopsis thaliana", Mol. Gen. Genet. 213 (2–3): 435–443, 1988.

GenBank Acc. No. T09267, Adams et al., US National Library of Medicine, Bathesda, MD, Aug. 1993.

GenBank Acc. No. T07161, Adams et al., US National Library of Medicine, Bathesda, MD, Jun. 1993.

Apperson et al., "A yeast protein, homologous to the proteolipid of teh chromaffin granule proton–ATPase, is important for cell growth", Biochem. Biophys. Res. Commun. 168 (2): 574–579, Apr. 1990.

Nielsen et al., "The Mouse Protein Synthesis Initiation Factor 4A Gene Family Includes Two Related Functional Genes Which Are Differentially Expressed", The EMBO Journal, vol. 7, No. 7, 1988, pp. 2097–2105.

Huhtala et al., "Complete Structure of the Human Gene for 92–kDa Type IV Collagenase", The Journal of Biological Chemistry, vol. 266, No. 25, Sep. 5, 1991, pp. 16485–16490.

Adams et al., "Sequence Identification of 2,375 Human Brain Genes", Nature, vol. 355, Feb. 13, 1992, pp. 632–634.

Rothofsky et al., "DNA–binding protein", GenBank No. AAB72016, US National Library of Medicine, Feb. 1998.

Faria et al., Enterocyte differentiation associated factor EDAF–1, GenBank No. AAB04758, US National Library of Medicine, May 1999.

Imai et al., "Splicing factor—human", GenBank No. 155595, US. National Library of Medicine, Feb. 1997.

Tassan et al., "Cell division protein kinase 7 (CDK–activating kinase) (CAK) (39 kD protein kinase) (P39 MO15) (STK1) (CAK1)", GenBank No. P50613, US National Library of Medicine, Nov. 1997.

*Primary Examiner*—Scott D. Priebe
*Attorney, Agent, or Firm*—Foley & Lardner

[57] ABSTRACT

Isolated cDNAs derived from mRNAs expressed in human cells are provided, as are DNAs and RNAs comprising their nucleotide sequences, and vectors for expressing the cDNAs. The cDNAs encode proteins which have functions similar to known proteins.

8 Claims, 1 Drawing Sheet

SEQUENCE LISTING (1) GENERAL INFORMATION:

(iii) NUMBER OF SEQUENCES: 253

(2) INFORMATION FOR SEQ ID NO:1:

(i) SEQUENCE CHARACTERISTICS:
      (A) LENGTH: 432 base pairs
      (B) TYPE: nucleic acid
      (C) STRANDEDNESS: double
      (D) TOPOLOGY: linear (ii) MOLECULE TYPE: cDNA to mRNA (ix) FEATURE:
      (A) NAME/KEY: CDS
      (B) LOCATION: 1..432

(xi) SEQUENCE DESCRIPTION: SEQ ID NO:1:

```
CCT GGT GTA GAC TCC ATC TCC TGC ACT GGC ATG GCG ACA TTC TGC AAC        48
Pro Gly Val Asp Ser Ile Ser Cys Thr Gly Met Ala Thr Phe Cys Asn
 1               5                  10                  15

ATG GGT GCA GAA ATT GGG GCC ACC ACT TCC GTG TTC CCT TAC AAC CAC        96
Met Gly Ala Glu Ile Gly Ala Thr Thr Ser Val Phe Pro Tyr Asn His
            20                  25                  30

AGG ATG AAG AAG TAC CTG AGC AAG ACC GGC CGG GAA GAC ATT GCC AAT       144
Arg Met Lys Lys Tyr Leu Ser Lys Thr Gly Arg Glu Asp Ile Ala Asn
        35                  40                  45

CTA GCT GAT GAA TTC AAG GAT CAC TTG GTG CCT GAC CCT GGC TGC CAT       192
Leu Ala Asp Glu Phe Lys Asp His Leu Val Pro Asp Pro Gly Cys His
    50                  55                  60

TAT GAC CAA CTA ATT GAA ATT AAC CTC AGT GAG CTG AAG CCA CAC ATC       240
Tyr Asp Gln Leu Ile Glu Ile Asn Leu Ser Glu Leu Lys Pro His Ile
65                  70                  75                  80

AAT GGG CCC TTC ACC CCT GAC CTG GCT CAC CCT GTG GCA GAA GTG GGC       288
Asn Gly Pro Phe Thr Pro Asp Leu Ala His Pro Val Ala Glu Val Gly
                85                  90                  95

AAG GTG GCA GAG AAG GAA GGA TGG CCT CTG GAC ATC CGA GTG GGT CTA       336
Lys Val Ala Glu Lys Glu Gly Trp Pro Leu Asp Ile Arg Val Gly Leu
           100                 105                 110

ATT GGT AGC TGC ACC AAT TCA AGC TAT GAA GAT ATG GGG CGC TCA GCA       384
Ile Gly Ser Cys Thr Asn Ser Ser Tyr Glu Asp Met Gly Arg Ser Ala
       115                 120                 125

GCT GTG GCC AAG CAG GCA CTG GCC CAT GGC CTC AAG TGC AAG TCC CAG       432
Ala Val Ala Lys Gln Ala Leu Ala His Gly Leu Lys Cys Lys Ser Gln
   130                 135                 140
```

(2) INFORMATION FOR SEQ ID NO:2:

(i) SEQUENCE CHARACTERISTICS:

(A) LENGTH: 144 amino acids
        (B) TYPE: amino acid
        (D) TOPOLOGY: linear (ii) MOLECULE TYPE: protein (xi) SEQUENCE DESCRIPTION: SEQ ID NO:2:

Pro Gly Val Asp Ser Ile Ser Cys Thr Gly Met Ala Thr Phe Cys Asn
 1               5                  10                  15

Met Gly Ala Glu Ile Gly Ala Thr Thr Ser Val Phe Pro Tyr Asn His
             20                  25                  30

Arg Met Lys Lys Tyr Leu Ser Lys Thr Gly Arg Glu Asp Ile Ala Asn
         35                  40                  45

Leu Ala Asp Glu Phe Lys Asp His Leu Val Pro Asp Pro Gly Cys His
     50                  55                  60

Tyr Asp Gln Leu Ile Glu Ile Asn Leu Ser Glu Leu Lys Pro His Ile
 65                  70                  75                  80

Asn Gly Pro Phe Thr Pro Asp Leu Ala His Pro Val Ala Glu Val Gly
                 85                  90                  95

Lys Val Ala Glu Lys Gly Trp Pro Leu Asp Ile Arg Val Gly Leu
            100                 105                 110

Ile Gly Ser Cys Thr Asn Ser Ser Tyr Glu Asp Met Gly Arg Ser Ala
            115                 120                 125

Ala Val Ala Lys Gln Ala Leu Ala His Gly Leu Lys Cys Lys Ser Gln
        130                 135                 140

(2) INFORMATION FOR SEQ ID NO:3:

(i) SEQUENCE CHARACTERISTICS:
        (A) LENGTH: 201 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..201

(xi) SEQUENCE DESCRIPTION: SEQ ID NO:3:

ATG GCA GCA AAG GCT GTA GCA AAT ACA ATG AGA ACA TCA CTT GGA CCA        48
Met Ala Ala Lys Ala Val Ala Asn Thr Met Arg Thr Ser Leu Gly Pro
145                 150                 155                 160

AAT GGG CTT GAT AAG ATG ATG GTG GAT AAG GAT GGG GAT GTG ACT GTA        96
Asn Gly Leu Asp Lys Met Met Val Asp Lys Asp Gly Asp Val Thr Val
                165                 170                 175

ACT AAT GAT GGG GCC ACC ATC TTA AGC ATG ATG GAT GTT GAT CAT CAG       144
Thr Asn Asp Gly Ala Thr Ile Leu Ser Met Met Asp Val Asp His Gln
            180                 185                 190

ATT GCC AAG CTG ATG GTG GAA CTG TCC AAG TCT CAG GAT GAT GAA ATT       192
Ile Ala Lys Leu Met Val Glu Leu Ser Lys Ser Gln Asp Asp Glu Ile
        195                 200                 205

GGA GAT GGA                                                           201
Gly Asp Gly
    210

(2) INFORMATION FOR SEQ ID NO:4:

(i) SEQUENCE CHARACTERISTICS:
        (A) LENGTH: 67 amino acids
        (B) TYPE: amino acid
        (D) TOPOLOGY: linear (ii) MOLECULE TYPE: protein (xi) SEQUENCE DESCRIPTION: SEQ ID NO:4:

Met Ala Ala Lys Ala Val Ala Asn Thr Met Arg Thr Ser Leu Gly Pro
1               5                   10                  15

Asn Gly Leu Asp Lys Met Met Val Asp Lys Asp Gly Asp Val Thr Val
            20                  25                  30

Thr Asn Asp Gly Ala Thr Ile Leu Ser Met Met Asp Val Asp His Gln
        35                  40                  45

Ile Ala Lys Leu Met Val Glu Leu Ser Lys Ser Gln Asp Asp Glu Ile
    50                  55                  60

Gly Asp Gly
65

(2) INFORMATION FOR SEQ ID NO:5:

(i) SEQUENCE CHARACTERISTICS:
        (A) LENGTH: 234 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..234

(xi) SEQUENCE DESCRIPTION: SEQ ID NO:5:

CTG GGG AAT GCG GGC TCT CTG ATG GTC CTC TTT GGC ACC CCA GAA TTT      48
Leu Gly Asn Ala Gly Ser Leu Met Val Leu Phe Gly Thr Pro Glu Phe
            70                  75                  80

GTG GCT CCT GAA GTG ATC AAC TAT GAG CCC ATC GGC TAC GGC ACA GAC      96
Val Ala Pro Glu Val Ile Asn Tyr Glu Pro Ile Gly Tyr Gly Thr Asp
        85                  90                  95

ATG TGG AGC ATC GGG GTC ATC TGC TAC ATC CTA GTC AGT GGC CTT NCC     144
Met Trp Ser Ile Gly Val Ile Cys Tyr Ile Leu Val Ser Gly Leu Xaa
100                 105                 110                 115

CCC TTC ATG GGA GAC AAC GAT AAC GAA ACC TTG GCC AAC GTT ACC TCA     192
Pro Phe Met Gly Asp Asn Asp Asn Glu Thr Leu Ala Asn Val Thr Ser
            120                 125                 130

GCC ACC TGG GAC TTC GAC GAC GAG GCA TTC GAT GAG ATC TCC             234
Ala Thr Trp Asp Phe Asp Asp Glu Ala Phe Asp Glu Ile Ser
        135                 140                 145

(2) INFORMATION FOR SEQ ID NO:6:

(i) SEQUENCE CHARACTERISTICS:
        (A) LENGTH: 78 amino acids
        (B) TYPE: amino acid
        (D) TOPOLOGY: linear (ii) MOLECULE TYPE: protein (xi) SEQUENCE DESCRIPTION: SEQ ID NO:6:

Leu Gly Asn Ala Gly Ser Leu Met Val Leu Phe Gly Thr Pro Glu Phe
1               5                   10                  15

Val Ala Pro Glu Val Ile Asn Tyr Glu Pro Ile Gly Tyr Gly Thr Asp
            20                  25                  30

Met Trp Ser Ile Gly Val Ile Cys Tyr Ile Leu Val Ser Gly Leu Xaa
        35                  40                  45

Pro Phe Met Gly Asp Asn Asp Asn Glu Thr Leu Ala Asn Val Thr Ser

```
                50                  55                  60
Ala Thr Trp Asp Phe Asp Asp Glu Ala Phe Asp Glu Ile Ser
 65                  70                  75
```

(2) INFORMATION FOR SEQ ID NO:7:

(i) SEQUENCE CHARACTERISTICS:
        (A) LENGTH: 135 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..135

(xi) SEQUENCE DESCRIPTION: SEQ ID NO:7:

```
ATC CAA GTG AAA GAT GCA AAT GAC AAC AGC CCG GTC TTT GAA TCT AGT      48
Ile Gln Val Lys Asp Ala Asn Asp Asn Ser Pro Val Phe Glu Ser Ser
        80                  85                  90

CCA TAT GAG GCA TTC ATT GTT GAA AAC CTG CCA GGG GGA AGT AGA GTA      96
Pro Tyr Glu Ala Phe Ile Val Glu Asn Leu Pro Gly Gly Ser Arg Val
 95                 100                 105                 110

ATT CAG ATC AGG GCA TCT GAT GCT GAC TCA GGA ACC AAC                 135
Ile Gln Ile Arg Ala Ser Asp Ala Asp Ser Gly Thr Asn
                115                 120
```

(2) INFORMATION FOR SEQ ID NO:8:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO:8:

```
Ile Gln Val Lys Asp Ala Asn Asp Asn Ser Pro Val Phe Glu Ser Ser
  1               5                  10                  15

Pro Tyr Glu Ala Phe Ile Val Glu Asn Leu Pro Gly Gly Ser Arg Val
             20                  25                  30

Ile Gln Ile Arg Ala Ser Asp Ala Asp Ser Gly Thr Asn
             35                  40                  45
```

(2) INFORMATION FOR SEQ ID NO:9:

(i) SEQUENCE CHARACTERISTICS:
        (A) LENGTH: 369 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..369

(xi) SEQUENCE DESCRIPTION: SEQ ID NO:9:

```
GAA ACC GTA GAT CTG GTT CAT GTT GTC TGT CTC GTG GTT GAG GTG AAG      48
Glu Thr Val Asp Leu Val His Val Val Cys Leu Val Val Glu Val Lys
                 50                  55                  60

GCC AAG TAC ACA GCC CAG ATG TAC GAG CTC TTT AGC GAG GTG TTC GAG      96
Ala Lys Tyr Thr Ala Gln Met Tyr Glu Leu Phe Ser Glu Val Phe Glu
             65                  70                  75
```

```
TGG CTC CCG TTG GCC CAG TGC ATC AAC GGC AAA GTG CTG ATC ATG CAC        144
Trp Leu Pro Leu Ala Gln Cys Ile Asn Gly Lys Val Leu Ile Met His
         80                  85                  90

GGA GGC CTG TTC AGT GAA GAC GGT GTC ACC CTG GAT GAC ATC CGG AAA        192
Gly Gly Leu Phe Ser Glu Asp Gly Val Thr Leu Asp Asp Ile Arg Lys
 95                 100                 105

ATT GAG CGG AAT CGA CAA CCC CCA GAT TCA GGG CCC ATG TGT GAC CTG        240
Ile Glu Arg Asn Arg Gln Pro Pro Asp Ser Gly Pro Met Cys Asp Leu
110             115                 120                 125

CTC TGG TCA GAT CCA CAG CCA CAG AAC GGG CGC TCG ATC AGC AAG CGG        288
Leu Trp Ser Asp Pro Gln Pro Gln Asn Gly Arg Ser Ile Ser Lys Arg
             130                 135                 140

GGC GTG AGC TGT CAG TTT GGG CCT GAC GTC ACC AAG GCC TTC TTG GAA        336
Gly Val Ser Cys Gln Phe Gly Pro Asp Val Thr Lys Ala Phe Leu Glu
                 145                 150                 155

GAG AAC AAC CTG GAC TAT ATC ATC CGC AGC CAC                            369
Glu Asn Asn Leu Asp Tyr Ile Ile Arg Ser His
             160                 165

(2) INFORMATION FOR SEQ ID NO:10:

(i) SEQUENCE CHARACTERISTICS:
        (A) LENGTH: 123 amino acids
        (B) TYPE: amino acid
        (D) TOPOLOGY: linear (ii) MOLECULE TYPE: protein (xi) SEQUENCE DESCRIPTION: SEQ ID NO:10:

Glu Thr Val Asp Leu Val His Val Val Cys Leu Val Val Glu Val Lys
 1               5                  10                  15

Ala Lys Tyr Thr Ala Gln Met Tyr Glu Leu Phe Ser Glu Val Phe Glu
             20                  25                  30

Trp Leu Pro Leu Ala Gln Cys Ile Asn Gly Lys Val Leu Ile Met His
         35                  40                  45

Gly Gly Leu Phe Ser Glu Asp Gly Val Thr Leu Asp Asp Ile Arg Lys
 50                  55                  60

Ile Glu Arg Asn Arg Gln Pro Pro Asp Ser Gly Pro Met Cys Asp Leu
65              70                  75                  80

Leu Trp Ser Asp Pro Gln Pro Gln Asn Gly Arg Ser Ile Ser Lys Arg
             85                  90                  95

Gly Val Ser Cys Gln Phe Gly Pro Asp Val Thr Lys Ala Phe Leu Glu
                 100                 105                 110

Glu Asn Asn Leu Asp Tyr Ile Ile Arg Ser His
             115                 120

(2) INFORMATION FOR SEQ ID NO:11:

(i) SEQUENCE CHARACTERISTICS:
        (A) LENGTH: 210 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..210

(xi) SEQUENCE DESCRIPTION: SEQ ID NO:11:

ATG GCC CGA ACC AAG CAG ACT GCT CGT AAG TCC ACC GGT GGG AAA GCC         48
```

```
Met Ala Arg Thr Lys Gln Thr Ala Arg Lys Ser Thr Gly Gly Lys Ala
    125                 130                 135

CCC CGC AAA CAG CTG GCC ACG AAA GCC GCC AGG AAA AGC GCT CCC TCT        96
Pro Arg Lys Gln Leu Ala Thr Lys Ala Ala Arg Lys Ser Ala Pro Ser
140                 145                 150                 155

ACC GGC GGG GTG AAG AAG CCT CAT CGC TAC AGG CCC GGG ACC GTG GCG       144
Thr Gly Gly Val Lys Lys Pro His Arg Tyr Arg Pro Gly Thr Val Ala
                160                 165                 170

CTT CGA GAG ATT CGT CGT TAT CAG AAG TCG ACC GAG CTG CTC ATC CGG       192
Leu Arg Glu Ile Arg Arg Tyr Gln Lys Ser Thr Glu Leu Leu Ile Arg
            175                 180                 185

AAG CTG CCC TTC CAG AGG                                               210
Lys Leu Pro Phe Gln Arg
        190
```

(2) INFORMATION FOR SEQ ID NO:12:

(i) SEQUENCE CHARACTERISTICS:
        (A) LENGTH: 70 amino acids
        (B) TYPE: amino acid
        (D) TOPOLOGY: linear (ii) MOLECULE TYPE: protein (xi) SEQUENCE DESCRIPTION: SEQ ID NO:12:

```
Met Ala Arg Thr Lys Gln Thr Ala Arg Lys Ser Thr Gly Gly Lys Ala
 1               5                  10                  15

Pro Arg Lys Gln Leu Ala Thr Lys Ala Ala Arg Lys Ser Ala Pro Ser
                20                  25                  30

Thr Gly Gly Val Lys Lys Pro His Arg Tyr Arg Pro Gly Thr Val Ala
            35                  40                  45

Leu Arg Glu Ile Arg Arg Tyr Gln Lys Ser Thr Glu Leu Leu Ile Arg
        50                  55                  60

Lys Leu Pro Phe Gln Arg
65                  70
```

(2) INFORMATION FOR SEQ ID NO:13:

(i) SEQUENCE CHARACTERISTICS:
        (A) LENGTH: 213 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..213

(xi) SEQUENCE DESCRIPTION: SEQ ID NO:13:

```
TTG GAT GTC CCT CAG GTG TCC CTC ATC ATT AAC TAT GAT CTC CCT AAT        48
Leu Asp Val Pro Gln Val Ser Leu Ile Ile Asn Tyr Asp Leu Pro Asn
                 75                  80                  85

AAC AGA GAA TTG TAC ATA CAC AGA ATT GGG AGA TCA GGT CGA TAC GGC        96
Asn Arg Glu Leu Tyr Ile His Arg Ile Gly Arg Ser Gly Arg Tyr Gly
             90                  95                 100

CGG AAG GGT GTG GCC ATT AAC TTT GTA AAG AAT GAC GAC ATC CGC ATC       144
Arg Lys Gly Val Ala Ile Asn Phe Val Lys Asn Asp Asp Ile Arg Ile
        105                 110                 115

CTC AGA GAT ATC GAG CAG TAC TAT TCC ACT CAG ATT GAT GAG ATG CCG       192
Leu Arg Asp Ile Glu Gln Tyr Tyr Ser Thr Gln Ile Asp Glu Met Pro
    120                 125                 130
```

```
ATG AAC GTT GCT GAT CTT ATC                                              213
Met Asn Val Ala Asp Leu Ile
135             140
```

(2) INFORMATION FOR SEQ ID NO:14:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO:14:

```
Leu Asp Val Pro Gln Val Ser Leu Ile Ile Asn Tyr Asp Leu Pro Asn
1               5                   10                  15

Asn Arg Glu Leu Tyr Ile His Arg Ile Gly Arg Ser Gly Arg Tyr Gly
            20                  25                  30

Arg Lys Gly Val Ala Ile Asn Phe Val Lys Asn Asp Asp Ile Arg Ile
            35                  40                  45

Leu Arg Asp Ile Glu Gln Tyr Tyr Ser Thr Gln Ile Asp Glu Met Pro
            50                  55                  60

Met Asn Val Ala Asp Leu Ile
65                  70
```

(2) INFORMATION FOR SEQ ID NO:15:

(i) SEQUENCE CHARACTERISTICS:
        (A) LENGTH: 342 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..342

(xi) SEQUENCE DESCRIPTION: SEQ ID NO:15:

```
ATG TTC TCT CGC GCG GGT GTC GCT GGG CTG TCG GCC TGG ACC TTG CAG          48
Met Phe Ser Arg Ala Gly Val Ala Gly Leu Ser Ala Trp Thr Leu Gln
            75                  80                  85

CCG CAA TGG ATT CAA GTT CGA AAT ATG GCA ACT TTG AAA GAT ATC ACC          96
Pro Gln Trp Ile Gln Val Arg Asn Met Ala Thr Leu Lys Asp Ile Thr
            90                  95                  100

AGG AGA CTA AAG TCC ATC AAA AAC ATC CAG AAA ATT ACC AAG TCT ATG          144
Arg Arg Leu Lys Ser Ile Lys Asn Ile Gln Lys Ile Thr Lys Ser Met
        105                 110                 115

AAA ATG GTA GCG GCA GCA AAA TAT GCC CGA GCT GAG AGA GAG CTG AAA          192
Lys Met Val Ala Ala Ala Lys Tyr Ala Arg Ala Glu Arg Glu Leu Lys
120                 125                 130                 135

CCA GCT CGA ATA TAT GGA TTG GGA TCT TTA GCT CTG TAT GAA AAA GCT          240
Pro Ala Arg Ile Tyr Gly Leu Gly Ser Leu Ala Leu Tyr Glu Lys Ala
                140                 145                 150

GAT ATC AAG GGG CCT GAA GAC AAG AAG AAA CAC CTC CTT ATT GGT GTG          288
Asp Ile Lys Gly Pro Glu Asp Lys Lys Lys His Leu Leu Ile Gly Val
                155                 160                 165

TCC TCA GAT CGA GGA CTG TGT GGT GCT ATT CAT TCC TCC ATT GCT AAA          336
Ser Ser Asp Arg Gly Leu Cys Gly Ala Ile His Ser Ser Ile Ala Lys
            170                 175                 180

CAG ATG                                                                  342
Gln Met
    185
```

(2) INFORMATION FOR SEQ ID NO:16:

(i) SEQUENCE CHARACTERISTICS:
        (A) LENGTH: 114 amino acids
        (B) TYPE: amino acid
        (D) TOPOLOGY: linear (ii) MOLECULE TYPE: protein (xi) SEQUENCE DESCRIPTION: SEQ ID NO:16:

```
Met Phe Ser Arg Ala Gly Val Ala Gly Leu Ser Ala Trp Thr Leu Gln
 1               5                  10                  15

Pro Gln Trp Ile Gln Val Arg Asn Met Ala Thr Leu Lys Asp Ile Thr
            20                  25                  30

Arg Arg Leu Lys Ser Ile Lys Asn Ile Gln Lys Ile Thr Lys Ser Met
        35                  40                  45

Lys Met Val Ala Ala Ala Lys Tyr Ala Arg Ala Glu Arg Glu Leu Lys
 50                  55                  60

Pro Ala Arg Ile Tyr Gly Leu Gly Ser Leu Ala Leu Tyr Glu Lys Ala
 65                  70                  75                  80

Asp Ile Lys Gly Pro Glu Asp Lys Lys Lys His Leu Leu Ile Gly Val
                85                  90                  95

Ser Ser Asp Arg Gly Leu Cys Gly Ala Ile His Ser Ser Ile Ala Lys
                100                 105                 110

Gln Met
```

(2) INFORMATION FOR SEQ ID NO:17:

(i) SEQUENCE CHARACTERISTICS:
        (A) LENGTH: 372 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..372

(xi) SEQUENCE DESCRIPTION: SEQ ID NO:17:

```
TCC ACC GCT CTG AAG GGG ATC TGC AGA GCT CAG TCA GAG GGC AGA CCC        48
Ser Thr Ala Leu Lys Gly Ile Cys Arg Ala Gln Ser Glu Gly Arg Pro
115             120                 125                 130

TGT GAA TAT AAC TCC AGA ATC TAC CAA AAC GGG GAA AGT TTC CAG CCC        96
Cys Glu Tyr Asn Ser Arg Ile Tyr Gln Asn Gly Glu Ser Phe Gln Pro
                135                 140                 145

AAC TGT AAA CAT CAG TGC ACA TGT ATT GAT GGC GCC GTG GGC TGC ATT       144
Asn Cys Lys His Gln Cys Thr Cys Ile Asp Gly Ala Val Gly Cys Ile
            150                 155                 160

CCT CTG TGT CCC CAA GAA CTA TCT CTC CCC AAC TTG GGC TGT CCC AAC       192
Pro Leu Cys Pro Gln Glu Leu Ser Leu Pro Asn Leu Gly Cys Pro Asn
        165                 170                 175

CCT CGG CTG GTC AAA GTT ACC GGG CAG TGC TGC GAG GAG TGG GTC TGT       240
Pro Arg Leu Val Lys Val Thr Gly Gln Cys Cys Glu Glu Trp Val Cys
180                 185                 190

GAC GAG GAT AGT ATC AAG GAC CCC ATG GAG GAC CAG GAC GGC CTC CTT       288
Asp Glu Asp Ser Ile Lys Asp Pro Met Glu Asp Gln Asp Gly Leu Leu
195                 200                 205                 210

GGC AAG GAG CTG GGA TTC GAT GCC TCC GAG GTG GAG TTG ACG AGA AAC       336
Gly Lys Glu Leu Gly Phe Asp Ala Ser Glu Val Glu Leu Thr Arg Asn
```

```
                    215                 220                 225
AAT GAA TTG ATT GCA GTT GGA AAA GGC AGC TCA CTG                          372
Asn Glu Leu Ile Ala Val Gly Lys Gly Ser Ser Leu
            230                 235
```

(2) INFORMATION FOR SEQ ID NO:18:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO:18:

```
Ser Thr Ala Leu Lys Gly Ile Cys Arg Ala Gln Ser Glu Gly Arg Pro
 1               5                  10                  15

Cys Glu Tyr Asn Ser Arg Ile Tyr Gln Asn Gly Glu Ser Phe Gln Pro
                20                  25                  30

Asn Cys Lys His Gln Cys Thr Cys Ile Asp Gly Ala Val Gly Cys Ile
            35                  40                  45

Pro Leu Cys Pro Gln Glu Leu Ser Leu Pro Asn Leu Gly Cys Pro Asn
        50                  55                  60

Pro Arg Leu Val Lys Val Thr Gly Gln Cys Cys Glu Glu Trp Val Cys
65                  70                  75                  80

Asp Glu Asp Ser Ile Lys Asp Pro Met Glu Asp Gln Asp Gly Leu Leu
                85                  90                  95

Gly Lys Glu Leu Gly Phe Asp Ala Ser Glu Val Glu Leu Thr Arg Asn
                100                 105                 110

Asn Glu Leu Ile Ala Val Gly Lys Gly Ser Ser Leu
            115                 120
```

(2) INFORMATION FOR SEQ ID NO:19:

(i) SEQUENCE CHARACTERISTICS:
        (A) LENGTH: 288 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..288

(xi) SEQUENCE DESCRIPTION: SEQ ID NO:19:

```
ATG GTG CGC ATG AAT GTC CTG GCA GAT GCT CTC AAG AGT ATC AAC AAT          48
Met Val Arg Met Asn Val Leu Ala Asp Ala Leu Lys Ser Ile Asn Asn
125                 130                 135                 140

GCC GAA AAG AGA GGC AAA CGC CAG GTG CTT ATT AGG CCG TGC TCC AAA          96
Ala Glu Lys Arg Gly Lys Arg Gln Val Leu Ile Arg Pro Cys Ser Lys
                145                 150                 155

GTC ATC GTC CGG TTT CTC ACT GTG ATG ATG AAG CAT GGT TAC ATT GGC         144
Val Ile Val Arg Phe Leu Thr Val Met Met Lys His Gly Tyr Ile Gly
            160                 165                 170

GAA TTT GAA ATC ATT GAT GAC CAC AGA GCT GGG AAA ATT GTT GTG AAC         192
Glu Phe Glu Ile Ile Asp Asp His Arg Ala Gly Lys Ile Val Val Asn
        175                 180                 185

CTC ACA GGC AGG CTA AAC AAG TGT GGG GTG ATC AGC CCC AGA TTT GAC         240
Leu Thr Gly Arg Leu Asn Lys Cys Gly Val Ile Ser Pro Arg Phe Asp
    190                 195                 200
```

```
GTG CAA CTC AAA GAC TGG GAA AAA TGG CAG AAT AAT CTG CTT CCA TCC         288
Val Gln Leu Lys Asp Trp Glu Lys Trp Gln Asn Asn Leu Leu Pro Ser
205                 210                 215                 220
```

(2) INFORMATION FOR SEQ ID NO:20:

(i) SEQUENCE CHARACTERISTICS:
        (A) LENGTH: 96 amino acids
        (B) TYPE: amino acid
        (D) TOPOLOGY: linear (ii) MOLECULE TYPE: protein (xi) SEQUENCE DESCRIPTION: SEQ ID NO:20:

```
Met Val Arg Met Asn Val Leu Ala Asp Ala Leu Lys Ser Ile Asn Asn
1               5                   10                  15

Ala Glu Lys Arg Gly Lys Arg Gln Val Leu Ile Arg Pro Cys Ser Lys
                20                  25                  30

Val Ile Val Arg Phe Leu Thr Val Met Met Lys His Gly Tyr Ile Gly
                35                  40                  45

Glu Phe Glu Ile Ile Asp Asp His Arg Ala Gly Lys Ile Val Val Asn
                50                  55                  60

Leu Thr Gly Arg Leu Asn Lys Cys Gly Val Ile Ser Pro Arg Phe Asp
65                  70                  75                  80

Val Gln Leu Lys Asp Trp Glu Lys Trp Gln Asn Asn Leu Leu Pro Ser
                85                  90                  95
```

(2) INFORMATION FOR SEQ ID NO:21:

(i) SEQUENCE CHARACTERISTICS:
        (A) LENGTH: 282 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..282

(xi) SEQUENCE DESCRIPTION: SEQ ID NO:21:

```
ATG GCG TGT GCT CGC CCA CTG ATA TCG GTG TAC TCC GAA AAG GGG GAG         48
Met Ala Cys Ala Arg Pro Leu Ile Ser Val Tyr Ser Glu Lys Gly Glu
                100                 105                 110

TCA TCT GGC AAA AAT GTC ACT TTG CCT GCT GTA TTC AAG GCT CCT ATT         96
Ser Ser Gly Lys Asn Val Thr Leu Pro Ala Val Phe Lys Ala Pro Ile
        115                 120                 125

CGA CCA GAT ATT GTG AAC TTT GTT CAC ACC AAC TTG CGC AAA AAC AAC         144
Arg Pro Asp Ile Val Asn Phe Val His Thr Asn Leu Arg Lys Asn Asn
130                 135                 140

AGA CAG CCC TAT GCT GTC AGT GAA TTA GCA GGT CAT CAG ACT AGT GCT         192
Arg Gln Pro Tyr Ala Val Ser Glu Leu Ala Gly His Gln Thr Ser Ala
145                 150                 155                 160

GAG TCT TGG GGT ACT GGC AGA GCT GTG GCT CGA ATT CCC AGA GTT CGA         240
Glu Ser Trp Gly Thr Gly Arg Ala Val Ala Arg Ile Pro Arg Val Arg
                165                 170                 175

GGT GGT GGG ACT CAC CGC TCT GGC CAG GGT GCT TTT GGA AAC                 282
Gly Gly Gly Thr His Arg Ser Gly Gln Gly Ala Phe Gly Asn
                180                 185                 190
```

(2) INFORMATION FOR SEQ ID NO:22:

(i) SEQUENCE CHARACTERISTICS:

```
        (A) LENGTH: 94 amino acids
        (B) TYPE: amino acid
        (D) TOPOLOGY: linear (ii) MOLECULE TYPE: protein (xi) SEQUENCE DESCRIPTION: SEQ ID NO:22:

Met Ala Cys Ala Arg Pro Leu Ile Ser Val Tyr Ser Glu Lys Gly Glu
 1               5                  10                  15

Ser Ser Gly Lys Asn Val Thr Leu Pro Ala Val Phe Lys Ala Pro Ile
            20                  25                  30

Arg Pro Asp Ile Val Asn Phe Val His Thr Asn Leu Arg Lys Asn Asn
        35                  40                  45

Arg Gln Pro Tyr Ala Val Ser Glu Leu Ala Gly His Gln Thr Ser Ala
    50                  55                  60

Glu Ser Trp Gly Thr Gly Arg Ala Val Ala Arg Ile Pro Arg Val Arg
65                  70                  75                  80

Gly Gly Gly Thr His Arg Ser Gly Gln Gly Ala Phe Gly Asn
                85                  90

(2) INFORMATION FOR SEQ ID NO:23:

(i) SEQUENCE CHARACTERISTICS:
        (A) LENGTH: 201 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..201

(xi) SEQUENCE DESCRIPTION: SEQ ID NO:23:

GAT GGG CCC GTT GTG ATT GGC TCT ACC AGT GCA CCT GGA CAG GGA GGA          48
Asp Gly Pro Val Val Ile Gly Ser Thr Ser Ala Pro Gly Gln Gly Gly
 95              100                 105                 110

ATC CTG GCT CAG CGG GAG TTT GAC AGG CGA TTC TCC CCT CAT TTT CTG          96
Ile Leu Ala Gln Arg Glu Phe Asp Arg Arg Phe Ser Pro His Phe Leu
                115                 120                 125

GAC TGG GCA GCC TTT GGG GTC ATG ACC CTT CCC TCC ATC GGC ATC CCC         144
Asp Trp Ala Ala Phe Gly Val Met Thr Leu Pro Ser Ile Gly Ile Pro
        130                 135                 140

CTG CTA TTG TGG TAC TCC AGC AAG AGG AAA TAT GAC ACT CCC AAA ACG         192
Leu Leu Leu Trp Tyr Ser Ser Lys Arg Lys Tyr Asp Thr Pro Lys Thr
    145                 150                 155

AAG AAG AAC                                                             201
Lys Lys Asn
    160

(2) INFORMATION FOR SEQ ID NO:24:

(i) SEQUENCE CHARACTERISTICS:
        (A) LENGTH: 67 amino acids
        (B) TYPE: amino acid
        (D) TOPOLOGY: linear (ii) MOLECULE TYPE: protein (xi) SEQUENCE DESCRIPTION: SEQ ID NO:24:

Asp Gly Pro Val Val Ile Gly Ser Thr Ser Ala Pro Gly Gln Gly Gly
 1               5                  10                  15

Ile Leu Ala Gln Arg Glu Phe Asp Arg Arg Phe Ser Pro His Phe Leu
```

```
                   20                  25                  30
Asp Trp Ala Ala Phe Gly Val Met Thr Leu Pro Ser Ile Gly Ile Pro
            35                  40                  45

Leu Leu Leu Trp Tyr Ser Ser Lys Arg Lys Tyr Asp Thr Pro Lys Thr
        50                  55                  60

Lys Lys Asn
 65
```

(2) INFORMATION FOR SEQ ID NO:25:

(i) SEQUENCE CHARACTERISTICS:
        (A) LENGTH: 204 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..204

(xi) SEQUENCE DESCRIPTION: SEQ ID NO:25:

```
CTG GAC TTC CCT GCC ATC CAC CAC GTC ATC AAT TAT GAC ATG CCA GAG      48
Leu Asp Phe Pro Ala Ile His His Val Ile Asn Tyr Asp Met Pro Glu
         70                  75                  80

GAG ATT GAG AAC TAT GTA CAC CGG ATT GGC CGC ACC GGG CGC TCG GGA      96
Glu Ile Glu Asn Tyr Val His Arg Ile Gly Arg Thr Gly Arg Ser Gly
     85                  90                  95

AAC ACA GGC ATC GCC ACT ACC TTC ATC AAC AAA GCG TGT GAT GAG TCA     144
Asn Thr Gly Ile Ala Thr Thr Phe Ile Asn Lys Ala Cys Asp Glu Ser
100                 105                 110                 115

GTG CTG ATG GAC CTC AAA GCG CTG CTG CTA GAA GCC AAG CAG AAG GTG     192
Val Leu Met Asp Leu Lys Ala Leu Leu Leu Glu Ala Lys Gln Lys Val
                120                 125                 130

CCG CCC GTG CTG                                                     204
Pro Pro Val Leu
            135
```

(2) INFORMATION FOR SEQ ID NO:26:

(i) SEQUENCE CHARACTERISTICS:
        (A) LENGTH: 68 amino acids
        (B) TYPE: amino acid
        (D) TOPOLOGY: linear (ii) MOLECULE TYPE: protein (xi) SEQUENCE DESCRIPTION: SEQ ID NO:26:

```
Leu Asp Phe Pro Ala Ile His His Val Ile Asn Tyr Asp Met Pro Glu
 1               5                  10                  15

Glu Ile Glu Asn Tyr Val His Arg Ile Gly Arg Thr Gly Arg Ser Gly
             20                  25                  30

Asn Thr Gly Ile Ala Thr Thr Phe Ile Asn Lys Ala Cys Asp Glu Ser
         35                  40                  45

Val Leu Met Asp Leu Lys Ala Leu Leu Leu Glu Ala Lys Gln Lys Val
     50                  55                  60

Pro Pro Val Leu
 65
```

(2) INFORMATION FOR SEQ ID NO:27:

(i) SEQUENCE CHARACTERISTICS:

(A) LENGTH: 243 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..243

(xi) SEQUENCE DESCRIPTION: SEQ ID NO:27:

```
AGT GAT CAA ATC AGA AGT GCC GTC CTT ATC TCA TCA AAG CCA GGC TGC        48
Ser Asp Gln Ile Arg Ser Ala Val Leu Ile Ser Ser Lys Pro Gly Cys
 70                  75                  80

TTT ATT GCA GGT GCT GAT ATC AAC ATG TTA GCC GCT TGC AAG ACC CTT        96
Phe Ile Ala Gly Ala Asp Ile Asn Met Leu Ala Ala Cys Lys Thr Leu
 85                  90                  95                 100

CAA GAA GTA ACA CAG CTA TCA CAA GAG GCA CAG AGA ATA GTT GAG AAA       144
Gln Glu Val Thr Gln Leu Ser Gln Glu Ala Gln Arg Ile Val Glu Lys
                105                 110                 115

CTT GAA AAG TCC ACA AAG CCT ATT GTG GCT GCC ATC AAT GGA TCC TGC       192
Leu Glu Lys Ser Thr Lys Pro Ile Val Ala Ala Ile Asn Gly Ser Cys
            120                 125                 130

CTG GGA GGC GGA CTT GAG GTT GCC ATT TCA TGC CAA TAC AGA AAT AGC       240
Leu Gly Gly Gly Leu Glu Val Ala Ile Ser Cys Gln Tyr Arg Asn Ser
        135                 140                 145

AAC                                                                   243
Asn
```

(2) INFORMATION FOR SEQ ID NO:28:

(i) SEQUENCE CHARACTERISTICS:
        (A) LENGTH: 81 amino acids
        (B) TYPE: amino acid
        (D) TOPOLOGY: linear (ii) MOLECULE TYPE: protein (xi) SEQUENCE DESCRIPTION: SEQ ID NO:28:

```
Ser Asp Gln Ile Arg Ser Ala Val Leu Ile Ser Ser Lys Pro Gly Cys
  1               5                  10                  15

Phe Ile Ala Gly Ala Asp Ile Asn Met Leu Ala Ala Cys Lys Thr Leu
                 20                  25                  30

Gln Glu Val Thr Gln Leu Ser Gln Glu Ala Gln Arg Ile Val Glu Lys
             35                  40                  45

Leu Glu Lys Ser Thr Lys Pro Ile Val Ala Ala Ile Asn Gly Ser Cys
         50                  55                  60

Leu Gly Gly Gly Leu Glu Val Ala Ile Ser Cys Gln Tyr Arg Asn Ser
 65                  70                  75                  80

Asn
```

(2) INFORMATION FOR SEQ ID NO:29:

(i) SEQUENCE CHARACTERISTICS:
        (A) LENGTH: 108 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..108

(xi) SEQUENCE DESCRIPTION: SEQ ID NO:29:

```
ATG ACG AAG GGA ACG TCA TCG TTT GGA AAG CGT CGC AAT AAG ACG CAC        48
Met Thr Lys Gly Thr Ser Ser Phe Gly Lys Arg Arg Asn Lys Thr His
            85                  90                  95

ACG TTG TGC CGC CGC TGT GGC TCT AAG GCC TAC CAC CTT CAG AAG TCG        96
Thr Leu Cys Arg Arg Cys Gly Ser Lys Ala Tyr His Leu Gln Lys Ser
        100                 105                 110

ACC TGT GGC AAA                                                       108
Thr Cys Gly Lys
    115
```

(2) INFORMATION FOR SEQ ID NO:30:

(i) SEQUENCE CHARACTERISTICS:
        (A) LENGTH: 36 amino acids
        (B) TYPE: amino acid
        (D) TOPOLOGY: linear (ii) MOLECULE TYPE: protein (xi) SEQUENCE DESCRIPTION: SEQ ID NO:30:

```
Met Thr Lys Gly Thr Ser Ser Phe Gly Lys Arg Arg Asn Lys Thr His
 1               5                  10                  15

Thr Leu Cys Arg Arg Cys Gly Ser Lys Ala Tyr His Leu Gln Lys Ser
            20                  25                  30

Thr Cys Gly Lys
        35
```

(2) INFORMATION FOR SEQ ID NO:31:

(i) SEQUENCE CHARACTERISTICS:
        (A) LENGTH: 165 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..165

(xi) SEQUENCE DESCRIPTION: SEQ ID NO:31:

```
ATG GCG CTG AAA CGG ATT AAT AAG GAA CTT AAT GAT TTG GCC CGT GAC        48
Met Ala Leu Lys Arg Ile Asn Lys Glu Leu Asn Asp Leu Ala Arg Asp
            40                  45                  50

CCT CCA GCA CAA TGT TCT GCA GGT CCA GTT GGG GAT GAT ATG TTT CAT        96
Pro Pro Ala Gln Cys Ser Ala Gly Pro Val Gly Asp Asp Met Phe His
        55                  60                  65

TGG CAA GCC ACA ATT ATG GGA CCT AAT GAC AGC CCA TAT CAA GGC GGT       144
Trp Gln Ala Thr Ile Met Gly Pro Asn Asp Ser Pro Tyr Gln Gly Gly
    70                  75                  80

GTA TTC TTT TTG ACA ATT CAT                                           165
Val Phe Phe Leu Thr Ile His
 85                  90
```

(2) INFORMATION FOR SEQ ID NO:32:

(i) SEQUENCE CHARACTERISTICS:
        (A) LENGTH: 55 amino acids
        (B) TYPE: amino acid
        (D) TOPOLOGY: linear (ii) MOLECULE TYPE: protein (xi) SEQUENCE DESCRIPTION: SEQ ID NO:32:

Met Ala Leu Lys Arg Ile Asn Lys Glu Leu Asn Asp Leu Ala Arg Asp
  1               5                  10                  15

Pro Pro Ala Gln Cys Ser Ala Gly Pro Val Gly Asp Asp Met Phe His
             20                  25                  30

Trp Gln Ala Thr Ile Met Gly Pro Asn Asp Ser Pro Tyr Gln Gly Gly
         35                  40                  45

Val Phe Phe Leu Thr Ile His
     50              55

(2) INFORMATION FOR SEQ ID NO:33:

(i) SEQUENCE CHARACTERISTICS:
        (A) LENGTH: 168 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..168

(xi) SEQUENCE DESCRIPTION: SEQ ID NO:33:

TTT TCC TTT GGG AAT TCA GAG CAA ACC AAG GAT GAG AAT TCT TCA AAG        48
Phe Ser Phe Gly Asn Ser Glu Gln Thr Lys Asp Glu Asn Ser Ser Lys
             60                  65                  70

TCC ACA TTT AGT TTT AGT ATG ACA AAA CCA TCT GAG AAG GAA TCT GAA        96
Ser Thr Phe Ser Phe Ser Met Thr Lys Pro Ser Glu Lys Glu Ser Glu
         75                  80                  85

CAG CCA GCA AAA GCC ACT TTT GCC TTT GGA GCT CAA ACT AGT ACT ACA       144
Gln Pro Ala Lys Ala Thr Phe Ala Phe Gly Ala Gln Thr Ser Thr Thr
         90                  95                 100

GCT GAT CAA GGT GCA GCA AAG CCA                                       168
Ala Asp Gln Gly Ala Ala Lys Pro
        105                 110

(2) INFORMATION FOR SEQ ID NO:34:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO:34:

Phe Ser Phe Gly Asn Ser Glu Gln Thr Lys Asp Glu Asn Ser Ser Lys
  1               5                  10                  15

Ser Thr Phe Ser Phe Ser Met Thr Lys Pro Ser Glu Lys Glu Ser Glu
             20                  25                  30

Gln Pro Ala Lys Ala Thr Phe Ala Phe Gly Ala Gln Thr Ser Thr Thr
         35                  40                  45

Ala Asp Gln Gly Ala Ala Lys Pro
     50              55

(2) INFORMATION FOR SEQ ID NO:35:

(i) SEQUENCE CHARACTERISTICS:
        (A) LENGTH: 306 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..306

(xi) SEQUENCE DESCRIPTION: SEQ ID NO:35:

| ATG | TTT | TTC | GAT | AGC | ACT | GCC | ATT | TTG | GCT | GGA | CTG | GCA | GCT | TCT | GTT | 48 |
|-----|-----|-----|-----|-----|-----|-----|-----|-----|-----|-----|-----|-----|-----|-----|-----|-----|
| Met | Phe | Phe | Asp | Ser | Thr | Ala | Ile | Leu | Ala | Gly | Leu | Ala | Ala | Ser | Val | |
| | | | | 60 | | | | 65 | | | | 70 | | | | |

| ATT | TCA | AAA | TGG | AGA | GAT | AAT | GAT | GCT | TTC | TCC | TAT | GGG | TAT | GTT | AGA | 96 |
|-----|-----|-----|-----|-----|-----|-----|-----|-----|-----|-----|-----|-----|-----|-----|-----|-----|
| Ile | Ser | Lys | Trp | Arg | Asp | Asn | Asp | Ala | Phe | Ser | Tyr | Gly | Tyr | Val | Arg | |
| | | 75 | | | | | 80 | | | | | 85 | | | | |

| GCG | GAA | GTT | CTG | GCT | GGC | TTT | GTC | AAT | GGC | CTA | TTT | TTG | ATC | TTC | ACT | 144 |
|-----|-----|-----|-----|-----|-----|-----|-----|-----|-----|-----|-----|-----|-----|-----|-----|-----|
| Ala | Glu | Val | Leu | Ala | Gly | Phe | Val | Asn | Gly | Leu | Phe | Leu | Ile | Phe | Thr | |
| | 90 | | | | | 95 | | | | | 100 | | | | | |

| GCT | TTT | TTT | ATT | TTC | TCA | GAA | GGA | GTT | GAG | AGA | GCA | TTA | GCC | CCT | CCA | 192 |
|-----|-----|-----|-----|-----|-----|-----|-----|-----|-----|-----|-----|-----|-----|-----|-----|-----|
| Ala | Phe | Phe | Ile | Phe | Ser | Glu | Gly | Val | Glu | Arg | Ala | Leu | Ala | Pro | Pro | |
| 105 | | | | | 110 | | | | | 115 | | | | | 120 | |

| GAT | GTC | CAC | CAT | GAG | AGA | CTG | CTT | CTT | GTT | TCC | ATT | CTT | GGG | TTT | GTG | 240 |
|-----|-----|-----|-----|-----|-----|-----|-----|-----|-----|-----|-----|-----|-----|-----|-----|-----|
| Asp | Val | His | His | Glu | Arg | Leu | Leu | Leu | Val | Ser | Ile | Leu | Gly | Phe | Val | |
| | | | | 125 | | | | | 130 | | | | | 135 | | |

| GTA | AAC | CTA | ATA | GGA | ATA | TTT | GTT | TTC | AAA | CAT | GGA | GGT | CAT | GGA | CAT | 288 |
|-----|-----|-----|-----|-----|-----|-----|-----|-----|-----|-----|-----|-----|-----|-----|-----|-----|
| Val | Asn | Leu | Ile | Gly | Ile | Phe | Val | Phe | Lys | His | Gly | Gly | His | Gly | His | |
| | | | 140 | | | | | 145 | | | | | 150 | | | |

| TCT | CAT | GGC | TCT | TGG | CAC | | | | | | | | | | | 306 |
|-----|-----|-----|-----|-----|-----|---|---|---|---|---|---|---|---|---|---|-----|
| Ser | His | Gly | Ser | Trp | His | | | | | | | | | | | |
| | | 155 | | | | | | | | | | | | | | |

(2) INFORMATION FOR SEQ ID NO:36:

(i) SEQUENCE CHARACTERISTICS:
        (A) LENGTH: 102 amino acids
        (B) TYPE: amino acid
        (D) TOPOLOGY: linear (ii) MOLECULE TYPE: protein (xi) SEQUENCE DESCRIPTION: SEQ ID NO:36:

Met Phe Phe Asp Ser Thr Ala Ile Leu Ala Gly Leu Ala Ala Ser Val
 1               5                  10                  15

Ile Ser Lys Trp Arg Asp Asn Asp Ala Phe Ser Tyr Gly Tyr Val Arg
                20                  25                  30

Ala Glu Val Leu Ala Gly Phe Val Asn Gly Leu Phe Leu Ile Phe Thr
            35                  40                  45

Ala Phe Phe Ile Phe Ser Glu Gly Val Glu Arg Ala Leu Ala Pro Pro
    50                  55                  60

Asp Val His His Glu Arg Leu Leu Leu Val Ser Ile Leu Gly Phe Val
65                  70                  75                  80

Val Asn Leu Ile Gly Ile Phe Val Phe Lys His Gly Gly His Gly His
                85                  90                  95

Ser His Gly Ser Trp His
            100

(2) INFORMATION FOR SEQ ID NO:37:

(i) SEQUENCE CHARACTERISTICS:
        (A) LENGTH: 102 base pairs
        (B) TYPE: nucleic acid
        (C) STRANDEDNESS: double
        (D) TOPOLOGY: linear (ii) MOLECULE TYPE: cDNA to mRNA (ix) FEATURE:
    (A) NAME/KEY: CDS
    (B) LOCATION: 1..102

(xi) SEQUENCE DESCRIPTION: SEQ ID NO:37:

```
ATG GCC AAA CGT ACC AAG AAA GTC GGG ATC GTC GGT AAA TAC GGG ACC        48
Met Ala Lys Arg Thr Lys Lys Val Gly Ile Val Gly Lys Tyr Gly Thr
        105                 110                 115

CGC TAT GGG GCC TCC CTC CGG AAA ATG GTG AAG AAA ATT GAA ATC AGC        96
Arg Tyr Gly Ala Ser Leu Arg Lys Met Val Lys Lys Ile Glu Ile Ser
    120                 125                 130

CAG CAC                                                               102
Gln His
135
```

(2) INFORMATION FOR SEQ ID NO:38:

(i) SEQUENCE CHARACTERISTICS:
        (A) LENGTH: 34 amino acids
        (B) TYPE: amino acid
        (D) TOPOLOGY: linear (ii) MOLECULE TYPE: protein (xi) SEQUENCE DESCRIPTION: SEQ ID NO:38:

```
Met Ala Lys Arg Thr Lys Lys Val Gly Ile Val Gly Lys Tyr Gly Thr
 1               5                  10                  15

Arg Tyr Gly Ala Ser Leu Arg Lys Met Val Lys Lys Ile Glu Ile Ser
            20                  25                  30

Gln His
```

(2) INFORMATION FOR SEQ ID NO:39:

(i) SEQUENCE CHARACTERISTICS:
        (A) LENGTH: 144 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..144

(xi) SEQUENCE DESCRIPTION: SEQ ID NO:39:

```
GAA GAT GAA ATG GCA AAA GCA CTT CTT ACC TTT GGC CCT TTG GTA GTC        48
Glu Asp Glu Met Ala Lys Ala Leu Leu Thr Phe Gly Pro Leu Val Val
 35                  40                  45                  50

ATA GTA GAT GCA GTG AGC TGG CAA GAT TAT CTG GGA GGC ATT ATA CAG        96
Ile Val Asp Ala Val Ser Trp Gln Asp Tyr Leu Gly Gly Ile Ile Gln
                55                  60                  65

CAT CAC TGC TCT AGT GGA GAA GCA AAT CAT GCA GTT CTC ATA ACT GGG       144
His His Cys Ser Ser Gly Glu Ala Asn His Ala Val Leu Ile Thr Gly
            70                  75                  80
```

(2) INFORMATION FOR SEQ ID NO:40:

(i) SEQUENCE CHARACTERISTICS:
        (A) LENGTH: 48 amino acids
        (B) TYPE: amino acid
        (D) TOPOLOGY: linear (ii) MOLECULE TYPE: protein (xi) SEQUENCE DESCRIPTION: SEQ ID NO:40:

```
Glu Asp Glu Met Ala Lys Ala Leu Leu Thr Phe Gly Pro Leu Val Val
 1               5                  10                  15

Ile Val Asp Ala Val Ser Trp Gln Asp Tyr Leu Gly Gly Ile Ile Gln
                20                  25                  30

His His Cys Ser Ser Gly Glu Ala Asn His Ala Val Leu Ile Thr Gly
            35                  40                  45
```

(2) INFORMATION FOR SEQ ID NO:41:

(i) SEQUENCE CHARACTERISTICS:
        (A) LENGTH: 1191 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..1191

(xi) SEQUENCE DESCRIPTION: SEQ ID NO:41:

```
ATG GTG AAA GAA ACA ACT TAC TAC GAT GTT TTG GGG GTC AAA CCC AAT      48
Met Val Lys Glu Thr Thr Tyr Tyr Asp Val Leu Gly Val Lys Pro Asn
     50                  55                  60

GCT ACT CAG GAA GAA TTG AAA AAG GCT TAT AGG AAA CTG GCC TTG AAG      96
Ala Thr Gln Glu Glu Leu Lys Lys Ala Tyr Arg Lys Leu Ala Leu Lys
 65                  70                  75                  80

TAC CAT CCT GAT AAG AAC CCA AAT GAA GGA GAG AAG TTT AAA CAG ATT     144
Tyr His Pro Asp Lys Asn Pro Asn Glu Gly Glu Lys Phe Lys Gln Ile
                 85                  90                  95

TCT CAA GCT TAC GAA GTT CTC TCT GAT GCA AAG AAA AGG GAA TTA TAT     192
Ser Gln Ala Tyr Glu Val Leu Ser Asp Ala Lys Lys Arg Glu Leu Tyr
            100                 105                 110

GAC AAA GGA GGA GAA CAG GCA ATT AAA GAG GGT GGA GCA GGT GGC GGT     240
Asp Lys Gly Gly Glu Gln Ala Ile Lys Glu Gly Gly Ala Gly Gly Gly
        115                 120                 125

TTT GGC TCC CCC ATG GAC ATC TTT GAT ATG TTT TTT GGA GGA GGA GGA     288
Phe Gly Ser Pro Met Asp Ile Phe Asp Met Phe Phe Gly Gly Gly Gly
130                 135                 140

AGG ATG CAG AGA GAA AGG AGA GGT AAA AAT GTT GTA CAT CAG CTC TCA     336
Arg Met Gln Arg Glu Arg Arg Gly Lys Asn Val Val His Gln Leu Ser
145                 150                 155                 160

GTA ACC CTA GAA GAC TTA TAT AAT GGT GCA ACA AGA AAA CTG GCT CTG     384
Val Thr Leu Glu Asp Leu Tyr Asn Gly Ala Thr Arg Lys Leu Ala Leu
                165                 170                 175

CAA AAG AAT GTG ATT TGT GAC AAA TGT GAA GGT AGA GGA GGT AAG AAA     432
Gln Lys Asn Val Ile Cys Asp Lys Cys Glu Gly Arg Gly Gly Lys Lys
            180                 185                 190

GGA GCA GTA GAG TGC TGT CCC AAT TGC CGA GGT ACT GGA ATG CAA ATA     480
Gly Ala Val Glu Cys Cys Pro Asn Cys Arg Gly Thr Gly Met Gln Ile
        195                 200                 205

AGA ATT CAT CAG ATA GGA CCT GGA ATG GTT CAG CAA ATT CAG TCT GTG     528
Arg Ile His Gln Ile Gly Pro Gly Met Val Gln Gln Ile Gln Ser Val
    210                 215                 220

TGC ATG GAG TGC CAG GGC CAT GGG GAG CGG ATC AGT CCT AAA GAT AGA     576
Cys Met Glu Cys Gln Gly His Gly Glu Arg Ile Ser Pro Lys Asp Arg
225                 230                 235                 240

TGT AAA AGC TGC AAC GGA AGG AAG ATA GTT CGA GAG AAA AAA ATT TTA     624
Cys Lys Ser Cys Asn Gly Arg Lys Ile Val Arg Glu Lys Lys Ile Leu
                245                 250                 255
```

```
GAA GTT CAT ATT GAC AAA GGC ATG AAA GAT GGC CAG AAG ATA ACA TTC      672
Glu Val His Ile Asp Lys Gly Met Lys Asp Gly Gln Lys Ile Thr Phe
            260                 265                 270

CAT GGT GAA GGA GAC CAA GAA CCA GGA CTG GAG CCA GGC GAT ATT ATC      720
His Gly Glu Gly Asp Gln Glu Pro Gly Leu Glu Pro Gly Asp Ile Ile
            275                 280                 285

ATT GTG TTA GAT CAG AAG GAC CAT GCT GTT TTT ACT CGA CGA GGA GAA      768
Ile Val Leu Asp Gln Lys Asp His Ala Val Phe Thr Arg Arg Gly Glu
            290                 295                 300

GAC CTT TTC ATG TGT ATG GAC ATA CAG CTC GTT GAA GCA CTG TGT GGC      816
Asp Leu Phe Met Cys Met Asp Ile Gln Leu Val Glu Ala Leu Cys Gly
305                 310                 315                 320

TTC CAC AAG CCA ATA TCT ACT CTT GAC AAC CGA ACC ATC GTC ATC ACC      864
Phe His Lys Pro Ile Ser Thr Leu Asp Asn Arg Thr Ile Val Ile Thr
            325                 330                 335

TCT CAT CCA GGT CAG ATT GTC AAG CAT GGA GAT ATC AAG TGT GTA CTA      912
Ser His Pro Gly Gln Ile Val Lys His Gly Asp Ile Lys Cys Val Leu
            340                 345                 350

AAT GAA GGC ATG CCA ATT TAT CGT AGA CCA TAT GAA AAG GGT CGC CTA      960
Asn Glu Gly Met Pro Ile Tyr Arg Arg Pro Tyr Glu Lys Gly Arg Leu
            355                 360                 365

ATC ATC GAA TTT AAG GTA AAC TTT CCT GAG AAT GGC TTT CTC TCT CCT     1008
Ile Ile Glu Phe Lys Val Asn Phe Pro Glu Asn Gly Phe Leu Ser Pro
            370                 375                 380

GAT AAA CTG TCT TTG CTG GAA AAA CTC CTA CCC GAG AGG AAG GAA GTG     1056
Asp Lys Leu Ser Leu Leu Glu Lys Leu Leu Pro Glu Arg Lys Glu Val
385                 390                 395                 400

GAA GAG ACT GAT GAG ATG GAC CAA GTA GAA CTG GTG GAC TTT GAT CCA     1104
Glu Glu Thr Asp Glu Met Asp Gln Val Glu Leu Val Asp Phe Asp Pro
                405                 410                 415

AAT CAG GAA AGA CGG CGC CAC TAC AAT GGA GAA GCA TAT GAG GAT GAT     1152
Asn Gln Glu Arg Arg Arg His Tyr Asn Gly Glu Ala Tyr Glu Asp Asp
            420                 425                 430

GAA CAT CAT CCC AGA GGT GGT GTT CAG TGT CAG ACC TCT                 1191
Glu His His Pro Arg Gly Gly Val Gln Cys Gln Thr Ser
            435                 440                 445

(2) INFORMATION FOR SEQ ID NO:42:

(i) SEQUENCE CHARACTERISTICS:
        (A) LENGTH: 397 amino acids
        (B) TYPE: amino acid
        (D) TOPOLOGY: linear (ii) MOLECULE TYPE: protein (xi) SEQUENCE DESCRIPTION: SEQ ID NO:42:

Met Val Lys Glu Thr Thr Tyr Tyr Asp Val Leu Gly Val Lys Pro Asn
 1               5                  10                  15

Ala Thr Gln Glu Glu Leu Lys Lys Ala Tyr Arg Lys Leu Ala Leu Lys
                20                  25                  30

Tyr His Pro Asp Lys Asn Pro Asn Glu Gly Glu Lys Phe Lys Gln Ile
             35                  40                  45

Ser Gln Ala Tyr Glu Val Leu Ser Asp Ala Lys Lys Arg Glu Leu Tyr
         50                  55                  60

Asp Lys Gly Gly Glu Gln Ala Ile Lys Glu Gly Gly Ala Gly Gly Gly
 65                  70                  75                  80

Phe Gly Ser Pro Met Asp Ile Phe Asp Met Phe Phe Gly Gly Gly Gly
                 85                  90                  95
```

```
Arg Met Gln Arg Glu Arg Arg Gly Lys Asn Val Val His Gln Leu Ser
            100                 105                 110

Val Thr Leu Glu Asp Leu Tyr Asn Gly Ala Thr Arg Lys Leu Ala Leu
            115                 120                 125

Gln Lys Asn Val Ile Cys Asp Lys Cys Glu Gly Arg Gly Gly Lys Lys
            130                 135                 140

Gly Ala Val Glu Cys Cys Pro Asn Cys Arg Gly Thr Gly Met Gln Ile
145                 150                 155                 160

Arg Ile His Gln Ile Gly Pro Gly Met Val Gln Gln Ile Gln Ser Val
                165                 170                 175

Cys Met Glu Cys Gln Gly His Gly Glu Arg Ile Ser Pro Lys Asp Arg
            180                 185                 190

Cys Lys Ser Cys Asn Gly Arg Lys Ile Val Arg Glu Lys Lys Ile Leu
            195                 200                 205

Glu Val His Ile Asp Lys Gly Met Lys Asp Gly Gln Lys Ile Thr Phe
            210                 215                 220

His Gly Glu Gly Asp Gln Glu Pro Gly Leu Glu Pro Gly Asp Ile Ile
225                 230                 235                 240

Ile Val Leu Asp Gln Lys Asp His Ala Val Phe Thr Arg Arg Gly Glu
                245                 250                 255

Asp Leu Phe Met Cys Met Asp Ile Gln Leu Val Glu Ala Leu Cys Gly
            260                 265                 270

Phe His Lys Pro Ile Ser Thr Leu Asp Asn Arg Thr Ile Val Ile Thr
            275                 280                 285

Ser His Pro Gly Gln Ile Val Lys His Gly Asp Ile Lys Cys Val Leu
            290                 295                 300

Asn Glu Gly Met Pro Ile Tyr Arg Arg Pro Tyr Glu Lys Gly Arg Leu
305                 310                 315                 320

Ile Ile Glu Phe Lys Val Asn Phe Pro Glu Asn Gly Phe Leu Ser Pro
                325                 330                 335

Asp Lys Leu Ser Leu Leu Glu Lys Leu Leu Pro Glu Arg Lys Glu Val
            340                 345                 350

Glu Glu Thr Asp Glu Met Asp Gln Val Glu Leu Val Asp Phe Asp Pro
            355                 360                 365

Asn Gln Glu Arg Arg Arg His Tyr Asn Gly Glu Ala Tyr Glu Asp Asp
            370                 375                 380

Glu His His Pro Arg Gly Gly Val Gln Cys Gln Thr Ser
385                 390                 395

(2) INFORMATION FOR SEQ ID NO:43:

(i) SEQUENCE CHARACTERISTICS:
        (A) LENGTH: 243 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..243

(xi) SEQUENCE DESCRIPTION: SEQ ID NO:43:

ATG GCA GCA GAA CCA CTG ACA GAG CTA GAG GAG TCC ATT GAG ACC GTG      48
Met Ala Ala Glu Pro Leu Thr Glu Leu Glu Glu Ser Ile Glu Thr Val
                400                 405                 410

GTC ACC ACC TTC TTC ACC TTT GCA AGG CAG GAG GGC CGG AAG GAT AGC      96
```

```
Val Thr Thr Phe Phe Thr Phe Ala Arg Gln Glu Gly Arg Lys Asp Ser
415                 420                 425

CTC AGC GTC AAC GAG TTC AAA GAG CTG GTT ACC CAG CAG TTG CCC CAT      144
Leu Ser Val Asn Glu Phe Lys Glu Leu Val Thr Gln Gln Leu Pro His
430                 435                 440                 445

CTG CTC AAG GAT GTG GGC TCT CTT GAT GAG AAG ATG AAG AGC TTG GAT      192
Leu Leu Lys Asp Val Gly Ser Leu Asp Glu Lys Met Lys Ser Leu Asp
            450                 455                 460

GTG AAT CAG GAC TCG GAG CTC AAG TTC AAT GAG TAC TGG AGA TTG ATT      240
Val Asn Gln Asp Ser Glu Leu Lys Phe Asn Glu Tyr Trp Arg Leu Ile
            465                 470                 475

GGG                                                                   243
Gly (2) INFORMATION FOR SEQ ID NO:44:

(i) SEQUENCE CHARACTERISTICS:
        (A) LENGTH: 81 amino acids
        (B) TYPE: amino acid
        (D) TOPOLOGY: linear (ii) MOLECULE TYPE: protein (xi) SEQUENCE DESCRIPTION: SEQ ID NO:44:

Met Ala Ala Glu Pro Leu Thr Glu Leu Glu Ser Ile Glu Thr Val
 1               5                  10                  15

Val Thr Thr Phe Phe Thr Phe Ala Arg Gln Glu Gly Arg Lys Asp Ser
                20                  25                  30

Leu Ser Val Asn Glu Phe Lys Glu Leu Val Thr Gln Gln Leu Pro His
                35                  40                  45

Leu Leu Lys Asp Val Gly Ser Leu Asp Glu Lys Met Lys Ser Leu Asp
        50                  55                  60

Val Asn Gln Asp Ser Glu Leu Lys Phe Asn Glu Tyr Trp Arg Leu Ile
 65                 70                  75                  80

Gly (2) INFORMATION FOR SEQ ID NO:45:

(i) SEQUENCE CHARACTERISTICS:
        (A) LENGTH: 282 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..282

(xi) SEQUENCE DESCRIPTION: SEQ ID NO:45:

ATG GCG CAG GAT CAA GGT GAA AAG GAG AAC CCC ATG CGG GAA CTT CGC       48
Met Ala Gln Asp Gln Gly Glu Lys Glu Asn Pro Met Arg Glu Leu Arg
                85                  90                  95

ATC CGC AAA CTC TGT CTC AAC ATC TGT GTT GGG GAG AGT GGA GAC AGA       96
Ile Arg Lys Leu Cys Leu Asn Ile Cys Val Gly Glu Ser Gly Asp Arg
            100                 105                 110

CTG ACG CGA GCA GCC AAG GTG TTG GAG CAG CTC ACA GGG CAG ACC CCT      144
Leu Thr Arg Ala Ala Lys Val Leu Glu Gln Leu Thr Gly Gln Thr Pro
115                 120                 125

GTG TTT TCC AAA GCT AGA TAC ACT GTC AGA TCC TTT GGC ATC CGG AGA      192
Val Phe Ser Lys Ala Arg Tyr Thr Val Arg Ser Phe Gly Ile Arg Arg
130                 135                 140                 145
```

```
AAT GAA AAG ATT GCT GTC CAC TGC ACA GTT CGA GGG GCC AAG GCA GAA       240
Asn Glu Lys Ile Ala Val His Cys Thr Val Arg Gly Ala Lys Ala Glu
            150                 155                 160

GAA ATC TTG GAG AAG GGT CTA AAG GTG CGG GAG TAT GAG TTA               282
Glu Ile Leu Glu Lys Gly Leu Lys Val Arg Glu Tyr Glu Leu
        165                 170                 175
```

(2) INFORMATION FOR SEQ ID NO:46:

(i) SEQUENCE CHARACTERISTICS:
        (A) LENGTH: 94 amino acids
        (B) TYPE: amino acid
        (D) TOPOLOGY: linear (ii) MOLECULE TYPE: protein (xi) SEQUENCE DESCRIPTION: SEQ ID NO:46:

```
Met Ala Gln Asp Gln Gly Glu Lys Glu Asn Pro Met Arg Glu Leu Arg
 1               5                  10                  15

Ile Arg Lys Leu Cys Leu Asn Ile Cys Val Gly Glu Ser Gly Asp Arg
            20                  25                  30

Leu Thr Arg Ala Ala Lys Val Leu Glu Gln Leu Thr Gly Gln Thr Pro
            35                  40                  45

Val Phe Ser Lys Ala Arg Tyr Thr Val Arg Ser Phe Gly Ile Arg Arg
 50                  55                  60

Asn Glu Lys Ile Ala Val His Cys Thr Val Arg Gly Ala Lys Ala Glu
 65                  70                  75                  80

Glu Ile Leu Glu Lys Gly Leu Lys Val Arg Glu Tyr Glu Leu
             85                  90
```

(2) INFORMATION FOR SEQ ID NO:47:

(i) SEQUENCE CHARACTERISTICS:
        (A) LENGTH: 345 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..345

(xi) SEQUENCE DESCRIPTION: SEQ ID NO:47:

```
ATG GCT TTT AAG GAT ACC GGA AAA ACA CCC GTG GAG CCG GAG GTG GCA       48
Met Ala Phe Lys Asp Thr Gly Lys Thr Pro Val Glu Pro Glu Val Ala
 95                  100                 105                 110

ATT CAC CGA ATT CGA ATC ACC CTA ACA AGC CGC AAC GTA AAA TCC TTG       96
Ile His Arg Ile Arg Ile Thr Leu Thr Ser Arg Asn Val Lys Ser Leu
             115                 120                 125

GAA AAG GTG TGT GCT GAC TTG ATA AGA GGC GCA AAA GAA AAG AAT CTC      144
Glu Lys Val Cys Ala Asp Leu Ile Arg Gly Ala Lys Glu Lys Asn Leu
             130                 135                 140

AAA GTG AAA GGA CCA GTT CGA ATG CCT ACC AAG ACT TTG AGA ATC ACT      192
Lys Val Lys Gly Pro Val Arg Met Pro Thr Lys Thr Leu Arg Ile Thr
             145                 150                 155

ACG AGA AAA ACT CCT TGT GGT GAA GGT TCT AAG ACG TGG GAT CGT TTC      240
Thr Arg Lys Thr Pro Cys Gly Glu Gly Ser Lys Thr Trp Asp Arg Phe
         160                 165                 170

CAG ATG AGA ATT CAC AAG CGA CTC ATT GAC TTG CAC AGT CCT TCT GAG      288
Gln Met Arg Ile His Lys Arg Leu Ile Asp Leu His Ser Pro Ser Glu
175                 180                 185                 190
```

```
ATT GTT AAG CAG ATT ACT TCC ATC AGT ATT GAG CCA GGT GTT GAG GTG         336
Ile Val Lys Gln Ile Thr Ser Ile Ser Ile Glu Pro Gly Val Glu Val
            195                 200                 205

GAA GTC ACC                                                              345
Glu Val Thr
```

(2) INFORMATION FOR SEQ ID NO:48:

(i) SEQUENCE CHARACTERISTICS:
        (A) LENGTH: 115 amino acids
        (B) TYPE: amino acid
        (D) TOPOLOGY: linear (ii) MOLECULE TYPE: protein (xi) SEQUENCE DESCRIPTION: SEQ ID NO:48:

```
Met Ala Phe Lys Asp Thr Gly Lys Thr Pro Val Glu Pro Glu Val Ala
 1               5                  10                  15

Ile His Arg Ile Arg Ile Thr Leu Thr Ser Arg Asn Val Lys Ser Leu
                20                  25                  30

Glu Lys Val Cys Ala Asp Leu Ile Arg Gly Ala Lys Glu Lys Asn Leu
            35                  40                  45

Lys Val Lys Gly Pro Val Arg Met Pro Thr Lys Thr Leu Arg Ile Thr
        50                  55                  60

Thr Arg Lys Thr Pro Cys Gly Glu Gly Ser Lys Thr Trp Asp Arg Phe
65                  70                  75                  80

Gln Met Arg Ile His Lys Arg Leu Ile Asp Leu His Ser Pro Ser Glu
                85                  90                  95

Ile Val Lys Gln Ile Thr Ser Ile Ser Ile Glu Pro Gly Val Glu Val
            100                 105                 110

Glu Val Thr
        115
```

(2) INFORMATION FOR SEQ ID NO:49:

(i) SEQUENCE CHARACTERISTICS:
        (A) LENGTH: 330 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..330

(xi) SEQUENCE DESCRIPTION: SEQ ID NO:49:

```
CTT CAT ATG GTT TTG CGT CCA TTC CTC CTT CGT CGA ATT AAG GCT GAT          48
Leu His Met Val Leu Arg Pro Phe Leu Leu Arg Arg Ile Lys Ala Asp
            120                 125                 130

GTT GAA AAG AGT TTG CCT CCA AAG AAG GAA GTA AAA ATC TAT GTG GGC          96
Val Glu Lys Ser Leu Pro Pro Lys Lys Glu Val Lys Ile Tyr Val Gly
        135                 140                 145

CTC AGC AAA ATG CAA AGG GAA TGG TAT ACT CGG ATA TTA ATG AAG GAT         144
Leu Ser Lys Met Gln Arg Glu Trp Tyr Thr Arg Ile Leu Met Lys Asp
    150                 155                 160

ATA GAT ATA CTC AAC TCA GCA GGC AAG ATG GAC AAA ATG AGG TTA TTG         192
Ile Asp Ile Leu Asn Ser Ala Gly Lys Met Asp Lys Met Arg Leu Leu
165                 170                 175

AAC ATC CTA ATG CAG TTG AGA AAA TGT TGT AAT CAT CCA TAT CTC TTT         240
Asn Ile Leu Met Gln Leu Arg Lys Cys Cys Asn His Pro Tyr Leu Phe
```

```
                 180                   185                   190                   195
GAT  GGA  GCA  GAA  CCT  GGT  CCA  CCT  TAT  ACA  ACA  GAT  ATG  CAT  CTA  GTA           288
Asp  Gly  Ala  Glu  Pro  Gly  Pro  Pro  Tyr  Thr  Thr  Asp  Met  His  Leu  Val
                    200                       205                      210

ACC  AAC  AGT  GGC  AAA  ATG  GTG  GTT  TTA  GAC  AAG  CTG  CTC  CCT                     330
Thr  Asn  Ser  Gly  Lys  Met  Val  Val  Leu  Asp  Lys  Leu  Leu  Pro
               215                      220                      225
```

(2) INFORMATION FOR SEQ ID NO:50:

(i) SEQUENCE CHARACTERISTICS:
        (A) LENGTH: 110 amino acids
        (B) TYPE: amino acid
        (D) TOPOLOGY: linear (ii) MOLECULE TYPE: protein (xi) SEQUENCE DESCRIPTION: SEQ ID NO:50:

```
Leu  His  Met  Val  Leu  Arg  Pro  Phe  Leu  Leu  Arg  Arg  Ile  Lys  Ala  Asp
 1                  5                        10                       15

Val  Glu  Lys  Ser  Leu  Pro  Pro  Lys  Lys  Glu  Val  Lys  Ile  Tyr  Val  Gly
                    20                       25                       30

Leu  Ser  Lys  Met  Gln  Arg  Glu  Trp  Tyr  Thr  Arg  Ile  Leu  Met  Lys  Asp
               35                       40                       45

Ile  Asp  Ile  Leu  Asn  Ser  Ala  Gly  Lys  Met  Asp  Lys  Met  Arg  Leu  Leu
 50                      55                       60

Asn  Ile  Leu  Met  Gln  Leu  Arg  Lys  Cys  Cys  Asn  His  Pro  Tyr  Leu  Phe
 65                      70                       75                       80

Asp  Gly  Ala  Glu  Pro  Gly  Pro  Pro  Tyr  Thr  Thr  Asp  Met  His  Leu  Val
                    85                       90                       95

Thr  Asn  Ser  Gly  Lys  Met  Val  Val  Leu  Asp  Lys  Leu  Leu  Pro
                    100                      105                      110
```

(2) INFORMATION FOR SEQ ID NO:51:

(i) SEQUENCE CHARACTERISTICS:
        (A) LENGTH: 312 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..312

(xi) SEQUENCE DESCRIPTION: SEQ ID NO:51:

```
CTG  GCC  ACC  TCT  GTC  CTG  CTG  TCA  CCG  GAC  TTC  CTC  TGG  GAT  GTG  CCT          48
Leu  Ala  Thr  Ser  Val  Leu  Leu  Ser  Pro  Asp  Phe  Leu  Trp  Asp  Val  Pro
                    115                      120                      125

TCC  AAC  TGG  ACG  CTG  GAG  GAG  GCG  GCC  TCG  GTG  CCT  GTC  GTC  TAC  AGC          96
Ser  Asn  Trp  Thr  Leu  Glu  Glu  Ala  Ala  Ser  Val  Pro  Val  Val  Tyr  Ser
                    130                      135                      140

ACG  GCC  TAC  TAC  GCG  CTG  GTG  GTG  CGT  GGG  CGG  GTG  CGC  CCC  GGG  GAG         144
Thr  Ala  Tyr  Tyr  Ala  Leu  Val  Val  Arg  Gly  Arg  Val  Arg  Pro  Gly  Glu
                    145                      150                      155

ACG  CTG  CTC  ATC  CAC  TCG  GGC  TCG  GGC  GGC  GTG  GGC  CAG  GCC  GCC  ATC         192
Thr  Leu  Leu  Ile  His  Ser  Gly  Ser  Gly  Gly  Val  Gly  Gln  Ala  Ala  Ile
               160                      165                      170

GCC  ATC  GCC  CTC  AGT  CTG  GGC  TGC  CGC  GTC  TTC  ANC  ACC  GTG  GGG  TCG         240
Ala  Ile  Ala  Leu  Ser  Leu  Gly  Cys  Arg  Val  Phe  Xaa  Thr  Val  Gly  Ser
 175                     180                      185                      190
```

```
GCT GAG AAG CGG GCG TAC CTC CAG GCC AGG TTC CCC AAG TTC GAC AGA      288
Ala Glu Lys Arg Ala Tyr Leu Gln Ala Arg Phe Pro Lys Phe Asp Arg
            195                 200                 205

ACC AGT TTG GCA AAC TCC CGG GAC                                      312
Thr Ser Leu Ala Asn Ser Arg Asp
            210
```

(2) INFORMATION FOR SEQ ID NO:52:

(i) SEQUENCE CHARACTERISTICS:
        (A) LENGTH: 104 amino acids
        (B) TYPE: amino acid
        (D) TOPOLOGY: linear (ii) MOLECULE TYPE: protein (xi) SEQUENCE DESCRIPTION: SEQ ID NO:52:

```
Leu Ala Thr Ser Val Leu Leu Ser Pro Asp Phe Leu Trp Asp Val Pro
 1               5                  10                  15

Ser Asn Trp Thr Leu Glu Glu Ala Ala Ser Val Pro Val Val Tyr Ser
                20                  25                  30

Thr Ala Tyr Tyr Ala Leu Val Val Arg Gly Arg Val Arg Pro Gly Glu
            35                  40                  45

Thr Leu Leu Ile His Ser Gly Ser Gly Gly Val Gly Gln Ala Ala Ile
        50                  55                  60

Ala Ile Ala Leu Ser Leu Gly Cys Arg Val Phe Xaa Thr Val Gly Ser
65                  70                  75                  80

Ala Glu Lys Arg Ala Tyr Leu Gln Ala Arg Phe Pro Lys Phe Asp Arg
                85                  90                  95

Thr Ser Leu Ala Asn Ser Arg Asp
            100
```

(2) INFORMATION FOR SEQ ID NO:53:

(i) SEQUENCE CHARACTERISTICS:
        (A) LENGTH: 342 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..342

(xi) SEQUENCE DESCRIPTION: SEQ ID NO:53:

```
CTG GAT GGA GCT CGG GCT GAG CGG GTG CTA GAG CTT GTA TCC ATC ACT       48
Leu Asp Gly Ala Arg Ala Glu Arg Val Leu Glu Leu Val Ser Ile Thr
105                 110                 115                 120

GCC AAC AAG AAC ACC TGT CCT GGA GAC CGA AGT GCC ATC ACA CCG GGC       96
Ala Asn Lys Asn Thr Cys Pro Gly Asp Arg Ser Ala Ile Thr Pro Gly
                125                 130                 135

GGC CTG CGG CTT GGG GCC CCA GCC TTA ACT TCT CGA CAG TTC CGT GAG      144
Gly Leu Arg Leu Gly Ala Pro Ala Leu Thr Ser Arg Gln Phe Arg Glu
            140                 145                 150

GAT GAC TTC CGG AGA GTT GTG GAC TTT ATA GAT GAA GGG GTC AAC ATT      192
Asp Asp Phe Arg Arg Val Val Asp Phe Ile Asp Glu Gly Val Asn Ile
        155                 160                 165

GGC TTA GAG GTG AAG AGC AAG ACT GCC AAG CTC CAG GAT TTC AAA TCC      240
Gly Leu Glu Val Lys Ser Lys Thr Ala Lys Leu Gln Asp Phe Lys Ser
170                 175                 180
```

```
TTC CTG CTT AAG GAC TCA GAA ACA AGT CAG CGT CTG GCC AAC CTC AGG      288
Phe Leu Leu Lys Asp Ser Glu Thr Ser Gln Arg Leu Ala Asn Leu Arg
185                 190                 195                 200

CAA CGG GTG GAG CAG TTT GCC AGG GCC TTC CCC ATG CCT GGT TTT GAT      336
Gln Arg Val Glu Gln Phe Ala Arg Ala Phe Pro Met Pro Gly Phe Asp
            205                 210                 215

GAG CAT                                                              342
Glu His
```

(2) INFORMATION FOR SEQ ID NO:54:

(i) SEQUENCE CHARACTERISTICS:
        (A) LENGTH: 114 amino acids
        (B) TYPE: amino acid
        (D) TOPOLOGY: linear (ii) MOLECULE TYPE: protein (xi) SEQUENCE DESCRIPTION: SEQ ID NO:54:

```
Leu Asp Gly Ala Arg Ala Glu Arg Val Leu Glu Leu Val Ser Ile Thr
 1               5                  10                  15

Ala Asn Lys Asn Thr Cys Pro Gly Asp Arg Ser Ala Ile Thr Pro Gly
            20                  25                  30

Gly Leu Arg Leu Gly Ala Pro Ala Leu Thr Ser Arg Gln Phe Arg Glu
        35                  40                  45

Asp Asp Phe Arg Arg Val Val Asp Phe Ile Asp Glu Gly Val Asn Ile
    50                  55                  60

Gly Leu Glu Val Lys Ser Lys Thr Ala Lys Leu Gln Asp Phe Lys Ser
65                  70                  75                  80

Phe Leu Leu Lys Asp Ser Glu Thr Ser Gln Arg Leu Ala Asn Leu Arg
                85                  90                  95

Gln Arg Val Glu Gln Phe Ala Arg Ala Phe Pro Met Pro Gly Phe Asp
            100                 105                 110

Glu His
```

(2) INFORMATION FOR SEQ ID NO:55:

(i) SEQUENCE CHARACTERISTICS:
        (A) LENGTH: 219 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..219

(xi) SEQUENCE DESCRIPTION: SEQ ID NO:55:

```
CTC TTT GTA ACT GGA GTC CAT GAG GAA GCC ACC GAA GAA GAC ATA CAC       48
Leu Phe Val Thr Gly Val His Glu Glu Ala Thr Glu Glu Asp Ile His
115                 120                 125                 130

GAC AAA TTC GCA GAA TAT GGG GAA ATT AAA AAC ATT CAT CTC AAC CTC       96
Asp Lys Phe Ala Glu Tyr Gly Glu Ile Lys Asn Ile His Leu Asn Leu
                135                 140                 145

GAC AGG CGA ACA GGA TAT CTG AAG GGG TAT ACT CTA GTT GAA TAT GAA      144
Asp Arg Arg Thr Gly Tyr Leu Lys Gly Tyr Thr Leu Val Glu Tyr Glu
            150                 155                 160

ACA TAC AAG GAA GCC CAG GCT GCT ATG GAG GGA CTC AAT GGC CAG GAT      192
Thr Tyr Lys Glu Ala Gln Ala Ala Met Glu Gly Leu Asn Gly Gln Asp
        165                 170                 175
```

```
TTG ATG GGA CAG CCC ATC AGC GTT GAC                                       219
Leu Met Gly Gln Pro Ile Ser Val Asp
    180                 185
```

(2) INFORMATION FOR SEQ ID NO:56:

(i) SEQUENCE CHARACTERISTICS:
        (A) LENGTH: 73 amino acids
        (B) TYPE: amino acid
        (D) TOPOLOGY: linear (ii) MOLECULE TYPE: protein (xi) SEQUENCE DESCRIPTION: SEQ ID NO:56:

```
Leu Phe Val Thr Gly Val His Glu Glu Ala Thr Glu Glu Asp Ile His
1               5                   10                  15

Asp Lys Phe Ala Glu Tyr Gly Glu Ile Lys Asn Ile His Leu Asn Leu
            20                  25                  30

Asp Arg Arg Thr Gly Tyr Leu Lys Gly Tyr Thr Leu Val Glu Tyr Glu
            35                  40                  45

Thr Tyr Lys Glu Ala Gln Ala Ala Met Glu Gly Leu Asn Gly Gln Asp
        50                  55                  60

Leu Met Gly Gln Pro Ile Ser Val Asp
65                  70
```

(2) INFORMATION FOR SEQ ID NO:57:

(i) SEQUENCE CHARACTERISTICS:
        (A) LENGTH: 153 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..153

(xi) SEQUENCE DESCRIPTION: SEQ ID NO:57:

```
AAG ATT CAT GAA GCC ACA AGC ATG CCT GCA GGG AAA CAG AAG CTA CAG        48
Lys Ile His Glu Ala Thr Ser Met Pro Ala Gly Lys Gln Lys Leu Gln
    75                  80                  85

TAT GAG GGT ATC TTC ATC AAA GAT TCC AAC TCA CTG GCT TAC TAC AAC        96
Tyr Glu Gly Ile Phe Ile Lys Asp Ser Asn Ser Leu Ala Tyr Tyr Asn
90                  95                  100                 105

ATG GCC AAT GGC GCA GTC ATC CAC CTG GCC CTC AAG GAG AGA GGC GGG       144
Met Ala Asn Gly Ala Val Ile His Leu Ala Leu Lys Glu Arg Gly Gly
                110                 115                 120

AGG AAG AAG                                                           153
Arg Lys Lys
```

(2) INFORMATION FOR SEQ ID NO:58:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO:58:

```
Lys Ile His Glu Ala Thr Ser Met Pro Ala Gly Lys Gln Lys Leu Gln
1               5                   10                  15

Tyr Glu Gly Ile Phe Ile Lys Asp Ser Asn Ser Leu Ala Tyr Tyr Asn
```

```
                        20                  25                  30
Met Ala Asn Gly Ala Val Ile His Leu Ala Leu Lys Glu Arg Gly Gly
                35                  40                  45

Arg Lys Lys
        50
```

(2) INFORMATION FOR SEQ ID NO:59:

(i) SEQUENCE CHARACTERISTICS:
        (A) LENGTH: 231 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..231

(xi) SEQUENCE DESCRIPTION: SEQ ID NO:59:

```
ATG GGG TTT GTT AAA GTT GTT AAG AAT AAG GCC TAC TTT AAG AGA TAC        48
Met Gly Phe Val Lys Val Val Lys Asn Lys Ala Tyr Phe Lys Arg Tyr
            55                  60                  65

CAA GTG AAA TTT AGA AGA CGA CGA GAG GGT AAA ACT GAT TAT TAT GCT        96
Gln Val Lys Phe Arg Arg Arg Arg Glu Gly Lys Thr Asp Tyr Tyr Ala
        70                  75                  80

CGG AAA CGC TTG GTG ATA CAA GAT AAA AAT AAA TAC AAC ACA CCC AAA       144
Arg Lys Arg Leu Val Ile Gln Asp Lys Asn Lys Tyr Asn Thr Pro Lys
    85                  90                  95

TAC AGG ATG ATA GTT CGT GTG ACA AAC AGA GAT ATC ATT TGT CAG ATT       192
Tyr Arg Met Ile Val Arg Val Thr Asn Arg Asp Ile Ile Cys Gln Ile
100                 105                 110                 115

GCT TAT GCC CGT ATA GAG GGG GAT ATG ATA GTC TGC GCA                   231
Ala Tyr Ala Arg Ile Glu Gly Asp Met Ile Val Cys Ala
                120                 125
```

(2) INFORMATION FOR SEQ ID NO:60:

(i) SEQUENCE CHARACTERISTICS:
        (A) LENGTH: 77 amino acids
        (B) TYPE: amino acid
        (D) TOPOLOGY: linear (ii) MOLECULE TYPE: protein (xi) SEQUENCE DESCRIPTION: SEQ ID NO:60:

```
Met Gly Phe Val Lys Val Val Lys Asn Lys Ala Tyr Phe Lys Arg Tyr
  1               5                  10                  15

Gln Val Lys Phe Arg Arg Arg Arg Glu Gly Lys Thr Asp Tyr Tyr Ala
                20                  25                  30

Arg Lys Arg Leu Val Ile Gln Asp Lys Asn Lys Tyr Asn Thr Pro Lys
            35                  40                  45

Tyr Arg Met Ile Val Arg Val Thr Asn Arg Asp Ile Ile Cys Gln Ile
        50                  55                  60

Ala Tyr Ala Arg Ile Glu Gly Asp Met Ile Val Cys Ala
 65                 70                  75
```

(2) INFORMATION FOR SEQ ID NO:61:

(i) SEQUENCE CHARACTERISTICS:
        (A) LENGTH: 225 base pairs
        (B) TYPE: nucleic acid
        (C) STRANDEDNESS: double (D) TOPOLOGY: linear (ii) MOLECULE TYPE: cDNA to mRNA (ix) FEATURE:
            (A) NAME/KEY: CDS
            (B) LOCATION: 1..225

(xi) SEQUENCE DESCRIPTION: SEQ ID NO:61:

```
ATC GAT CCC CCC CGA GGC GTC CTC ATG TAT GGA CCA CCT GGC TGT GGG       48
Ile Asp Pro Pro Arg Gly Val Leu Met Tyr Gly Pro Pro Gly Cys Gly
         80                  85                  90

AAG ACC ATG TTG GCA AAG GCG GTG GCA CAT CAC ACA ACA GCT GCA TTC       96
Lys Thr Met Leu Ala Lys Ala Val Ala His His Thr Thr Ala Ala Phe
     95                 100                 105

ATC CGG GTC GTG GGC TCG GAG TTT GTA CAG AAG TAT CTG GGT GAG GGC      144
Ile Arg Val Val Gly Ser Glu Phe Val Gln Lys Tyr Leu Gly Glu Gly
110                 115                 120                 125

CCC CGC ATG GTC CGG GAT GTG TTC CGC CTG GCC AAG GAG AAT GCA CCT      192
Pro Arg Met Val Arg Asp Val Phe Arg Leu Ala Lys Glu Asn Ala Pro
                130                 135                 140

GCC ATC ATC TTC ATA GAC GAG ATT GAT GCC ATC                          225
Ala Ile Ile Phe Ile Asp Glu Ile Asp Ala Ile
            145                 150
```

(2) INFORMATION FOR SEQ ID NO:62:

(i) SEQUENCE CHARACTERISTICS:
            (A) LENGTH: 75 amino acids
            (B) TYPE: amino acid
            (D) TOPOLOGY: linear (ii) MOLECULE TYPE: protein (xi) SEQUENCE DESCRIPTION: SEQ ID NO:62:

```
Ile Asp Pro Pro Arg Gly Val Leu Met Tyr Gly Pro Pro Gly Cys Gly
 1               5                  10                  15

Lys Thr Met Leu Ala Lys Ala Val Ala His His Thr Thr Ala Ala Phe
             20                  25                  30

Ile Arg Val Val Gly Ser Glu Phe Val Gln Lys Tyr Leu Gly Glu Gly
         35                  40                  45

Pro Arg Met Val Arg Asp Val Phe Arg Leu Ala Lys Glu Asn Ala Pro
     50                  55                  60

Ala Ile Ile Phe Ile Asp Glu Ile Asp Ala Ile
65                  70                  75
```

(2) INFORMATION FOR SEQ ID NO:63:

(i) SEQUENCE CHARACTERISTICS:
            (A) LENGTH: 288 base pairs
            (B) TYPE: nucleic acid
            (C) STRANDEDNESS: double
            (D) TOPOLOGY: linear (ii) MOLECULE TYPE: cDNA to mRNA (ix) FEATURE:
            (A) NAME/KEY: CDS
            (B) LOCATION: 1..288

(xi) SEQUENCE DESCRIPTION: SEQ ID NO:63:

```
TTC CAG CTG CAC ACA CAT GTG AAC GAT GGC ACT GAA TTT GGA GGT TCT       48
Phe Gln Leu His Thr His Val Asn Asp Gly Thr Glu Phe Gly Gly Ser
         80                  85                  90

ATC TAC CAG AAG GTG AAT GAG AAG ATT GAA ACA TCC ATA AAC CTT GCT       96
```

```
Ile Tyr Gln Lys Val Asn Glu Lys Ile Glu Thr Ser Ile Asn Leu Ala
             95                 100                 105

TGG ACA GCT GGG AGT AAC AAC ACC CGT TTT GGC ATT GCT GCT AAG TAC        144
Trp Thr Ala Gly Ser Asn Asn Thr Arg Phe Gly Ile Ala Ala Lys Tyr
         110                 115                 120

ATG CTG GAT TGT AGA ACT TCT CTC TCT GCT AAA GTA AAT AAT GCC AGC        192
Met Leu Asp Cys Arg Thr Ser Leu Ser Ala Lys Val Asn Asn Ala Ser
         125                 130                 135

CTG ATT GGA CTG GGT TAT ACT CAG ACC CTT CGA CCA GGA GTC AAA TTG        240
Leu Ile Gly Leu Gly Tyr Thr Gln Thr Leu Arg Pro Gly Val Lys Leu
140                 145                 150                 155

ACT TTA TCA GCT TTA ATC GAT GGG AAG AAC TTC AGT GCA GGA GGT CAC        288
Thr Leu Ser Ala Leu Ile Asp Gly Lys Asn Phe Ser Ala Gly Gly His
                 160                 165                 170

(2) INFORMATION FOR SEQ ID NO:64:

(i) SEQUENCE CHARACTERISTICS:
        (A) LENGTH: 96 amino acids
        (B) TYPE: amino acid
        (D) TOPOLOGY: linear (ii) MOLECULE TYPE: protein (xi) SEQUENCE DESCRIPTION: SEQ ID NO:64:

Phe Gln Leu His Thr His Val Asn Asp Gly Thr Glu Phe Gly Gly Ser
 1               5                  10                  15

Ile Tyr Gln Lys Val Asn Glu Lys Ile Glu Thr Ser Ile Asn Leu Ala
                20                  25                  30

Trp Thr Ala Gly Ser Asn Asn Thr Arg Phe Gly Ile Ala Ala Lys Tyr
             35                  40                  45

Met Leu Asp Cys Arg Thr Ser Leu Ser Ala Lys Val Asn Asn Ala Ser
         50                  55                  60

Leu Ile Gly Leu Gly Tyr Thr Gln Thr Leu Arg Pro Gly Val Lys Leu
65                  70                  75                  80

Thr Leu Ser Ala Leu Ile Asp Gly Lys Asn Phe Ser Ala Gly Gly His
                 85                  90                  95

(2) INFORMATION FOR SEQ ID NO:65:

(i) SEQUENCE CHARACTERISTICS:
        (A) LENGTH: 372 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..372

(xi) SEQUENCE DESCRIPTION: SEQ ID NO:65:

AGG CTG GTC GTG CTC GCC ACC CCT CAG GTC TCA GAC TCC ATG AGA AAA         48
Arg Leu Val Val Leu Ala Thr Pro Gln Val Ser Asp Ser Met Arg Lys
             100                 105                 110

GTT TTA GAG ACA GTC TTT GAT GAA GTC ATC ATG GTA GAT GTC TTG GAC         96
Val Leu Glu Thr Val Phe Asp Glu Val Ile Met Val Asp Val Leu Asp
         115                 120                 125

AGT GGC GAT TCT GCT CAT CTA ACC TTA ATG AAG AGG CCA GAG TTG GGT        144
Ser Gly Asp Ser Ala His Leu Thr Leu Met Lys Arg Pro Glu Leu Gly
         130                 135                 140

GTC ACG CTG ACA AAG CTC CAC TGC TGG TCG CTT ACA CAG TAT TCA AAA        192
```

```
Val Thr Leu Thr Lys Leu His Cys Trp Ser Leu Thr Gln Tyr Ser Lys
145                 150                 155                 160

TGT GTA TTC ATG GAT GCA GAT ACT CTG GTC CTA GCA AAT ATT GAT GAT    240
Cys Val Phe Met Asp Ala Asp Thr Leu Val Leu Ala Asn Ile Asp Asp
                165                 170                 175

CTT TTT GAC AGA GAA GAA TTG TCA GCA GCA CCA GAC CCA GGG TGG CCT    288
Leu Phe Asp Arg Glu Glu Leu Ser Ala Ala Pro Asp Pro Gly Trp Pro
            180                 185                 190

GAC TGC TTC AAT TCC GGA GTC TTC GTT TAT CAG CCT TCA GTT GAA ACA    336
Asp Cys Phe Asn Ser Gly Val Phe Val Tyr Gln Pro Ser Val Glu Thr
        195                 200                 205

TAC AAT CAG CTG TTG CAT CTT GCT TCT GAG CAA GGT                    372
Tyr Asn Gln Leu Leu His Leu Ala Ser Glu Gln Gly
    210                 215                 220

(2) INFORMATION FOR SEQ ID NO:66:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO:66:

Arg Leu Val Val Leu Ala Thr Pro Gln Val Ser Asp Ser Met Arg Lys
 1               5                  10                  15

Val Leu Glu Thr Val Phe Asp Glu Val Ile Met Val Asp Val Leu Asp
                20                  25                  30

Ser Gly Asp Ser Ala His Leu Thr Leu Met Lys Arg Pro Glu Leu Gly
            35                  40                  45

Val Thr Leu Thr Lys Leu His Cys Trp Ser Leu Thr Gln Tyr Ser Lys
        50                  55                  60

Cys Val Phe Met Asp Ala Asp Thr Leu Val Leu Ala Asn Ile Asp Asp
65                  70                  75                  80

Leu Phe Asp Arg Glu Glu Leu Ser Ala Ala Pro Asp Pro Gly Trp Pro
                85                  90                  95

Asp Cys Phe Asn Ser Gly Val Phe Val Tyr Gln Pro Ser Val Glu Thr
            100                 105                 110

Tyr Asn Gln Leu Leu His Leu Ala Ser Glu Gln Gly
        115                 120

(2) INFORMATION FOR SEQ ID NO:67:

(i) SEQUENCE CHARACTERISTICS:
        (A) LENGTH: 186 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..186

(xi) SEQUENCE DESCRIPTION: SEQ ID NO:67:

GGA TAC AAA GGA AGC ACC TTC CAC AGG GTC ATA AAG GAT TTC ATG ATT     48
Gly Tyr Lys Gly Ser Thr Phe His Arg Val Ile Lys Asp Phe Met Ile
125                 130                 135                 140

CAG GGT GGA GAT TTT GTT AAT GGA GAT GGT ACT GGA GTC GCC AGT ATT     96
Gln Gly Gly Asp Phe Val Asn Gly Asp Gly Thr Gly Val Ala Ser Ile
                145                 150                 155
```

```
TAC CGG GGG CCA TTT GCA GAT GAA AAT TTT AAA CTT AGA CAC TCA GCT        144
Tyr Arg Gly Pro Phe Ala Asp Glu Asn Phe Lys Leu Arg His Ser Ala
            160                 165                 170

CCA GGC CTG CTT TCC ATG GCG AAC AGT GGT CCA AGT ACA AAT                186
Pro Gly Leu Leu Ser Met Ala Asn Ser Gly Pro Ser Thr Asn
        175                 180                 185

(2) INFORMATION FOR SEQ ID NO:68:

(i) SEQUENCE CHARACTERISTICS:
        (A) LENGTH: 62 amino acids
        (B) TYPE: amino acid
        (D) TOPOLOGY: linear (ii) MOLECULE TYPE: protein (xi) SEQUENCE DESCRIPTION: SEQ ID NO:68:

Gly Tyr Lys Gly Ser Thr Phe His Arg Val Ile Lys Asp Phe Met Ile
 1               5                  10                  15

Gln Gly Gly Asp Phe Val Asn Gly Asp Gly Thr Gly Val Ala Ser Ile
            20                  25                  30

Tyr Arg Gly Pro Phe Ala Asp Glu Asn Phe Lys Leu Arg His Ser Ala
        35                  40                  45

Pro Gly Leu Leu Ser Met Ala Asn Ser Gly Pro Ser Thr Asn
    50                  55                  60

(2) INFORMATION FOR SEQ ID NO:69:

(i) SEQUENCE CHARACTERISTICS:
        (A) LENGTH: 63 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..63

(xi) SEQUENCE DESCRIPTION: SEQ ID NO:69:

ATT CAT TTC AGA GTT CAC ACG GGA GAG AAA CCC TAT AAA TGT AAG GAG         48
Ile His Phe Arg Val His Thr Gly Glu Lys Pro Tyr Lys Cys Lys Glu
            65                  70                  75

TGT GGT AAG GGC TTC                                                     63
Cys Gly Lys Gly Phe
        80

(2) INFORMATION FOR SEQ ID NO:70:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:70:

Ile His Phe Arg Val His Thr Gly Glu Lys Pro Tyr Lys Cys Lys Glu
 1               5                  10                  15

Cys Gly Lys Gly Phe
            20

(2) INFORMATION FOR SEQ ID NO:71:
```

```
    (i) SEQUENCE CHARACTERISTICS:
        (A) LENGTH: 168 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..168

(xi) SEQUENCE DESCRIPTION: SEQ ID NO:71:

AAG CAG AAC CTT AGC AAA GAG GAG CTG ATA GCG GAG CTG CAC GAC TGT         48
Lys Gln Asn Leu Ser Lys Glu Glu Leu Ile Ala Glu Leu His Asp Cys
             25                  30                  35

GAA GGC CTT ATT GTT CGC TCT GCC ACC AAG GTG ACC GCT GAT GTC ATC         96
Glu Gly Leu Ile Val Arg Ser Ala Thr Lys Val Thr Ala Asp Val Ile
         40                  45                  50

AAC GCA GCT GAG ATA CTC CAG GTG GTG GGC AGG GCT GGC ACA GGT GTG        144
Asn Ala Ala Glu Ile Leu Gln Val Val Gly Arg Ala Gly Thr Gly Val
     55                  60                  65

GAC AAT GTG GAT CTG GAG GCC GCA                                        168
Asp Asn Val Asp Leu Glu Ala Ala
 70                  75

(2) INFORMATION FOR SEQ ID NO:72:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO:72:

Lys Gln Asn Leu Ser Lys Glu Glu Leu Ile Ala Glu Leu His Asp Cys
 1               5                  10                  15

Glu Gly Leu Ile Val Arg Ser Ala Thr Lys Val Thr Ala Asp Val Ile
             20                  25                  30

Asn Ala Ala Glu Ile Leu Gln Val Val Gly Arg Ala Gly Thr Gly Val
         35                  40                  45

Asp Asn Val Asp Leu Glu Ala Ala
     50                  55

(2) INFORMATION FOR SEQ ID NO:73:

(i) SEQUENCE CHARACTERISTICS:
        (A) LENGTH: 792 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..792

(xi) SEQUENCE DESCRIPTION: SEQ ID NO:73:

ATG GAA TCA GGC TTC ACC TCC AAG GAC ACC TAT CTA AGC CAT TTT AAC         48
Met Glu Ser Gly Phe Thr Ser Lys Asp Thr Tyr Leu Ser His Phe Asn
             60                  65                  70

CCT CGG GAT TAC CTA GAA AAA TAT TAC AAG TTT GGT TCT AGG CAC TCT         96
Pro Arg Asp Tyr Leu Glu Lys Tyr Tyr Lys Phe Gly Ser Arg His Ser
         75                  80                  85
```

```
GCA AAA AGC CAG ATT CTT AAG CAC CTT CTG AAA AAT CTT TTC AAG ATA       144
Ala Glu Ser Gln Ile Leu Lys His Leu Leu Lys Asn Leu Phe Lys Ile
     90                   95                  100

TTC TGC CTA GAC GGT GTG AAG GGA GAC CTG CTG ATT GAC ATC GGC TCT       192
Phe Cys Leu Asp Gly Val Lys Gly Asp Leu Leu Ile Asp Ile Gly Ser
105                 110                 115                 120

GGC CCC ACT ATC TAT CAG CTC CTC TCT GCT TGT GAA TCC TTT AAG GAG       240
Gly Pro Thr Ile Tyr Gln Leu Leu Ser Ala Cys Glu Ser Phe Lys Glu
                125                 130                 135

ATC GTC GTC ACT GAC TAC TCA GAC CAG AAC CTG CAG GAG CTG GAG AAG       288
Ile Val Val Thr Asp Tyr Ser Asp Gln Asn Leu Gln Glu Leu Glu Lys
            140                 145                 150

TGG CTG AAG AAA GAG CCA GAG GCC TTT GAC TGG TCC CCA GTG GTG ACC       336
Trp Leu Lys Lys Glu Pro Glu Ala Phe Asp Trp Ser Pro Val Val Thr
                155                 160                 165

TAT GTG TGT GAT CTT GAA GGG AAC AGA GTC AAG GGT CCA GAG AAG GAG       384
Tyr Val Cys Asp Leu Glu Gly Asn Arg Val Lys Gly Pro Glu Lys Glu
170                 175                 180

GAG AAG TTG AGA CAG GCG GTC AAG CAG GTG CTG AAG TGT GAT GTG ACT       432
Glu Lys Leu Arg Gln Ala Val Lys Gln Val Leu Lys Cys Asp Val Thr
185                 190                 195                 200

CAG AGC CAG CCA CTG GGG GCC CTC CCC TTA CCC CCG GCT GAC TGC GTG       480
Gln Ser Gln Pro Leu Gly Ala Leu Pro Leu Pro Pro Ala Asp Cys Val
                205                 210                 215

CTC AGC ACA CTG TGT CTG GAT GCC GCC TGC CCA GAC CTC CCC ACC TAC       528
Leu Ser Thr Leu Cys Leu Asp Ala Ala Cys Pro Asp Leu Pro Thr Tyr
            220                 225                 230

TGC AGG GCG CTC AGG AAC CTC GGC AGC CTA CTG AAG CCA GGG GGC TTC       576
Cys Arg Ala Leu Arg Asn Leu Gly Ser Leu Leu Lys Pro Gly Gly Phe
                235                 240                 245

CTG GTG ATC ATG GAT GCG CTC AAG AGC AGC TAC TAC ATG ATT GGT GAG       624
Leu Val Ile Met Asp Ala Leu Lys Ser Ser Tyr Tyr Met Ile Gly Glu
250                 255                 260

CAG AAG TTC TCC AGC CTC CCC CTG GGC CGG GAG GCA GTA GAG GCT GCT       672
Gln Lys Phe Ser Ser Leu Pro Leu Gly Arg Glu Ala Val Glu Ala Ala
265                 270                 275                 280

GTG AAA GAG GCT GGC TAC ACA ATC GAA TGG TTT GAG GTG ATC TCG CAA       720
Val Lys Glu Ala Gly Tyr Thr Ile Glu Trp Phe Glu Val Ile Ser Gln
                285                 290                 295

AGT TAT TCT TCC ACC ATG GCC AAC AAC GAA GGA CTT TTC TCC CTG GTG       768
Ser Tyr Ser Ser Thr Met Ala Asn Asn Glu Gly Leu Phe Ser Leu Val
                300                 305                 310

GCG AGG AAG CTG AGC AGA CCC CTG                                       792
Ala Arg Lys Leu Ser Arg Pro Leu
                315                 320

(2) INFORMATION FOR SEQ ID NO:74:

(i) SEQUENCE CHARACTERISTICS:
        (A) LENGTH: 264 amino acids
        (B) TYPE: amino acid
        (D) TOPOLOGY: linear (ii) MOLECULE TYPE: protein (xi) SEQUENCE DESCRIPTION: SEQ ID NO:74:

Met Glu Ser Gly Phe Thr Ser Lys Asp Thr Tyr Leu Ser His Phe Asn
 1               5                  10                  15

Pro Arg Asp Tyr Leu Glu Lys Tyr Tyr Lys Phe Gly Ser Arg His Ser
                20                  25                  30

Ala Glu Ser Gln Ile Leu Lys His Leu Leu Lys Asn Leu Phe Lys Ile
```

```
                35                  40                  45
Phe Cys Leu Asp Gly Val Lys Gly Asp Leu Leu Ile Asp Ile Gly Ser
 50                  55                  60

Gly Pro Thr Ile Tyr Gln Leu Leu Ser Ala Cys Glu Ser Phe Lys Glu
 65                  70                  75                  80

Ile Val Val Thr Asp Tyr Ser Asp Gln Asn Leu Gln Glu Leu Glu Lys
                 85                  90                  95

Trp Leu Lys Lys Glu Pro Glu Ala Phe Asp Trp Ser Pro Val Val Thr
            100                 105                 110

Tyr Val Cys Asp Leu Glu Gly Asn Arg Val Lys Gly Pro Glu Lys Glu
            115                 120                 125

Glu Lys Leu Arg Gln Ala Val Lys Gln Val Leu Lys Cys Asp Val Thr
        130                 135                 140

Gln Ser Gln Pro Leu Gly Ala Leu Pro Leu Pro Ala Asp Cys Val
145                 150                 155                 160

Leu Ser Thr Leu Cys Leu Asp Ala Ala Cys Pro Asp Leu Pro Thr Tyr
                165                 170                 175

Cys Arg Ala Leu Arg Asn Leu Gly Ser Leu Leu Lys Pro Gly Gly Phe
            180                 185                 190

Leu Val Ile Met Asp Ala Leu Lys Ser Ser Tyr Tyr Met Ile Gly Glu
        195                 200                 205

Gln Lys Phe Ser Ser Leu Pro Leu Gly Arg Glu Ala Val Glu Ala Ala
210                 215                 220

Val Lys Glu Ala Gly Tyr Thr Ile Glu Trp Phe Glu Val Ile Ser Gln
225                 230                 235                 240

Ser Tyr Ser Ser Thr Met Ala Asn Asn Glu Gly Leu Phe Ser Leu Val
                245                 250                 255

Ala Arg Lys Leu Ser Arg Pro Leu
            260

(2) INFORMATION FOR SEQ ID NO:75:

(i) SEQUENCE CHARACTERISTICS:
        (A) LENGTH: 252 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..252

(xi) SEQUENCE DESCRIPTION: SEQ ID NO:75:

TTT AAG AAA GGA GAT TAT ATA GAA GCT GAA AGT TCT TAT AGT CGA GCC      48
Phe Lys Lys Gly Asp Tyr Ile Glu Ala Glu Ser Ser Tyr Ser Arg Ala
265                 270                 275                 280

CTC GAA ATG TGC CCA TCC TGC TTC CAA AAG GAG AGG TTG ATT CTA TTT      96
Leu Glu Met Cys Pro Ser Cys Phe Gln Lys Glu Arg Leu Ile Leu Phe
                285                 290                 295

TCA AAT AGA GCT GCA GCA AGG ATG AAA CAG GAC AAG AAA GAA ATG GCC     144
Ser Asn Arg Ala Ala Ala Arg Met Lys Gln Asp Lys Lys Glu Met Ala
            300                 305                 310

ATC AAT GAC TGC AGC AAA GCA ATT CAA TTA AAC CCC AGC TAT ATC AGG     192
Ile Asn Asp Cys Ser Lys Ala Ile Gln Leu Asn Pro Ser Tyr Ile Arg
        315                 320                 325

GCA ATA TTG AGG AGA GCA GAG TTG TAT GAG AAG ACG GAC AAG CTA GAT     240
Ala Ile Leu Arg Arg Ala Glu Leu Tyr Glu Lys Thr Asp Lys Leu Asp
```

```
                    330              335              340
GAA GCC CTG GAA                                                                     252
Glu Ala Leu Glu
345

(2) INFORMATION FOR SEQ ID NO:76:

(i) SEQUENCE CHARACTERISTICS:
        (A) LENGTH: 84 amino acids
        (B) TYPE: amino acid
        (D) TOPOLOGY: linear (ii) MOLECULE TYPE: protein (xi) SEQUENCE DESCRIPTION: SEQ ID NO:76:

Phe Lys Lys Gly Asp Tyr Ile Glu Ala Glu Ser Ser Tyr Ser Arg Ala
1               5                   10                  15

Leu Glu Met Cys Pro Ser Cys Phe Gln Lys Glu Arg Leu Ile Leu Phe
            20                  25                  30

Ser Asn Arg Ala Ala Ala Arg Met Lys Gln Asp Lys Lys Glu Met Ala
        35                  40                  45

Ile Asn Asp Cys Ser Lys Ala Ile Gln Leu Asn Pro Ser Tyr Ile Arg
    50                  55                  60

Ala Ile Leu Arg Arg Ala Glu Leu Tyr Glu Lys Thr Asp Lys Leu Asp
65                  70                  75                  80

Glu Ala Leu Glu (2) INFORMATION FOR SEQ ID NO:77:

(i) SEQUENCE CHARACTERISTICS:
        (A) LENGTH: 252 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..252

(xi) SEQUENCE DESCRIPTION: SEQ ID NO:77:

CTG AAG CTG ACG GTG GAG GAG GCT GTG CGT ATG GGC ATT GTG GGC CCC        48
Leu Lys Leu Thr Val Glu Glu Ala Val Arg Met Gly Ile Val Gly Pro
85                  90                  95                  100

GAG TTC AAG GAC AAG CTG CTG TCG GCC GAG CGC GCC GTC ACT GGG TAC        96
Glu Phe Lys Asp Lys Leu Leu Ser Ala Glu Arg Ala Val Thr Gly Tyr
                105                 110                 115

AAG GAC CCC TAC TCT GGG AAG CTC ATC TCC CTC TTC CAG GCC ATG AAG       144
Lys Asp Pro Tyr Ser Gly Lys Leu Ile Ser Leu Phe Gln Ala Met Lys
            120                 125                 130

AAG GGC CTG ATC CTG AAG GAC CAT GGC ATC CGC CTG CTG GAG GCC CAG       192
Lys Gly Leu Ile Leu Lys Asp His Gly Ile Arg Leu Leu Glu Ala Gln
        135                 140                 145

ATC GCC ACG GGC GGC ATC ATC GAC CCT GAG GAG AGC CAC CGG CTG CCC       240
Ile Ala Thr Gly Gly Ile Ile Asp Pro Glu Glu Ser His Arg Leu Pro
    150                 155                 160

GTG GAG GTG GCC                                                       252
Val Glu Val Ala
165

(2) INFORMATION FOR SEQ ID NO:78:
```

(i) SEQUENCE CHARACTERISTICS:
    (A) LENGTH: 84 amino acids
    (B) TYPE: amino acid
    (D) TOPOLOGY: linear (ii) MOLECULE TYPE: protein (xi) SEQUENCE DESCRIPTION: SEQ ID NO:78:

Leu Lys Leu Thr Val Glu Glu Ala Val Arg Met Gly Ile Val Gly Pro
 1               5                  10                  15

Glu Phe Lys Asp Lys Leu Leu Ser Ala Glu Arg Ala Val Thr Gly Tyr
                20                  25                  30

Lys Asp Pro Tyr Ser Gly Lys Leu Ile Ser Leu Phe Gln Ala Met Lys
            35                  40                  45

Lys Gly Leu Ile Leu Lys Asp His Gly Ile Arg Leu Leu Glu Ala Gln
    50                  55                  60

Ile Ala Thr Gly Gly Ile Ile Asp Pro Glu Glu Ser His Arg Leu Pro
65                  70                  75                  80

Val Glu Val Ala (2) INFORMATION FOR SEQ ID NO:79:

(i) SEQUENCE CHARACTERISTICS:
        (A) LENGTH: 213 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..213

(xi) SEQUENCE DESCRIPTION: SEQ ID NO:79:

CCA GGT GCC CTG GTG CTG GCA GTT GGG GGT GGG GGT CTC CTG GCC GGG        48
Pro Gly Ala Leu Val Leu Ala Val Gly Gly Gly Gly Leu Leu Ala Gly
 85              90                  95                  100

GTG GTG GCT GGC CTG CTG GAG GTG GGC TGG CAG CAT GTA CCC ATC ATT        96
Val Val Ala Gly Leu Leu Glu Val Gly Trp Gln His Val Pro Ile Ile
            105                 110                 115

GCC ATG GAG ACC CAT GGG GCA CAC TGC TTC AAT GCG GCC ATC ACA GCC       144
Ala Met Glu Thr His Gly Ala His Cys Phe Asn Ala Ala Ile Thr Ala
        120                 125                 130

GGC AAG CTG GTC ACA CTT CCA GAC ATC ACC AGT GTG GCC AAG AGC CTG       192
Gly Lys Leu Val Thr Leu Pro Asp Ile Thr Ser Val Ala Lys Ser Leu
    135                 140                 145

GGT GCC AAG ACG GTG GCC GCT                                            213
Gly Ala Lys Thr Val Ala Ala
150                 155

(2) INFORMATION FOR SEQ ID NO:80:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO:80:

Pro Gly Ala Leu Val Leu Ala Val Gly Gly Gly Gly Leu Leu Ala Gly
 1               5                  10                  15

Val Val Ala Gly Leu Leu Glu Val Gly Trp Gln His Val Pro Ile Ile

```
                    20                  25                  30
Ala Met Glu Thr His Gly Ala His Cys Phe Asn Ala Ala Ile Thr Ala
            35                  40                  45
Gly Lys Leu Val Thr Leu Pro Asp Ile Thr Ser Val Ala Lys Ser Leu
        50                  55                  60
Gly Ala Lys Thr Val Ala Ala
65                  70
```

(2) INFORMATION FOR SEQ ID NO:81:

(i) SEQUENCE CHARACTERISTICS:
        (A) LENGTH: 186 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..186

(xi) SEQUENCE DESCRIPTION: SEQ ID NO:81:

```
CTT AAG AAG CTT GAA CTA AGC GAT AAC AGA GTC TCA GGG GGC CTG AAA        48
Leu Lys Lys Leu Glu Leu Ser Asp Asn Arg Val Ser Gly Gly Leu Glu
              75                  80                  85

GTA TTG GCA GAA AAG TGT CCG AAC CTC ACG CAT CTA AAT TTA AGT GGC        96
Val Leu Ala Glu Lys Cys Pro Asn Leu Thr His Leu Asn Leu Ser Gly
          90                  95                 100

AAC AAA ATT AAA GAC CTC AGC ACA ATA GAG CCA CTG AAA AAG TTA GAA       144
Asn Lys Ile Lys Asp Leu Ser Thr Ile Glu Pro Leu Lys Lys Leu Glu
     105                 110                 115

AAC CTC AAG AGC TTA GAC CTT TTC AAT TGC GAG GTA ACC AAC               186
Asn Leu Lys Ser Leu Asp Leu Phe Asn Cys Glu Val Thr Asn
120                 125                 130
```

(2) INFORMATION FOR SEQ ID NO:82:

(i) SEQUENCE CHARACTERISTICS:
        (A) LENGTH: 62 amino acids
        (B) TYPE: amino acid
        (D) TOPOLOGY: linear (ii) MOLECULE TYPE: protein (xi) SEQUENCE DESCRIPTION: SEQ ID NO:82:

```
Leu Lys Lys Leu Glu Leu Ser Asp Asn Arg Val Ser Gly Gly Leu Glu
 1               5                  10                  15
Val Leu Ala Glu Lys Cys Pro Asn Leu Thr His Leu Asn Leu Ser Gly
             20                  25                  30
Asn Lys Ile Lys Asp Leu Ser Thr Ile Glu Pro Leu Lys Lys Leu Glu
         35                  40                  45
Asn Leu Lys Ser Leu Asp Leu Phe Asn Cys Glu Val Thr Asn
     50                  55                  60
```

(2) INFORMATION FOR SEQ ID NO:83:

(i) SEQUENCE CHARACTERISTICS:
        (A) LENGTH: 114 base pairs
        (B) TYPE: nucleic acid
        (C) STRANDEDNESS: double
        (D) TOPOLOGY: linear (ii) MOLECULE TYPE: cDNA to mRNA (ix) FEATURE:
              (A) NAME/KEY: CDS
              (B) LOCATION: 1..114

(xi) SEQUENCE DESCRIPTION: SEQ ID NO:83:

```
TGG ACA GGC ATG ATT ATT GGG CCA CCA AGG ACA AAT TAT GAA AAC AGA         48
Trp Thr Gly Met Ile Ile Gly Pro Pro Arg Thr Asn Tyr Glu Asn Arg
         65                  70                  75

ATA TAT AGC CTG AAA GTA GAA TGT GGA CCT AAA TAC CCA GAA GCT CCT         96
Ile Tyr Ser Leu Lys Val Glu Cys Gly Pro Lys Tyr Pro Glu Ala Pro
     80                  85                  90

CCG TCA GTT AGA TTT GTA                                                114
Pro Ser Val Arg Phe Val
 95                 100
```

(2) INFORMATION FOR SEQ ID NO:84:

(i) SEQUENCE CHARACTERISTICS:
              (A) LENGTH: 38 amino acids
              (B) TYPE: amino acid
              (D) TOPOLOGY: linear (ii) MOLECULE TYPE: protein (xi) SEQUENCE DESCRIPTION: SEQ ID NO:84:

```
Trp Thr Gly Met Ile Ile Gly Pro Pro Arg Thr Asn Tyr Glu Asn Arg
 1               5                  10                  15

Ile Tyr Ser Leu Lys Val Glu Cys Gly Pro Lys Tyr Pro Glu Ala Pro
             20                  25                  30

Pro Ser Val Arg Phe Val
         35
```

(2) INFORMATION FOR SEQ ID NO:85:

(i) SEQUENCE CHARACTERISTICS:
              (A) LENGTH: 255 base pairs
              (B) TYPE: nucleic acid
              (C) STRANDEDNESS: double
              (D) TOPOLOGY: linear (ii) MOLECULE TYPE: cDNA to mRNA (ix) FEATURE:
              (A) NAME/KEY: CDS
              (B) LOCATION: 1..255

(xi) SEQUENCE DESCRIPTION: SEQ ID NO:85:

```
AAA CCT TAT AAT CCT ATA CTT GGC GAG ACT TTC CGT TGT TTA TGG ATT         48
Lys Pro Tyr Asn Pro Ile Leu Gly Glu Thr Phe Arg Cys Leu Trp Ile
         40                  45                  50

CAT CCC AGA ACA AAC AGC AAA ACT TTT TAT ATT GCT GAA CAG GTG TCC         96
His Pro Arg Thr Asn Ser Lys Thr Phe Tyr Ile Ala Glu Gln Val Ser
 55                  60                  65                  70

CAT CAT CCA CCA ATA TCT GCC TTT TAT GTT AGT AAT CGA AAA GAT GGA        144
His His Pro Pro Ile Ser Ala Phe Tyr Val Ser Asn Arg Lys Asp Gly
             75                  80                  85

TTT TGC CTT AGC GGT AGT ATC CTG GCT AAG TCT AAG TTT TAT GGA AAC        192
Phe Cys Leu Ser Gly Ser Ile Leu Ala Lys Ser Lys Phe Tyr Gly Asn
         90                  95                 100

TCA TTA TCT GCA ATA TTA GAG GGA GAA GCA CGG TTA ACT TTC TTG AAT        240
Ser Leu Ser Ala Ile Leu Glu Gly Glu Ala Arg Leu Thr Phe Leu Asn
     105                 110                 115

AGA GGT GAA GAT TAT                                                    255
Arg Gly Glu Asp Tyr
        120
```

(2) INFORMATION FOR SEQ ID NO:86:

(i) SEQUENCE CHARACTERISTICS:
        (A) LENGTH: 85 amino acids
        (B) TYPE: amino acid
        (D) TOPOLOGY: linear (ii) MOLECULE TYPE: protein (xi) SEQUENCE DESCRIPTION: SEQ ID NO:86:

```
Lys Pro Tyr Asn Pro Ile Leu Gly Glu Thr Phe Arg Cys Leu Trp Ile
  1               5                  10                  15

His Pro Arg Thr Asn Ser Lys Thr Phe Tyr Ile Ala Glu Gln Val Ser
             20                  25                  30

His His Pro Pro Ile Ser Ala Phe Tyr Val Ser Asn Arg Lys Asp Gly
         35                  40                  45

Phe Cys Leu Ser Gly Ser Ile Leu Ala Lys Ser Lys Phe Tyr Gly Asn
     50                  55                  60

Ser Leu Ser Ala Ile Leu Glu Gly Glu Ala Arg Leu Thr Phe Leu Asn
 65                  70                  75                  80

Arg Gly Glu Asp Tyr
             85
```

(2) INFORMATION FOR SEQ ID NO:87:

(i) SEQUENCE CHARACTERISTICS:
        (A) LENGTH: 198 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..198

(xi) SEQUENCE DESCRIPTION: SEQ ID NO:87:

```
CTG GGC AAG ATG GCT CCC AGT TCT GCC CAC TTC GTC ACC CTG AAT GGG        48
Leu Gly Lys Met Ala Pro Ser Ser Ala His Phe Val Thr Leu Asn Gly
             90                  95                 100

AGT ACA GTG CCA TTA GGA CCA GCA AGT GAC ACA GGA ATT CTG AAT CCA        96
Ser Thr Val Pro Leu Gly Pro Ala Ser Asp Thr Gly Ile Leu Asn Pro
            105                 110                 115

GAT GGT TAT ACC CTC AAC TAC AAT GAA TAT ATT GTA TAT AAC CCC AAC       144
Asp Gly Tyr Thr Leu Asn Tyr Asn Glu Tyr Ile Val Tyr Asn Pro Asn
            120                 125                 130

CAG GTC CGT ATG CGG TAC CTT TTA AAG GTT CAG TTT AAT TTC CTT CAG       192
Gln Val Arg Met Arg Tyr Leu Leu Lys Val Gln Phe Asn Phe Leu Gln
            135                 140                 145

CTG TGG                                                                198
Leu Trp
150
```

(2) INFORMATION FOR SEQ ID NO:88:

(i) SEQUENCE CHARACTERISTICS:
        (A) LENGTH: 66 amino acids
        (B) TYPE: amino acid
        (D) TOPOLOGY: linear (ii) MOLECULE TYPE: protein (xi) SEQUENCE DESCRIPTION: SEQ ID NO:88:

```
Leu Gly Lys Met Ala Pro Ser Ser Ala His Phe Val Thr Leu Asn Gly
  1               5                  10                  15

Ser Thr Val Pro Leu Gly Pro Ala Ser Asp Thr Gly Ile Leu Asn Pro
             20                  25                  30

Asp Gly Tyr Thr Leu Asn Tyr Asn Glu Tyr Ile Val Tyr Asn Pro Asn
             35                  40                  45

Gln Val Arg Met Arg Tyr Leu Leu Lys Val Gln Phe Asn Phe Leu Gln
         50                  55                  60

Leu Trp
 65
```

(2) INFORMATION FOR SEQ ID NO:89:

(i) SEQUENCE CHARACTERISTICS:
        (A) LENGTH: 372 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..372

(xi) SEQUENCE DESCRIPTION: SEQ ID NO:89:

```
GAA ATT AAA GTG TGT CAG GGT GAA AGA GAG ATG GCT GGA GAC AAC AAA    48
Glu Ile Lys Val Cys Gln Gly Glu Arg Glu Met Ala Gly Asp Asn Lys
             70                  75                  80

CTC CTT GGA CAG TTT ACT TTG ATT GGA ATT CCA CCA GCC CCT CGT GGA    96
Leu Leu Gly Gln Phe Thr Leu Ile Gly Ile Pro Pro Ala Pro Arg Gly
             85                  90                  95

GTT CCT CAG ATT GAA GTT ACA TTT GAC ATT GAT GCC AAT GGG ATA GTA   144
Val Pro Gln Ile Glu Val Thr Phe Asp Ile Asp Ala Asn Gly Ile Val
         100                 105                 110

CAT GTT TCT GCT AAA GAT AAA GGC ACA GGA CGT GAG CAG CAG ATT GTA   192
His Val Ser Ala Lys Asp Lys Gly Thr Gly Arg Glu Gln Gln Ile Val
115                 120                 125                 130

ATC CAG TCT TCT GGT GGA TTA AGC AAA GAT GAT ATT GAA AAT ATG GTT   240
Ile Gln Ser Ser Gly Gly Leu Ser Lys Asp Asp Ile Glu Asn Met Val
                135                 140                 145

AAA AAT GCA GAG AAA TAT GCT GAA GAA GAC CGG CGA AAG AAG GAA CGA   288
Lys Asn Ala Glu Lys Tyr Ala Glu Glu Asp Arg Arg Lys Lys Glu Arg
            150                 155                 160

GTT GAA GCA GTT AAT ATG GCT GAA GGA ATC ATT CAC GAC ACA GAA ACC   336
Val Glu Ala Val Asn Met Ala Glu Gly Ile Ile His Asp Thr Glu Thr
            165                 170                 175

AAG ATG GAA GAA TTC AAG GAC CAA TTA CCT GCT GAT                   372
Lys Met Glu Glu Phe Lys Asp Gln Leu Pro Ala Asp
            180                 185                 190
```

(2) INFORMATION FOR SEQ ID NO:90:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO:90:

```
Glu Ile Lys Val Cys Gln Gly Glu Arg Glu Met Ala Gly Asp Asn Lys
  1               5                  10                  15
```

```
Leu Leu Gly Gln Phe Thr Leu Ile Gly Ile Pro Pro Ala Pro Arg Gly
             20                  25                  30

Val Pro Gln Ile Glu Val Thr Phe Asp Ile Asp Ala Asn Gly Ile Val
         35                  40                  45

His Val Ser Ala Lys Asp Lys Gly Thr Gly Arg Glu Gln Gln Ile Val
     50                  55                  60

Ile Gln Ser Ser Gly Gly Leu Ser Lys Asp Asp Ile Glu Asn Met Val
 65                  70                  75                  80

Lys Asn Ala Glu Lys Tyr Ala Glu Glu Asp Arg Arg Lys Lys Glu Arg
                 85                  90                  95

Val Glu Ala Val Asn Met Ala Glu Gly Ile Ile His Asp Thr Glu Thr
            100                 105                 110

Lys Met Glu Glu Phe Lys Asp Gln Leu Pro Ala Asp
        115                 120
```

(2) INFORMATION FOR SEQ ID NO:91:

(i) SEQUENCE CHARACTERISTICS:
       (A) LENGTH: 1218 base pairs
       (B) TYPE: nucleic acid
       (C) STRANDEDNESS: double
       (D) TOPOLOGY: linear (ii) MOLECULE TYPE: cDNA to mRNA (ix) FEATURE:
       (A) NAME/KEY: CDS
       (B) LOCATION: 1..1218

(xi) SEQUENCE DESCRIPTION: SEQ ID NO:91:

```
ATG TCT GCG AGC CAG GAT TCC CGA TCC AGA GAC AAT GGC CCC GAT GGG       48
Met Ser Ala Ser Gln Asp Ser Arg Ser Arg Asp Asn Gly Pro Asp Gly
125             130                 135                 140

ATG GAG CCC GAA GGC GTC ATC GAG AGT AAC TGG AAT GAG ATT GTT GAC       96
Met Glu Pro Glu Gly Val Ile Glu Ser Asn Trp Asn Glu Ile Val Asp
                145                 150                 155

AGC TTT GAT GAC ATG AAC CTC TCG GAG TCC CTT CTC CGT GGC ATC TAC      144
Ser Phe Asp Asp Met Asn Leu Ser Glu Ser Leu Leu Arg Gly Ile Tyr
            160                 165                 170

GCC TAT GGT TTT GAG AAG CCC TCT GCC ATC CAG CAG CGA GCC ATT CTA      192
Ala Tyr Gly Phe Glu Lys Pro Ser Ala Ile Gln Gln Arg Ala Ile Leu
        175                 180                 185

CCT TGT ATC AAG GGT TAT GAT GTG ATT GCT CAA GCC CAA TCT GGG ACT      240
Pro Cys Ile Lys Gly Tyr Asp Val Ile Ala Gln Ala Gln Ser Gly Thr
    190                 195                 200

GGG AAA ACG GCC ACA TTT GCC ATA TCG ATT CTG CAG CAG ATT GAA TTA      288
Gly Lys Thr Ala Thr Phe Ala Ile Ser Ile Leu Gln Gln Ile Glu Leu
205                 210                 215                 220

GAT CTA AAA GCC ACC CAG GCC TTG GTC CTA GCA CCC ACT CGA GAA TTG      336
Asp Leu Lys Ala Thr Gln Ala Leu Val Leu Ala Pro Thr Arg Glu Leu
                225                 230                 235

GCT CAG CAG ATA CAG AAG GTG GTC ATG GCA CTA GGA GAC TAC ATG GGC      384
Ala Gln Gln Ile Gln Lys Val Val Met Ala Leu Gly Asp Tyr Met Gly
            240                 245                 250

GCC TCC TGT CAC GCC TGT ATC GGG GGC ACC AAC GTG CGT GCT GAG GTG      432
Ala Ser Cys His Ala Cys Ile Gly Gly Thr Asn Val Arg Ala Glu Val
        255                 260                 265

CAG AAA CTG CAG ATG GAA GCT CCC CAC ATC ATC GTG GGT ACC CCT GGC      480
Gln Lys Leu Gln Met Glu Ala Pro His Ile Ile Val Gly Thr Pro Gly
    270                 275                 280
```

```
CGT GTG TTT GAT ATG CTT AAC CGG AGA TAC CTG TCC CCC AAA TAC ATC        528
Arg Val Phe Asp Met Leu Asn Arg Arg Tyr Leu Ser Pro Lys Tyr Ile
285                 290                 295                 300

AAG ATG TTT GTA CTG GAT GAA GCT GAC GAA ATG TTA AGC CGT GGA TTC        576
Lys Met Phe Val Leu Asp Glu Ala Asp Glu Met Leu Ser Arg Gly Phe
                305                 310                 315

AAG GAC CAG ATC TAT GAC ATA TTC CAA AAG CTC AAC AGC AAC ACC CAG        624
Lys Asp Gln Ile Tyr Asp Ile Phe Gln Lys Leu Asn Ser Asn Thr Gln
            320                 325                 330

GTA GTT TTG CTG TCA GCC ACA ATG CCT TCT GAT GTG CTT GAG GTG ACC        672
Val Val Leu Leu Ser Ala Thr Met Pro Ser Asp Val Leu Glu Val Thr
                335                 340                 345

AAG AAG TTC ATG AGG GAC CCC ATT CGG ATT CTT GTC AAG AAG GAA GAG        720
Lys Lys Phe Met Arg Asp Pro Ile Arg Ile Leu Val Lys Lys Glu Glu
            350                 355                 360

TTG ACC CTG GAG GGT ATC CGC CAG TTC TAC ATC AAC GTG GAA CGA GAG        768
Leu Thr Leu Glu Gly Ile Arg Gln Phe Tyr Ile Asn Val Glu Arg Glu
365                 370                 375                 380

GAG TGG AAG CTG GAC ACA CTA TGT GAC TTG TAT GAA ACC CTG ACC ATC        816
Glu Trp Lys Leu Asp Thr Leu Cys Asp Leu Tyr Glu Thr Leu Thr Ile
                385                 390                 395

ACC CAG GCA GTC ATC TTC ATC AAC ACC CGG AGG AAG GTG GAC TGG CTC        864
Thr Gln Ala Val Ile Phe Ile Asn Thr Arg Arg Lys Val Asp Trp Leu
            400                 405                 410

ACC GAG AAG ATG CAT GCT CGA GAT TTC ACT GTA TCC GCC ATG CAT GGA        912
Thr Glu Lys Met His Ala Arg Asp Phe Thr Val Ser Ala Met His Gly
                415                 420                 425

GAT ATG GAC CAA AAG GAA CGA GAC GTG ATT ATG AGG GAG TTT CGT TCT        960
Asp Met Asp Gln Lys Glu Arg Asp Val Ile Met Arg Glu Phe Arg Ser
430                 435                 440

GGC TCT AGC AGA GTT TTG ATT ACC ACT GAC CTG CTG GCC AGA GGC ATT       1008
Gly Ser Ser Arg Val Leu Ile Thr Thr Asp Leu Leu Ala Arg Gly Ile
445                 450                 455                 460

GAT GTG CAG CAG GTT TCT TTA GTC ATC AAC TAT GAC CTT CCC ACC AAC       1056
Asp Val Gln Gln Val Ser Leu Val Ile Asn Tyr Asp Leu Pro Thr Asn
                465                 470                 475

AGG GAA AAC TAT ATC CAC AGA ATC GGT CGA GGT GGA CGG TTT GGC CGT       1104
Arg Glu Asn Tyr Ile His Arg Ile Gly Arg Gly Gly Arg Phe Gly Arg
            480                 485                 490

AAA GGT GTG GCT ATT AAC ATG GTG ACA GAA GAA GAC AAG AGG ACT CTT       1152
Lys Gly Val Ala Ile Asn Met Val Thr Glu Glu Asp Lys Arg Thr Leu
                495                 500                 505

CGA GAC ATT GAG ACC TTC TAC AAC ACC TCC ATT GAG GAA ATG CCC CTC       1200
Arg Asp Ile Glu Thr Phe Tyr Asn Thr Ser Ile Glu Glu Met Pro Leu
510                 515                 520

AAT GTT GCT GAC CTC ATC                                               1218
Asn Val Ala Asp Leu Ile
525             530

(2) INFORMATION FOR SEQ ID NO:92:

(i) SEQUENCE CHARACTERISTICS:
        (A) LENGTH: 406 amino acids
        (B) TYPE: amino acid
        (D) TOPOLOGY: linear (ii) MOLECULE TYPE: protein (xi) SEQUENCE DESCRIPTION: SEQ ID NO:92:

Met Ser Ala Ser Gln Asp Ser Arg Ser Arg Asp Asn Gly Pro Asp Gly
1               5                   10                  15
```

Met Glu Pro Glu Gly Val Ile Glu Ser Asn Trp Asn Glu Ile Val Asp
            20                  25                  30

Ser Phe Asp Asp Met Asn Leu Ser Glu Ser Leu Leu Arg Gly Ile Tyr
        35                  40                  45

Ala Tyr Gly Phe Glu Lys Pro Ser Ala Ile Gln Gln Arg Ala Ile Leu
    50                  55                  60

Pro Cys Ile Lys Gly Tyr Asp Val Ile Ala Gln Ala Gln Ser Gly Thr
65                  70                  75                  80

Gly Lys Thr Ala Thr Phe Ala Ile Ser Ile Leu Gln Gln Ile Glu Leu
                85                  90                  95

Asp Leu Lys Ala Thr Gln Ala Leu Val Leu Ala Pro Thr Arg Glu Leu
            100                 105                 110

Ala Gln Gln Ile Gln Lys Val Val Met Ala Leu Gly Asp Tyr Met Gly
        115                 120                 125

Ala Ser Cys His Ala Cys Ile Gly Gly Thr Asn Val Arg Ala Glu Val
    130                 135                 140

Gln Lys Leu Gln Met Glu Ala Pro His Ile Ile Val Gly Thr Pro Gly
145                 150                 155                 160

Arg Val Phe Asp Met Leu Asn Arg Arg Tyr Leu Ser Pro Lys Tyr Ile
                165                 170                 175

Lys Met Phe Val Leu Asp Glu Ala Asp Glu Met Leu Ser Arg Gly Phe
            180                 185                 190

Lys Asp Gln Ile Tyr Asp Ile Phe Gln Lys Leu Asn Ser Asn Thr Gln
        195                 200                 205

Val Val Leu Leu Ser Ala Thr Met Pro Ser Asp Val Leu Glu Val Thr
    210                 215                 220

Lys Lys Phe Met Arg Asp Pro Ile Arg Ile Leu Val Lys Lys Glu Glu
225                 230                 235                 240

Leu Thr Leu Glu Gly Ile Arg Gln Phe Tyr Ile Asn Val Glu Arg Glu
                245                 250                 255

Glu Trp Lys Leu Asp Thr Leu Cys Asp Leu Tyr Glu Thr Leu Thr Ile
            260                 265                 270

Thr Gln Ala Val Ile Phe Ile Asn Thr Arg Arg Lys Val Asp Trp Leu
        275                 280                 285

Thr Glu Lys Met His Ala Arg Asp Phe Thr Val Ser Ala Met His Gly
    290                 295                 300

Asp Met Asp Gln Lys Glu Arg Asp Val Ile Met Arg Glu Phe Arg Ser
305                 310                 315                 320

Gly Ser Ser Arg Val Leu Ile Thr Thr Asp Leu Leu Ala Arg Gly Ile
                325                 330                 335

Asp Val Gln Gln Val Ser Leu Val Ile Asn Tyr Asp Leu Pro Thr Asn
            340                 345                 350

Arg Glu Asn Tyr Ile His Arg Ile Gly Arg Gly Arg Phe Gly Arg
        355                 360                 365

Lys Gly Val Ala Ile Asn Met Val Thr Glu Glu Asp Lys Arg Thr Leu
    370                 375                 380

Arg Asp Ile Glu Thr Phe Tyr Asn Thr Ser Ile Glu Glu Met Pro Leu
385                 390                 395                 400

Asn Val Ala Asp Leu Ile
                405

(2) INFORMATION FOR SEQ ID NO:93:

(i) SEQUENCE CHARACTERISTICS:

(A) LENGTH: 207 base pairs
           (B) TYPE: nucleic acid
           (C) STRANDEDNESS: double
           (D) TOPOLOGY: linear (ii) MOLECULE TYPE: cDNA to mRNA (ix) FEATURE:
           (A) NAME/KEY: CDS
           (B) LOCATION: 1..207

(xi) SEQUENCE DESCRIPTION: SEQ ID NO:93:

```
CCT CAA GTG GAA AAG AAG CTC AAG TGT ACA GTT GAA GGT TGT GAC CGG          48
Pro Gln Val Glu Lys Lys Leu Lys Cys Thr Val Glu Gly Cys Asp Arg
410                 415                 420

ACA TTT GTA TGG CCA GCT CAC TTT AAA TAC CAC CTC AAG ACT CAT CGA          96
Thr Phe Val Trp Pro Ala His Phe Lys Tyr His Leu Lys Thr His Arg
            425                 430                 435

AAT GAC CGC TCC TTC ATC TGT TCT GCA GAA GGT TGT GGG AAA AGC TTC         144
Asn Asp Arg Ser Phe Ile Cys Ser Ala Glu Gly Cys Gly Lys Ser Phe
        440                 445                 450

TAT GTT CTG CAG AGG CTG AAG GTG CAC ATG AGG ACC CAC AAT GGA GAG         192
Tyr Val Leu Gln Arg Leu Lys Val His Met Arg Thr His Asn Gly Glu
455                 460                 465                 470

AAG CCC TTT ATG TGC                                                     207
Lys Pro Phe Met Cys
            475
```

(2) INFORMATION FOR SEQ ID NO:94:

(i) SEQUENCE CHARACTERISTICS:
           (A) LENGTH: 69 amino acids
           (B) TYPE: amino acid
           (D) TOPOLOGY: linear (ii) MOLECULE TYPE: protein (xi) SEQUENCE DESCRIPTION: SEQ ID NO:94:

```
Pro Gln Val Glu Lys Lys Leu Lys Cys Thr Val Glu Gly Cys Asp Arg
1               5                   10                  15

Thr Phe Val Trp Pro Ala His Phe Lys Tyr His Leu Lys Thr His Arg
            20                  25                  30

Asn Asp Arg Ser Phe Ile Cys Ser Ala Glu Gly Cys Gly Lys Ser Phe
        35                  40                  45

Tyr Val Leu Gln Arg Leu Lys Val His Met Arg Thr His Asn Gly Glu
    50                  55                  60

Lys Pro Phe Met Cys
65
```

(2) INFORMATION FOR SEQ ID NO:95:

(i) SEQUENCE CHARACTERISTICS:
           (A) LENGTH: 165 base pairs
           (B) TYPE: nucleic acid
           (C) STRANDEDNESS: double
           (D) TOPOLOGY: linear (ii) MOLECULE TYPE: cDNA to mRNA (ix) FEATURE:
           (A) NAME/KEY: CDS
           (B) LOCATION: 1..165

(xi) SEQUENCE DESCRIPTION: SEQ ID NO:95:

```
ATG GAG CCG TAC ATC TTT GGG AGC CGC CTG GAC CAC GAC ATC ATC GAC          48
Met Glu Pro Tyr Ile Phe Gly Ser Arg Leu Asp His Asp Ile Ile Asp
```

```
                       70                    75                  80                    85
CTG GAA CAG ACA GCC ACG TAC CTC CAG CTG GCC TTG AAC TTC ACC GCC          96
Leu Glu Gln Thr Ala Thr Tyr Leu Gln Leu Ala Leu Asn Phe Thr Ala
                    90                   95                  100

CAC ATG GCC TAC CGC AAG GGC ATC ATC TTG TTT ATA AGC CGC AAC CGG          144
His Met Ala Tyr Arg Lys Gly Ile Ile Leu Phe Ile Ser Arg Asn Arg
                105                  110                  115

CAG TTC TCG TAC CTG ATT GAG                                              165
Gln Phe Ser Tyr Leu Ile Glu
        120
```

(2) INFORMATION FOR SEQ ID NO:96:

(i) SEQUENCE CHARACTERISTICS:
        (A) LENGTH: 55 amino acids
        (B) TYPE: amino acid
        (D) TOPOLOGY: linear (ii) MOLECULE TYPE: protein (xi) SEQUENCE DESCRIPTION: SEQ ID NO:96:

```
Met Glu Pro Tyr Ile Phe Gly Ser Arg Leu Asp His Asp Ile Ile Asp
 1               5                  10                  15

Leu Glu Gln Thr Ala Thr Tyr Leu Gln Leu Ala Leu Asn Phe Thr Ala
                20                  25                  30

His Met Ala Tyr Arg Lys Gly Ile Ile Leu Phe Ile Ser Arg Asn Arg
            35                  40                  45

Gln Phe Ser Tyr Leu Ile Glu
        50                  55
```

(2) INFORMATION FOR SEQ ID NO:97:

(i) SEQUENCE CHARACTERISTICS:
        (A) LENGTH: 249 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..249

(xi) SEQUENCE DESCRIPTION: SEQ ID NO:97:

```
ATG GCA AAC AAT TTA CAA AAG GGA AGT GCT GGA CCT ATG AGG CTT TAT          48
Met Ala Asn Asn Leu Gln Lys Gly Ser Ala Gly Pro Met Arg Leu Tyr
                    60                  65                  70

GTG GGC TCA TTA CAC TTC AAC ATA ACT GAA GAT ATG CTT CGT GGG ATC          96
Val Gly Ser Leu His Phe Asn Ile Thr Glu Asp Met Leu Arg Gly Ile
                75                  80                  85

TTT GAG CCT TTT GGA AGA ATT GAA AGT ATC CAG CTG ATG ATG GAC AGT          144
Phe Glu Pro Phe Gly Arg Ile Glu Ser Ile Gln Leu Met Met Asp Ser
            90                  95                 100

GAA ACT GGT CGA TCC AAG GGA TAT GGA TTT ATT ACA TTT TCT GAC TCA          192
Glu Thr Gly Arg Ser Lys Gly Tyr Gly Phe Ile Thr Phe Ser Asp Ser
        105                 110                 115

GAA TGT GCC AAA AAG GCT TTG GAA CAA CTT AAT GGA TTT GAA CTA GCA          240
Glu Cys Ala Lys Lys Ala Leu Glu Gln Leu Asn Gly Phe Glu Leu Ala
120                 125                 130                 135

GGA AGA CCA                                                              249
Gly Arg Pro
```

(2) INFORMATION FOR SEQ ID NO:98:

(i) SEQUENCE CHARACTERISTICS:
        (A) LENGTH: 83 amino acids
        (B) TYPE: amino acid
        (D) TOPOLOGY: linear (ii) MOLECULE TYPE: protein (xi) SEQUENCE DESCRIPTION: SEQ ID NO:98:

```
Met Ala Asn Asn Leu Gln Lys Gly Ser Ala Gly Pro Met Arg Leu Tyr
  1               5                  10                  15

Val Gly Ser Leu His Phe Asn Ile Thr Glu Asp Met Leu Arg Gly Ile
             20                  25                  30

Phe Glu Pro Phe Gly Arg Ile Glu Ser Ile Gln Leu Met Met Asp Ser
         35                  40                  45

Glu Thr Gly Arg Ser Lys Gly Tyr Gly Phe Ile Thr Phe Ser Asp Ser
     50                  55                  60

Glu Cys Ala Lys Lys Ala Leu Glu Gln Leu Asn Gly Phe Glu Leu Ala
 65                  70                  75                  80

Gly Arg Pro
```

(2) INFORMATION FOR SEQ ID NO:99:

(i) SEQUENCE CHARACTERISTICS:
        (A) LENGTH: 204 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..204

(xi) SEQUENCE DESCRIPTION: SEQ ID NO:99:

```
CCA GAA AAG GCC CTT TCT GGT TAC TGT GGC TTT ATG GCA GCC AAC CTT      48
Pro Glu Lys Ala Leu Ser Gly Tyr Cys Gly Phe Met Ala Ala Asn Leu
     85                  90                  95

TAT GCT CGT TCC ATA TTT GGT GAA GAT GCA CTT GCA AAT GTC AGC ATT      96
Tyr Ala Arg Ser Ile Phe Gly Glu Asp Ala Leu Ala Asn Val Ser Ile
100             105                 110                 115

GAG AAG CCA ATT CAC CAG GGA CCA GAT GCT GCT GTT ACC GGC CAT ATA     144
Glu Lys Pro Ile His Gln Gly Pro Asp Ala Ala Val Thr Gly His Ile
            120                 125                 130

AGA ATT CGT GCA AAG AGC CAG GGA ATG GCC TTA AGT CTT GGA GAT AAA     192
Arg Ile Arg Ala Lys Ser Gln Gly Met Ala Leu Ser Leu Gly Asp Lys
        135                 140                 145

ATC AAC TTG TCA                                                     204
Ile Asn Leu Ser
        150
```

(2) INFORMATION FOR SEQ ID NO:100:

(i) SEQUENCE CHARACTERISTICS:
        (A) LENGTH: 68 amino acids
        (B) TYPE: amino acid
        (D) TOPOLOGY: linear (ii) MOLECULE TYPE: protein (xi) SEQUENCE DESCRIPTION: SEQ ID NO:100:

```
Pro Glu Lys Ala Leu Ser Gly Tyr Cys Gly Phe Met Ala Ala Asn Leu
  1               5                  10                  15
```

```
Tyr Ala Arg Ser Ile Phe Gly Glu Asp Ala Leu Ala Asn Val Ser Ile
            20                  25                  30

Glu Lys Pro Ile His Gln Gly Pro Asp Ala Ala Val Thr Gly His Ile
        35                  40                  45

Arg Ile Arg Ala Lys Ser Gln Gly Met Ala Leu Ser Leu Gly Asp Lys
    50                  55                  60

Ile Asn Leu Ser
65
```

(2) INFORMATION FOR SEQ ID NO:101:

(i) SEQUENCE CHARACTERISTICS:
        (A) LENGTH: 123 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..123

(xi) SEQUENCE DESCRIPTION: SEQ ID NO:101:

```
ATG GCC AAC AGG GGA CCT GCA TAT GGC CTG AGC CGG GAC GTG CAG CAG        48
Met Ala Asn Arg Gly Pro Ala Tyr Gly Leu Ser Arg Asp Val Gln Gln
    70                  75                  80

AAG ATT GAG AAA CAA TAT GAT GCA GAT CTG GAG CAG ATC CTG ATC CAG        96
Lys Ile Glu Lys Gln Tyr Asp Ala Asp Leu Glu Gln Ile Leu Ile Gln
85                  90                  95                  100

TGG ATC ACC ACC CAG TGC CGA AAG GAT                                   123
Trp Ile Thr Thr Gln Cys Arg Lys Asp
                105
```

(2) INFORMATION FOR SEQ ID NO:102:

(i) SEQUENCE CHARACTERISTICS:
        (A) LENGTH: 41 amino acids
        (B) TYPE: amino acid
        (D) TOPOLOGY: linear (ii) MOLECULE TYPE: protein (xi) SEQUENCE DESCRIPTION: SEQ ID NO:102:

```
Met Ala Asn Arg Gly Pro Ala Tyr Gly Leu Ser Arg Asp Val Gln Gln
1               5                   10                  15

Lys Ile Glu Lys Gln Tyr Asp Ala Asp Leu Glu Gln Ile Leu Ile Gln
            20                  25                  30

Trp Ile Thr Thr Gln Cys Arg Lys Asp
        35                  40
```

(2) INFORMATION FOR SEQ ID NO:103:

(i) SEQUENCE CHARACTERISTICS:
        (A) LENGTH: 225 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..225

(xi) SEQUENCE DESCRIPTION: SEQ ID NO:103:

```
GGG CGA CCC TCC GTT CTG TTG CTG CCG GTG AGG CGG GAG AGC GCC GGG        48
Gly Arg Pro Ser Val Leu Leu Leu Pro Val Arg Arg Glu Ser Ala Gly
             45                  50                  55

GCC GAC ACG CGC CCC ACT GTC AGA CCA CGG AAT GAT GTG GCC CAC AAG        96
Ala Asp Thr Arg Pro Thr Val Arg Pro Arg Asn Asp Val Ala His Lys
         60                  65                  70

CAG CTC TCA GAT TTT GGA GAG TAT GTG GCT GAA ATC TTG CCC AAG TAT       144
Gln Leu Ser Asp Phe Gly Glu Tyr Val Ala Glu Ile Leu Pro Lys Tyr
         75                  80                  85

GTC CAA CAA GTT CAG GTG TCC TGC TTC AAT GAG TTA GAG GTC TGT ATC       192
Val Gln Gln Val Gln Val Ser Cys Phe Asn Glu Leu Glu Val Cys Ile
 90                  95                 100                 105

CAT CCT GAT GGC GTC ATC CCA GTG CTG ACT TTC                           225
His Pro Asp Gly Val Ile Pro Val Leu Thr Phe
                 110                 115

(2) INFORMATION FOR SEQ ID NO:104:

(i) SEQUENCE CHARACTERISTICS:
        (A) LENGTH: 75 amino acids
        (B) TYPE: amino acid
        (D) TOPOLOGY: linear (ii) MOLECULE TYPE: protein (xi) SEQUENCE DESCRIPTION: SEQ ID NO:104:

Gly Arg Pro Ser Val Leu Leu Pro Val Arg Arg Glu Ser Ala Gly
 1               5                  10                  15

Ala Asp Thr Arg Pro Thr Val Arg Pro Arg Asn Asp Val Ala His Lys
                 20                  25                  30

Gln Leu Ser Asp Phe Gly Glu Tyr Val Ala Glu Ile Leu Pro Lys Tyr
             35                  40                  45

Val Gln Gln Val Gln Val Ser Cys Phe Asn Glu Leu Glu Val Cys Ile
         50                  55                  60

His Pro Asp Gly Val Ile Pro Val Leu Thr Phe
 65                  70                  75

(2) INFORMATION FOR SEQ ID NO:105:

(i) SEQUENCE CHARACTERISTICS:
        (A) LENGTH: 162 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..162

(xi) SEQUENCE DESCRIPTION: SEQ ID NO:105:

ATG GCG GGT GAA AAA GTT GAG AAG CCA GAT ACT AAA GAG AAG AAA CCC        48
Met Ala Gly Glu Lys Val Glu Lys Pro Asp Thr Lys Glu Lys Lys Pro
                 80                  85                  90

GAA GCC AAG AAG GTT GAT GCT GGT GGC AAG GTG AAA AAG GGT AAC CTC        96
Glu Ala Lys Lys Val Asp Ala Gly Gly Lys Val Lys Lys Gly Asn Leu
             95                 100                 105

AAA GCT AAA AAG CCC AAG AAG GGG AAG CCC CAT TGC AGC CGC AAC CCT       144
Lys Ala Lys Lys Pro Lys Lys Gly Lys Pro His Cys Ser Arg Asn Pro
         110                 115                 120

GTC CTT GTC AGA GGA ATT                                               162
Val Leu Val Arg Gly Ile
```

125

(2) INFORMATION FOR SEQ ID NO:106:

(i) SEQUENCE CHARACTERISTICS:
        (A) LENGTH: 54 amino acids
        (B) TYPE: amino acid
        (D) TOPOLOGY: linear (ii) MOLECULE TYPE: protein (xi) SEQUENCE DESCRIPTION: SEQ ID NO:106:

```
Met Ala Gly Glu Lys Val Glu Lys Pro Asp Thr Lys Glu Lys Lys Pro
 1               5                  10                  15

Glu Ala Lys Lys Val Asp Ala Gly Gly Lys Val Lys Lys Gly Asn Leu
            20                  25                  30

Lys Ala Lys Lys Pro Lys Lys Gly Lys Pro His Cys Ser Arg Asn Pro
        35                  40                  45

Val Leu Val Arg Gly Ile
        50
```

(2) INFORMATION FOR SEQ ID NO:107:

(i) SEQUENCE CHARACTERISTICS:
        (A) LENGTH: 315 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..315

(xi) SEQUENCE DESCRIPTION: SEQ ID NO:107:

```
AGC CCC GGG TAC CTT ACA TCT CCT GGT TAT CCT CAT TCT TAT CAC CCA        48
Ser Pro Gly Tyr Leu Thr Ser Pro Gly Tyr Pro His Ser Tyr His Pro
 55              60                  65                  70

AGT GAA AAA TGC GAA TGG CTG ATT CAG GCT CCG GAC CCA TAC CAG AGA        96
Ser Glu Lys Cys Glu Trp Leu Ile Gln Ala Pro Asp Pro Tyr Gln Arg
                75                  80                  85

ATT ATG ATC AAC TTC AAC CCT CAC TTC GAT TTG GAG GAC AGA GAC TGC       144
Ile Met Ile Asn Phe Asn Pro His Phe Asp Leu Glu Asp Arg Asp Cys
            90                  95                  100

AAG TAT GAC TAC GTG GAA GTC TTC GAT GGA GAC AAT GAA AAT GGA CAT       192
Lys Tyr Asp Tyr Val Glu Val Phe Asp Gly Asp Asn Glu Asn Gly His
        105                 110                 115

TTT AGG GGA AAG TTC TGT GGA AAG ATA GCC CCT CCT CCT GTT GTG TCT       240
Phe Arg Gly Lys Phe Cys Gly Lys Ile Ala Pro Pro Pro Val Val Ser
    120                 125                 130

TCA GGG CCA TTT CTT TTT ATC AAA TTT GTC TCT GAC TAC GAA ACA CAT       288
Ser Gly Pro Phe Leu Phe Ile Lys Phe Val Ser Asp Tyr Glu Thr His
135                 140                 145                 150

GGT GCA GGA TTT TCC ATA CGT TAT GAA                                   315
Gly Ala Gly Phe Ser Ile Arg Tyr Glu
                155
```

(2) INFORMATION FOR SEQ ID NO:108:

(i) SEQUENCE CHARACTERISTICS:
        (A) LENGTH: 105 amino acids
        (B) TYPE: amino acid
        (D) TOPOLOGY: linear (ii) MOLECULE TYPE: protein (xi) SEQUENCE DESCRIPTION: SEQ ID NO:108:

```
Ser Pro Gly Tyr Leu Thr Ser Pro Gly Tyr Pro His Ser Tyr His Pro
 1               5                  10                  15

Ser Glu Lys Cys Glu Trp Leu Ile Gln Ala Pro Asp Pro Tyr Gln Arg
            20                  25                  30

Ile Met Ile Asn Phe Asn Pro His Phe Asp Leu Glu Asp Arg Asp Cys
            35                  40                  45

Lys Tyr Asp Tyr Val Glu Val Phe Asp Gly Asp Asn Glu Asn Gly His
        50                  55                  60

Phe Arg Gly Lys Phe Cys Gly Lys Ile Ala Pro Pro Val Val Ser
 65                 70                  75                  80

Ser Gly Pro Phe Leu Phe Ile Lys Phe Val Ser Asp Tyr Glu Thr His
                85                  90                  95

Gly Ala Gly Phe Ser Ile Arg Tyr Glu
                100                 105
```

(2) INFORMATION FOR SEQ ID NO:109:

(i) SEQUENCE CHARACTERISTICS:
        (A) LENGTH: 294 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..294

(xi) SEQUENCE DESCRIPTION: SEQ ID NO:109:

```
GAC AAG TAC TGC CAC TAT GTT GCT GGG CTG GTC GGA ATT GGC CTT TCC      48
Asp Lys Tyr Cys His Tyr Val Ala Gly Leu Val Gly Ile Gly Leu Ser
                110                 115                 120

CGT CTT TTC TCA GCC TCA GAG TTT GAA GAC CCC TTA GTT GGT GAA GAT      96
Arg Leu Phe Ser Ala Ser Glu Phe Glu Asp Pro Leu Val Gly Glu Asp
                125                 130                 135

ACA GAA CAT GCC AAC TCT ATG GGC CTG TTT CTG CAG AAA ACA AAC ATC      144
Thr Glu His Ala Asn Ser Met Gly Leu Phe Leu Gln Lys Thr Asn Ile
            140                 145                 150

ATC CGT GAC TAT CTG GAA GAC CAG CAA GGA GGA AGA GAG TTC TGG CCT      192
Ile Arg Asp Tyr Leu Glu Asp Gln Gln Gly Gly Arg Glu Phe Trp Pro
    155                 160                 165

CAA GAG GTT TGG AGC AGG TAT GTT AAG AAG TTA GGG GAT TTT GCT AAG      240
Gln Glu Val Trp Ser Arg Tyr Val Lys Lys Leu Gly Asp Phe Ala Lys
170                 175                 180                 185

CCG GAG AAT ATT GAC TTG GCC GTG CAG TGC CTG AAT GAA CTT ATA ACC      288
Pro Glu Asn Ile Asp Leu Ala Val Gln Cys Leu Asn Glu Leu Ile Thr
                190                 195                 200

AAT GCA                                                              294
Asn Ala
```

(2) INFORMATION FOR SEQ ID NO:110:

(i) SEQUENCE CHARACTERISTICS:
        (A) LENGTH: 98 amino acids
        (B) TYPE: amino acid
        (D) TOPOLOGY: linear (ii) MOLECULE TYPE: protein (xi) SEQUENCE DESCRIPTION: SEQ ID NO:110:

| Asp | Lys | Tyr | Cys | His | Tyr | Val | Ala | Gly | Leu | Val | Gly | Ile | Gly | Leu | Ser |
|---|---|---|---|---|---|---|---|---|---|---|---|---|---|---|---|
| 1 | | | | 5 | | | | | 10 | | | | | 15 | |

| Arg | Leu | Phe | Ser | Ala | Ser | Glu | Phe | Glu | Asp | Pro | Leu | Val | Gly | Glu | Asp |
|---|---|---|---|---|---|---|---|---|---|---|---|---|---|---|---|
| | | | 20 | | | | | 25 | | | | | 30 | | |

| Thr | Glu | His | Ala | Asn | Ser | Met | Gly | Leu | Phe | Leu | Gln | Lys | Thr | Asn | Ile |
|---|---|---|---|---|---|---|---|---|---|---|---|---|---|---|---|
| | | 35 | | | | | 40 | | | | | 45 | | | |

| Ile | Arg | Asp | Tyr | Leu | Glu | Asp | Gln | Gln | Gly | Arg | Glu | Phe | Trp | Pro |
|---|---|---|---|---|---|---|---|---|---|---|---|---|---|---|
| 50 | | | | | 55 | | | | | 60 | | | | |

| Gln | Glu | Val | Trp | Ser | Arg | Tyr | Val | Lys | Lys | Leu | Gly | Asp | Phe | Ala | Lys |
|---|---|---|---|---|---|---|---|---|---|---|---|---|---|---|---|
| 65 | | | | | 70 | | | | | 75 | | | | | 80 |

| Pro | Glu | Asn | Ile | Asp | Leu | Ala | Val | Gln | Cys | Leu | Asn | Glu | Leu | Ile | Thr |
|---|---|---|---|---|---|---|---|---|---|---|---|---|---|---|---|
| | | | | 85 | | | | | 90 | | | | | 95 | |

Asn Ala (2) INFORMATION FOR SEQ ID NO:111:

(i) SEQUENCE CHARACTERISTICS:
        (A) LENGTH: 282 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..282

(xi) SEQUENCE DESCRIPTION: SEQ ID NO:111:

| TAC | ATT | GCC | TCC | CAG | ACG | GTG | AAG | AAG | GTG | ATA | GAG | ATC | AAC | CCA | TAC | 48 |
|---|---|---|---|---|---|---|---|---|---|---|---|---|---|---|---|---|
| Tyr | Ile | Ala | Ser | Gln | Thr | Val | Lys | Lys | Val | Ile | Glu | Ile | Asn | Pro | Tyr | |
| 100 | | | | | 105 | | | | | 110 | | | | | | |

| CTG | CTA | GGC | ACC | ATG | GCT | GGG | GGC | GCA | CGG | GAT | TGC | AGC | TTC | TGG | GAA | 96 |
|---|---|---|---|---|---|---|---|---|---|---|---|---|---|---|---|---|
| Leu | Leu | Gly | Thr | Met | Ala | Gly | Gly | Ala | Arg | Asp | Cys | Ser | Phe | Trp | Glu | |
| 115 | | | | | 120 | | | | | 125 | | | | | 130 | |

| CGG | CTG | TTG | GCT | CGG | CAA | TGT | CGA | ATC | TAT | GAG | CTT | CGA | AAT | AAG | GAA | 144 |
|---|---|---|---|---|---|---|---|---|---|---|---|---|---|---|---|---|
| Arg | Leu | Leu | Ala | Arg | Gln | Cys | Arg | Ile | Tyr | Glu | Leu | Arg | Asn | Lys | Glu | |
| | | | | 135 | | | | | 140 | | | | | 145 | | |

| CGC | ATC | TCT | GTA | GCA | GCT | GCC | TCC | AAA | CTG | CTT | GCC | AAC | ATG | GTG | TAT | 192 |
|---|---|---|---|---|---|---|---|---|---|---|---|---|---|---|---|---|
| Arg | Ile | Ser | Val | Ala | Ala | Ala | Ser | Lys | Leu | Leu | Ala | Asn | Met | Val | Tyr | |
| | | 150 | | | | | 155 | | | | | 160 | | | | |

| CAG | TAC | AAA | GGC | ATG | GGG | CTG | TCC | ATG | GGC | ACC | ATG | ATC | TGT | GGC | TGG | 240 |
|---|---|---|---|---|---|---|---|---|---|---|---|---|---|---|---|---|
| Gln | Tyr | Lys | Gly | Met | Gly | Leu | Ser | Met | Gly | Thr | Met | Ile | Cys | Gly | Trp | |
| | | 165 | | | | | 170 | | | | | 175 | | | | |

| GAT | AAG | AGA | GGC | CCT | GGC | CTC | TAC | TAC | GTG | GAC | AGT | GAA | GGG | | | 282 |
|---|---|---|---|---|---|---|---|---|---|---|---|---|---|---|---|---|
| Asp | Lys | Arg | Gly | Pro | Gly | Leu | Tyr | Tyr | Val | Asp | Ser | Glu | Gly | | | |
| | 180 | | | | | 185 | | | | | 190 | | | | | |

(2) INFORMATION FOR SEQ ID NO:112:

(i) SEQUENCE CHARACTERISTICS:
        (A) LENGTH: 94 amino acids
        (B) TYPE: amino acid
        (D) TOPOLOGY: linear (ii) MOLECULE TYPE: protein (xi) SEQUENCE DESCRIPTION: SEQ ID NO:112:

| Tyr | Ile | Ala | Ser | Gln | Thr | Val | Lys | Lys | Val | Ile | Glu | Ile | Asn | Pro | Tyr |
|---|---|---|---|---|---|---|---|---|---|---|---|---|---|---|---|
| 1 | | | | 5 | | | | | 10 | | | | | 15 | |

Leu Leu Gly Thr Met Ala Gly Gly Ala Arg Asp Cys Ser Phe Trp Glu

```
                    20                  25                  30

Arg Leu Leu Ala Arg Gln Cys Arg Ile Tyr Glu Leu Arg Asn Lys Glu
         35                  40                  45

Arg Ile Ser Val Ala Ala Ala Ser Lys Leu Leu Ala Asn Met Val Tyr
         50                  55                  60

Gln Tyr Lys Gly Met Gly Leu Ser Met Gly Thr Met Ile Cys Gly Trp
 65                  70                  75                  80

Asp Lys Arg Gly Pro Gly Leu Tyr Tyr Val Asp Ser Glu Gly
                 85                  90
```

(2) INFORMATION FOR SEQ ID NO:113:

(i) SEQUENCE CHARACTERISTICS:
        (A) LENGTH: 105 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..105

(xi) SEQUENCE DESCRIPTION: SEQ ID NO:113:

```
AGC GAC ATG CCT CCT TTG ACG TTA GAG GGC ATC CAG GAC CGT GTT CTT        48
Ser Asp Met Pro Pro Leu Thr Leu Glu Gly Ile Gln Asp Arg Val Leu
 95              100                 105                 110

TAC GTA TTG AAA CTC TAT GAC AAG ATT GAC CCA GAG AAG CTT TCA GTA        96
Tyr Val Leu Lys Leu Tyr Asp Lys Ile Asp Pro Glu Lys Leu Ser Val
                 115                 120                 125

AAT TCT CAT                                                           105
Asn Ser His
```

(2) INFORMATION FOR SEQ ID NO:114:

(i) SEQUENCE CHARACTERISTICS:
        (A) LENGTH: 35 amino acids
        (B) TYPE: amino acid
        (D) TOPOLOGY: linear (ii) MOLECULE TYPE: protein (xi) SEQUENCE DESCRIPTION: SEQ ID NO:114:

```
Ser Asp Met Pro Pro Leu Thr Leu Glu Gly Ile Gln Asp Arg Val Leu
 1               5                   10                  15

Tyr Val Leu Lys Leu Tyr Asp Lys Ile Asp Pro Glu Lys Leu Ser Val
                 20                  25                  30

Asn Ser His
         35
```

(2) INFORMATION FOR SEQ ID NO:115:

(i) SEQUENCE CHARACTERISTICS:
        (A) LENGTH: 213 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..213

(xi) SEQUENCE DESCRIPTION: SEQ ID NO:115:

```
AAG AGA GCA GAA ATC TCC AAT GCC ATC GAT CAA TAT GTG ACT GGA ACC          48
Lys Arg Ala Glu Ile Ser Asn Ala Ile Asp Gln Tyr Val Thr Gly Thr
             40                  45                  50

ATT GGC GAG GAT GAA GAT TTG ATA AAG TGG AAG GCA CTG TTT GAG GAA          96
Ile Gly Glu Asp Glu Asp Leu Ile Lys Trp Lys Ala Leu Phe Glu Glu
             55                  60                  65

GTC CCT GAG TTA CTC ACT GAG GCA GAG AAG AAG GAA TGG GTT GAG AAA         144
Val Pro Glu Leu Leu Thr Glu Ala Glu Lys Lys Glu Trp Val Glu Lys
         70                  75                  80

CTG ACT GAA GTT TCT ATC AGC TCT GAT GCC TCC TTC CCT TTC CGA GAT         192
Leu Thr Glu Val Ser Ile Ser Ser Asp Ala Ser Phe Pro Phe Arg Asp
         85                  90                  95

AAC GTA GAC AGA GCT AAA AGG                                             213
Asn Val Asp Arg Ala Lys Arg
100             105

(2) INFORMATION FOR SEQ ID NO:116:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO:116:

Lys Arg Ala Glu Ile Ser Asn Ala Ile Asp Gln Tyr Val Thr Gly Thr
 1               5                  10                  15

Ile Gly Glu Asp Glu Asp Leu Ile Lys Trp Lys Ala Leu Phe Glu Glu
             20                  25                  30

Val Pro Glu Leu Leu Thr Glu Ala Glu Lys Lys Glu Trp Val Glu Lys
         35                  40                  45

Leu Thr Glu Val Ser Ile Ser Ser Asp Ala Ser Phe Pro Phe Arg Asp
         50                  55                  60

Asn Val Asp Arg Ala Lys Arg
65              70

(2) INFORMATION FOR SEQ ID NO:117:

(i) SEQUENCE CHARACTERISTICS:
        (A) LENGTH: 315 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..315

(xi) SEQUENCE DESCRIPTION: SEQ ID NO:117:

GGG GCT CTA GCA AAA GGA AAG TTT GGC CGT GTG GAT GTA GCT GTC AAC          48
Gly Ala Leu Ala Lys Gly Lys Phe Gly Arg Val Asp Val Ala Val Asn
             75                  80                  85

TGT GCA GGC ATC GCG GTG GCT AGC AAG ACG TAC AAC TTA AAG AAG GGC          96
Cys Ala Gly Ile Ala Val Ala Ser Lys Thr Tyr Asn Leu Lys Lys Gly
             90                  95                 100

CAG ACC CAT ACC TTG GAA GAC TTC CAG CGA GTT CTT GAT GTG AAT CTC         144
Gln Thr His Thr Leu Glu Asp Phe Gln Arg Val Leu Asp Val Asn Leu
        105                 110                 115

ATG GGC ACC TTC AAT GTG ATC CGC CTG GTG GCT GGT GAG ATG GGC CAG         192
Met Gly Thr Phe Asn Val Ile Arg Leu Val Ala Gly Glu Met Gly Gln
```

-continued

```
       120                 125                 130                 135
AAT GAA CCA GAC CAG GGA GGC CAA CGT GGG GTC ATC ATC AAC ACT GCC         240
Asn Glu Pro Asp Gln Gly Gly Gln Arg Gly Val Ile Ile Asn Thr Ala
                140                 145                 150

AGT GTG GCT GCC TTC GAG GGT CAG GTT GGA CAA GCT GCA TAC TCT GCT         288
Ser Val Ala Ala Phe Glu Gly Gln Val Gly Gln Ala Ala Tyr Ser Ala
            155                 160                 165

TCC AAG GGG GGA ATA GTG GGC ATG ACA                                     315
Ser Lys Gly Gly Ile Val Gly Met Thr
        170                 175
```

(2) INFORMATION FOR SEQ ID NO:118:

(i) SEQUENCE CHARACTERISTICS:
        (A) LENGTH: 105 amino acids
        (B) TYPE: amino acid
        (D) TOPOLOGY: linear (ii) MOLECULE TYPE: protein (xi) SEQUENCE DESCRIPTION: SEQ ID NO:118:

```
Gly Ala Leu Ala Lys Gly Lys Phe Gly Arg Val Asp Val Ala Val Asn
 1               5                  10                  15

Cys Ala Gly Ile Ala Val Ala Ser Lys Thr Tyr Asn Leu Lys Lys Gly
            20                  25                  30

Gln Thr His Thr Leu Glu Asp Phe Gln Arg Val Leu Asp Val Asn Leu
        35                  40                  45

Met Gly Thr Phe Asn Val Ile Arg Leu Val Ala Gly Glu Met Gly Gln
    50                  55                  60

Asn Glu Pro Asp Gln Gly Gly Gln Arg Gly Val Ile Ile Asn Thr Ala
65                  70                  75                  80

Ser Val Ala Ala Phe Glu Gly Gln Val Gly Gln Ala Ala Tyr Ser Ala
                85                  90                  95

Ser Lys Gly Gly Ile Val Gly Met Thr
            100                 105
```

(2) INFORMATION FOR SEQ ID NO:119:

(i) SEQUENCE CHARACTERISTICS:
        (A) LENGTH: 207 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..207

(xi) SEQUENCE DESCRIPTION: SEQ ID NO:119:

```
GGA AAG AAT CTC TAT ACA AAT GAA TAC GTG GCT ATC AAA TTG GAG CCG         48
Gly Lys Asn Leu Tyr Thr Asn Glu Tyr Val Ala Ile Lys Leu Glu Pro
                110                 115                 120

ATC AAG TCC CGG GCC CCG CAG CTG CAC CTG GAG TAC CGG TTC TAC AAG         96
Ile Lys Ser Arg Ala Pro Gln Leu His Leu Glu Tyr Arg Phe Tyr Lys
            125                 130                 135

CAG CTC AGC GCC ACA GAG GGC GTC CCT CAG GTC TAC TAC TTC GGT CCG         144
Gln Leu Ser Ala Thr Glu Gly Val Pro Gln Val Tyr Tyr Phe Gly Pro
        140                 145                 150

TGC GGG AAG TAC AAC GCC ATG GTG CTG GAG CTG CTG GGG CCC AGC CTG         192
Cys Gly Lys Tyr Asn Ala Met Val Leu Glu Leu Leu Gly Pro Ser Leu
    155                 160                 165
```

```
GAG GAC CTG TTC GAC                                                              207
Glu Asp Leu Phe Asp
170
```

(2) INFORMATION FOR SEQ ID NO:120:

(i) SEQUENCE CHARACTERISTICS:
        (A) LENGTH: 69 amino acids
        (B) TYPE: amino acid
        (D) TOPOLOGY: linear (ii) MOLECULE TYPE: protein (xi) SEQUENCE DESCRIPTION: SEQ ID NO:120:

```
Gly Lys Asn Leu Tyr Thr Asn Glu Tyr Val Ala Ile Lys Leu Glu Pro
 1               5                  10                  15

Ile Lys Ser Arg Ala Pro Gln Leu His Leu Glu Tyr Arg Phe Tyr Lys
             20                  25                  30

Gln Leu Ser Ala Thr Glu Gly Val Pro Gln Val Tyr Tyr Phe Gly Pro
             35                  40                  45

Cys Gly Lys Tyr Asn Ala Met Val Leu Glu Leu Leu Gly Pro Ser Leu
 50                  55                  60

Glu Asp Leu Phe Asp
 65
```

(2) INFORMATION FOR SEQ ID NO:121:

(i) SEQUENCE CHARACTERISTICS:
        (A) LENGTH: 324 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..324

(xi) SEQUENCE DESCRIPTION: SEQ ID NO:121:

```
GAT GTT TGC AAA GAG GCA GCA GAC ATG ATC CTA GTG GAT GAT GAT TTT         48
Asp Val Cys Lys Glu Ala Ala Asp Met Ile Leu Val Asp Asp Asp Phe
 70                  75                  80                  85

CAA ACC ATA ATG TCT GCA ATC GAA GAG GGT AAA GGG ATT TAT AAT AAC         96
Gln Thr Ile Met Ser Ala Ile Glu Glu Gly Lys Gly Ile Tyr Asn Asn
                 90                  95                 100

ATT AAA AAT TTC GTT AGA TTC CAG CTG AGC ACG AGT ATA GCA GCA TTA        144
Ile Lys Asn Phe Val Arg Phe Gln Leu Ser Thr Ser Ile Ala Ala Leu
             105                 110                 115

ACT TTA ATC TCA TTG GCT ACA TTA ATG AAC TTT CCT AAT CCT CTC AAT        192
Thr Leu Ile Ser Leu Ala Thr Leu Met Asn Phe Pro Asn Pro Leu Asn
         120                 125                 130

GCC ATG CAG ATT TTG TGG ATC AAT ATT ATT ATG GAT GGA CCC CCA GCT        240
Ala Met Gln Ile Leu Trp Ile Asn Ile Ile Met Asp Gly Pro Pro Ala
 135                 140                 145

CAG AGC CTT GGA GTA GAA CCA GTG GAT AAA GAT GTC ATT CGT AAA CCT        288
Gln Ser Leu Gly Val Glu Pro Val Asp Lys Asp Val Ile Arg Lys Pro
150                 155                 160                 165

CCT CGC AAC TGG AAA GAC AGC ATT TTG ACT AAA AAC                        324
Pro Arg Asn Trp Lys Asp Ser Ile Leu Thr Lys Asn
                 170                 175
```

(2) INFORMATION FOR SEQ ID NO:122:

(i) SEQUENCE CHARACTERISTICS:
   (A) LENGTH: 108 amino acids
   (B) TYPE: amino acid
   (D) TOPOLOGY: linear (ii) MOLECULE TYPE: protein (xi) SEQUENCE DESCRIPTION: SEQ ID NO:122:

```
Asp Val Cys Lys Glu Ala Ala Asp Met Ile Leu Val Asp Asp Asp Phe
 1               5                  10                  15

Gln Thr Ile Met Ser Ala Ile Glu Glu Gly Lys Gly Ile Tyr Asn Asn
            20                  25                  30

Ile Lys Asn Phe Val Arg Phe Gln Leu Ser Thr Ser Ile Ala Ala Leu
        35                  40                  45

Thr Leu Ile Ser Leu Ala Thr Leu Met Asn Phe Pro Asn Pro Leu Asn
    50                  55                  60

Ala Met Gln Ile Leu Trp Ile Asn Ile Ile Met Asp Gly Pro Pro Ala
65                  70                  75                  80

Gln Ser Leu Gly Val Glu Pro Val Asp Lys Asp Val Ile Arg Lys Pro
                85                  90                  95

Pro Arg Asn Trp Lys Asp Ser Ile Leu Thr Lys Asn
            100                 105
```

(2) INFORMATION FOR SEQ ID NO:123:

(i) SEQUENCE CHARACTERISTICS:
      (A) LENGTH: 162 base pairs
      (B) TYPE: nucleic acid
      (C) STRANDEDNESS: double
      (D) TOPOLOGY: linear (ii) MOLECULE TYPE: cDNA to mRNA (ix) FEATURE:
      (A) NAME/KEY: CDS
      (B) LOCATION: 1..162

(xi) SEQUENCE DESCRIPTION: SEQ ID NO:123:

```
GCA GCA GCC AGG CTG GAC CAG AAG CAG CTG CAG TCT GGC AAG GCC CTT      48
Ala Ala Ala Arg Leu Asp Gln Lys Gln Leu Gln Ser Gly Lys Ala Leu
    110                 115                 120

GCC GAC TGG AAG CAG AAG CAC GAG GAG TCC CAG GCG TTG CTG GAT GCC      96
Ala Asp Trp Lys Gln Lys His Glu Glu Ser Gln Ala Leu Leu Asp Ala
125                 130                 135                 140

TCT CAG AAG GAA GTT CAG GCT CTC AGT ACA GAG CTC CTC AAG CTC AAG     144
Ser Gln Lys Glu Val Gln Ala Leu Ser Thr Glu Leu Leu Lys Leu Lys
                145                 150                 155

AAC ACC TAT GAG GAG AGC                                              162
Asn Thr Tyr Glu Glu Ser
            160
```

(2) INFORMATION FOR SEQ ID NO:124:

(i) SEQUENCE CHARACTERISTICS:
      (A) LENGTH: 54 amino acids
      (B) TYPE: amino acid
      (D) TOPOLOGY: linear (ii) MOLECULE TYPE: protein (xi) SEQUENCE DESCRIPTION: SEQ ID NO:124:

```
Ala Ala Ala Arg Leu Asp Gln Lys Gln Leu Gln Ser Gly Lys Ala Leu
 1               5                  10                  15
```

```
Ala Asp Trp Lys Gln Lys His Glu Glu Ser Gln Ala Leu Leu Asp Ala
         20                  25                  30

Ser Gln Lys Glu Val Gln Ala Leu Ser Thr Glu Leu Leu Lys Leu Lys
         35                  40                  45

Asn Thr Tyr Glu Glu Ser
         50
```

(2) INFORMATION FOR SEQ ID NO:125:

(i) SEQUENCE CHARACTERISTICS:
        (A) LENGTH: 129 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..129

(xi) SEQUENCE DESCRIPTION: SEQ ID NO:125:

```
ATC AGA AGG CAA AGA GCC CAG CCT AAC CAT GAC CCA AAT ACT CAT CAT      48
Ile Arg Arg Gln Arg Ala Gln Pro Asn His Asp Pro Asn Thr His His
 55                  60                  65                  70

TGT TTA TGT GGA GCA GAT GCT GAT CTC ATT ATG CTT GGC CTT GCC ACA      96
Cys Leu Cys Gly Ala Asp Ala Asp Leu Ile Met Leu Gly Leu Ala Thr
                 75                  80                  85

CAT GAA CCG AAC TTT ACC ATT ATT AGA GAA GAA                         129
His Glu Pro Asn Phe Thr Ile Ile Arg Glu Glu
         90                  95
```

(2) INFORMATION FOR SEQ ID NO:126:

(i) SEQUENCE CHARACTERISTICS:
        (A) LENGTH: 43 amino acids
        (B) TYPE: amino acid
        (D) TOPOLOGY: linear (ii) MOLECULE TYPE: protein (xi) SEQUENCE DESCRIPTION: SEQ ID NO:126:

```
Ile Arg Arg Gln Arg Ala Gln Pro Asn His Asp Pro Asn Thr His His
 1               5                  10                  15

Cys Leu Cys Gly Ala Asp Ala Asp Leu Ile Met Leu Gly Leu Ala Thr
                 20                  25                  30

His Glu Pro Asn Phe Thr Ile Ile Arg Glu Glu
         35                  40
```

(2) INFORMATION FOR SEQ ID NO:127:

(i) SEQUENCE CHARACTERISTICS:
        (A) LENGTH: 240 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..240

(xi) SEQUENCE DESCRIPTION: SEQ ID NO:127:

```
ATA GTA CTT CGA GGC TCT ACA GAC AAT CTG ATG GAT GAC ATA GAA AGG      48
Ile Val Leu Arg Gly Ser Thr Asp Asn Leu Met Asp Asp Ile Glu Arg
 45                  50                  55
```

```
GCA GTA GAC GAT GGT GTT AAT ACT TTC AAA GTT CTT ACA AGG GAT AAA        96
Ala Val Asp Asp Gly Val Asn Thr Phe Lys Val Leu Thr Arg Asp Lys
 60              65                  70                  75

CGT CTT GTA CCC GGA GGT GGA GCA ACA GAA ATT GAA TTA GCC AAA CAG       144
Arg Leu Val Pro Gly Gly Gly Ala Thr Glu Ile Glu Leu Ala Lys Gln
                 80                  85                  90

ATC ACA TCA TAT GGA GAG ACA TGT CCT GGA CTT GAA CAG TAT GCT ATT       192
Ile Thr Ser Tyr Gly Glu Thr Cys Pro Gly Leu Glu Gln Tyr Ala Ile
                     95                 100                 105

AAG AAG TTT GCT GAG GCA TTT GAA GCT ATT CCC CGC GCA CTG GCA GAA       240
Lys Lys Phe Ala Glu Ala Phe Glu Ala Ile Pro Arg Ala Leu Ala Glu
             110                 115                 120

(2) INFORMATION FOR SEQ ID NO:128:

(i) SEQUENCE CHARACTERISTICS:
        (A) LENGTH: 80 amino acids
        (B) TYPE: amino acid
        (D) TOPOLOGY: linear (ii) MOLECULE TYPE: protein (xi) SEQUENCE DESCRIPTION: SEQ ID NO:128:

Ile Val Leu Arg Gly Ser Thr Asp Asn Leu Met Asp Asp Ile Glu Arg
 1               5                  10                  15

Ala Val Asp Asp Gly Val Asn Thr Phe Lys Val Leu Thr Arg Asp Lys
                 20                  25                  30

Arg Leu Val Pro Gly Gly Gly Ala Thr Glu Ile Glu Leu Ala Lys Gln
             35                  40                  45

Ile Thr Ser Tyr Gly Glu Thr Cys Pro Gly Leu Glu Gln Tyr Ala Ile
         50                  55                  60

Lys Lys Phe Ala Glu Ala Phe Glu Ala Ile Pro Arg Ala Leu Ala Glu
 65                  70                  75                  80

(2) INFORMATION FOR SEQ ID NO:129:

(i) SEQUENCE CHARACTERISTICS:
        (A) LENGTH: 318 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..318

(xi) SEQUENCE DESCRIPTION: SEQ ID NO:129:

ATG GGC AAG TGT CGT GGA CTT CGT ACT CCT AGG AAG CTC CGT AGT CAC        48
Met Gly Lys Cys Arg Gly Leu Arg Thr Pro Arg Lys Leu Arg Ser His
                 85                  90                  95

CGA CGA GAC CAG AAG TGG CAT GAT AAA CAG TAT AAG AAA GCT CAT TTG        96
Arg Arg Asp Gln Lys Trp His Asp Lys Gln Tyr Lys Lys Ala His Leu
             100                 105                 110

GGC ACA GCC CTA AAG GCC AAC CCT TTT GGA GGT GCT TCT CAT GCA AAA       144
Gly Thr Ala Leu Lys Ala Asn Pro Phe Gly Gly Ala Ser His Ala Lys
         115                 120                 125

GGA ATC GTG CTG GAA AAA GTA GGA GTT GAA GCC AAA CAG CCA AAT TCT       192
Gly Ile Val Leu Glu Lys Val Gly Val Glu Ala Lys Gln Pro Asn Ser
 130                 135                 140

GCC ATT AGG AAG TGT GTA AGG GTC CAG CTG ATC AAG AAT GGC AGG AAA       240
Ala Ile Arg Lys Cys Val Arg Val Gln Leu Ile Lys Asn Gly Arg Lys
```

```
145                 150                 155                 160
ATC ACA GCC TTT GTA CCC CAT GAC GGT TGC TTG AAC TTT ATT GAG GAA       288
Ile Thr Ala Phe Val Pro His Asp Gly Cys Leu Asn Phe Ile Glu Glu
                165                 170                 175

AAT GAT GAA GTT CTG GTT GCT GGA TTT GGT                               318
Asn Asp Glu Val Leu Val Ala Gly Phe Gly
        180                 185
```

(2) INFORMATION FOR SEQ ID NO:130:

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO:130:

```
Met Gly Lys Cys Arg Gly Leu Arg Thr Pro Arg Lys Leu Arg Ser His
 1               5                  10                  15

Arg Arg Asp Gln Lys Trp His Asp Lys Gln Tyr Lys Lys Ala His Leu
             20                  25                  30

Gly Thr Ala Leu Lys Ala Asn Pro Phe Gly Gly Ala Ser His Ala Lys
         35                  40                  45

Gly Ile Val Leu Glu Lys Val Gly Val Glu Ala Lys Gln Pro Asn Ser
     50                  55                  60

Ala Ile Arg Lys Cys Val Arg Val Gln Leu Ile Lys Asn Gly Arg Lys
 65                  70                  75                  80

Ile Thr Ala Phe Val Pro His Asp Gly Cys Leu Asn Phe Ile Glu Glu
                 85                  90                  95

Asn Asp Glu Val Leu Val Ala Gly Phe Gly
            100                 105
```

(2) INFORMATION FOR SEQ ID NO:131:

(i) SEQUENCE CHARACTERISTICS:
        (A) LENGTH: 264 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..264

(xi) SEQUENCE DESCRIPTION: SEQ ID NO:131:

```
GCA GCA GGA AGC TGT TTT AGG TTA TGT GAA AGA GAT GTT TCC TCA TCT       48
Ala Ala Gly Ser Cys Phe Arg Leu Cys Glu Arg Asp Val Ser Ser Ser
            110                 115                 120

CTA AGG CTT ACC AGA AGC TCT GAT TTG AAG AGA ATA AAT GGA TTT TGC       96
Leu Arg Leu Thr Arg Ser Ser Asp Leu Lys Arg Ile Asn Gly Phe Cys
        125                 130                 135

ACA AAA CCA CAG GAA AGT CCC GGA GCT CCA TCC CGC ACT TAC AAC AGA      144
Thr Lys Pro Gln Glu Ser Pro Gly Ala Pro Ser Arg Thr Tyr Asn Arg
    140                 145                 150

GTG CCT TTA CAC AAA CCT ACG GAT TGG CAG AAA ACG ATC CTC ATA TGG      192
Val Pro Leu His Lys Pro Thr Asp Trp Gln Lys Thr Ile Leu Ile Trp
155                 160                 165                 170

TCA GGT CGC TTC AAA AAG GAA GAT GAA ATC CCA GAG ACT GTC TCG TTG      240
Ser Gly Arg Phe Lys Lys Glu Asp Glu Ile Pro Glu Thr Val Ser Leu
                175                 180                 185
```

```
GAG ATG CTT GAT GCT GCA AAG AAC                                                  264
Glu Met Leu Asp Ala Ala Lys Asn
            190
```

(2) INFORMATION FOR SEQ ID NO:132:

(i) SEQUENCE CHARACTERISTICS:
        (A) LENGTH: 88 amino acids
        (B) TYPE: amino acid
        (D) TOPOLOGY: linear (ii) MOLECULE TYPE: protein (xi) SEQUENCE DESCRIPTION: SEQ ID NO:132:

```
Ala Ala Gly Ser Cys Phe Arg Leu Cys Glu Arg Asp Val Ser Ser Ser
 1               5                  10                  15

Leu Arg Leu Thr Arg Ser Ser Asp Leu Lys Arg Ile Asn Gly Phe Cys
                20                  25                  30

Thr Lys Pro Gln Glu Ser Pro Gly Ala Pro Ser Arg Thr Tyr Asn Arg
            35                  40                  45

Val Pro Leu His Lys Pro Thr Asp Trp Gln Lys Thr Ile Leu Ile Trp
     50                  55                  60

Ser Gly Arg Phe Lys Lys Glu Asp Glu Ile Pro Glu Thr Val Ser Leu
 65                  70                  75                  80

Glu Met Leu Asp Ala Ala Lys Asn
                85
```

(2) INFORMATION FOR SEQ ID NO:133:

(i) SEQUENCE CHARACTERISTICS:
        (A) LENGTH: 297 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..297

(xi) SEQUENCE DESCRIPTION: SEQ ID NO:133:

```
TGC TGC CGT CTG CAC ACG GTC CGC GCG TCG CTG GAA GAC CTG GGC TGG            48
Cys Cys Arg Leu His Thr Val Arg Ala Ser Leu Glu Asp Leu Gly Trp
 90                  95                 100

GCC GAT TGG GTG CTG TCG CCA CGG GAG GTG CAA GTG ACC ATG TGC ATC            96
Ala Asp Trp Val Leu Ser Pro Arg Glu Val Gln Val Thr Met Cys Ile
105                 110                 115                 120

GGC GCG TGC CCG AGC CAG TTC CGG GCG GCA AAC ATG CAC GCG CAG ATC           144
Gly Ala Cys Pro Ser Gln Phe Arg Ala Ala Asn Met His Ala Gln Ile
                125                 130                 135

AAG ACG AGC CTG CAC CGC CTG AAG CCC GAC ACG GTG CCA GCG CCC TGC           192
Lys Thr Ser Leu His Arg Leu Lys Pro Asp Thr Val Pro Ala Pro Cys
            140                 145                 150

TGC GTG CCC GCC AGC TAC AAT CCC ATG GTG CTC ATT CAA AAG ACC GAC           240
Cys Val Pro Ala Ser Tyr Asn Pro Met Val Leu Ile Gln Lys Thr Asp
        155                 160                 165

ACC GGG GTG TCG CTC CAG ACC TAT GAT GAC TTG TTA GCC AAA GAC TGC           288
Thr Gly Val Ser Leu Gln Thr Tyr Asp Asp Leu Leu Ala Lys Asp Cys
170                 175                 180

CAC TGC ATA                                                               297
His Cys Ile
185
```

(2) INFORMATION FOR SEQ ID NO:134:

(i) SEQUENCE CHARACTERISTICS:
        (A) LENGTH: 99 amino acids
        (B) TYPE: amino acid
        (D) TOPOLOGY: linear (ii) MOLECULE TYPE: protein (xi) SEQUENCE DESCRIPTION: SEQ ID NO:134:

```
Cys Cys Arg Leu His Thr Val Arg Ala Ser Leu Glu Asp Leu Gly Trp
  1               5                  10                  15

Ala Asp Trp Val Leu Ser Pro Arg Glu Val Gln Val Thr Met Cys Ile
             20                  25                  30

Gly Ala Cys Pro Ser Gln Phe Arg Ala Ala Asn Met His Ala Gln Ile
             35                  40                  45

Lys Thr Ser Leu His Arg Leu Lys Pro Asp Thr Val Pro Ala Pro Cys
 50                  55                  60

Cys Val Pro Ala Ser Tyr Asn Pro Met Val Leu Ile Gln Lys Thr Asp
 65                  70                  75                  80

Thr Gly Val Ser Leu Gln Thr Tyr Asp Asp Leu Leu Ala Lys Asp Cys
                 85                  90                  95

His Cys Ile
```

(2) INFORMATION FOR SEQ ID NO:135:

(i) SEQUENCE CHARACTERISTICS:
        (A) LENGTH: 276 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..276

(xi) SEQUENCE DESCRIPTION: SEQ ID NO:135:

```
TGC GAC ATT CGC TGC CAG AAG GGC TAC GAG CTG CAT GGC TCT TCC CTA      48
Cys Asp Ile Arg Cys Gln Lys Gly Tyr Glu Leu His Gly Ser Ser Leu
100              105                 110                 115

CTG ATC TGC CAG TCA AAC AAA CGA TGG TCT GAC AAG GTC ATC TGC AAA      96
Leu Ile Cys Gln Ser Asn Lys Arg Trp Ser Asp Lys Val Ile Cys Lys
                 120                 125                 130

CAA AAG CGA TGT CCT ACC CTT GCC ATG CCA GCA AAT GGA GGG TTT AAG     144
Gln Lys Arg Cys Pro Thr Leu Ala Met Pro Ala Asn Gly Gly Phe Lys
             135                 140                 145

TGT GTA GAT GGT GCC TAC TTT AAC TCC CGG TGT GAG TAT TAT TGT TCA     192
Cys Val Asp Gly Ala Tyr Phe Asn Ser Arg Cys Glu Tyr Tyr Cys Ser
             150                 155                 160

CCA GGA TAC ACG TTG AAA GGG GAG CGG ACC GTC ACA TGT ATG GAC AAC     240
Pro Gly Tyr Thr Leu Lys Gly Glu Arg Thr Val Thr Cys Met Asp Asn
             165                 170                 175

AAG GCC TGG AGC GGC CGG CCA GCC TCC TGT GTG GAT                     276
Lys Ala Trp Ser Gly Arg Pro Ala Ser Cys Val Asp
180                 185                 190
```

(2) INFORMATION FOR SEQ ID NO:136:

(i) SEQUENCE CHARACTERISTICS:
        (A) LENGTH: 92 amino acids (B) TYPE: amino acid
        (D) TOPOLOGY: linear (ii) MOLECULE TYPE: protein (xi) SEQUENCE DESCRIPTION: SEQ ID NO:136:

Cys Asp Ile Arg Cys Gln Lys Gly Tyr Glu Leu His Gly Ser Ser Leu
 1               5                  10                  15

Leu Ile Cys Gln Ser Asn Lys Arg Trp Ser Asp Lys Val Ile Cys Lys
             20                  25                  30

Gln Lys Arg Cys Pro Thr Leu Ala Met Pro Ala Asn Gly Gly Phe Lys
         35                  40                  45

Cys Val Asp Gly Ala Tyr Phe Asn Ser Arg Cys Glu Tyr Tyr Cys Ser
     50                  55                  60

Pro Gly Tyr Thr Leu Lys Gly Glu Arg Thr Val Thr Cys Met Asp Asn
 65                  70                  75                  80

Lys Ala Trp Ser Gly Arg Pro Ala Ser Cys Val Asp
                 85                  90

(2) INFORMATION FOR SEQ ID NO:137:

(i) SEQUENCE CHARACTERISTICS:
        (A) LENGTH: 210 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..210

(xi) SEQUENCE DESCRIPTION: SEQ ID NO:137:

ACC AGC CTC TCA GAA TAC GCC AGC CGC ATG CGG GCC GGC ACC CGC AAC        48
Thr Ser Leu Ser Glu Tyr Ala Ser Arg Met Arg Ala Gly Thr Arg Asn
         95                 100                 105

ATC TAC TAC CTG TGC GCC CCC AAC CGT CAC CTG GCA GAG CAC TCA CCC        96
Ile Tyr Tyr Leu Cys Ala Pro Asn Arg His Leu Ala Glu His Ser Pro
 110                 115                 120

TAC TAT GAG GCC ATG AAG AAG AAA GAC ACA GAG GTT CTC TTC TGC TTT       144
Tyr Tyr Glu Ala Met Lys Lys Lys Asp Thr Glu Val Leu Phe Cys Phe
125                 130                 135                 140

GAG CAG TTT GAT GAG CTC ACC CTG CTG CAC CTT CGT GAG TTT GAC AAG       192
Glu Gln Phe Asp Glu Leu Thr Leu Leu His Leu Arg Glu Phe Asp Lys
                145                 150                 155

AAG AAG CTG ATC TCT GTG                                               210
Lys Lys Leu Ile Ser Val
            160

(2) INFORMATION FOR SEQ ID NO:138:

(i) SEQUENCE CHARACTERISTICS:
        (A) LENGTH: 70 amino acids
        (B) TYPE: amino acid
        (D) TOPOLOGY: linear (ii) MOLECULE TYPE: protein (xi) SEQUENCE DESCRIPTION: SEQ ID NO:138:

Thr Ser Leu Ser Glu Tyr Ala Ser Arg Met Arg Ala Gly Thr Arg Asn
 1               5                  10                  15

Ile Tyr Tyr Leu Cys Ala Pro Asn Arg His Leu Ala Glu His Ser Pro
             20                  25                  30

```
Tyr Tyr Glu Ala Met Lys Lys Asp Thr Glu Val Leu Phe Cys Phe
        35                  40                  45

Glu Gln Phe Asp Glu Leu Thr Leu Leu His Leu Arg Glu Phe Asp Lys
 50                  55                  60

Lys Lys Leu Ile Ser Val
 65                  70

(2) INFORMATION FOR SEQ ID NO:139:

(i) SEQUENCE CHARACTERISTICS:
        (A) LENGTH: 363 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..363

(xi) SEQUENCE DESCRIPTION: SEQ ID NO:139:

CTG CTT CTG GCT GGC ATC TTC CCT TTT GCA CCT CCG GGA GCT GCT GCT        48
Leu Leu Leu Ala Gly Ile Phe Pro Phe Ala Pro Pro Gly Ala Ala Ala
                 75                  80                  85

GAG CCC CAC AGT CTT CGT TAT AAC CTC ACG GTG CTG TCC TGG GAT GGA        96
Glu Pro His Ser Leu Arg Tyr Asn Leu Thr Val Leu Ser Trp Asp Gly
                 90                  95                 100

TCT GTG CAG TCA GGG TTT CTC GCT GAG GTA CAT CTG GAT GGT CAG CCC       144
Ser Val Gln Ser Gly Phe Leu Ala Glu Val His Leu Asp Gly Gln Pro
                105                 110                 115

TTC CTG CGC TGT GAC AGG CAG AAA TGC AGG GCA AAG CCC CAG GGA CAG       192
Phe Leu Arg Cys Asp Arg Gln Lys Cys Arg Ala Lys Pro Gln Gly Gln
            120                 125                 130

TGG GCA GAA GAT GTC CTG GGA AAT AAG ACA TGG GAC AGA GAG ACC AGG       240
Trp Ala Glu Asp Val Leu Gly Asn Lys Thr Trp Asp Arg Glu Thr Arg
135                 140                 145                 150

GAC TTG ACA GGG AAC GGA AAG GAC CTC AGG ATG ACC CTG GCT CAT ATC       288
Asp Leu Thr Gly Asn Gly Lys Asp Leu Arg Met Thr Leu Ala His Ile
                155                 160                 165

AAG GAC CAG AAA GAA GGC TTG CAT TCC CTC CAG GAG ATT AGG GTC TGT       336
Lys Asp Gln Lys Glu Gly Leu His Ser Leu Gln Glu Ile Arg Val Cys
                170                 175                 180

GAG ATC CAT GAA GAC AAC AGC ACC AGG                                   363
Glu Ile His Glu Asp Asn Ser Thr Arg
            185                 190

(2) INFORMATION FOR SEQ ID NO:140:

(i) SEQUENCE CHARACTERISTICS:
        (A) LENGTH: 121 amino acids
        (B) TYPE: amino acid
        (D) TOPOLOGY: linear (ii) MOLECULE TYPE: protein (xi) SEQUENCE DESCRIPTION: SEQ ID NO:140:

Leu Leu Leu Ala Gly Ile Phe Pro Phe Ala Pro Pro Gly Ala Ala Ala
 1               5                  10                  15

Glu Pro His Ser Leu Arg Tyr Asn Leu Thr Val Leu Ser Trp Asp Gly
                20                  25                  30

Ser Val Gln Ser Gly Phe Leu Ala Glu Val His Leu Asp Gly Gln Pro
                35                  40                  45
```

```
        Phe Leu Arg Cys Asp Arg Gln Lys Cys Arg Ala Lys Pro Gln Gly Gln
            50                  55                  60

Trp Ala Glu Asp Val Leu Gly Asn Lys Thr Trp Asp Arg Glu Thr Arg
         65                  70                  75                  80

Asp Leu Thr Gly Asn Gly Lys Asp Leu Arg Met Thr Leu Ala His Ile
                         85                  90                  95

Lys Asp Gln Lys Glu Gly Leu His Ser Leu Gln Glu Ile Arg Val Cys
                    100                 105                 110

Glu Ile His Glu Asp Asn Ser Thr Arg
                    115                 120

(2) INFORMATION FOR SEQ ID NO:141:

(i) SEQUENCE CHARACTERISTICS:
          (A) LENGTH: 267 base pairs
          (B) TYPE: nucleic acid
          (C) STRANDEDNESS: double
          (D) TOPOLOGY: linear (ii) MOLECULE TYPE: cDNA to mRNA (ix) FEATURE:
          (A) NAME/KEY: CDS
          (B) LOCATION: 1..267

(xi) SEQUENCE DESCRIPTION: SEQ ID NO:141:

ATG ACA AAG AAA AGA AGG AAC AAT GGT CGT GCC AAA AAG GGC CGC GGC         48
Met Thr Lys Lys Arg Arg Asn Asn Gly Arg Ala Lys Lys Gly Arg Gly
                125                 130                 135

CAC GTG CAG CCT ATT CGC TGC ACT AAC TGT GCC CGA TGC GTG CCC AAG         96
His Val Gln Pro Ile Arg Cys Thr Asn Cys Ala Arg Cys Val Pro Lys
            140                 145                 150

GAC AAG GCC ATT AAG AAA TTC GTC ATT CGA AAC ATA GTG GAG GCC GCA        144
Asp Lys Ala Ile Lys Lys Phe Val Ile Arg Asn Ile Val Glu Ala Ala
        155                 160                 165

GCA GTC AGG GAC ATT TCT GAA GCG AGC GTC TTC GAT GCC TAT GTG CTT        192
Ala Val Arg Asp Ile Ser Glu Ala Ser Val Phe Asp Ala Tyr Val Leu
170                 175                 180                 185

CCC AAG CTG TAT GTG AAG CTA CAT TAC TGT GTG AGT TGT GCA ATT CAC        240
Pro Lys Leu Tyr Val Lys Leu His Tyr Cys Val Ser Cys Ala Ile His
                190                 195                 200

AGC AAA GTA GTC AGG AAT CGA TCT CGT                                    267
Ser Lys Val Val Arg Asn Arg Ser Arg
            205                 210

(2) INFORMATION FOR SEQ ID NO:142:

(i) SEQUENCE CHARACTERISTICS:
          (A) LENGTH: 89 amino acids
          (B) TYPE: amino acid
          (D) TOPOLOGY: linear (ii) MOLECULE TYPE: protein (xi) SEQUENCE DESCRIPTION: SEQ ID NO:142:

Met Thr Lys Lys Arg Arg Asn Asn Gly Arg Ala Lys Lys Gly Arg Gly
 1               5                  10                  15

His Val Gln Pro Ile Arg Cys Thr Asn Cys Ala Arg Cys Val Pro Lys
             20                  25                  30

Asp Lys Ala Ile Lys Lys Phe Val Ile Arg Asn Ile Val Glu Ala Ala
         35                  40                  45

Ala Val Arg Asp Ile Ser Glu Ala Ser Val Phe Asp Ala Tyr Val Leu
```

```
              50                  55                  60
Pro Lys Leu Tyr Val Lys Leu His Tyr Cys Val Ser Cys Ala Ile His
 65                  70                  75                  80

Ser Lys Val Val Arg Asn Arg Ser Arg
                 85

(2) INFORMATION FOR SEQ ID NO:143:

(i) SEQUENCE CHARACTERISTICS:
        (A) LENGTH: 300 base pairs
        (B) TYPE: nucleic acid
        (C) STRANDEDNESS: double
        (D) TOPOLOGY: linear (ii) MOLECULE TYPE: cDNA to mRNA (ix) FEATURE:
         (A) NAME/KEY: CDS
         (B) LOCATION: 1..300

(xi) SEQUENCE DESCRIPTION: SEQ ID NO:143:

CTG GGC TTT GCT GGT CTT GTA CAG GAG ATC TCA TTT GGG ACA ACT AAG         48
Leu Gly Phe Ala Gly Leu Val Gln Glu Ile Ser Phe Gly Thr Thr Lys
 90                  95                 100                 105

GAT AAA ATG CTG GTC ATC GAG CAG TGT AAG AAC TCC AGA GCT GTA ACC         96
Asp Lys Met Leu Val Ile Glu Gln Cys Lys Asn Ser Arg Ala Val Thr
                110                 115                 120

ATT TTT ATT AGA GGA GGA AAT AAG ATG ATC ATT GAG GAG GCG AAA CGA        144
Ile Phe Ile Arg Gly Gly Asn Lys Met Ile Ile Glu Glu Ala Lys Arg
            125                 130                 135

TCC CTT CAC GAT GCT TTG TGT GTC ATC CGG AAC CTC ATC CGC GAT AAT        192
Ser Leu His Asp Ala Leu Cys Val Ile Arg Asn Leu Ile Arg Asp Asn
        140                 145                 150

CGT GTG GTG TAT GGA GGA GGG GCT GCT GAG ATA TCC TGT GCC CTG GCA        240
Arg Val Val Tyr Gly Gly Gly Ala Ala Glu Ile Ser Cys Ala Leu Ala
    155                 160                 165

GTT AGC CAA GAG GCG GAT AAG TGC CCC ACC TTA GAA CAG TAT GCC ATG        288
Val Ser Gln Glu Ala Asp Lys Cys Pro Thr Leu Glu Gln Tyr Ala Met
170                 175                 180                 185

AGA GCG TTT GCC                                                         300
Arg Ala Phe Ala (2) INFORMATION FOR SEQ ID NO:144:

(i) SEQUENCE CHARACTERISTICS:
        (A) LENGTH: 100 amino acids
        (B) TYPE: amino acid
        (D) TOPOLOGY: linear (ii) MOLECULE TYPE: protein (xi) SEQUENCE DESCRIPTION: SEQ ID NO:144:

Leu Gly Phe Ala Gly Leu Val Gln Glu Ile Ser Phe Gly Thr Thr Lys
  1               5                  10                  15

Asp Lys Met Leu Val Ile Glu Gln Cys Lys Asn Ser Arg Ala Val Thr
                 20                  25                  30

Ile Phe Ile Arg Gly Gly Asn Lys Met Ile Ile Glu Glu Ala Lys Arg
             35                  40                  45

Ser Leu His Asp Ala Leu Cys Val Ile Arg Asn Leu Ile Arg Asp Asn
         50                  55                  60

Arg Val Val Tyr Gly Gly Gly Ala Ala Glu Ile Ser Cys Ala Leu Ala
 65                  70                  75                  80
```

```
Val Ser Gln Glu Ala Asp Lys Cys Pro Thr Leu Glu Gln Tyr Ala Met
            85                  90                  95
Arg Ala Phe Ala
            100
```

(2) INFORMATION FOR SEQ ID NO:145:

(i) SEQUENCE CHARACTERISTICS:
        (A) LENGTH: 201 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..201

(xi) SEQUENCE DESCRIPTION: SEQ ID NO:145:

```
GTA GCT GGG CTT ACA GTT ACA TAT TCT CAT TTG GCC CAA GGC CTT TGG      48
Val Ala Gly Leu Thr Val Thr Tyr Ser His Leu Ala Gln Gly Leu Trp
                105                 110                 115

CCA GAG CAG GGC ATA AAA GAT TCT TTC CAA GAA GTC ATA TTG AGA AGA      96
Pro Glu Gln Gly Ile Lys Asp Ser Phe Gln Glu Val Ile Leu Arg Arg
            120                 125                 130

TAT GGA CAA TGT GGA CAT GAA GAT TTC CAG TTA AGA ACA GGC TGT AAA     144
Tyr Gly Gln Cys Gly His Glu Asp Phe Gln Leu Arg Thr Gly Cys Lys
            135                 140                 145

AGT GTG GAT GGG TGT AAT CTG CAC AAC GAA TGT TAT GAT GGA CTA AAC     192
Ser Val Asp Gly Cys Asn Leu His Asn Glu Cys Tyr Asp Gly Leu Asn
            150                 155                 160

CAG TGT TTG                                                         201
Gln Cys Leu
165
```

(2) INFORMATION FOR SEQ ID NO:146:

(i) SEQUENCE CHARACTERISTICS:
        (A) LENGTH: 67 amino acids
        (B) TYPE: amino acid
        (D) TOPOLOGY: linear (ii) MOLECULE TYPE: protein (xi) SEQUENCE DESCRIPTION: SEQ ID NO:146:

```
Val Ala Gly Leu Thr Val Thr Tyr Ser His Leu Ala Gln Gly Leu Trp
 1               5                  10                  15

Pro Glu Gln Gly Ile Lys Asp Ser Phe Gln Glu Val Ile Leu Arg Arg
            20                  25                  30

Tyr Gly Gln Cys Gly His Glu Asp Phe Gln Leu Arg Thr Gly Cys Lys
            35                  40                  45

Ser Val Asp Gly Cys Asn Leu His Asn Glu Cys Tyr Asp Gly Leu Asn
            50                  55                  60

Gln Cys Leu
65
```

(2) INFORMATION FOR SEQ ID NO:147:

(i) SEQUENCE CHARACTERISTICS:
        (A) LENGTH: 213 base pairs
        (B) TYPE: nucleic acid
        (C) STRANDEDNESS: double
        (D) TOPOLOGY: linear (ii) MOLECULE TYPE: cDNA to mRNA (ix) FEATURE:
   (A) NAME/KEY: CDS
   (B) LOCATION: 1..213

(xi) SEQUENCE DESCRIPTION: SEQ ID NO:147:

```
ATG AAG ACT ATT CTC AGC AAT CAG ACT GTC GAC ATT CCA GAA AAT GTC      48
Met Lys Thr Ile Leu Ser Asn Gln Thr Val Asp Ile Pro Glu Asn Val
        70                  75                  80

GAC ATT ACT CTG AAG GGA CGC ACA GTT ATC GTG AAG GGC CCC AGA GGA      96
Asp Ile Thr Leu Lys Gly Arg Thr Val Ile Val Lys Gly Pro Arg Gly
    85                  90                  95

ACC CTG CGG AGG GAC TTC AAT CAC ATC AAT GTA GAA CTC AGC CTT CTT     144
Thr Leu Arg Arg Asp Phe Asn His Ile Asn Val Glu Leu Ser Leu Leu
100                 105                 110                 115

GGA AAG AAA AAA AAG AGG CTC CGG GTT GAC AAA TGG TGG GGT AAC AGA     192
Gly Lys Lys Lys Lys Arg Leu Arg Val Asp Lys Trp Trp Gly Asn Arg
            120                 125                 130

AAG GAA CTG GCT ACC GTT CGG                                         213
Lys Glu Leu Ala Thr Val Arg
        135
```

(2) INFORMATION FOR SEQ ID NO:148:

(i) SEQUENCE CHARACTERISTICS:
       (A) LENGTH: 71 amino acids
       (B) TYPE: amino acid
       (D) TOPOLOGY: linear (ii) MOLECULE TYPE: protein (xi) SEQUENCE DESCRIPTION: SEQ ID NO:148:

```
Met Lys Thr Ile Leu Ser Asn Gln Thr Val Asp Ile Pro Glu Asn Val
 1               5                  10                  15

Asp Ile Thr Leu Lys Gly Arg Thr Val Ile Val Lys Gly Pro Arg Gly
             20                  25                  30

Thr Leu Arg Arg Asp Phe Asn His Ile Asn Val Glu Leu Ser Leu Leu
         35                  40                  45

Gly Lys Lys Lys Lys Arg Leu Arg Val Asp Lys Trp Trp Gly Asn Arg
     50                  55                  60

Lys Glu Leu Ala Thr Val Arg
 65              70
```

(2) INFORMATION FOR SEQ ID NO:149:

(i) SEQUENCE CHARACTERISTICS:
       (A) LENGTH: 192 base pairs
       (B) TYPE: nucleic acid
       (C) STRANDEDNESS: double
       (D) TOPOLOGY: linear (ii) MOLECULE TYPE: cDNA to mRNA (ix) FEATURE:
       (A) NAME/KEY: CDS
       (B) LOCATION: 1..192

(xi) SEQUENCE DESCRIPTION: SEQ ID NO:149:

```
ATG AAG GTC GAG CTG TGC AGT TTT AGC GGG TAC AAG ATC TAC CCC GGA      48
Met Lys Val Glu Leu Cys Ser Phe Ser Gly Tyr Lys Ile Tyr Pro Gly
        75                  80                  85

CAC GGG AGG CGC TAC GCC AGG ACC GAC GGG AAG GTT TTC CAG TTT CTT      96
His Gly Arg Arg Tyr Ala Arg Thr Asp Gly Lys Val Phe Gln Phe Leu
    90                  95                 100
```

-continued

```
AAT GCG AAA TGC GAG TCG GCT TTC CTT TCC AAG AGG AAT CCT CGG CAG        144
Asn Ala Lys Cys Glu Ser Ala Phe Leu Ser Lys Arg Asn Pro Arg Gln
    105                 110                 115

ATA AAC TGG ACT GTC CTC TAC AGA AGG AAG CAC AAA AAG GGA CAG TCG        192
Ile Asn Trp Thr Val Leu Tyr Arg Arg Lys His Lys Lys Gly Gln Ser
120                 125                 130                 135
```

(2) INFORMATION FOR SEQ ID NO:150:

(i) SEQUENCE CHARACTERISTICS:
        (A) LENGTH: 64 amino acids
        (B) TYPE: amino acid
        (D) TOPOLOGY: linear (ii) MOLECULE TYPE: protein (xi) SEQUENCE DESCRIPTION: SEQ ID NO:150:

```
Met Lys Val Glu Leu Cys Ser Phe Ser Gly Tyr Lys Ile Tyr Pro Gly
1               5                   10                  15

His Gly Arg Arg Tyr Ala Arg Thr Asp Gly Lys Val Phe Gln Phe Leu
                20                  25                  30

Asn Ala Lys Cys Glu Ser Ala Phe Leu Ser Lys Arg Asn Pro Arg Gln
            35                  40                  45

Ile Asn Trp Thr Val Leu Tyr Arg Arg Lys His Lys Lys Gly Gln Ser
        50                  55                  60
```

(2) INFORMATION FOR SEQ ID NO:151:

(i) SEQUENCE CHARACTERISTICS:
        (A) LENGTH: 132 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..132

(xi) SEQUENCE DESCRIPTION: SEQ ID NO:151:

```
ATG GTG GGA GAC CTA CCT GAT GCA GAT ATT AAA CCT CCA GAA AAT GTA         48
Met Val Gly Asp Leu Pro Asp Ala Asp Ile Lys Pro Pro Glu Asn Val
65                  70                  75                  80

CTG TTT GTG TGT AAA TTG AAC CCA GTG ACC ACA GAT GAG GAT CTG GAA         96
Leu Phe Val Cys Lys Leu Asn Pro Val Thr Thr Asp Glu Asp Leu Glu
                85                  90                  95

ATA ATA TTC TCT AGA TTT GGG CCA ATA AGA AGT TGT                        132
Ile Ile Phe Ser Arg Phe Gly Pro Ile Arg Ser Cys
            100                 105
```

(2) INFORMATION FOR SEQ ID NO:152:

(i) SEQUENCE CHARACTERISTICS:
        (A) LENGTH: 44 amino acids
        (B) TYPE: amino acid
        (D) TOPOLOGY: linear (ii) MOLECULE TYPE: protein (xi) SEQUENCE DESCRIPTION: SEQ ID NO:152:

```
Met Val Gly Asp Leu Pro Asp Ala Asp Ile Lys Pro Pro Glu Asn Val
1               5                   10                  15

Leu Phe Val Cys Lys Leu Asn Pro Val Thr Thr Asp Glu Asp Leu Glu
                20                  25                  30
```

```
Ile Ile Phe Ser Arg Phe Gly Pro Ile Arg Ser Cys
        35                  40
```

(2) INFORMATION FOR SEQ ID NO:153:

(i) SEQUENCE CHARACTERISTICS:
        (A) LENGTH: 249 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..249

(xi) SEQUENCE DESCRIPTION: SEQ ID NO:153:

```
ATG GCG CCG AAA GCG AAG AAG GAA GCT CCT GCC CCT CCT AAA GCT GAA        48
Met Ala Pro Lys Ala Lys Lys Glu Ala Pro Ala Pro Pro Lys Ala Glu
 45                  50                  55                  60

GCC AAA GCG AAG GCT TTA AAG GCC AAG AAG GCA GTG TTG AAA GGT GTC        96
Ala Lys Ala Lys Ala Leu Lys Ala Lys Lys Ala Val Leu Lys Gly Val
                 65                  70                  75

CAC AGC CAC AAA AAG AAG AAG ATC CGC ACG TCA CCC ACC TTC CGG CGG       144
His Ser His Lys Lys Lys Lys Ile Arg Thr Ser Pro Thr Phe Arg Arg
                     80                  85                  90

CCG AAG ACA CTG CGA CTC CGG AGA CAG CCC AAA TAT CCT CGG AAG AGC       192
Pro Lys Thr Leu Arg Leu Arg Arg Gln Pro Lys Tyr Pro Arg Lys Ser
             95                 100                 105

GCT CCC AGG AGA AAC AAG CTT GAC CAC TAT GCT ATC ATC AAG TTT CCG       240
Ala Pro Arg Arg Asn Lys Leu Asp His Tyr Ala Ile Ile Lys Phe Pro
        110                 115                 120

CTG ACC ACT                                                           249
Leu Thr Thr
125
```

(2) INFORMATION FOR SEQ ID NO:154:

(i) SEQUENCE CHARACTERISTICS:
        (A) LENGTH: 83 amino acids
        (B) TYPE: amino acid
        (D) TOPOLOGY: linear (ii) MOLECULE TYPE: protein (xi) SEQUENCE DESCRIPTION: SEQ ID NO:154:

```
Met Ala Pro Lys Ala Lys Lys Glu Ala Pro Ala Pro Pro Lys Ala Glu
 1               5                  10                  15

Ala Lys Ala Lys Ala Leu Lys Ala Lys Lys Ala Val Leu Lys Gly Val
                 20                  25                  30

His Ser His Lys Lys Lys Lys Ile Arg Thr Ser Pro Thr Phe Arg Arg
                 35                  40                  45

Pro Lys Thr Leu Arg Leu Arg Arg Gln Pro Lys Tyr Pro Arg Lys Ser
             50                  55                  60

Ala Pro Arg Arg Asn Lys Leu Asp His Tyr Ala Ile Ile Lys Phe Pro
 65                  70                  75                  80

Leu Thr Thr
```

(2) INFORMATION FOR SEQ ID NO:155:

(i) SEQUENCE CHARACTERISTICS:
        (A) LENGTH: 306 base pairs (B) TYPE: nucleic acid
            (C) STRANDEDNESS: double
            (D) TOPOLOGY: linear (ii) MOLECULE TYPE: cDNA to mRNA (ix) FEATURE:
            (A) NAME/KEY: CDS
            (B) LOCATION: 1..306

(xi) SEQUENCE DESCRIPTION: SEQ ID NO:155:

| | | | | | | | | | | | | | | | | |
|---|---|---|---|---|---|---|---|---|---|---|---|---|---|---|---|---|
| ATG | TTC | GCC | TGC | TCC | AAG | TTT | GTC | TCC | ACT | CCC | TCC | TTG | GTC | AAG | AGC | 48 |
| Met | Phe | Ala | Cys | Ser | Lys | Phe | Val | Ser | Thr | Pro | Ser | Leu | Val | Lys | Ser | |
| 85 | | | | 90 | | | | | 95 | | | | | | | |

| | | | | | | | | | | | | | | | | |
|---|---|---|---|---|---|---|---|---|---|---|---|---|---|---|---|---|
| ACC | TCA | CAG | CTG | CTG | AGC | CGT | CCG | CTA | TCT | GCA | GTG | GTG | CTG | AAA | CGA | 96 |
| Thr | Ser | Gln | Leu | Leu | Ser | Arg | Pro | Leu | Ser | Ala | Val | Val | Leu | Lys | Arg | |
| 100 | | | | | 105 | | | | | 110 | | | | | 115 | |

| | | | | | | | | | | | | | | | | |
|---|---|---|---|---|---|---|---|---|---|---|---|---|---|---|---|---|
| CCG | GAG | ATA | CTG | ACA | GAT | GAG | AGC | CTC | AGC | AGC | TTG | GCA | GTC | TCA | TGT | 144 |
| Pro | Glu | Ile | Leu | Thr | Asp | Glu | Ser | Leu | Ser | Ser | Leu | Ala | Val | Ser | Cys | |
| | | | | 120 | | | | | 125 | | | | | 130 | | |

| | | | | | | | | | | | | | | | | |
|---|---|---|---|---|---|---|---|---|---|---|---|---|---|---|---|---|
| CCC | CTT | ACC | TCA | CTT | GTC | TCT | AGC | CGC | AGC | TTC | CAA | ACC | AGC | GCC | ATT | 192 |
| Pro | Leu | Thr | Ser | Leu | Val | Ser | Ser | Arg | Ser | Phe | Gln | Thr | Ser | Ala | Ile | |
| | | | 135 | | | | | 140 | | | | | 145 | | | |

| | | | | | | | | | | | | | | | | |
|---|---|---|---|---|---|---|---|---|---|---|---|---|---|---|---|---|
| TCA | AGG | GAC | ATC | GAC | ACA | GCA | GCC | AAG | TTC | ATT | GGA | GCT | GGG | GCT | GCC | 240 |
| Ser | Arg | Asp | Ile | Asp | Thr | Ala | Ala | Lys | Phe | Ile | Gly | Ala | Gly | Ala | Ala | |
| | | | 150 | | | | | 155 | | | | | 160 | | | |

| | | | | | | | | | | | | | | | | |
|---|---|---|---|---|---|---|---|---|---|---|---|---|---|---|---|---|
| ACA | GTT | GGG | GTG | GCT | GGT | TCT | GGG | GCT | GGG | ATT | GGA | ACT | GTG | TTT | GGG | 288 |
| Thr | Val | Gly | Val | Ala | Gly | Ser | Gly | Ala | Gly | Ile | Gly | Thr | Val | Phe | Gly | |
| 165 | | | | | 170 | | | | | 175 | | | | | | |

| | | | | | |
|---|---|---|---|---|---|
| AGC | CTC | ATC | ATT | GGT | TAT | 306 |
| Ser | Leu | Ile | Ile | Gly | Tyr | |
| 180 | | | | 185 | | |

(2) INFORMATION FOR SEQ ID NO:156:

(i) SEQUENCE CHARACTERISTICS:
            (A) LENGTH: 102 amino acids
            (B) TYPE: amino acid
            (D) TOPOLOGY: linear (ii) MOLECULE TYPE: protein (xi) SEQUENCE DESCRIPTION: SEQ ID NO:156:

Met Phe Ala Cys Ser Lys Phe Val Ser Thr Pro Ser Leu Val Lys Ser
 1               5                  10                  15

Thr Ser Gln Leu Leu Ser Arg Pro Leu Ser Ala Val Val Leu Lys Arg
            20                  25                  30

Pro Glu Ile Leu Thr Asp Glu Ser Leu Ser Ser Leu Ala Val Ser Cys
        35                  40                  45

Pro Leu Thr Ser Leu Val Ser Ser Arg Ser Phe Gln Thr Ser Ala Ile
    50                  55                  60

Ser Arg Asp Ile Asp Thr Ala Ala Lys Phe Ile Gly Ala Gly Ala Ala
65                  70                  75                  80

Thr Val Gly Val Ala Gly Ser Gly Ala Gly Ile Gly Thr Val Phe Gly
                85                  90                  95

Ser Leu Ile Ile Gly Tyr
            100

(2) INFORMATION FOR SEQ ID NO:157:

(i) SEQUENCE CHARACTERISTICS:
            (A) LENGTH: 261 base pairs
            (B) TYPE: nucleic acid (C) STRANDEDNESS: double
(D) TOPOLOGY: linear (ii) MOLECULE TYPE: cDNA to mRNA (ix) FEATURE:
(A) NAME/KEY: CDS
(B) LOCATION: 1..261

(xi) SEQUENCE DESCRIPTION: SEQ ID NO:157:

```
ATG ACG AAC ACA AAG GGA AAG AGG AGA GGC ACC CGA TAT ATG TTC TCT      48
Met Thr Asn Thr Lys Gly Lys Arg Arg Gly Thr Arg Tyr Met Phe Ser
        105                 110                 115

AGG CCT TTT AGA AAA CAT GGA GTT GTT CCT TTG GCC ACA TAT ATG CGA      96
Arg Pro Phe Arg Lys His Gly Val Val Pro Leu Ala Thr Tyr Met Arg
    120                 125                 130

ATC TAT AAG AAA GGT GAT ATT GTA GAC ATC AAG GGA ATG GGT ACT GTT     144
Ile Tyr Lys Lys Gly Asp Ile Val Asp Ile Lys Gly Met Gly Thr Val
135                 140                 145                 150

CAA AAA GGA ATG CCC CAC AAG TGT TAC CAT GGC AAA ACT GGA AGA GTC     192
Gln Lys Gly Met Pro His Lys Cys Tyr His Gly Lys Thr Gly Arg Val
                155                 160                 165

TAC AAT GTT ACC CAG CAT GCT GTT GGC ATT GTT GTA AAC AAA CAA GTT     240
Tyr Asn Val Thr Gln His Ala Val Gly Ile Val Val Asn Lys Gln Val
            170                 175                 180

AAG GGC AAG ATT CTT GCC AAG                                         261
Lys Gly Lys Ile Leu Ala Lys
        185
```

(2) INFORMATION FOR SEQ ID NO:158:

(i) SEQUENCE CHARACTERISTICS:
(A) LENGTH: 87 amino acids
(B) TYPE: amino acid
(D) TOPOLOGY: linear (ii) MOLECULE TYPE: protein (xi) SEQUENCE DESCRIPTION: SEQ ID NO:158:

```
Met Thr Asn Thr Lys Gly Lys Arg Arg Gly Thr Arg Tyr Met Phe Ser
 1               5                  10                  15

Arg Pro Phe Arg Lys His Gly Val Val Pro Leu Ala Thr Tyr Met Arg
            20                  25                  30

Ile Tyr Lys Lys Gly Asp Ile Val Asp Ile Lys Gly Met Gly Thr Val
            35                  40                  45

Gln Lys Gly Met Pro His Lys Cys Tyr His Gly Lys Thr Gly Arg Val
        50                  55                  60

Tyr Asn Val Thr Gln His Ala Val Gly Ile Val Val Asn Lys Gln Val
65                  70                  75                  80

Lys Gly Lys Ile Leu Ala Lys
            85
```

(2) INFORMATION FOR SEQ ID NO:159:

(i) SEQUENCE CHARACTERISTICS:
(A) LENGTH: 279 base pairs
(B) TYPE: nucleic acid
(C) STRANDEDNESS: double
(D) TOPOLOGY: linear (ii) MOLECULE TYPE: cDNA to mRNA (ix) FEATURE:
(A) NAME/KEY: CDS
(B) LOCATION: 1..279

(xi) SEQUENCE DESCRIPTION: SEQ ID NO:159:

| | | | | | | | | | | | | | | | | |
|---|---|---|---|---|---|---|---|---|---|---|---|---|---|---|---|---|
| AAT | TGT | GAA | GTG | AAA | AAG | GCC | CTT | TCT | AAA | CAA | GAG | ATG | CAG | TCT | GCT | 48 |
| Asn | Cys | Glu | Val | Lys | Lys | Ala | Leu | Ser | Lys | Gln | Glu | Met | Gln | Ser | Ala | |
| | | 90 | | | 95 | | | | 100 | | | | | | | |

| | | | | | | | | | | | | | | | | |
|---|---|---|---|---|---|---|---|---|---|---|---|---|---|---|---|---|
| GGA | TCA | CAG | AGA | GGT | CGT | GGA | GGT | GGA | TCT | GGC | AAT | TTT | ATG | GGT | CGC | 96 |
| Gly | Ser | Gln | Arg | Gly | Arg | Gly | Gly | Gly | Ser | Gly | Asn | Phe | Met | Gly | Arg | |
| 105 | | | | | 110 | | | | 115 | | | | | | | |

| | | | | | | | | | | | | | | | | |
|---|---|---|---|---|---|---|---|---|---|---|---|---|---|---|---|---|
| GGA | GGG | AAC | TTT | GGA | GGT | GGT | GGA | GGT | AAT | TTT | GGC | CGT | GGT | GGA | AAC | 144 |
| Gly | Gly | Asn | Phe | Gly | Gly | Gly | Gly | Gly | Asn | Phe | Gly | Arg | Gly | Gly | Asn | |
| 120 | | | | 125 | | | | | 130 | | | | | | 135 | |

| | | | | | | | | | | | | | | | | |
|---|---|---|---|---|---|---|---|---|---|---|---|---|---|---|---|---|
| TTT | GGT | GGA | AGA | GGA | GGC | TAT | GGT | GGT | GGA | GGT | GGT | GGC | AGC | AGA | GGT | 192 |
| Phe | Gly | Gly | Arg | Gly | Gly | Tyr | Gly | Gly | Gly | Gly | Gly | Gly | Ser | Arg | Gly | |
| | | | 140 | | | | | 145 | | | | | 150 | | | |

| | | | | | | | | | | | | | | | | |
|---|---|---|---|---|---|---|---|---|---|---|---|---|---|---|---|---|
| AGT | TAT | GGA | GGA | GGT | GAT | GGT | GGA | TAT | AAT | GGA | TTT | GGA | GGT | GAT | GGT | 240 |
| Ser | Tyr | Gly | Gly | Gly | Asp | Gly | Gly | Tyr | Asn | Gly | Phe | Gly | Gly | Asp | Gly | |
| | | | 155 | | | | | 160 | | | | | 165 | | | |

| | | | | | | | | | | | | |
|---|---|---|---|---|---|---|---|---|---|---|---|---|
| GGC | AAC | TAT | GGC | GGT | GGT | CCT | GGT | TAT | AGT | AGT | AGA | GGG | 279 |
| Gly | Asn | Tyr | Gly | Gly | Gly | Pro | Gly | Tyr | Ser | Ser | Arg | Gly | |
| | | 170 | | | | 175 | | | | 180 | | | |

(2) INFORMATION FOR SEQ ID NO:160:

(i) SEQUENCE CHARACTERISTICS:
        (A) LENGTH: 93 amino acids
        (B) TYPE: amino acid
        (D) TOPOLOGY: linear (ii) MOLECULE TYPE: protein (xi) SEQUENCE DESCRIPTION: SEQ ID NO:160:

| | | | | | | | | | | | | | | | |
|---|---|---|---|---|---|---|---|---|---|---|---|---|---|---|---|
| Asn | Cys | Glu | Val | Lys | Lys | Ala | Leu | Ser | Lys | Gln | Glu | Met | Gln | Ser | Ala |
| 1 | | | | 5 | | | | | 10 | | | | | 15 | |

| | | | | | | | | | | | | | | | |
|---|---|---|---|---|---|---|---|---|---|---|---|---|---|---|---|
| Gly | Ser | Gln | Arg | Gly | Arg | Gly | Gly | Gly | Ser | Gly | Asn | Phe | Met | Gly | Arg |
| | | | 20 | | | | | 25 | | | | | 30 | | |

| | | | | | | | | | | | | | | | |
|---|---|---|---|---|---|---|---|---|---|---|---|---|---|---|---|
| Gly | Gly | Asn | Phe | Gly | Gly | Gly | Gly | Gly | Asn | Phe | Gly | Arg | Gly | Gly | Asn |
| | | | | 35 | | | | | 40 | | | | | 45 | |

| | | | | | | | | | | | | | | | |
|---|---|---|---|---|---|---|---|---|---|---|---|---|---|---|---|
| Phe | Gly | Gly | Arg | Gly | Gly | Tyr | Gly | Gly | Gly | Gly | Gly | Gly | Ser | Arg | Gly |
| | 50 | | | | | 55 | | | | | 60 | | | | |

| | | | | | | | | | | | | | | | |
|---|---|---|---|---|---|---|---|---|---|---|---|---|---|---|---|
| Ser | Tyr | Gly | Gly | Gly | Asp | Gly | Gly | Tyr | Asn | Gly | Phe | Gly | Gly | Asp | Gly |
| 65 | | | | | 70 | | | | | 75 | | | | | 80 |

| | | | | | | | | | | |
|---|---|---|---|---|---|---|---|---|---|---|
| Gly | Asn | Tyr | Gly | Gly | Gly | Pro | Gly | Tyr | Ser | Ser | Arg | Gly |
| | | | | 85 | | | | | 90 | | | |

(2) INFORMATION FOR SEQ ID NO:161:

(i) SEQUENCE CHARACTERISTICS:
        (A) LENGTH: 282 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..282

(xi) SEQUENCE DESCRIPTION: SEQ ID NO:161:

| | | | | | | | | | | | | | | | | |
|---|---|---|---|---|---|---|---|---|---|---|---|---|---|---|---|---|
| ATG | GCC | AAG | TCC | AAG | AAC | CAC | ACC | ACA | CAC | AAC | CAG | TCC | CGA | AAA | TGG | 48 |
| Met | Ala | Lys | Ser | Lys | Asn | His | Thr | Thr | His | Asn | Gln | Ser | Arg | Lys | Trp | |
| | | 95 | | | | | 100 | | | | | 105 | | | | |

| | | | | | | | | | | | | | | | | |
|---|---|---|---|---|---|---|---|---|---|---|---|---|---|---|---|---|
| CAC | AGA | AAT | GGT | ATC | AAG | AAA | CCC | CGA | TCA | CAA | AGA | TAC | GAA | TCT | CTT | 96 |

```
His Arg Asn Gly Ile Lys Lys Pro Arg Ser Gln Arg Tyr Glu Ser Leu
110                 115                 120                 125

AAG GGG GTG GAC CCC AAG TTC CTG AGG AAC ATG CGC TTT GCC AAG AAG        144
Lys Gly Val Asp Pro Lys Phe Leu Arg Asn Met Arg Phe Ala Lys Lys
                130                 135                 140

CAC AAC AAA AAG GGC CTA AAG AAG ATG CAG GCC AAC AAT GCC AAG GCC        192
His Asn Lys Lys Gly Leu Lys Lys Met Gln Ala Asn Asn Ala Lys Ala
            145                 150                 155

ATG AGT GCA CGT GCC GAG GCT ATC AAG GCC CTC GTA AAG CCC AAG GAG        240
Met Ser Ala Arg Ala Glu Ala Ile Lys Ala Leu Val Lys Pro Lys Glu
        160                 165                 170

GTT AAG CCC AAG ATC CCA AAG GGT GTC AGC CGC AAG CTC GAT                282
Val Lys Pro Lys Ile Pro Lys Gly Val Ser Arg Lys Leu Asp
    175                 180                 185

(2) INFORMATION FOR SEQ ID NO:162:

(i) SEQUENCE CHARACTERISTICS:
        (A) LENGTH: 94 amino acids
        (B) TYPE: amino acid
        (D) TOPOLOGY: linear (ii) MOLECULE TYPE: protein (xi) SEQUENCE DESCRIPTION: SEQ ID NO:162:

Met Ala Lys Ser Lys Asn His Thr Thr His Asn Gln Ser Arg Lys Trp
1               5                   10                  15

His Arg Asn Gly Ile Lys Lys Pro Arg Ser Gln Arg Tyr Glu Ser Leu
            20                  25                  30

Lys Gly Val Asp Pro Lys Phe Leu Arg Asn Met Arg Phe Ala Lys Lys
        35                  40                  45

His Asn Lys Lys Gly Leu Lys Lys Met Gln Ala Asn Asn Ala Lys Ala
    50                  55                  60

Met Ser Ala Arg Ala Glu Ala Ile Lys Ala Leu Val Lys Pro Lys Glu
65                  70                  75                  80

Val Lys Pro Lys Ile Pro Lys Gly Val Ser Arg Lys Leu Asp
            85                  90

(2) INFORMATION FOR SEQ ID NO:163:

(i) SEQUENCE CHARACTERISTICS:
        (A) LENGTH: 273 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..273

(xi) SEQUENCE DESCRIPTION: SEQ ID NO:163:

ATC AGT CAC CAG AGA GAT GGA CTG ACA AAT GCT GGA GAA CTG GAA AGT         48
Ile Ser His Gln Arg Asp Gly Leu Thr Asn Ala Gly Glu Leu Glu Ser
95                  100                 105                 110

GAC TCT GGG AGT GAC AAG GCC AAC AGC CCA GCA GGA GGT ATT CCC TCC         96
Asp Ser Gly Ser Asp Lys Ala Asn Ser Pro Ala Gly Gly Ile Pro Ser
                115                 120                 125

ACC TCT TCT TGT TTG CCT AGC CCC AGT ACT CCA GTG CAG TCT CCT CAT        144
Thr Ser Ser Cys Leu Pro Ser Pro Ser Thr Pro Val Gln Ser Pro His
            130                 135                 140

CCA CAG TTT CCT CAC ATT TCC AGT ACT ATG AAT GGA ACC AGC AAC AGC        192
```

```
                 Pro Gln Phe Pro His Ile Ser Ser Thr Met Asn Gly Thr Ser Asn Ser
                         145                 150                 155

CCC AGC GGT AAC CAC CAA TCT TCT TTT GCC AAT AGA CCT CGA AAA TCA                      240
Pro Ser Gly Asn His Gln Ser Ser Phe Ala Asn Arg Pro Arg Lys Ser
        160                 165                 170

TCA GTA AAT GGG TCA TCA GCA ACT TCT TCT GGT                                          273
Ser Val Asn Gly Ser Ser Ala Thr Ser Ser Gly
175                 180                 185
```

(2) INFORMATION FOR SEQ ID NO:164:

(i) SEQUENCE CHARACTERISTICS:
        (A) LENGTH: 91 amino acids
        (B) TYPE: amino acid
        (D) TOPOLOGY: linear (ii) MOLECULE TYPE: protein (xi) SEQUENCE DESCRIPTION: SEQ ID NO:164:

```
Ile Ser His Gln Arg Asp Gly Leu Thr Asn Ala Gly Glu Leu Glu Ser
 1               5                  10                  15

Asp Ser Gly Ser Asp Lys Ala Asn Ser Pro Ala Gly Ile Pro Ser
                20                  25                  30

Thr Ser Ser Cys Leu Pro Ser Pro Ser Thr Pro Val Gln Ser Pro His
            35                  40                  45

Pro Gln Phe Pro His Ile Ser Ser Thr Met Asn Gly Thr Ser Asn Ser
        50                  55                  60

Pro Ser Gly Asn His Gln Ser Ser Phe Ala Asn Arg Pro Arg Lys Ser
65                  70                  75                  80

Ser Val Asn Gly Ser Ser Ala Thr Ser Ser Gly
                85                  90
```

(2) INFORMATION FOR SEQ ID NO:165:

(i) SEQUENCE CHARACTERISTICS:
        (A) LENGTH: 285 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..285

(xi) SEQUENCE DESCRIPTION: SEQ ID NO:165:

```
ATG TCC GTA GTT CGC TCA TCC GTC CAT GCC AGA TGG ATT GTG GGG AAG              48
Met Ser Val Val Arg Ser Ser Val His Ala Arg Trp Ile Val Gly Lys
                 95                 100                 105

GTG ATT GGG ACA AAA ATG CAA AAG ACT GCT AAA GTG AGA GTG ACC AGG              96
Val Ile Gly Thr Lys Met Gln Lys Thr Ala Lys Val Arg Val Thr Arg
        110                 115                 120

CTT GTT CTG GAT CCC TAT TTA TTA AAG TAT TTT AAT AAG CGG AAA ACC             144
Leu Val Leu Asp Pro Tyr Leu Leu Lys Tyr Phe Asn Lys Arg Lys Thr
        125                 130                 135

TAC TTT GCT CAC GAT GCC CTT CAG CAG TGC ACA GTT GGG GAT ATT GTG             192
Tyr Phe Ala His Asp Ala Leu Gln Gln Cys Thr Val Gly Asp Ile Val
140                 145                 150                 155

CTT CTC AGA GCT TTA CCT GTT CCA CGA GCA AAG CAT GTG AAA CAT GAA             240
Leu Leu Arg Ala Leu Pro Val Pro Arg Ala Lys His Val Lys His Glu
                160                 165                 170

CTG GCT GAG ATC GTT TTC AAA GTT GGA AAA GTC ATA GAT CCA GTG                 285
```

-continued

```
Leu Ala Glu Ile Val Phe Lys Val Gly Lys Val Ile Asp Pro Val
            175                 180                 185
```

(2) INFORMATION FOR SEQ ID NO:166:

(i) SEQUENCE CHARACTERISTICS:
        (A) LENGTH: 95 amino acids
        (B) TYPE: amino acid
        (D) TOPOLOGY: linear (ii) MOLECULE TYPE: protein (xi) SEQUENCE DESCRIPTION: SEQ ID NO:166:

```
Met Ser Val Val Arg Ser Ser Val His Ala Arg Trp Ile Val Gly Lys
 1               5                  10                  15
Val Ile Gly Thr Lys Met Gln Lys Thr Ala Lys Val Arg Val Thr Arg
            20                  25                  30
Leu Val Leu Asp Pro Tyr Leu Leu Lys Tyr Phe Asn Lys Arg Lys Thr
            35                  40                  45
Tyr Phe Ala His Asp Ala Leu Gln Gln Cys Thr Val Gly Asp Ile Val
            50                  55                  60
Leu Leu Arg Ala Leu Pro Val Pro Arg Ala Lys His Val Lys His Glu
 65                 70                  75                  80
Leu Ala Glu Ile Val Phe Lys Val Gly Lys Val Ile Asp Pro Val
            85                  90                  95
```

(2) INFORMATION FOR SEQ ID NO:167:

(i) SEQUENCE CHARACTERISTICS:
        (A) LENGTH: 270 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..270

(xi) SEQUENCE DESCRIPTION: SEQ ID NO:167:

```
ATG AAG TTT AAT CCC TTT GTG ACT TCC GAC CGA AGC AAG AAT CGC AAA      48
Met Lys Phe Asn Pro Phe Val Thr Ser Asp Arg Ser Lys Asn Arg Lys
                100                 105                 110

AGG CAT TTC AAT GCA CCT TCC CAC ATT CGA AGG AAG ATT ATG TCT TCC      96
Arg His Phe Asn Ala Pro Ser His Ile Arg Arg Lys Ile Met Ser Ser
            115                 120                 125

CCT CTT TCC AAA GAG CTG AGA CAG AAG TAC AAC GTG CGA TCC ATG CCC     144
Pro Leu Ser Lys Glu Leu Arg Gln Lys Tyr Asn Val Arg Ser Met Pro
        130                 135                 140

ATC CGA AAG GAT GAT GAA GTT CAG GTT GTA CGT GGA CAC TAT AAA GGT     192
Ile Arg Lys Asp Asp Glu Val Gln Val Val Arg Gly His Tyr Lys Gly
        145                 150                 155

CAG CAA ATT GGC AAA GTA GTC CAG GTT TAC AGG AAG AAA TAT GTT ATC     240
Gln Gln Ile Gly Lys Val Val Gln Val Tyr Arg Lys Lys Tyr Val Ile
160                 165                 170                 175

TAC ATT GAA CGG GTG CAG CGG GAA AAG GCT                             270
Tyr Ile Glu Arg Val Gln Arg Glu Lys Ala
                180                 185
```

(2) INFORMATION FOR SEQ ID NO:168:

(i) SEQUENCE CHARACTERISTICS:
        (A) LENGTH: 90 amino acids (B) TYPE: amino acid
          (D) TOPOLOGY: linear (ii) MOLECULE TYPE: protein (xi) SEQUENCE DESCRIPTION: SEQ ID NO:168:

Met Lys Phe Asn Pro Phe Val Thr Ser Asp Arg Ser Lys Asn Arg Lys
 1               5                  10                  15

Arg His Phe Asn Ala Pro Ser His Ile Arg Arg Lys Ile Met Ser Ser
                 20                  25                  30

Pro Leu Ser Lys Glu Leu Arg Gln Lys Tyr Asn Val Arg Ser Met Pro
             35                  40                  45

Ile Arg Lys Asp Asp Glu Val Gln Val Val Arg Gly His Tyr Lys Gly
         50                  55                  60

Gln Gln Ile Gly Lys Val Val Gln Val Tyr Arg Lys Lys Tyr Val Ile
 65                  70                  75                  80

Tyr Ile Glu Arg Val Gln Arg Glu Lys Ala
                 85                  90

(2) INFORMATION FOR SEQ ID NO:169:

(i) SEQUENCE CHARACTERISTICS:
        (A) LENGTH: 261 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..261

(xi) SEQUENCE DESCRIPTION: SEQ ID NO:169:

ATG GCT CTG GAC GTG AAG TCT CGG GCA AAG CGT TAT GAG AAG CTG GAC      48
Met Ala Leu Asp Val Lys Ser Arg Ala Lys Arg Tyr Glu Lys Leu Asp
                 95                 100                 105

TTC CTT GGG GAG GGA CAG TTT GCC ACC GTT TAC AAG GCC AGA GAT AAG      96
Phe Leu Gly Glu Gly Gln Phe Ala Thr Val Tyr Lys Ala Arg Asp Lys
             110                 115                 120

AAC ACC AAC CAA ATT GTC GCC ATT AAG AAA ATC AAA CTT GGA CAT AGA     144
Asn Thr Asn Gln Ile Val Ala Ile Lys Lys Ile Lys Leu Gly His Arg
         125                 130                 135

TCA GAA GCT AAA GAT GGT ATA AAT AGA ACC GCC TTA AGA GAG ATA AAA     192
Ser Glu Ala Lys Asp Gly Ile Asn Arg Thr Ala Leu Arg Glu Ile Lys
     140                 145                 150

TTA TTA CAG GAG CTA AGT CAT CCA AAT ATA ATT GGT CTC CTT GAT GCT     240
Leu Leu Gln Glu Leu Ser His Pro Asn Ile Ile Gly Leu Leu Asp Ala
155                 160                 165                 170

TTT GGA CAT AAA TCT AAT ATT                                         261
Phe Gly His Lys Ser Asn Ile
                175

(2) INFORMATION FOR SEQ ID NO:170:

(i) SEQUENCE CHARACTERISTICS:
        (A) LENGTH: 87 amino acids
        (B) TYPE: amino acid
        (D) TOPOLOGY: linear (ii) MOLECULE TYPE: protein (xi) SEQUENCE DESCRIPTION: SEQ ID NO:170:

Met Ala Leu Asp Val Lys Ser Arg Ala Lys Arg Tyr Glu Lys Leu Asp

```
               1               5                  10                 15
           Phe Leu Gly Glu Gly Gln Phe Ala Thr Val Tyr Lys Ala Arg Asp Lys
                           20                  25                  30

Asn Thr Asn Gln Ile Val Ala Ile Lys Lys Ile Lys Leu Gly His Arg
                       35                  40                  45

Ser Glu Ala Lys Asp Gly Ile Asn Arg Thr Ala Leu Arg Glu Ile Lys
                   50                  55                  60

Leu Leu Gln Glu Leu Ser His Pro Asn Ile Ile Gly Leu Leu Asp Ala
            65                  70                  75                  80

Phe Gly His Lys Ser Asn Ile
                           85

(2) INFORMATION FOR SEQ ID NO:171:

(i) SEQUENCE CHARACTERISTICS:
        (A) LENGTH: 138 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..138

(xi) SEQUENCE DESCRIPTION: SEQ ID NO:171:

CTT ATA CTC CAT CGG GGT ATG AAT CTT TCC AAT GAT GGC CAC TTT GTT        48
Leu Ile Leu His Arg Gly Met Asn Leu Ser Asn Asp Gly His Phe Val
            90                  95                  100

CTC CTT CCT GGG TAT ATG ACT CGG CAC AAC AAT CTA GAC CTG GTG ATC        96
Leu Leu Pro Gly Tyr Met Thr Arg His Asn Asn Leu Asp Leu Val Ile
    105                 110                 115

ATT CGA GAC CAG ACA GAA GGG GAG TAC AGC TCT CTG GAA CAT               138
Ile Arg Asp Gln Thr Glu Gly Glu Tyr Ser Ser Leu Glu His
120                 125                 130

(2) INFORMATION FOR SEQ ID NO:172:

(i) SEQUENCE CHARACTERISTICS:
        (A) LENGTH: 46 amino acids
        (B) TYPE: amino acid
        (D) TOPOLOGY: linear (ii) MOLECULE TYPE: protein (xi) SEQUENCE DESCRIPTION: SEQ ID NO:172:

Leu Ile Leu His Arg Gly Met Asn Leu Ser Asn Asp Gly His Phe Val
 1               5                  10                 15

Leu Leu Pro Gly Tyr Met Thr Arg His Asn Asn Leu Asp Leu Val Ile
             20                  25                  30

Ile Arg Asp Gln Thr Glu Gly Glu Tyr Ser Ser Leu Glu His
            35                  40                  45

(2) INFORMATION FOR SEQ ID NO:173:

(i) SEQUENCE CHARACTERISTICS:
        (A) LENGTH: 318 base pairs
        (B) TYPE: nucleic acid
        (C) STRANDEDNESS: double
        (D) TOPOLOGY: linear (ii) MOLECULE TYPE: cDNA to mRNA (ix) FEATURE:
```

(A) NAME/KEY: CDS
          (B) LOCATION: 1..318

(xi) SEQUENCE DESCRIPTION: SEQ ID NO:173:

ATG GTT AAC GTC CCT AAA ACC CGC CGG ACT TTC TGT AAG AAG TGT GGC         48
Met Val Asn Val Pro Lys Thr Arg Arg Thr Phe Cys Lys Lys Cys Gly
             50                  55                  60

AAG CAC CAA CCC CAT AAA GTG ACA CAG TAC AAG AAG GGC AAG GAT TCT         96
Lys His Gln Pro His Lys Val Thr Gln Tyr Lys Lys Gly Lys Asp Ser
         65                  70                  75

CTG TAC GCC CAG GGA AAG CGG CGT TAT GAC AGG AAG CAG AGT GGC TAT        144
Leu Tyr Ala Gln Gly Lys Arg Arg Tyr Asp Arg Lys Gln Ser Gly Tyr
     80                  85                  90

GGT GGG CAA ACT AAG CCG ATT TTC CGG AAA AAG GCT AAA ACT ACA AAG        192
Gly Gly Gln Thr Lys Pro Ile Phe Arg Lys Lys Ala Lys Thr Thr Lys
 95                 100                 105                 110

AAG ATT GTG CTA AGG CTT GAG TGC GTT GAG CCC AAC TGC AGA TCT AAG        240
Lys Ile Val Leu Arg Leu Glu Cys Val Glu Pro Asn Cys Arg Ser Lys
                115                 120                 125

AGA ATG CTG GCT ATT AAA AGA TGC AAG CAT TTT GAA CTG GGA GGA GAT        288
Arg Met Leu Ala Ile Lys Arg Cys Lys His Phe Glu Leu Gly Gly Asp
            130                 135                 140

AAG AAG AGA AAG GGC CAA GTG ATC CAG TTC                                318
Lys Lys Arg Lys Gly Gln Val Ile Gln Phe
            145                 150

(2) INFORMATION FOR SEQ ID NO:174:

(i) SEQUENCE CHARACTERISTICS:
         (A) LENGTH: 106 amino acids
         (B) TYPE: amino acid
         (D) TOPOLOGY: linear (ii) MOLECULE TYPE: protein (xi) SEQUENCE DESCRIPTION: SEQ ID NO:174:

Met Val Asn Val Pro Lys Thr Arg Arg Thr Phe Cys Lys Lys Cys Gly
  1               5                  10                  15

Lys His Gln Pro His Lys Val Thr Gln Tyr Lys Lys Gly Lys Asp Ser
                 20                  25                  30

Leu Tyr Ala Gln Gly Lys Arg Arg Tyr Asp Arg Lys Gln Ser Gly Tyr
             35                  40                  45

Gly Gly Gln Thr Lys Pro Ile Phe Arg Lys Lys Ala Lys Thr Thr Lys
         50                  55                  60

Lys Ile Val Leu Arg Leu Glu Cys Val Glu Pro Asn Cys Arg Ser Lys
 65                  70                  75                  80

Arg Met Leu Ala Ile Lys Arg Cys Lys His Phe Glu Leu Gly Gly Asp
                 85                  90                  95

Lys Lys Arg Lys Gly Gln Val Ile Gln Phe
            100                 105

(2) INFORMATION FOR SEQ ID NO:175:

(i) SEQUENCE CHARACTERISTICS:
         (A) LENGTH: 417 base pairs
         (B) TYPE: nucleic acid
         (C) STRANDEDNESS: double
         (D) TOPOLOGY: linear (ii) MOLECULE TYPE: cDNA to mRNA (ix) FEATURE:
         (A) NAME/KEY: CDS (B) LOCATION: 1..417

(xi) SEQUENCE DESCRIPTION: SEQ ID NO:175:

```
ATG GCG GCT GTG TCG GTG TAT GCT CCA CCA GTT GGA GGC TTC TCT TTT        48
Met Ala Ala Val Ser Val Tyr Ala Pro Pro Val Gly Gly Phe Ser Phe
    110                 115                 120

GAT AAC TGC CGC AGG AAT GCC GTC TTG GAA GCC GAT TTT GCA AAG AGG        96
Asp Asn Cys Arg Arg Asn Ala Val Leu Glu Ala Asp Phe Ala Lys Arg
            125                 130                 135

GGA TAC AAG CTT CCA AAG GTC CGG AAA ACT GGC ACG ACC ATC GCT GGG       144
Gly Tyr Lys Leu Pro Lys Val Arg Lys Thr Gly Thr Thr Ile Ala Gly
        140                 145                 150

GTG GTC TAT AAG GAT GGC ATA GTT CTT GGA GCA GAT ACA AGA GCA ACT       192
Val Val Tyr Lys Asp Gly Ile Val Leu Gly Ala Asp Thr Arg Ala Thr
155                 160                 165                 170

GAA GGG ATG GTT GTT GCT GAC AAG AAC TGT TCA AAA ATA CAC TTC ATA       240
Glu Gly Met Val Val Ala Asp Lys Asn Cys Ser Lys Ile His Phe Ile
                175                 180                 185

TCT CCT AAT ATT TAT TGT TGT GGT GCT GGG ACA GCT GCA GAC ACA GAC       288
Ser Pro Asn Ile Tyr Cys Cys Gly Ala Gly Thr Ala Ala Asp Thr Asp
            190                 195                 200

ATG ACA ACC CAG CTC ATT TCT TCC AAC CTG GAG CTC CAC TCC CTC TCC       336
Met Thr Thr Gln Leu Ile Ser Ser Asn Leu Glu Leu His Ser Leu Ser
        205                 210                 215

ACT GGC CGT CTT CCC AGA GTT GTG ACA GCC AAT CGG ATG CTG AAG CAG       384
Thr Gly Arg Leu Pro Arg Val Val Thr Ala Asn Arg Met Leu Lys Gln
220                 225                 230

ATG CTT TTC AGG TAT CAA GGT TAC ATT GGT GCA                           417
Met Leu Phe Arg Tyr Gln Gly Tyr Ile Gly Ala
235                 240                 245
```

(2) INFORMATION FOR SEQ ID NO:176:

(i) SEQUENCE CHARACTERISTICS:
        (A) LENGTH: 139 amino acids
        (B) TYPE: amino acid
        (D) TOPOLOGY: linear (ii) MOLECULE TYPE: protein (xi) SEQUENCE DESCRIPTION: SEQ ID NO:176:

```
Met Ala Ala Val Ser Val Tyr Ala Pro Pro Val Gly Gly Phe Ser Phe
  1               5                  10                  15

Asp Asn Cys Arg Arg Asn Ala Val Leu Glu Ala Asp Phe Ala Lys Arg
            20                  25                  30

Gly Tyr Lys Leu Pro Lys Val Arg Lys Thr Gly Thr Thr Ile Ala Gly
        35                  40                  45

Val Val Tyr Lys Asp Gly Ile Val Leu Gly Ala Asp Thr Arg Ala Thr
    50                  55                  60

Glu Gly Met Val Val Ala Asp Lys Asn Cys Ser Lys Ile His Phe Ile
 65                 70                  75                  80

Ser Pro Asn Ile Tyr Cys Cys Gly Ala Gly Thr Ala Ala Asp Thr Asp
                85                  90                  95

Met Thr Thr Gln Leu Ile Ser Ser Asn Leu Glu Leu His Ser Leu Ser
            100                 105                 110

Thr Gly Arg Leu Pro Arg Val Val Thr Ala Asn Arg Met Leu Lys Gln
        115                 120                 125

Met Leu Phe Arg Tyr Gln Gly Tyr Ile Gly Ala
    130                 135
```

(2) INFORMATION FOR SEQ ID NO:177:

(i) SEQUENCE CHARACTERISTICS:
        (A) LENGTH: 105 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..105

(xi) SEQUENCE DESCRIPTION: SEQ ID NO:177:

```
CTG ACA GCA GGA CCC AGT GTT GCC GTC CCT CCC CAG GCA CCT TTT GGT        48
Leu Thr Ala Gly Pro Ser Val Ala Val Pro Pro Gln Ala Pro Phe Gly
140                 145                 150                 155

TAT GGT TAT ACC GCA CCA CCG TAT GGA CAG CCA CAG CCT GGC TTT GGG        96
Tyr Gly Tyr Thr Ala Pro Pro Tyr Gly Gln Pro Gln Pro Gly Phe Gly
                160                 165                 170

TAC AGC ATG                                                           105
Tyr Ser Met
```

(2) INFORMATION FOR SEQ ID NO:178:

(i) SEQUENCE CHARACTERISTICS:
        (A) LENGTH: 35 amino acids
        (B) TYPE: amino acid
        (D) TOPOLOGY: linear (ii) MOLECULE TYPE: protein (xi) SEQUENCE DESCRIPTION: SEQ ID NO:178:

```
Leu Thr Ala Gly Pro Ser Val Ala Val Pro Pro Gln Ala Pro Phe Gly
 1               5                  10                  15

Tyr Gly Tyr Thr Ala Pro Pro Tyr Gly Gln Pro Gln Pro Gly Phe Gly
                20                  25                  30

Tyr Ser Met
       35
```

(2) INFORMATION FOR SEQ ID NO:179:

(i) SEQUENCE CHARACTERISTICS:
        (A) LENGTH: 372 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..372

(xi) SEQUENCE DESCRIPTION: SEQ ID NO:179:

```
ATG GCG ACT TTT TCT GGC CCG GCT GGG CCA ATC CTG TCG CTT AAT CCG        48
Met Ala Thr Phe Ser Gly Pro Ala Gly Pro Ile Leu Ser Leu Asn Pro
                 40                  45                  50

CAG GAA GAT GTC GAG TTT CAA AAG GAG GTG GCG CAG GTT CGC AAG CGC        96
Gln Glu Asp Val Glu Phe Gln Lys Glu Val Ala Gln Val Arg Lys Arg
                 55                  60                  65

ATA ACC CAG CGA AAA AAA CAA GAA CAA CTT ACT CCT GGA GTA GTC TAT       144
Ile Thr Gln Arg Lys Lys Gln Glu Gln Leu Thr Pro Gly Val Val Tyr
         70                  75                  80

GTG CGC CAC CTA CCT AAC CTA CTT GAC GAA ACC AGA ATC TTT TCA TAT       192
```

| | | | | | | | | | | | | |
|---|---|---|---|---|---|---|---|---|---|---|---|---|
|Val|Arg|His|Leu|Pro|Asn|Leu|Leu|Asp|Glu|Thr|Gln|Ile|Phe|Ser|Tyr|
| |85| | | |90| | | | |95| | | | | |

```
TTC TCC CAG TTT GGC ACT GTG ACA CGG TTC AGG CTG TCC AGA AGT AAA        240
Phe Ser Gln Phe Gly Thr Val Thr Arg Phe Arg Leu Ser Arg Ser Lys
100             105                 110                 115

AGG ACT GGA AAT AGC AAA GGC TAT GCA TTT GTG GAG TTT GAG TCT GAG        288
Arg Thr Gly Asn Ser Lys Gly Tyr Ala Phe Val Glu Phe Glu Ser Glu
                120                 125                 130

GAT GTT GCC AAA ATA GTT GCT GAA ACA ATG AAC AAC TAC CTG TTT GGT        336
Asp Val Ala Lys Ile Val Ala Glu Thr Met Asn Asn Tyr Leu Phe Gly
        135                 140                 145

GAA AGA CTC TTG GAG TGT CAT TTT ATG CCA CCT GAA                        372
Glu Arg Leu Leu Glu Cys His Phe Met Pro Pro Glu
        150                 155
```

(2) INFORMATION FOR SEQ ID NO:180:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO:180:

```
Met Ala Thr Phe Ser Gly Pro Ala Gly Pro Ile Leu Ser Leu Asn Pro
1               5                   10                  15

Gln Glu Asp Val Glu Phe Gln Lys Glu Val Ala Gln Val Arg Lys Arg
                20                  25                  30

Ile Thr Gln Arg Lys Lys Gln Glu Gln Leu Thr Pro Gly Val Val Tyr
            35                  40                  45

Val Arg His Leu Pro Asn Leu Leu Asp Glu Thr Gln Ile Phe Ser Tyr
        50                  55                  60

Phe Ser Gln Phe Gly Thr Val Thr Arg Phe Arg Leu Ser Arg Ser Lys
65                  70                  75                  80

Arg Thr Gly Asn Ser Lys Gly Tyr Ala Phe Val Glu Phe Glu Ser Glu
                85                  90                  95

Asp Val Ala Lys Ile Val Ala Glu Thr Met Asn Asn Tyr Leu Phe Gly
            100                 105                 110

Glu Arg Leu Leu Glu Cys His Phe Met Pro Pro Glu
        115                 120
```

(2) INFORMATION FOR SEQ ID NO:181:

(i) SEQUENCE CHARACTERISTICS:
        (A) LENGTH: 243 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..243

(xi) SEQUENCE DESCRIPTION: SEQ ID NO:181:

```
ATG CTA ATT AAA GTG AAG ACG CTG ACC GGA AAG GAG ATT GAG ATT GAC        48
Met Leu Ile Lys Val Lys Thr Leu Thr Gly Lys Glu Ile Glu Ile Asp
125                 130                 135                 140

ATT GAA CCT ACA GAC AAG GTG GAG CGA ATC AAG GAG CGT GTG GAG GAG        96
Ile Glu Pro Thr Asp Lys Val Glu Arg Ile Lys Glu Arg Val Glu Glu
                145                 150                 155
```

```
AAA GAG GGA ATC CCC CCA CAA CAG CAG AGG CTC ATC TAC AGT GGC AAG         144
Lys Glu Gly Ile Pro Pro Gln Gln Gln Arg Leu Ile Tyr Ser Gly Lys
            160                 165                 170

CAG ATG AAT GAT GAG AAG ACA GCA GCT GAT TAC AAG ATT TTA GGT GGT         192
Gln Met Asn Asp Glu Lys Thr Ala Ala Asp Tyr Lys Ile Leu Gly Gly
        175                 180                 185

TCA GTC CTT CAC CTG GTG TTG GCT CTG AGA GGA GGA GGT GGT CTT AGG         240
Ser Val Leu His Leu Val Leu Ala Leu Arg Gly Gly Gly Gly Leu Arg
190                 195                 200

CAG                                                                      243
Gln
205
```

(2) INFORMATION FOR SEQ ID NO:182:

(i) SEQUENCE CHARACTERISTICS:
        (A) LENGTH: 81 amino acids
        (B) TYPE: amino acid
        (D) TOPOLOGY: linear (ii) MOLECULE TYPE: protein (xi) SEQUENCE DESCRIPTION: SEQ ID NO:182:

```
Met Leu Ile Lys Val Lys Thr Leu Thr Gly Lys Glu Ile Glu Ile Asp
 1               5                  10                  15

Ile Glu Pro Thr Asp Lys Val Glu Arg Ile Lys Glu Arg Val Glu Glu
            20                  25                  30

Lys Glu Gly Ile Pro Pro Gln Gln Gln Arg Leu Ile Tyr Ser Gly Lys
        35                  40                  45

Gln Met Asn Asp Glu Lys Thr Ala Ala Asp Tyr Lys Ile Leu Gly Gly
    50                  55                  60

Ser Val Leu His Leu Val Leu Ala Leu Arg Gly Gly Gly Gly Leu Arg
65                  70                  75                  80

Gln
```

(2) INFORMATION FOR SEQ ID NO:183:

(i) SEQUENCE CHARACTERISTICS:
        (A) LENGTH: 222 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..222

(xi) SEQUENCE DESCRIPTION: SEQ ID NO:183:

```
ATG GTC CAG CGT TTG ACA TAC CGA CGT AGG CTT TCC TAC AAT ACA GCC          48
Met Val Gln Arg Leu Thr Tyr Arg Arg Arg Leu Ser Tyr Asn Thr Ala
            85                  90                  95

TCT AAC AAA ACT AGG CTG TCC CGA ACC CCT GGT AAT AGA ATT GTT TAC          96
Ser Asn Lys Thr Arg Leu Ser Arg Thr Pro Gly Asn Arg Ile Val Tyr
        100                 105                 110

CTT TAT ACC AAG AAG GTT GGG AAA GCA CCA AAA TCT GCA TGT GGT GTG         144
Leu Tyr Thr Lys Lys Val Gly Lys Ala Pro Lys Ser Ala Cys Gly Val
    115                 120                 125

TGC CCA GGC AGA CTT CGA GGG GTT CGT GCT GTA AGA CCT AAA GTT CTT         192
Cys Pro Gly Arg Leu Arg Gly Val Arg Ala Val Arg Pro Lys Val Leu
130                 135                 140                 145
```

```
ATG AGA TTG TCC AAA ACA AAG AAA CAT GTC                              222
Met Arg Leu Ser Lys Thr Lys Lys His Val
                150                 155
```

(2) INFORMATION FOR SEQ ID NO:184:

(i) SEQUENCE CHARACTERISTICS:
        (A) LENGTH: 74 amino acids
        (B) TYPE: amino acid
        (D) TOPOLOGY: linear (ii) MOLECULE TYPE: protein (xi) SEQUENCE DESCRIPTION: SEQ ID NO:184:

```
Met Val Gln Arg Leu Thr Tyr Arg Arg Arg Leu Ser Tyr Asn Thr Ala
 1               5                  10                  15

Ser Asn Lys Thr Arg Leu Ser Arg Thr Pro Gly Asn Arg Ile Val Tyr
            20                  25                  30

Leu Tyr Thr Lys Lys Val Gly Lys Ala Pro Lys Ser Ala Cys Gly Val
            35                  40                  45

Cys Pro Gly Arg Leu Arg Gly Val Arg Ala Val Arg Pro Lys Val Leu
        50                  55                  60

Met Arg Leu Ser Lys Thr Lys Lys His Val
65                  70
```

(2) INFORMATION FOR SEQ ID NO:185:

(i) SEQUENCE CHARACTERISTICS:
        (A) LENGTH: 81 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..81

(xi) SEQUENCE DESCRIPTION: SEQ ID NO:185:

```
ATG GGC CGT GTG ATC CGT GGA CAG AGG AAG GGC GCC GGG TCT GTA TTC    48
Met Gly Arg Val Ile Arg Gly Gln Arg Lys Gly Ala Gly Ser Val Phe
 75              80                  85                  90

CGC GCG CAC GTA AAG CAC CGT AAA GAC GCT GCG                         81
Arg Ala His Val Lys His Arg Lys Asp Ala Ala
                95                  100
```

(2) INFORMATION FOR SEQ ID NO:186:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO:186:

```
Met Gly Arg Val Ile Arg Gly Gln Arg Lys Gly Ala Gly Ser Val Phe
 1               5                  10                  15

Arg Ala His Val Lys His Arg Lys Asp Ala Ala
            20                  25
```

(2) INFORMATION FOR SEQ ID NO:187:

(i) SEQUENCE CHARACTERISTICS:

(A) LENGTH: 186 base pairs
            (B) TYPE: nucleic acid
            (C) STRANDEDNESS: double
            (D) TOPOLOGY: linear (ii) MOLECULE TYPE: cDNA to mRNA (ix) FEATURE:
            (A) NAME/KEY: CDS
            (B) LOCATION: 1..186

(xi) SEQUENCE DESCRIPTION: SEQ ID NO:187:

```
ATG TCT GAA CCA ATC AGA GTC CTT GTG ACT GGA GCA GCT GGT CAA ATT        48
Met Ser Glu Pro Ile Arg Val Leu Val Thr Gly Ala Ala Gly Gln Ile
        30                  35                  40

GCA TAT TCA CTG CTG TAC AGT ATT GGA AAT GGA TCT GTC TTT GGT AAA        96
Ala Tyr Ser Leu Leu Tyr Ser Ile Gly Asn Gly Ser Val Phe Gly Lys
    45                  50                  55

GAT CAG CCT ATA ATT CTT GTG CTG TTG GAT ATC ACC CCC ATG ATG GGT       144
Asp Gln Pro Ile Ile Leu Val Leu Leu Asp Ile Thr Pro Met Met Gly
 60                  65                  70                  75

GTC CTG GAC GGT GTC CTA ATG GAT CTG CAA GAC TGT GCC CTT               186
Val Leu Asp Gly Val Leu Met Asp Leu Gln Asp Cys Ala Leu
                 80                  85
```

(2) INFORMATION FOR SEQ ID NO:188:

(i) SEQUENCE CHARACTERISTICS:
            (A) LENGTH: 62 amino acids
            (B) TYPE: amino acid
            (D) TOPOLOGY: linear (ii) MOLECULE TYPE: protein (xi) SEQUENCE DESCRIPTION: SEQ ID NO:188:

```
Met Ser Glu Pro Ile Arg Val Leu Val Thr Gly Ala Ala Gly Gln Ile
 1               5                  10                  15

Ala Tyr Ser Leu Leu Tyr Ser Ile Gly Asn Gly Ser Val Phe Gly Lys
             20                  25                  30

Asp Gln Pro Ile Ile Leu Val Leu Leu Asp Ile Thr Pro Met Met Gly
         35                  40                  45

Val Leu Asp Gly Val Leu Met Asp Leu Gln Asp Cys Ala Leu
     50                  55                  60
```

(2) INFORMATION FOR SEQ ID NO:189:

(i) SEQUENCE CHARACTERISTICS:
            (A) LENGTH: 342 base pairs
            (B) TYPE: nucleic acid
            (C) STRANDEDNESS: double
            (D) TOPOLOGY: linear (ii) MOLECULE TYPE: cDNA to mRNA (ix) FEATURE:
            (A) NAME/KEY: CDS
            (B) LOCATION: 1..342

(xi) SEQUENCE DESCRIPTION: SEQ ID NO:189:

```
CTC TTT GCA GAG TCC CTG CAG TGC AAG GTG GAC TGT GAG GCC AAT TTG        48
Leu Phe Ala Glu Ser Leu Gln Cys Lys Val Asp Cys Glu Ala Asn Leu
        65                  70                  75

ACC CCC AAT GTG GGT GGC TAC TTC GTG GAC AAG TTC GTG GCC ACC ATG        96
Thr Pro Asn Val Gly Gly Tyr Phe Val Asp Lys Phe Val Ala Thr Met
 80                  85                  90

TAC CAC TAC CTG CAG TTT GCC TAC TAT AAG TTG AAT GAT GTG CGC CAG       144
```

-continued

| | | | | | | | | | | | | | | |
|---|---|---|---|---|---|---|---|---|---|---|---|---|---|---|
|Tyr|His|Tyr|Leu|Gln|Phe|Ala|Tyr|Tyr|Lys|Leu|Asn|Asp|Val|Arg|Gln|
|95| | | |100| | | |105| | | |110| | |

```
GCT GCC CGC AGC GCC GCC AGC TAC ATG CTC TTC GAC CCC AAG GAC AGC      192
Ala Ala Arg Ser Ala Ala Ser Tyr Met Leu Phe Asp Pro Lys Asp Ser
                115                 120                 125

GTC ATG CAG CAG AAC CTG GTG TAT TAC CGG TTC CAC CGG GCT CGC TGG      240
Val Met Gln Gln Asn Leu Val Tyr Tyr Arg Phe His Arg Ala Arg Trp
            130                 135                 140

GGC CTG GAA GAG GAG GAC TTC CAG CCC CGG GAG GAG GCC ATG CTC TAC      288
Gly Leu Glu Glu Glu Asp Phe Gln Pro Arg Glu Glu Ala Met Leu Tyr
        145                 150                 155

CAC AAC CAG ACC GCC GAG CTG CGG GAG CTG CTG GAG TTC ACC CAC ATG      336
His Asn Gln Thr Ala Glu Leu Arg Glu Leu Leu Glu Phe Thr His Met
    160                 165                 170

TAC CTG                                                              342
Tyr Leu
175
```

(2) INFORMATION FOR SEQ ID NO:190:

(i) SEQUENCE CHARACTERISTICS:
        (A) LENGTH: 114 amino acids
        (B) TYPE: amino acid
        (D) TOPOLOGY: linear (ii) MOLECULE TYPE: protein (xi) SEQUENCE DESCRIPTION: SEQ ID NO:190:

```
Leu Phe Ala Glu Ser Leu Gln Cys Lys Val Asp Cys Glu Ala Asn Leu
 1               5                  10                  15

Thr Pro Asn Val Gly Gly Tyr Phe Val Asp Lys Phe Val Ala Thr Met
             20                  25                  30

Tyr His Tyr Leu Gln Phe Ala Tyr Tyr Lys Leu Asn Asp Val Arg Gln
         35                  40                  45

Ala Ala Arg Ser Ala Ala Ser Tyr Met Leu Phe Asp Pro Lys Asp Ser
     50                  55                  60

Val Met Gln Gln Asn Leu Val Tyr Tyr Arg Phe His Arg Ala Arg Trp
65                  70                  75                  80

Gly Leu Glu Glu Glu Asp Phe Gln Pro Arg Glu Glu Ala Met Leu Tyr
                 85                  90                  95

His Asn Gln Thr Ala Glu Leu Arg Glu Leu Leu Glu Phe Thr His Met
            100                 105                 110

Tyr Leu
```

(2) INFORMATION FOR SEQ ID NO:191:

(i) SEQUENCE CHARACTERISTICS:
        (A) LENGTH: 354 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..354

(xi) SEQUENCE DESCRIPTION: SEQ ID NO:191:

```
TTG GCA GAC AAA TAC AAA AAG AAA ATG TGG GGG TGG CTG TGG ACA GAA       48
Leu Ala Asp Lys Tyr Lys Lys Lys Met Trp Gly Trp Leu Trp Thr Glu
115                 120                 125                 130
```

```
GCT GGA GCC CAG TCT GAA CTT GAG ACC GCG TTG GGG ATT GGA GGG TTT          96
Ala Gly Ala Gln Ser Glu Leu Glu Thr Ala Leu Gly Ile Gly Gly Phe
            135                 140                 145

GGG TAC CCC GCC ATG GCC GCC ATC AAT GCA CGC AAG ATG AAA TTT GCT         144
Gly Tyr Pro Ala Met Ala Ala Ile Asn Ala Arg Lys Met Lys Phe Ala
        150                 155                 160

CTG CTA AAA GGC TCC TTC AGT GAG CAA GGC ATC AAC GAG TTT CTC AGG         192
Leu Leu Lys Gly Ser Phe Ser Glu Gln Gly Ile Asn Glu Phe Leu Arg
            165                 170                 175

GAG CTC TCT TTT GGG CGT GGC TCC ACG GCA CCT GTA GGA GGC GGG GCT         240
Glu Leu Ser Phe Gly Arg Gly Ser Thr Ala Pro Val Gly Gly Gly Ala
        180                 185                 190

TTC CCT ACC ATC GTT GAG AGA GAG CCT TGG GAC GGC AGG GAT GGC GAG         288
Phe Pro Thr Ile Val Glu Arg Glu Pro Trp Asp Gly Arg Asp Gly Glu
195                 200                 205                 210

CTT CCC GTG GAG GAT GAC ATT GAC CTC AGT GAT GTG GAG CTT GAT GAC         336
Leu Pro Val Glu Asp Asp Ile Asp Leu Ser Asp Val Glu Leu Asp Asp
            215                 220                 225

TTA GGG AAA GAT GAG TTG                                                 354
Leu Gly Lys Asp Glu Leu
            230

(2) INFORMATION FOR SEQ ID NO:192:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:192:

Leu Ala Asp Lys Tyr Lys Lys Met Trp Gly Trp Leu Trp Thr Glu
  1               5                  10                  15

Ala Gly Ala Gln Ser Glu Leu Glu Thr Ala Leu Gly Ile Gly Gly Phe
             20                  25                  30

Gly Tyr Pro Ala Met Ala Ala Ile Asn Ala Arg Lys Met Lys Phe Ala
         35                  40                  45

Leu Leu Lys Gly Ser Phe Ser Glu Gln Gly Ile Asn Glu Phe Leu Arg
     50                  55                  60

Glu Leu Ser Phe Gly Arg Gly Ser Thr Ala Pro Val Gly Gly Gly Ala
 65                  70                  75                  80

Phe Pro Thr Ile Val Glu Arg Glu Pro Trp Asp Gly Arg Asp Gly Glu
                 85                  90                  95

Leu Pro Val Glu Asp Asp Ile Asp Leu Ser Asp Val Glu Leu Asp Asp
             100                 105                 110

Leu Gly Lys Asp Glu Leu
         115

(2) INFORMATION FOR SEQ ID NO:193:

(i) SEQUENCE CHARACTERISTICS:
        (A) LENGTH: 312 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..312
```

(xi) SEQUENCE DESCRIPTION: SEQ ID NO:193:

| | | | | | | | | | | | | | | | |
|---|---|---|---|---|---|---|---|---|---|---|---|---|---|---|---|
| ATG | CTG | AGC | CGC | TGC | CGC | AGC | CGG | CTG | CTC | CAC | GTC | CTG | GGC | CTT | AGC | 48 |
| Met | Leu | Ser | Arg | Cys | Arg | Ser | Arg | Leu | Leu | His | Val | Leu | Gly | Leu | Ser |
| 120 | | | | | 125 | | | | | 130 | | | | | |

| TTC | CTG | CTG | CAG | ACC | CGC | CGG | CCG | ATT | CTC | CTC | TGC | TCT | CCA | CGT | CTC | 96 |
| Phe | Leu | Leu | Gln | Thr | Arg | Arg | Pro | Ile | Leu | Leu | Cys | Ser | Pro | Arg | Leu |
| 135 | | | | | 140 | | | | | 145 | | | | | 150 |

| ATG | AAG | CCG | CTG | GTC | GTG | TTC | GTC | CTC | GGC | GGC | CCC | GGC | GCC | GGC | AAG | 144 |
| Met | Lys | Pro | Leu | Val | Val | Phe | Val | Leu | Gly | Gly | Pro | Gly | Ala | Gly | Lys |
| | | | | 155 | | | | | 160 | | | | | 165 | |

| GGG | ACC | CAG | TGC | GCC | CGC | ATC | GTC | GAG | AAA | TAT | GGC | TAC | ACA | CAC | CTT | 192 |
| Gly | Thr | Gln | Cys | Ala | Arg | Ile | Val | Glu | Lys | Tyr | Gly | Tyr | Thr | His | Leu |
| | | 170 | | | | | 175 | | | | | 180 | | | |

| TCT | GCA | GGA | GAG | CTG | CTT | CGT | GAT | GAA | AGG | AAG | AAC | CCA | GAT | TCA | CAG | 240 |
| Ser | Ala | Gly | Glu | Leu | Leu | Arg | Asp | Glu | Arg | Lys | Asn | Pro | Asp | Ser | Gln |
| | | 185 | | | | | 190 | | | | | 195 | | | |

| TAT | GGT | GAA | CTT | ATT | GAA | AAG | TAC | ATT | AAA | GAA | GGA | AAG | ATT | GTA | CCA | 288 |
| Tyr | Gly | Glu | Leu | Ile | Glu | Lys | Tyr | Ile | Lys | Glu | Gly | Lys | Ile | Val | Pro |
| | 200 | | | | | 205 | | | | | 210 | | | | |

| GTT | GAG | ATA | ACC | ATC | AGT | TTA | TTA | | | | | | | | | 312 |
| Val | Glu | Ile | Thr | Ile | Ser | Leu | Leu |
| 215 | | | | | 220 | | |

(2) INFORMATION FOR SEQ ID NO:194:

(i) SEQUENCE CHARACTERISTICS:
        (A) LENGTH: 104 amino acids
        (B) TYPE: amino acid
        (D) TOPOLOGY: linear (ii) MOLECULE TYPE: protein (xi) SEQUENCE DESCRIPTION: SEQ ID NO:194:

Met Leu Ser Arg Cys Arg Ser Arg Leu Leu His Val Leu Gly Leu Ser
 1          5                10               15

Phe Leu Leu Gln Thr Arg Arg Pro Ile Leu Leu Cys Ser Pro Arg Leu
          20               25             30

Met Lys Pro Leu Val Val Phe Val Leu Gly Gly Pro Gly Ala Gly Lys
        35               40             45

Gly Thr Gln Cys Ala Arg Ile Val Glu Lys Tyr Gly Tyr Thr His Leu
 50                55             60

Ser Ala Gly Glu Leu Leu Arg Asp Glu Arg Lys Asn Pro Asp Ser Gln
 65                70             75             80

Tyr Gly Glu Leu Ile Glu Lys Tyr Ile Lys Glu Gly Lys Ile Val Pro
               85             90             95

Val Glu Ile Thr Ile Ser Leu Leu
          100

(2) INFORMATION FOR SEQ ID NO:195:

(i) SEQUENCE CHARACTERISTICS:
        (A) LENGTH: 267 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..267

(xi) SEQUENCE DESCRIPTION: SEQ ID NO:195:

```
ATG GAA GCG TTT TTG GGG TCG CGG TCC GGA CTT TGG GCG GGG GGT CCG      48
Met Glu Ala Phe Leu Gly Ser Arg Ser Gly Leu Trp Ala Gly Gly Pro
105             110                 115                 120

GCC CCA GGA CAG TTT TAC CGC ATT CCA TCC ACT CCC GAT TCC TTC ATG      96
Ala Pro Gly Gln Phe Tyr Arg Ile Pro Ser Thr Pro Asp Ser Phe Met
            125                 130                 135

GAT CCG GCG TCT GCA CTT TAC AGA GGT CCA ATC ACG CGG ACC CAG AAC     144
Asp Pro Ala Ser Ala Leu Tyr Arg Gly Pro Ile Thr Arg Thr Gln Asn
        140                 145                 150

CCC ATG GTG ACC GGG ACC TCA GTC CTC GGC GTT AAG TTC GAG GGC GGA     192
Pro Met Val Thr Gly Thr Ser Val Leu Gly Val Lys Phe Glu Gly Gly
            155                 160                 165

GTG GTG ATT GCC GCA GAC ATG CTG GGA TCC TAC GGC TCC TTG GCT CGT     240
Val Val Ile Ala Ala Asp Met Leu Gly Ser Tyr Gly Ser Leu Ala Arg
170                 175                 180

TTC CGC AAC ATC TCT CGC ATT ATG CGA                                  267
Phe Arg Asn Ile Ser Arg Ile Met Arg
185             190

(2) INFORMATION FOR SEQ ID NO:196:

(i) SEQUENCE CHARACTERISTICS:
        (A) LENGTH: 89 amino acids
        (B) TYPE: amino acid
        (D) TOPOLOGY: linear (ii) MOLECULE TYPE: protein (xi) SEQUENCE DESCRIPTION: SEQ ID NO:196:

Met Glu Ala Phe Leu Gly Ser Arg Ser Gly Leu Trp Ala Gly Gly Pro
  1               5                  10                  15

Ala Pro Gly Gln Phe Tyr Arg Ile Pro Ser Thr Pro Asp Ser Phe Met
                 20                  25                  30

Asp Pro Ala Ser Ala Leu Tyr Arg Gly Pro Ile Thr Arg Thr Gln Asn
             35                  40                  45

Pro Met Val Thr Gly Thr Ser Val Leu Gly Val Lys Phe Glu Gly Gly
         50                  55                  60

Val Val Ile Ala Ala Asp Met Leu Gly Ser Tyr Gly Ser Leu Ala Arg
 65                  70                  75                  80

Phe Arg Asn Ile Ser Arg Ile Met Arg
                 85

(2) INFORMATION FOR SEQ ID NO:197:

(i) SEQUENCE CHARACTERISTICS:
        (A) LENGTH: 234 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..234

(xi) SEQUENCE DESCRIPTION: SEQ ID NO:197:

ATG CAT CGT GAT TCC TGT CCA TTG GAC TGT AAG GTT TAT GTA GGC AAT      48
Met His Arg Asp Ser Cys Pro Leu Asp Cys Lys Val Tyr Val Gly Asn
 90              95                 100                 105

CTT GGA AAC AAT GGC AAC AAG ACG GAA TTG GAA CGG GCT TTT GGC TAC      96
Leu Gly Asn Asn Gly Asn Lys Thr Glu Leu Glu Arg Ala Phe Gly Tyr
                110                 115                 120
```

```
TAT GGA CCA CTC CGA AGT GTG TGG GTT GCT AGA AAC CCA CCC GGC TTT      144
Tyr Gly Pro Leu Arg Ser Val Trp Val Ala Arg Asn Pro Pro Gly Phe
            125                 130                 135

GCT TTT GTT GAA TTT GAA GAT CCC CGA GAT GCA GCT GAT GCA GTC CGA      192
Ala Phe Val Glu Phe Glu Asp Pro Arg Asp Ala Ala Asp Ala Val Arg
        140                 145                 150

GAG CTA GAT GGA AGA ACA CTA TGT GGC TGC CGT GTA AGA GTG              234
Glu Leu Asp Gly Arg Thr Leu Cys Gly Cys Arg Val Arg Val
    155                 160                 165
```

(2) INFORMATION FOR SEQ ID NO:198:

(i) SEQUENCE CHARACTERISTICS:
        (A) LENGTH: 78 amino acids
        (B) TYPE: amino acid
        (D) TOPOLOGY: linear (ii) MOLECULE TYPE: protein (xi) SEQUENCE DESCRIPTION: SEQ ID NO:198:

```
Met His Arg Asp Ser Cys Pro Leu Asp Cys Lys Val Tyr Val Gly Asn
  1               5                  10                  15

Leu Gly Asn Asn Gly Asn Lys Thr Glu Leu Glu Arg Ala Phe Gly Tyr
                20                  25                  30

Tyr Gly Pro Leu Arg Ser Val Trp Val Ala Arg Asn Pro Pro Gly Phe
            35                  40                  45

Ala Phe Val Glu Phe Glu Asp Pro Arg Asp Ala Ala Asp Ala Val Arg
        50                  55                  60

Glu Leu Asp Gly Arg Thr Leu Cys Gly Cys Arg Val Arg Val
 65                 70                  75
```

(2) INFORMATION FOR SEQ ID NO:199:

(i) SEQUENCE CHARACTERISTICS:
        (A) LENGTH: 198 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..198

(xi) SEQUENCE DESCRIPTION: SEQ ID NO:199:

```
ATG GAG CTG GAG GAG TTG GGG ATC CGA GAG GAA TGT GGC GTG TTC GGG      48
Met Glu Leu Glu Glu Leu Gly Ile Arg Glu Glu Cys Gly Val Phe Gly
 80                  85                  90

TGC ATC GCC TCA GGA GAG TGG CCC ACG CAG CTG GAT GTA CCG CAT GTG      96
Cys Ile Ala Ser Gly Glu Trp Pro Thr Gln Leu Asp Val Pro His Val
 95                 100                 105                 110

ATC ACT CTG GGA CTC GTG GGG CTG CAG CAC CGG GGT CAG GAG AGT GCT     144
Ile Thr Leu Gly Leu Val Gly Leu Gln His Arg Gly Gln Glu Ser Ala
                115                 120                 125

GGT ATT GTG ACT AGT GAT GGG AGT TCC GTG CCA ACA TTC AAA TCA CAC     192
Gly Ile Val Thr Ser Asp Gly Ser Ser Val Pro Thr Phe Lys Ser His
            130                 135                 140

AAG GGA                                                              198
Lys Gly
```

(2) INFORMATION FOR SEQ ID NO:200:

(i) SEQUENCE CHARACTERISTICS:
    (A) LENGTH: 66 amino acids
    (B) TYPE: amino acid
    (D) TOPOLOGY: linear (ii) MOLECULE TYPE: protein (xi) SEQUENCE DESCRIPTION: SEQ ID NO:200:

Met Glu Leu Glu Glu Leu Gly Ile Arg Glu Cys Gly Val Phe Gly
1               5                   10                  15

Cys Ile Ala Ser Gly Glu Trp Pro Thr Gln Leu Asp Val Pro His Val
            20                  25                  30

Ile Thr Leu Gly Leu Val Gly Leu Gln His Arg Gly Gln Glu Ser Ala
        35                  40                  45

Gly Ile Val Thr Ser Asp Gly Ser Ser Val Pro Thr Phe Lys Ser His
    50                  55                  60

Lys Gly
65

(2) INFORMATION FOR SEQ ID NO:201:

(i) SEQUENCE CHARACTERISTICS:
        (A) LENGTH: 270 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..270

(xi) SEQUENCE DESCRIPTION: SEQ ID NO:201:

ATG TTC GCC TGC GCC AAG CTC GCC TGC ACC CCC TCT CTG ATC CGA GCT     48
Met Phe Ala Cys Ala Lys Leu Ala Cys Thr Pro Ser Leu Ile Arg Ala
                70                  75                  80

GGA TCC AGA GTT GCA TAC AGA CCA ATT TCT GCA TCA GTG TTA TCT CGA     96
Gly Ser Arg Val Ala Tyr Arg Pro Ile Ser Ala Ser Val Leu Ser Arg
            85                  90                  95

CCA GAG GCT AGT AGG ACT GGA GAG GGC TCT ACG GTA TTT AAT GGG GCC    144
Pro Glu Ala Ser Arg Thr Gly Glu Gly Ser Thr Val Phe Asn Gly Ala
100                 105                 110

CAG AAT GGT GTG TCT CAG CTA ATC CAA AGG GAG TTT CAG ACC AGT GCA    192
Gln Asn Gly Val Ser Gln Leu Ile Gln Arg Glu Phe Gln Thr Ser Ala
115                 120                 125                 130

ATC AGC AGA GAC ATT GAT ACT GCT GCC AAA TTT ATT GGT GCA GGT GCT    240
Ile Ser Arg Asp Ile Asp Thr Ala Ala Lys Phe Ile Gly Ala Gly Ala
                135                 140                 145

GCA ACA GTA GGA GTG GCT GGT TCT GGT GCT                            270
Ala Thr Val Gly Val Ala Gly Ser Gly Ala
            150                 155

(2) INFORMATION FOR SEQ ID NO:202:

(i) SEQUENCE CHARACTERISTICS:
        (A) LENGTH: 90 amino acids
        (B) TYPE: amino acid
        (D) TOPOLOGY: linear (ii) MOLECULE TYPE: protein (xi) SEQUENCE DESCRIPTION: SEQ ID NO:202:

Met Phe Ala Cys Ala Lys Leu Ala Cys Thr Pro Ser Leu Ile Arg Ala
1               5                   10                  15

```
Gly Ser Arg Val Ala Tyr Arg Pro Ile Ser Ala Ser Val Leu Ser Arg
            20                  25                  30

Pro Glu Ala Ser Arg Thr Gly Glu Gly Ser Thr Val Phe Asn Gly Ala
        35                  40                  45

Gln Asn Gly Val Ser Gln Leu Ile Gln Arg Glu Phe Gln Thr Ser Ala
    50                  55                  60

Ile Ser Arg Asp Ile Asp Thr Ala Ala Lys Phe Ile Gly Ala Gly Ala
65                  70                  75                  80

Ala Thr Val Gly Val Ala Gly Ser Gly Ala
                85                  90

(2) INFORMATION FOR SEQ ID NO:203:

(i) SEQUENCE CHARACTERISTICS:
        (A) LENGTH: 273 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..273

(xi) SEQUENCE DESCRIPTION: SEQ ID NO:203:

ATG GCT GCC CCA GCA GTG TCC GGG CTC TCC CGG CAG GTG CGA TGC TTC        48
Met Ala Ala Pro Ala Val Ser Gly Leu Ser Arg Gln Val Arg Cys Phe
                 95                 100                 105

AGT ACC TCT GTG GTC AGA CCA TTT GCC AAG CTT GTG AGG CCT CCT GTT        96
Ser Thr Ser Val Val Arg Pro Phe Ala Lys Leu Val Arg Pro Pro Val
                110                 115                 120

CAG GTA TAC GGT ATT GAA GGT CGC TAT GCC ACA GCT CTT TAT TCT GCT       144
Gln Val Tyr Gly Ile Glu Gly Arg Tyr Ala Thr Ala Leu Tyr Ser Ala
                125                 130                 135

GCA TCA AAA CAG AAT AAG CTG GAG CAA GTA GAA AAG GAG TTG TTG AGA       192
Ala Ser Lys Gln Asn Lys Leu Glu Gln Val Glu Lys Glu Leu Leu Arg
                140                 145                 150

GTA GCA CAA ATC CTG AAG GAA CCC AAA GTG GCT GCT TCT GTT TTG AAT       240
Val Ala Gln Ile Leu Lys Glu Pro Lys Val Ala Ala Ser Val Leu Asn
155                 160                 165                 170

CCC TAT GTG AAG CGT TCC ATT AAA GTG AAA AGC                            273
Pro Tyr Val Lys Arg Ser Ile Lys Val Lys Ser
                175                 180

(2) INFORMATION FOR SEQ ID NO:204:

(i) SEQUENCE CHARACTERISTICS:
        (A) LENGTH: 91 amino acids
        (B) TYPE: amino acid
        (D) TOPOLOGY: linear (ii) MOLECULE TYPE: protein (xi) SEQUENCE DESCRIPTION: SEQ ID NO:204:

Met Ala Ala Pro Ala Val Ser Gly Leu Ser Arg Gln Val Arg Cys Phe
 1               5                  10                  15

Ser Thr Ser Val Val Arg Pro Phe Ala Lys Leu Val Arg Pro Pro Val
                20                  25                  30

Gln Val Tyr Gly Ile Glu Gly Arg Tyr Ala Thr Ala Leu Tyr Ser Ala
            35                  40                  45

Ala Ser Lys Gln Asn Lys Leu Glu Gln Val Glu Lys Glu Leu Leu Arg
```

```
              50                  55                  60
Val Ala Gln Ile Leu Lys Glu Pro Lys Val Ala Ser Val Leu Asn
 65                  70                  75                  80

Pro Tyr Val Lys Arg Ser Ile Lys Val Lys Ser
                 85                  90
```

(2) INFORMATION FOR SEQ ID NO:205:

(i) SEQUENCE CHARACTERISTICS:
        (A) LENGTH: 210 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..210

(xi) SEQUENCE DESCRIPTION: SEQ ID NO:205:

```
ATG CCT CGG AAA ATT GAG GAA ATC AAG GAC TTC CTG CTC ACA GCC CGA        48
Met Pro Arg Lys Ile Glu Glu Ile Lys Asp Phe Leu Leu Thr Ala Arg
             95                 100                 105

CGA AAG GAT GCC AAA TCT GTC AAG ATC AAG AAA AAT AAG GAC AAC GTG        96
Arg Lys Asp Ala Lys Ser Val Lys Ile Lys Lys Asn Lys Asp Asn Val
        110                 115                 120

AAG TTT AAA GTT CGA TGC AGC AGA TAC CTT TAC ACC CTG GTC ATC ACT       144
Lys Phe Lys Val Arg Cys Ser Arg Tyr Leu Tyr Thr Leu Val Ile Thr
    125                 130                 135

GAC AAA GAG AAG GCA GAG AAA CTG AAG CAG TCC CTG CCC CCC GGT TTG       192
Asp Lys Glu Lys Ala Glu Lys Leu Lys Gln Ser Leu Pro Pro Gly Leu
140                 145                 150                 155

GCA GTG AAG GAA CTG AAA                                               210
Ala Val Lys Glu Leu Lys
                160
```

(2) INFORMATION FOR SEQ ID NO:206:

(i) SEQUENCE CHARACTERISTICS:
        (A) LENGTH: 70 amino acids
        (B) TYPE: amino acid
        (D) TOPOLOGY: linear (ii) MOLECULE TYPE: protein (xi) SEQUENCE DESCRIPTION: SEQ ID NO:206:

```
Met Pro Arg Lys Ile Glu Glu Ile Lys Asp Phe Leu Leu Thr Ala Arg
  1               5                  10                  15

Arg Lys Asp Ala Lys Ser Val Lys Ile Lys Lys Asn Lys Asp Asn Val
                 20                  25                  30

Lys Phe Lys Val Arg Cys Ser Arg Tyr Leu Tyr Thr Leu Val Ile Thr
             35                  40                  45

Asp Lys Glu Lys Ala Glu Lys Leu Lys Gln Ser Leu Pro Pro Gly Leu
         50                  55                  60

Ala Val Lys Glu Leu Lys
 65                  70
```

(2) INFORMATION FOR SEQ ID NO:207:

(i) SEQUENCE CHARACTERISTICS:
        (A) LENGTH: 111 base pairs
        (B) TYPE: nucleic acid
        (C) STRANDEDNESS: double (D) TOPOLOGY: linear (ii) MOLECULE TYPE: cDNA to mRNA (ix) FEATURE:
    (A) NAME/KEY: CDS
    (B) LOCATION: 1..111

(xi) SEQUENCE DESCRIPTION: SEQ ID NO:207:

```
CTG GAT AAC GTG GCC ACC TAT GCG GGG CAG TTC AAC CAG GAC TAT CTC        48
Leu Asp Asn Val Ala Thr Tyr Ala Gly Gln Phe Asn Gln Asp Tyr Leu
            75                  80                  85

TCG GGA ATA GCG GCC AAC ATG TCT GGG ACA TTT GGA GGA GCC AAC ATG        96
Ser Gly Ile Ala Ala Asn Met Ser Gly Thr Phe Gly Gly Ala Asn Met
        90                  95                 100

CCC AAC CTG TAC CCT                                                   111
Pro Asn Leu Tyr Pro
    105
```

(2) INFORMATION FOR SEQ ID NO:208:

(i) SEQUENCE CHARACTERISTICS:
        (A) LENGTH: 37 amino acids
        (B) TYPE: amino acid
        (D) TOPOLOGY: linear (ii) MOLECULE TYPE: protein (xi) SEQUENCE DESCRIPTION: SEQ ID NO:208:

```
Leu Asp Asn Val Ala Thr Tyr Ala Gly Gln Phe Asn Gln Asp Tyr Leu
 1               5                  10                  15

Ser Gly Ile Ala Ala Asn Met Ser Gly Thr Phe Gly Gly Ala Asn Met
            20                  25                  30

Pro Asn Leu Tyr Pro
        35
```

(2) INFORMATION FOR SEQ ID NO:209:

(i) SEQUENCE CHARACTERISTICS:
        (A) LENGTH: 183 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..183

(xi) SEQUENCE DESCRIPTION: SEQ ID NO:209:

```
TCT TAC ATT TTC GTA AGT GTT ACT CAA GAA GCA GAA AGG GAA GAA TTT        48
Ser Tyr Ile Phe Val Ser Val Thr Gln Glu Ala Glu Arg Glu Glu Phe
            40                  45                  50

TTT GAT GAA ACA AGA CGA CTT TGT GAC CTT CGG CTT TTT CAA CCC TTT        96
Phe Asp Glu Thr Arg Arg Leu Cys Asp Leu Arg Leu Phe Gln Pro Phe
        55                  60                  65

TTA AAA GTA ATT GAA CCA GTA GGC AAC CGT GAA GAA AAG ATC CTC AAT       144
Leu Lys Val Ile Glu Pro Val Gly Asn Arg Glu Glu Lys Ile Leu Asn
 70                  75                  80                  85

CGA GAA ATT GGT TTT GCT ATC GGC ATG CCA GTG TGT GAA                   183
Arg Glu Ile Gly Phe Ala Ile Gly Met Pro Val Cys Glu
            90                  95
```

(2) INFORMATION FOR SEQ ID NO:210:

(i) SEQUENCE CHARACTERISTICS:
        (A) LENGTH: 61 amino acids
        (B) TYPE: amino acid
        (D) TOPOLOGY: linear (ii) MOLECULE TYPE: protein (xi) SEQUENCE DESCRIPTION: SEQ ID NO:210:

Ser Tyr Ile Phe Val Ser Val Thr Gln Glu Ala Glu Arg Glu Glu Phe
 1               5                  10                  15

Phe Asp Glu Thr Arg Arg Leu Cys Asp Leu Arg Leu Phe Gln Pro Phe
                20                  25                  30

Leu Lys Val Ile Glu Pro Val Gly Asn Arg Glu Glu Lys Ile Leu Asn
            35                  40                  45

Arg Glu Ile Gly Phe Ala Ile Gly Met Pro Val Cys Glu
        50                  55                  60

(2) INFORMATION FOR SEQ ID NO:211:

(i) SEQUENCE CHARACTERISTICS:
        (A) LENGTH: 330 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..330

(xi) SEQUENCE DESCRIPTION: SEQ ID NO:211:

ATG GCG GCT TCA GGA GAG AGC GGG ACT TCA GGC GGC GGA GGC AGC ACC        48
Met Ala Ala Ser Gly Glu Ser Gly Thr Ser Gly Gly Gly Gly Ser Thr
                65                  70                  75

GAG GAA GCA TTT ATG ACC TTC TAC AGT GAG GTG AAA CAA ATA GAG AAG        96
Glu Glu Ala Phe Met Thr Phe Tyr Ser Glu Val Lys Gln Ile Glu Lys
            80                  85                  90

AGA GAC TCG GTT CTA ACT TCG AAA AAT CAG ATT GAA AGA CTG ACC CGT       144
Arg Asp Ser Val Leu Thr Ser Lys Asn Gln Ile Glu Arg Leu Thr Arg
        95                  100                 105

CCT GGT TCC TCT TAC TTC AAT TTG AAC CCA TTT GAG GTT CTT CAG ATA       192
Pro Gly Ser Ser Tyr Phe Asn Leu Asn Pro Phe Glu Val Leu Gln Ile
110                 115                 120                 125

GAT CCT GAA GTT ACA GAT GAA GAA ATA AAA AAG AGG TTT CGG CAG TTA       240
Asp Pro Glu Val Thr Asp Glu Glu Ile Lys Lys Arg Phe Arg Gln Leu
                130                 135                 140

TCC ATC TTG GTG CAT CCT GAC AAA AAT CAA GAT GAT GCT GAC AGA GCA       288
Ser Ile Leu Val His Pro Asp Lys Asn Gln Asp Asp Ala Asp Arg Ala
            145                 150                 155

CAA AAG GCT TTT GAA GCT GTG GAC AAA GCT TAC AAG TTG CTA               330
Gln Lys Ala Phe Glu Ala Val Asp Lys Ala Tyr Lys Leu Leu
        160                 165                 170

(2) INFORMATION FOR SEQ ID NO:212:

(i) SEQUENCE CHARACTERISTICS:
        (A) LENGTH: 110 amino acids
        (B) TYPE: amino acid
        (D) TOPOLOGY: linear (ii) MOLECULE TYPE: protein (xi) SEQUENCE DESCRIPTION: SEQ ID NO:212:

Met Ala Ala Ser Gly Glu Ser Gly Thr Ser Gly Gly Gly Gly Ser Thr

```
                1               5                    10                   15
              Glu Glu Ala Phe Met Thr Phe Tyr Ser Glu Val Lys Gln Ile Glu Lys
                              20                   25                  30

Arg Asp Ser Val Leu Thr Ser Lys Asn Gln Ile Glu Arg Leu Thr Arg
                          35                  40                  45

Pro Gly Ser Ser Tyr Phe Asn Leu Asn Pro Phe Glu Val Leu Gln Ile
                      50                  55                  60

Asp Pro Glu Val Thr Asp Glu Ile Lys Lys Arg Phe Arg Gln Leu
              65                  70                  75                  80

Ser Ile Leu Val His Pro Asp Lys Asn Gln Asp Ala Asp Arg Ala
                              85                  90                  95

Gln Lys Ala Phe Glu Ala Val Asp Lys Ala Tyr Lys Leu Leu
                          100                 105                 110
```

(2) INFORMATION FOR SEQ ID NO:213:

(i) SEQUENCE CHARACTERISTICS:
        (A) LENGTH: 273 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..273

(xi) SEQUENCE DESCRIPTION: SEQ ID NO:213:

```
ATG AAT AAG CCC TCA GAT GGC AGG CCC AAG TAT CTG GTG GTG AAC GCA      48
Met Asn Lys Pro Ser Asp Gly Arg Pro Lys Tyr Leu Val Val Asn Ala
 1                 115                 120                 125

GAC GAG GGG GAG CCG GGC ACC TGC AAG GAC CGG GAG ATC TTA CGC CAT      96
Asp Glu Gly Glu Pro Gly Thr Cys Lys Asp Arg Glu Ile Leu Arg His
            130                 135                 140

GAT CCT CAC AAG CTG CTG GAA GGC TGC CTG GTG GGG GGC CGG GCC ATG     144
Asp Pro His Lys Leu Leu Glu Gly Cys Leu Val Gly Gly Arg Ala Met
        145                 150                 155

GGC GCC CGC GCT GCC TAT ATC TAC ATC CGA GGG GAA TTC TAC AAT GAG     192
Gly Ala Arg Ala Ala Tyr Ile Tyr Ile Arg Gly Glu Phe Tyr Asn Glu
    160                 165                 170

GCC TCC AAT CTG CAG GTG GCC ATC CGA GAG GCC TAT GAG GCA GGT CTG     240
Ala Ser Asn Leu Gln Val Ala Ile Arg Glu Ala Tyr Glu Ala Gly Leu
175                 180                 185                 190

ATT GGC AAG AAT GCT TGT GGC TCT GGC TAT GAT                         273
Ile Gly Lys Asn Ala Cys Gly Ser Gly Tyr Asp
                195                 200
```

(2) INFORMATION FOR SEQ ID NO:214:

(i) SEQUENCE CHARACTERISTICS:
        (A) LENGTH: 91 amino acids
        (B) TYPE: amino acid
        (D) TOPOLOGY: linear (ii) MOLECULE TYPE: protein (xi) SEQUENCE DESCRIPTION: SEQ ID NO:214:

```
Met Asn Lys Pro Ser Asp Gly Arg Pro Lys Tyr Leu Val Val Asn Ala
 1               5                  10                  15

Asp Glu Gly Glu Pro Gly Thr Cys Lys Asp Arg Glu Ile Leu Arg His
              20                  25                  30
```

```
Asp Pro His Lys Leu Leu Glu Gly Cys Leu Val Gly Gly Arg Ala Met
         35                  40                  45

Gly Ala Arg Ala Ala Tyr Ile Tyr Ile Arg Gly Glu Phe Tyr Asn Glu
     50                  55                  60

Ala Ser Asn Leu Gln Val Ala Ile Arg Glu Ala Tyr Glu Ala Gly Leu
 65                  70                  75                  80

Ile Gly Lys Asn Ala Cys Gly Ser Gly Tyr Asp
                 85                  90

(2) INFORMATION FOR SEQ ID NO:215:

(i) SEQUENCE CHARACTERISTICS:
        (A) LENGTH: 246 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..246

(xi) SEQUENCE DESCRIPTION: SEQ ID NO:215:

CCA GGA CAT GCT GCT TTC TCA GCA ATG AGA GCC AGA GGT GCT CAG GTC      48
Pro Gly His Ala Ala Phe Ser Ala Met Arg Ala Arg Gly Ala Gln Val
                 95                 100                 105

ACT GAC ATT GTC GTA TTG GTT GTA GCT GCA GAT GAT GGA GTG ATG AAA      96
Thr Asp Ile Val Val Leu Val Val Ala Ala Asp Asp Gly Val Met Lys
            110                 115                 120

CAA ACT GTA GAA TCT ATT CAG CAT GCC AAA GAT GCA CAG GTT CCT ATT     144
Gln Thr Val Glu Ser Ile Gln His Ala Lys Asp Ala Gln Val Pro Ile
        125                 130                 135

ATC CTT GCC GTA AAT AAA TGT GAC AAA GCT GAG GCT GAT CCT GAG AAA     192
Ile Leu Ala Val Asn Lys Cys Asp Lys Ala Glu Ala Asp Pro Glu Lys
140                 145                 150                 155

GTG AAA AAA GAG CTG CTG GCT TAT GAT GTG GTA TGT GAA GAT TAT GGA     240
Val Lys Lys Glu Leu Leu Ala Tyr Asp Val Val Cys Glu Asp Tyr Gly
                160                 165                 170

GGT GAT                                                              246
Gly Asp (2) INFORMATION FOR SEQ ID NO:216:

(i) SEQUENCE CHARACTERISTICS:
        (A) LENGTH: 82 amino acids
        (B) TYPE: amino acid
        (D) TOPOLOGY: linear (ii) MOLECULE TYPE: protein (xi) SEQUENCE DESCRIPTION: SEQ ID NO:216:

Pro Gly His Ala Ala Phe Ser Ala Met Arg Ala Arg Gly Ala Gln Val
 1               5                  10                  15

Thr Asp Ile Val Val Leu Val Val Ala Ala Asp Asp Gly Val Met Lys
             20                  25                  30

Gln Thr Val Glu Ser Ile Gln His Ala Lys Asp Ala Gln Val Pro Ile
         35                  40                  45

Ile Leu Ala Val Asn Lys Cys Asp Lys Ala Glu Ala Asp Pro Glu Lys
     50                  55                  60

Val Lys Lys Glu Leu Leu Ala Tyr Asp Val Val Cys Glu Asp Tyr Gly
 65                  70                  75                  80
```

Gly Asp (2) INFORMATION FOR SEQ ID NO:217:

(i) SEQUENCE CHARACTERISTICS:
        (A) LENGTH: 249 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..249

(xi) SEQUENCE DESCRIPTION: SEQ ID NO:217:

```
ATG CAA GCA CAG AAG GAA GAA GTT CTT AGC CAC ATG AAT GAT GTG CTA      48
Met Gln Ala Gln Lys Glu Glu Val Leu Ser His Met Asn Asp Val Leu
        85                  90                  95

GAG AAT GAG CTC CAA TGT ATT ATT TGT TCA GAA TAC TTC ATT GAG GCT      96
Glu Asn Glu Leu Gln Cys Ile Ile Cys Ser Glu Tyr Phe Ile Glu Ala
    100                 105                 110

GTC ACC TTG AAC TGT GCC CAC AGT TTC TGC TCC TAC TGT ATC AAT GAA     144
Val Thr Leu Asn Cys Ala His Ser Phe Cys Ser Tyr Cys Ile Asn Glu
115                 120                 125                 130

TGG ATG AAG CGG AAG ATA GAA TGC CCC ATT TGT CGG AAG GAC ATT AAG     192
Trp Met Lys Arg Lys Ile Glu Cys Pro Ile Cys Arg Lys Asp Ile Lys
                135                 140                 145

TCC AAA ACA TAC TCT TTG GTT CTG GAC AAT TGC ATT AAT AAG ATG GTA     240
Ser Lys Thr Tyr Ser Leu Val Leu Asp Asn Cys Ile Asn Lys Met Val
            150                 155                 160

AAT AAT CTG                                                         249
Asn Asn Leu
        165
```

(2) INFORMATION FOR SEQ ID NO:218:

(i) SEQUENCE CHARACTERISTICS:
        (A) LENGTH: 83 amino acids
        (B) TYPE: amino acid
        (D) TOPOLOGY: linear (ii) MOLECULE TYPE: protein (xi) SEQUENCE DESCRIPTION: SEQ ID NO:218:

```
Met Gln Ala Gln Lys Glu Glu Val Leu Ser His Met Asn Asp Val Leu
 1               5                  10                  15

Glu Asn Glu Leu Gln Cys Ile Ile Cys Ser Glu Tyr Phe Ile Glu Ala
            20                  25                  30

Val Thr Leu Asn Cys Ala His Ser Phe Cys Ser Tyr Cys Ile Asn Glu
        35                  40                  45

Trp Met Lys Arg Lys Ile Glu Cys Pro Ile Cys Arg Lys Asp Ile Lys
    50                  55                  60

Ser Lys Thr Tyr Ser Leu Val Leu Asp Asn Cys Ile Asn Lys Met Val
65                  70                  75                  80

Asn Asn Leu
```

(2) INFORMATION FOR SEQ ID NO:219:

(i) SEQUENCE CHARACTERISTICS:
        (A) LENGTH: 312 base pairs
        (B) TYPE: nucleic acid
        (C) STRANDEDNESS: double (D) TOPOLOGY: linear (ii) MOLECULE TYPE: cDNA to mRNA (ix) FEATURE:
         (A) NAME/KEY: CDS
         (B) LOCATION: 1..312

(xi) SEQUENCE DESCRIPTION: SEQ ID NO:219:

ATG CCA GTG GCC CGG AGC TGG GTT TGT CGC AAA ACT TAT GTG ACC CCG    48
Met Pro Val Ala Arg Ser Trp Val Cys Arg Lys Thr Tyr Val Thr Pro
 85              90              95

CGG AGA CCC TTC GAG AAA TCT CGT CTC GAC CAA GAG CTG AAG CTG ATC    96
Arg Arg Pro Phe Glu Lys Ser Arg Leu Asp Gln Glu Leu Lys Leu Ile
100             105             110             115

GGC GAG TAT GGG CTC CGG AAC AAA CGT GAG GTC TGG AGG GTC AAA TTT   144
Gly Glu Tyr Gly Leu Arg Asn Lys Arg Glu Val Trp Arg Val Lys Phe
            120             125             130

ACC CTG GCC AAG ATC CGC AAG GCC GCC CGG GAA CTG CTG ACG CTT GAT   192
Thr Leu Ala Lys Ile Arg Lys Ala Ala Arg Glu Leu Leu Thr Leu Asp
            135             140             145

GAG AAG GAC CCA CGG CGT CTG TTC GAA GGC AAC GCC CTG CTG CGG CGG   240
Glu Lys Asp Pro Arg Arg Leu Phe Glu Gly Asn Ala Leu Leu Arg Arg
        150             155             160

CTG GTC CGC ATT GGG GTG CTG GAT GAG GGC AAG ATG AAG CTG GAT TAC   288
Leu Val Arg Ile Gly Val Leu Asp Glu Gly Lys Met Lys Leu Asp Tyr
165             170             175

ATC CTG GGC CTG AAG ATA GAG GAT                                   312
Ile Leu Gly Leu Lys Ile Glu Asp
180             185

(2) INFORMATION FOR SEQ ID NO:220:

(i) SEQUENCE CHARACTERISTICS:
        (A) LENGTH: 104 amino acids
        (B) TYPE: amino acid
        (D) TOPOLOGY: linear (ii) MOLECULE TYPE: protein (xi) SEQUENCE DESCRIPTION: SEQ ID NO:220:

Met Pro Val Ala Arg Ser Trp Val Cys Arg Lys Thr Tyr Val Thr Pro
 1               5              10              15

Arg Arg Pro Phe Glu Lys Ser Arg Leu Asp Gln Glu Leu Lys Leu Ile
            20              25              30

Gly Glu Tyr Gly Leu Arg Asn Lys Arg Glu Val Trp Arg Val Lys Phe
        35              40              45

Thr Leu Ala Lys Ile Arg Lys Ala Ala Arg Glu Leu Leu Thr Leu Asp
    50              55              60

Glu Lys Asp Pro Arg Arg Leu Phe Glu Gly Asn Ala Leu Leu Arg Arg
65              70              75              80

Leu Val Arg Ile Gly Val Leu Asp Glu Gly Lys Met Lys Leu Asp Tyr
            85              90              95

Ile Leu Gly Leu Lys Ile Glu Asp
            100

(2) INFORMATION FOR SEQ ID NO:221:

(i) SEQUENCE CHARACTERISTICS:
        (A) LENGTH: 87 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..87

(xi) SEQUENCE DESCRIPTION: SEQ ID NO:221:

| ATG | ACG | GCG | GCT | GAG | AAC | GTA | TGC | TAC | ACG | TTA | ATT | AAC | GTG | CCA | ATG | 48 |
|---|---|---|---|---|---|---|---|---|---|---|---|---|---|---|---|---|
| Met | Thr | Ala | Ala | Glu | Asn | Val | Cys | Tyr | Thr | Leu | Ile | Asn | Val | Pro | Met | |
| 105 | | | | 110 | | | | | 115 | | | | | 120 | | |

| GAT | TCA | GAA | CCA | CCA | TCT | GAA | ATT | AGC | TTA | AAA | AAT | GAT | 87 |
|---|---|---|---|---|---|---|---|---|---|---|---|---|---|
| Asp | Ser | Glu | Pro | Pro | Ser | Glu | Ile | Ser | Leu | Lys | Asn | Asp | |
| | | | 125 | | | | | 130 | | | | | |

(2) INFORMATION FOR SEQ ID NO:222:

(i) SEQUENCE CHARACTERISTICS:
        (A) LENGTH: 29 amino acids
        (B) TYPE: amino acid
        (D) TOPOLOGY: linear (ii) MOLECULE TYPE: protein (xi) SEQUENCE DESCRIPTION: SEQ ID NO:222:

Met Thr Ala Ala Glu Asn Val Cys Tyr Thr Leu Ile Asn Val Pro Met
 1               5                  10                  15

Asp Ser Glu Pro Pro Ser Glu Ile Ser Leu Lys Asn Asp
            20                  25

(2) INFORMATION FOR SEQ ID NO:223:

(i) SEQUENCE CHARACTERISTICS:
        (A) LENGTH: 252 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..252

(xi) SEQUENCE DESCRIPTION: SEQ ID NO:223:

| TAC | TTT | CAC | ATC | GGA | GAG | ACG | GAG | AAG | AAG | TGC | TTT | ATT | GAG | GAG | ATC | 48 |
|---|---|---|---|---|---|---|---|---|---|---|---|---|---|---|---|---|
| Tyr | Phe | His | Ile | Gly | Glu | Thr | Glu | Lys | Lys | Cys | Phe | Ile | Glu | Glu | Ile | |
| 30 | | | | | 35 | | | | | 40 | | | | | 45 | |

| CCG | GAC | GAG | ACC | ATG | GTC | ATA | GGA | AAC | TAC | CGG | ACG | CAG | CTG | TAT | GAC | 96 |
|---|---|---|---|---|---|---|---|---|---|---|---|---|---|---|---|---|
| Pro | Asp | Glu | Thr | Met | Val | Ile | Gly | Asn | Tyr | Arg | Thr | Gln | Leu | Tyr | Asp | |
| | | | | 50 | | | | | 55 | | | | | 60 | | |

| AAG | CAG | CGG | GAG | GAG | TAC | CAG | CCG | GCC | ACC | CCG | GGG | CTT | GGC | ATG | TTT | 144 |
|---|---|---|---|---|---|---|---|---|---|---|---|---|---|---|---|---|
| Lys | Gln | Arg | Glu | Glu | Tyr | Gln | Pro | Ala | Thr | Pro | Gly | Leu | Gly | Met | Phe | |
| | | | 65 | | | | | 70 | | | | | 75 | | | |

| TTG | GAG | GTG | AAG | GAC | CCA | GAG | GAC | AAG | GTC | ATC | CTG | GCC | CGG | CAG | TAT | 192 |
|---|---|---|---|---|---|---|---|---|---|---|---|---|---|---|---|---|
| Leu | Glu | Val | Lys | Asp | Pro | Glu | Asp | Lys | Val | Ile | Leu | Ala | Arg | Gln | Tyr | |
| | | 80 | | | | | 85 | | | | | 90 | | | | |

| GGC | TCC | GAG | GGC | AGG | TTC | ACT | TTC | ACT | TCC | CAT | ACC | CCT | GGT | GAG | CAC | 240 |
|---|---|---|---|---|---|---|---|---|---|---|---|---|---|---|---|---|
| Gly | Ser | Glu | Gly | Arg | Phe | Thr | Phe | Thr | Ser | His | Thr | Pro | Gly | Glu | His | |
| | | 95 | | | | | 100 | | | | | 105 | | | | |

| CAG | ATC | TGT | CTT | 252 |
|---|---|---|---|---|
| Gln | Ile | Cys | Leu | |
| 110 | | | | |

(2) INFORMATION FOR SEQ ID NO:224:

(i) SEQUENCE CHARACTERISTICS:
(A) LENGTH: 84 amino acids
(B) TYPE: amino acid
(D) TOPOLOGY: linear (ii) MOLECULE TYPE: protein (xi) SEQUENCE DESCRIPTION: SEQ ID NO:224:

```
Tyr Phe His Ile Gly Glu Thr Glu Lys Lys Cys Phe Ile Glu Glu Ile
 1               5                  10                  15

Pro Asp Glu Thr Met Val Ile Gly Asn Tyr Arg Thr Gln Leu Tyr Asp
                20                  25                  30

Lys Gln Arg Glu Glu Tyr Gln Pro Ala Thr Pro Gly Leu Gly Met Phe
            35                  40                  45

Leu Glu Val Lys Asp Pro Glu Asp Lys Val Ile Leu Ala Arg Gln Tyr
        50                  55                  60

Gly Ser Glu Gly Arg Phe Thr Phe Thr Ser His Thr Pro Gly Glu His
 65                  70                  75                  80

Gln Ile Cys Leu
```

(2) INFORMATION FOR SEQ ID NO:225:

(i) SEQUENCE CHARACTERISTICS:
(A) LENGTH: 354 base pairs
(B) TYPE: nucleic acid
(C) STRANDEDNESS: double
(D) TOPOLOGY: linear (ii) MOLECULE TYPE: cDNA to mRNA (ix) FEATURE:
(A) NAME/KEY: CDS
(B) LOCATION: 1..354

(xi) SEQUENCE DESCRIPTION: SEQ ID NO:225:

```
ATG GCG GTG CTG TCA GCT CCT GGC CTG CGC GGC TTC CGG ATC CTT GGT      48
Met Ala Val Leu Ser Ala Pro Gly Leu Arg Gly Phe Arg Ile Leu Gly
 85                  90                  95                 100

CTG CGC TCC AGC GTG GGC CCG GCT GTG CAG GCA CGA GGT GTC CAT CAG      96
Leu Arg Ser Ser Val Gly Pro Ala Val Gln Ala Arg Gly Val His Gln
                105                 110                 115

AGC GTG GCC ACC GAT GGC CCA AGC AGC ACC CAG CCT GCC CTG CCA AAG     144
Ser Val Ala Thr Asp Gly Pro Ser Ser Thr Gln Pro Ala Leu Pro Lys
            120                 125                 130

GCC AGA GCC GTG GCT CCC AAA CCC AGC AGC CGG GGC GAG TAT GTA GTG     192
Ala Arg Ala Val Ala Pro Lys Pro Ser Ser Arg Gly Glu Tyr Val Val
        135                 140                 145

GCC AAG CTG GAT GAC CTC GTC AAC TGG GCC CGC CGG AGT TCT CTG TGG     240
Ala Lys Leu Asp Asp Leu Val Asn Trp Ala Arg Arg Ser Ser Leu Trp
150                 155                 160

CCC ATG ACC TTC GGC CTG GCC TGC TGC GCC GTG GAG ATG ATG CAC ATG     288
Pro Met Thr Phe Gly Leu Ala Cys Cys Ala Val Glu Met Met His Met
165                 170                 175                 180

GCA GCA CCC CGC TAC GAC ATG GAC CGC TTT GGC GTG GTC TTT CGC GCC     336
Ala Ala Pro Arg Tyr Asp Met Asp Arg Phe Gly Val Val Phe Arg Ala
                185                 190                 195

AGC CCG CGC CAG TCC GAC                                              354
Ser Pro Arg Gln Ser Asp
                200
```

(2) INFORMATION FOR SEQ ID NO:226:

(i) SEQUENCE CHARACTERISTICS:

(A) LENGTH: 118 amino acids
            (B) TYPE: amino acid
            (D) TOPOLOGY: linear (ii) MOLECULE TYPE: protein (xi) SEQUENCE DESCRIPTION: SEQ ID NO:226:

```
Met Ala Val Leu Ser Ala Pro Gly Leu Arg Gly Phe Arg Ile Leu Gly
 1               5                  10                  15

Leu Arg Ser Ser Val Gly Pro Ala Val Gln Ala Arg Gly Val His Gln
             20                  25                  30

Ser Val Ala Thr Asp Gly Pro Ser Thr Gln Pro Ala Leu Pro Lys
             35                  40                  45

Ala Arg Ala Val Ala Pro Lys Pro Ser Ser Arg Gly Glu Tyr Val Val
         50                  55                  60

Ala Lys Leu Asp Asp Leu Val Asn Trp Ala Arg Arg Ser Ser Leu Trp
 65                  70                  75                  80

Pro Met Thr Phe Gly Leu Ala Cys Cys Ala Val Glu Met Met His Met
             85                  90                  95

Ala Ala Pro Arg Tyr Asp Met Asp Arg Phe Gly Val Val Phe Arg Ala
            100                 105                 110

Ser Pro Arg Gln Ser Asp
            115
```

(2) INFORMATION FOR SEQ ID NO:227:

(i) SEQUENCE CHARACTERISTICS:
            (A) LENGTH: 330 base pairs
            (B) TYPE: nucleic acid
            (C) STRANDEDNESS: double
            (D) TOPOLOGY: linear (ii) MOLECULE TYPE: cDNA to mRNA (ix) FEATURE:
            (A) NAME/KEY: CDS
            (B) LOCATION: 1..330

(xi) SEQUENCE DESCRIPTION: SEQ ID NO:227:

```
ATG ACG GGG CTA GCA CTG CTC TAC TCC GGG GTC TTC GTG GCC TTC TGG    48
Met Thr Gly Leu Ala Leu Leu Tyr Ser Gly Val Phe Val Ala Phe Trp
120                 125                 130

GCC TGC GCG CTG GCC GTG GGA GTC TGC TAC ACC ATT TTT GAT TTG GGC    96
Ala Cys Ala Leu Ala Val Gly Val Cys Tyr Thr Ile Phe Asp Leu Gly
135                 140                 145                 150

TTC CGC TTT GAT GTG GCA TGG TTC CTG ACG GAG ACT TCG CCC TTC ATG   144
Phe Arg Phe Asp Val Ala Trp Phe Leu Thr Glu Thr Ser Pro Phe Met
                155                 160                 165

TGG TCC AAC CTG GGC ATT GGC CTA GCT ATC TCC CTG TCT GTG GTT GGG   192
Trp Ser Asn Leu Gly Ile Gly Leu Ala Ile Ser Leu Ser Val Val Gly
            170                 175                 180

GCA GCC TGG GGC ATC TAT ATT ACC GGC TCC TCC ATC ATT GGT GGA GGA   240
Ala Ala Trp Gly Ile Tyr Ile Thr Gly Ser Ser Ile Ile Gly Gly Gly
            185                 190                 195

GTG AAG GCC CCC AGG ATC AAG ACC AAG AAC CTG GTC AGC ATC ATC TTC   288
Val Lys Ala Pro Arg Ile Lys Thr Lys Asn Leu Val Ser Ile Ile Phe
200                 205                 210

TGT GAG GCT GTG GCC ATC TAC GGC ATC ATC ATG GCA ATT GTC           330
Cys Glu Ala Val Ala Ile Tyr Gly Ile Ile Met Ala Ile Val
215                 220                 225
```

(2) INFORMATION FOR SEQ ID NO:228:

(i) SEQUENCE CHARACTERISTICS:
    (A) LENGTH: 110 amino acids
    (B) TYPE: amino acid
    (D) TOPOLOGY: linear (ii) MOLECULE TYPE: protein (xi) SEQUENCE DESCRIPTION: SEQ ID NO:228:

```
Met Thr Gly Leu Ala Leu Leu Tyr Ser Gly Val Phe Val Ala Phe Trp
 1               5                  10                  15

Ala Cys Ala Leu Ala Val Gly Val Cys Tyr Thr Ile Phe Asp Leu Gly
            20                  25                  30

Phe Arg Phe Asp Val Ala Trp Phe Leu Thr Glu Thr Ser Pro Phe Met
        35                  40                  45

Trp Ser Asn Leu Gly Ile Gly Leu Ala Ile Ser Leu Ser Val Val Gly
    50                  55                  60

Ala Ala Trp Gly Ile Tyr Ile Thr Gly Ser Ser Ile Ile Gly Gly Gly
65                  70                  75                  80

Val Lys Ala Pro Arg Ile Lys Thr Lys Asn Leu Val Ser Ile Ile Phe
            85                  90                  95

Cys Glu Ala Val Ala Ile Tyr Gly Ile Ile Met Ala Ile Val
            100                 105                 110
```

(2) INFORMATION FOR SEQ ID NO:229:

(i) SEQUENCE CHARACTERISTICS:
       (A) LENGTH: 228 base pairs
       (B) TYPE: nucleic acid
       (C) STRANDEDNESS: double
       (D) TOPOLOGY: linear (ii) MOLECULE TYPE: cDNA to mRNA (ix) FEATURE:
       (A) NAME/KEY: CDS
       (B) LOCATION: 1..228

(xi) SEQUENCE DESCRIPTION: SEQ ID NO:229:

```
ATG AGC AAA GCT CAC CCT CCC GAG TTG AAA AAA TTT ATG GAC AAG AAG      48
Met Ser Lys Ala His Pro Pro Glu Leu Lys Lys Phe Met Asp Lys Lys
                115                 120                 125

TTA TCA TTG AAA TTA AAT GGT GGC AGA CAT GTC CAA GGA ATA TTG CGG      96
Leu Ser Leu Lys Leu Asn Gly Gly Arg His Val Gln Gly Ile Leu Arg
        130                 135                 140

GGA TTT GAT CCC TTT ATG AAC CTT GTG ATA GAT GAA TGT GTG GAG ATG     144
Gly Phe Asp Pro Phe Met Asn Leu Val Ile Asp Glu Cys Val Glu Met
    145                 150                 155

GCG ACT AGT GGA CAA CAG AAC AAT ATT GGA ATG GTG GTA ATA CGA GGA     192
Ala Thr Ser Gly Gln Gln Asn Asn Ile Gly Met Val Val Ile Arg Gly
160                 165                 170

AAT AGT ATC ATC ATG TTA GAA GCC TTG GAA CGA GTA                     228
Asn Ser Ile Ile Met Leu Glu Ala Leu Glu Arg Val
175                 180                 185
```

(2) INFORMATION FOR SEQ ID NO:230:

(i) SEQUENCE CHARACTERISTICS:
       (A) LENGTH: 76 amino acids
       (B) TYPE: amino acid
       (D) TOPOLOGY: linear (ii) MOLECULE TYPE: protein (xi) SEQUENCE DESCRIPTION: SEQ ID NO:230:

```
Met Ser Lys Ala His Pro Pro Glu Leu Lys Lys Phe Met Asp Lys Lys
 1               5                  10                  15

Leu Ser Leu Lys Leu Asn Gly Gly Arg His Val Gln Gly Ile Leu Arg
             20                  25                  30

Gly Phe Asp Pro Phe Met Asn Leu Val Ile Asp Glu Cys Val Glu Met
         35                  40                  45

Ala Thr Ser Gly Gln Gln Asn Asn Ile Gly Met Val Val Ile Arg Gly
     50                  55                  60

Asn Ser Ile Ile Met Leu Glu Ala Leu Glu Arg Val
 65                  70                  75
```

(2) INFORMATION FOR SEQ ID NO:231:

(i) SEQUENCE CHARACTERISTICS:
        (A) LENGTH: 234 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..234

(xi) SEQUENCE DESCRIPTION: SEQ ID NO:231:

```
ATG GCC AAG ATC AAG GCT CGA GAT CTT CGC GGG AAG AAG AAG GAG GAG      48
Met Ala Lys Ile Lys Ala Arg Asp Leu Arg Gly Lys Lys Lys Glu Glu
                 80                  85                  90

CTG CTG AAA CAG CTG GAC GAC CTG AAG GTG GAG CTG TCC CAG CTG CGC      96
Leu Leu Lys Gln Leu Asp Asp Leu Lys Val Glu Leu Ser Gln Leu Arg
         95                 100                 105

GTC GCC AAA GTG ACA GGC GGT GCG GCC TCC AAG CTC TCT AAG ATC CGA     144
Val Ala Lys Val Thr Gly Gly Ala Ala Ser Lys Leu Ser Lys Ile Arg
     110                 115                 120

GTC GTC CGG AAA TCC ATT GCC CGT GTT CTC ACA GTT ATT AAC CAG ACT     192
Val Val Arg Lys Ser Ile Ala Arg Val Leu Thr Val Ile Asn Gln Thr
125                 130                 135                 140

CAG AAA GAA AAC CTC AGG AAA TTC TAC AAG GGC AAG AAG TAC             234
Gln Lys Glu Asn Leu Arg Lys Phe Tyr Lys Gly Lys Lys Tyr
                145                 150
```

(2) INFORMATION FOR SEQ ID NO:232:

(i) SEQUENCE CHARACTERISTICS:
        (A) LENGTH: 78 amino acids
        (B) TYPE: amino acid
        (D) TOPOLOGY: linear (ii) MOLECULE TYPE: protein (xi) SEQUENCE DESCRIPTION: SEQ ID NO:232:

```
Met Ala Lys Ile Lys Ala Arg Asp Leu Arg Gly Lys Lys Lys Glu Glu
 1               5                  10                  15

Leu Leu Lys Gln Leu Asp Asp Leu Lys Val Glu Leu Ser Gln Leu Arg
             20                  25                  30

Val Ala Lys Val Thr Gly Gly Ala Ala Ser Lys Leu Ser Lys Ile Arg
         35                  40                  45

Val Val Arg Lys Ser Ile Ala Arg Val Leu Thr Val Ile Asn Gln Thr
     50                  55                  60

Gln Lys Glu Asn Leu Arg Lys Phe Tyr Lys Gly Lys Lys Tyr
 65                  70                  75
```

(2) INFORMATION FOR SEQ ID NO:233:

(i) SEQUENCE CHARACTERISTICS:
        (A) LENGTH: 195 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..195

(xi) SEQUENCE DESCRIPTION: SEQ ID NO:233:

```
ATG GCG CCG AAA GCG AAG AAG GAA GCT CCT GCC CCT CCT AAA GGT GAA      48
Met Ala Pro Lys Ala Lys Lys Glu Ala Pro Ala Pro Pro Lys Gly Glu
    80              85                  90

GCC AAA GCG AAG GCT TTA AAG GCC AAG AAG GCA GTG TTG AAA GGT GTC      96
Ala Lys Ala Lys Ala Leu Lys Ala Lys Lys Ala Val Leu Lys Gly Val
 95              100                 105                 110

CAC AGC CAC AAA AAG AAG AAG ATC CGC ACG TCA CCC ACC TTC CGG CGG     144
His Ser His Lys Lys Lys Lys Ile Arg Thr Ser Pro Thr Phe Arg Arg
                115                 120                 125

CCG AAG ACA CTG CGA CTC CGG AGA CAG CCC AAA TAT CCT CGG AAG AGC     192
Pro Lys Thr Leu Arg Leu Arg Arg Gln Pro Lys Tyr Pro Arg Lys Ser
            130                 135                 140

GCT                                                                  195
Ala
```

(2) INFORMATION FOR SEQ ID NO:234:

(i) SEQUENCE CHARACTERISTICS:
        (A) LENGTH: 65 amino acids
        (B) TYPE: amino acid
        (D) TOPOLOGY: linear (ii) MOLECULE TYPE: protein (xi) SEQUENCE DESCRIPTION: SEQ ID NO:234:

```
Met Ala Pro Lys Ala Lys Lys Glu Ala Pro Ala Pro Pro Lys Gly Glu
 1               5                  10                  15

Ala Lys Ala Lys Ala Leu Lys Ala Lys Lys Ala Val Leu Lys Gly Val
                20                  25                  30

His Ser His Lys Lys Lys Lys Ile Arg Thr Ser Pro Thr Phe Arg Arg
                35                  40                  45

Pro Lys Thr Leu Arg Leu Arg Arg Gln Pro Lys Tyr Pro Arg Lys Ser
            50                  55                  60

Ala
65
```

(2) INFORMATION FOR SEQ ID NO:235:

(i) SEQUENCE CHARACTERISTICS:
        (A) LENGTH: 306 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..306

(xi) SEQUENCE DESCRIPTION: SEQ ID NO:235:

| | | | | | | | | | | | | | | | | |
|---|---|---|---|---|---|---|---|---|---|---|---|---|---|---|---|---|
| ATG | AGT | AGA | TGC | TCA | GTA | AGT | GGT | GCA | CAG | GGT | TGG | TCC | CTA | TGG | TGG | 48 |
| Met | Ser | Arg | Cys | Ser | Val | Ser | Gly | Ala | Gln | Gly | Trp | Ser | Leu | Trp | Trp | |
| | | | 70 | | | | | 75 | | | | | | 80 | | |
| AGG | CCC | CCT | AAC | ACC | GCC | CAA | CCC | CCC | TCC | ATG | TTC | TCA | CAG | CTC | CAC | 96 |
| Arg | Pro | Pro | Asn | Thr | Ala | Gln | Pro | Pro | Ser | Met | Phe | Ser | Gln | Leu | His | |
| | | | | 85 | | | | | 90 | | | | | 95 | | |
| GCA | CTG | AGC | ACG | GGC | ATG | AAG | GCC | ATG | ATG | TCA | GAA | TTC | TGC | ACC | CAG | 144 |
| Ala | Leu | Ser | Thr | Gly | Met | Lys | Ala | Met | Met | Ser | Glu | Phe | Cys | Thr | Gln | |
| | | | 100 | | | | | 105 | | | | | 110 | | | |
| GGA | GCT | GAG | ATG | TGC | CGC | AGG | GCC | TGT | GGC | GGA | CAT | GGC | TAC | TCA | AAG | 192 |
| Gly | Ala | Glu | Met | Cys | Arg | Arg | Ala | Cys | Gly | Gly | His | Gly | Tyr | Ser | Lys | |
| | | 115 | | | | | 120 | | | | | 125 | | | | |
| CTG | AGT | GGC | CTG | CCA | TCA | CTG | GTC | ACC | AAA | TTG | TCG | GCC | TCC | TGT | ACC | 240 |
| Leu | Ser | Gly | Leu | Pro | Ser | Leu | Val | Thr | Lys | Leu | Ser | Ala | Ser | Cys | Thr | |
| 130 | | | | | 135 | | | | | 140 | | | | | 145 | |
| TAC | GAG | GGT | GAG | AAC | ACA | GTG | CTC | TAC | CTG | CAG | GTG | GCC | AGG | TTC | CTG | 288 |
| Tyr | Glu | Gly | Glu | Asn | Thr | Val | Leu | Tyr | Leu | Gln | Val | Ala | Arg | Phe | Leu | |
| | | | | 150 | | | | | 155 | | | | | 160 | | |
| GTG | AAG | AGC | TAC | CTG | CAG | | | | | | | | | | | 306 |
| Val | Lys | Ser | Tyr | Leu | Gln | | | | | | | | | | | |
| | | | 165 | | | | | | | | | | | | | |

(2) INFORMATION FOR SEQ ID NO:236:

(i) SEQUENCE CHARACTERISTICS:
        (A) LENGTH: 102 amino acids
        (B) TYPE: amino acid
        (D) TOPOLOGY: linear (ii) MOLECULE TYPE: protein (xi) SEQUENCE DESCRIPTION: SEQ ID NO:236:

Met Ser Arg Cys Ser Val Ser Gly Ala Gln Gly Trp Ser Leu Trp Trp
 1            5                    10               15

Arg Pro Pro Asn Thr Ala Gln Pro Pro Ser Met Phe Ser Gln Leu His
           20                 25               30

Ala Leu Ser Thr Gly Met Lys Ala Met Met Ser Glu Phe Cys Thr Gln
        35                 40               45

Gly Ala Glu Met Cys Arg Arg Ala Cys Gly Gly His Gly Tyr Ser Lys
 50                  55                   60

Leu Ser Gly Leu Pro Ser Leu Val Thr Lys Leu Ser Ala Ser Cys Thr
 65                  70                75               80

Tyr Glu Gly Glu Asn Thr Val Leu Tyr Leu Gln Val Ala Arg Phe Leu
           85                 90               95

Val Lys Ser Tyr Leu Gln
        100

(2) INFORMATION FOR SEQ ID NO:237:

(i) SEQUENCE CHARACTERISTICS:
        (A) LENGTH: 141 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..141

(xi) SEQUENCE DESCRIPTION: SEQ ID NO:237:

```
ATG AGT GAT CAG CAG CTG GAC TGT GCC TTG GAC CTA ATG AGG CGC CTG      48
Met Ser Asp Gln Gln Leu Asp Cys Ala Leu Asp Leu Met Arg Arg Leu
        105                 110                 115

CCT CCC CAG CAA ATC GAG AAA AAC CTC AGC GAC CTG ATC GAC CTG GTC      96
Pro Pro Gln Gln Ile Glu Lys Asn Leu Ser Asp Leu Ile Asp Leu Val
        120                 125                 130

CCC AGT CTA TGT GAG GAT CTC CTG TCT TCT GTT GAC CAG CCA CTG         141
Pro Ser Leu Cys Glu Asp Leu Leu Ser Ser Val Asp Gln Pro Leu
135                 140                 145
```

(2) INFORMATION FOR SEQ ID NO:238:

(i) SEQUENCE CHARACTERISTICS:
        (A) LENGTH: 47 amino acids
        (B) TYPE: amino acid
        (D) TOPOLOGY: linear (ii) MOLECULE TYPE: protein (xi) SEQUENCE DESCRIPTION: SEQ ID NO:238:

```
Met Ser Asp Gln Gln Leu Asp Cys Ala Leu Asp Leu Met Arg Arg Leu
 1               5                  10                  15

Pro Pro Gln Gln Ile Glu Lys Asn Leu Ser Asp Leu Ile Asp Leu Val
            20                  25                  30

Pro Ser Leu Cys Glu Asp Leu Leu Ser Ser Val Asp Gln Pro Leu
            35                  40                  45
```

(2) INFORMATION FOR SEQ ID NO:239:

(i) SEQUENCE CHARACTERISTICS:
        (A) LENGTH: 138 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..138

(xi) SEQUENCE DESCRIPTION: SEQ ID NO:239:

```
ATG AAA GTC GCC AGT GGC AGC ACC GCC ACC GCC GCC GCG GGC CCC AGC      48
Met Lys Val Ala Ser Gly Ser Thr Ala Thr Ala Ala Ala Gly Pro Ser
        50                  55                  60

TGC GCG CTG AAG GCC GGC AAG ACA GCG AGC GGT GCG GGC GAG GTG GTG      96
Cys Ala Leu Lys Ala Gly Lys Thr Ala Ser Gly Ala Gly Glu Val Val
        65                  70                  75

CGC TGT CTG TCT GAG CAG AGC GTG GCC ATC TCG CGC TGC GCC            138
Arg Cys Leu Ser Glu Gln Ser Val Ala Ile Ser Arg Cys Ala
 80                  85                  90
```

(2) INFORMATION FOR SEQ ID NO:240:

(i) SEQUENCE CHARACTERISTICS:
        (A) LENGTH: 46 amino acids
        (B) TYPE: amino acid
        (D) TOPOLOGY: linear (ii) MOLECULE TYPE: protein (xi) SEQUENCE DESCRIPTION: SEQ ID NO:240:

```
Met Lys Val Ala Ser Gly Ser Thr Ala Thr Ala Ala Ala Gly Pro Ser
 1               5                  10                  15

Cys Ala Leu Lys Ala Gly Lys Thr Ala Ser Gly Ala Gly Glu Val Val
```

```
                         20                  25                  30
Arg Cys Leu Ser Glu Gln Ser Val Ala Ile Ser Arg Cys Ala
             35                  40                  45

(2) INFORMATION FOR SEQ ID NO:241:

(i) SEQUENCE CHARACTERISTICS:
        (A) LENGTH: 84 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..84

(xi) SEQUENCE DESCRIPTION: SEQ ID NO:241:

ATG ATT GGA GGC TTA TTC ATC TAT AAT CAC AAG GGG GAG GTG CTC ATC        48
Met Ile Gly Gly Leu Phe Ile Tyr Asn His Lys Gly Glu Val Leu Ile
             50                  55                  60

TCC CGA GTC TAC CGA GAT GAC ATC GGG AGG AAC GCA                         84
Ser Arg Val Tyr Arg Asp Asp Ile Gly Arg Asn Ala
             65                  70

(2) INFORMATION FOR SEQ ID NO:242:

(i) SEQUENCE CHARACTERISTICS:
        (A) LENGTH: 28 amino acids
        (B) TYPE: amino acid
        (D) TOPOLOGY: linear (ii) MOLECULE TYPE: protein (xi) SEQUENCE DESCRIPTION: SEQ ID NO:242:

Met Ile Gly Gly Leu Phe Ile Tyr Asn His Lys Gly Glu Val Leu Ile
 1               5                  10                  15

Ser Arg Val Tyr Arg Asp Asp Ile Gly Arg Asn Ala
             20                  25

(2) INFORMATION FOR SEQ ID NO:243:

(i) SEQUENCE CHARACTERISTICS:
        (A) LENGTH: 282 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..282

(xi) SEQUENCE DESCRIPTION: SEQ ID NO:243:

GAC CCC ATG TTT AAG TTG GTT GCT CAG CTG TAC AAG ATT GTG CCC AAT        48
Asp Pro Met Phe Lys Leu Val Ala Gln Leu Tyr Lys Ile Val Pro Asn
             30                  35                  40

GTC CTC TTA GAG CAG GGT AAA GCC AAG AAT CCT TGG CCC AAT GTA GAT        96
Val Leu Leu Glu Gln Gly Lys Ala Lys Asn Pro Trp Pro Asn Val Asp
 45                  50                  55                  60

GCT CAC AGT GGG GTG CTG CTC CAG TAT TAT GGC ATG ACG GAG ATG AAT       144
Ala His Ser Gly Val Leu Leu Gln Tyr Tyr Gly Met Thr Glu Met Asn
             65                  70                  75

TAC TAC ACG GTC CTG TTT GGG GTG TCA CGA GCA TTG GGT GTA CTG GCA       192
Tyr Tyr Thr Val Leu Phe Gly Val Ser Arg Ala Leu Gly Val Leu Ala
```

```
            80                  85                  90
CAG CTC ATC TGG AGC CGA GCC TTA GGC TTC CCT CTA GAA AGG CCC AAG        240
Gln Leu Ile Trp Ser Arg Ala Leu Gly Phe Pro Leu Glu Arg Pro Lys
         95                 100                 105

TCC ATG AGC ACA GAG GGT CTG ATG AAG TTT GTG GAC TCT AAG                282
Ser Met Ser Thr Glu Gly Leu Met Lys Phe Val Asp Ser Lys
        110                 115                 120

(2) INFORMATION FOR SEQ ID NO:244:

(i) SEQUENCE CHARACTERISTICS:
        (A) LENGTH: 94 amino acids
        (B) TYPE: amino acid
        (D) TOPOLOGY: linear (ii) MOLECULE TYPE: protein (xi) SEQUENCE DESCRIPTION: SEQ ID NO:244:

Asp Pro Met Phe Lys Leu Val Ala Gln Leu Tyr Lys Ile Val Pro Asn
  1               5                  10                  15

Val Leu Leu Glu Gln Gly Lys Ala Lys Asn Pro Trp Pro Asn Val Asp
             20                  25                  30

Ala His Ser Gly Val Leu Leu Gln Tyr Tyr Gly Met Thr Glu Met Asn
         35                  40                  45

Tyr Tyr Thr Val Leu Phe Gly Val Ser Arg Ala Leu Gly Val Leu Ala
 50                  55                  60

Gln Leu Ile Trp Ser Arg Ala Leu Gly Phe Pro Leu Glu Arg Pro Lys
 65                  70                  75                  80

Ser Met Ser Thr Glu Gly Leu Met Lys Phe Val Asp Ser Lys
                 85                  90

(2) INFORMATION FOR SEQ ID NO:245:

(i) SEQUENCE CHARACTERISTICS:
        (A) LENGTH: 144 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..144

(xi) SEQUENCE DESCRIPTION: SEQ ID NO:245:

ATG AAT CTA CTA AAG CAG CAC CTG GAG ATT ACT GGT GGG CAG GTA CGT         48
Met Asn Leu Leu Lys Gln His Leu Glu Ile Thr Gly Gly Gln Val Arg
 95                 100                 105                 110

ACC CGG TTC CCG CCA GAA CCC AAT GGA ATC CTG CAT ATT GGA CAT GCC         96
Thr Arg Phe Pro Pro Glu Pro Asn Gly Ile Leu His Ile Gly His Ala
                115                 120                 125

AAA GCC ATC AAT TTC AAC TTT GGC TAT GCC AAG GCC AAC AAT GGC ATC        144
Lys Ala Ile Asn Phe Asn Phe Gly Tyr Ala Lys Ala Asn Asn Gly Ile
            130                 135                 140

(2) INFORMATION FOR SEQ ID NO:246:

(i) SEQUENCE CHARACTERISTICS:
        (A) LENGTH: 48 amino acids
        (B) TYPE: amino acid
        (D) TOPOLOGY: linear (ii) MOLECULE TYPE: protein
```

(xi) SEQUENCE DESCRIPTION: SEQ ID NO:246:

Met Asn Leu Leu Lys Gln His Leu Glu Ile Thr Gly Gly Gln Val Arg
1               5                   10                  15

Thr Arg Phe Pro Pro Glu Pro Asn Gly Ile Leu His Ile Gly His Ala
                20                  25                  30

Lys Ala Ile Asn Phe Asn Phe Gly Tyr Ala Lys Ala Asn Asn Gly Ile
            35                  40                  45

(2) INFORMATION FOR SEQ ID NO:247:

(i) SEQUENCE CHARACTERISTICS:
      (A) LENGTH: 174 base pairs
      (B) TYPE: nucleic acid
      (C) STRANDEDNESS: double
      (D) TOPOLOGY: linear (ii) MOLECULE TYPE: cDNA to mRNA (ix) FEATURE:
      (A) NAME/KEY: CDS
      (B) LOCATION: 1..174

(xi) SEQUENCE DESCRIPTION: SEQ ID NO:247:

```
ATG CTT CAA AGT ATT ATT AAA AAC ATA TGG ATC CCC ATG AAG CCC TAC      48
Met Leu Gln Ser Ile Ile Lys Asn Ile Trp Ile Pro Met Lys Pro Tyr
 50                  55                  60

TAC ACC AAA GTT TAC CAG GAG ATT TGG ATA GGA ATG GGG CTG ATG GGC      96
Tyr Thr Lys Val Tyr Gln Glu Ile Trp Ile Gly Met Gly Leu Met Gly
 65                  70                  75                  80

TTC ATC GTT TAT AAA ATC CGG GCT GCT GAT AAA AGA AGT AAG GCT TTG     144
Phe Ile Val Tyr Lys Ile Arg Ala Ala Asp Lys Arg Ser Lys Ala Leu
                 85                  90                  95

AAA GCT TCA GCG CCT GCT CCT GGT CAT CAC                             174
Lys Ala Ser Ala Pro Ala Pro Gly His His
                100                 105
```

(2) INFORMATION FOR SEQ ID NO:248:

(i) SEQUENCE CHARACTERISTICS:
      (A) LENGTH: 58 amino acids
      (B) TYPE: amino acid
      (D) TOPOLOGY: linear (ii) MOLECULE TYPE: protein (xi) SEQUENCE DESCRIPTION: SEQ ID NO:248:

Met Leu Gln Ser Ile Ile Lys Asn Ile Trp Ile Pro Met Lys Pro Tyr
1               5                   10                  15

Tyr Thr Lys Val Tyr Gln Glu Ile Trp Ile Gly Met Gly Leu Met Gly
                20                  25                  30

Phe Ile Val Tyr Lys Ile Arg Ala Ala Asp Lys Arg Ser Lys Ala Leu
            35                  40                  45

Lys Ala Ser Ala Pro Ala Pro Gly His His
    50                  55

(2) INFORMATION FOR SEQ ID NO:249:

(i) SEQUENCE CHARACTERISTICS:
      (A) LENGTH: 168 base pairs
      (B) TYPE: nucleic acid
      (C) STRANDEDNESS: double
      (D) TOPOLOGY: linear (ii) MOLECULE TYPE: cDNA to mRNA (ix) FEATURE:
    (A) NAME/KEY: CDS
    (B) LOCATION: 1..168

(xi) SEQUENCE DESCRIPTION: SEQ ID NO:249:

| | | | | | | | | | | | | |
|---|---|---|---|---|---|---|---|---|---|---|---|---|
| ATG | GGT | CAC | CAG | CAG | CTG | TAC | TGG | AGC | CAC | CCG | CGA | AAA | TTC | GGC | CAG | 48 |
| Met | Gly | His | Gln | Gln | Leu | Tyr | Trp | Ser | His | Pro | Arg | Lys | Phe | Gly | Gln |
|   | 60 |     |     |     | 65  |     |     |     | 70  |     |     |     |     |     |     |

GGT TCT CGC TCT TGT CGT GTC TGT TCA AAC CGG CAC GGT CTG ATC CGG    96
Gly Ser Arg Ser Cys Arg Val Cys Ser Asn Arg His Gly Leu Ile Arg
    75              80              85              90

AAA TAT GGC CTC AAT ATG TGC CGC CAG TGT TTC CGT CAG TAC GCG AAG   144
Lys Tyr Gly Leu Asn Met Cys Arg Gln Cys Phe Arg Gln Tyr Ala Lys
            95              100             105

GAT ATC GGT TTC ATT AAG TTG GAC                                   168
Asp Ile Gly Phe Ile Lys Leu Asp
            110

(2) INFORMATION FOR SEQ ID NO:250:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO:250:

Met Gly His Gln Gln Leu Tyr Trp Ser His Pro Arg Lys Phe Gly Gln
 1               5                   10                  15

Gly Ser Arg Ser Cys Arg Val Cys Ser Asn Arg His Gly Leu Ile Arg
                20                  25                  30

Lys Tyr Gly Leu Asn Met Cys Arg Gln Cys Phe Arg Gln Tyr Ala Lys
            35                  40                  45

Asp Ile Gly Phe Ile Lys Leu Asp
            50                  55

(2) INFORMATION FOR SEQ ID NO:251:

(i) SEQUENCE CHARACTERISTICS:
        (A) LENGTH: 924 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..924

(xi) SEQUENCE DESCRIPTION: SEQ ID NO:251:

ATG CCC GGG CAA GAA CTC AGG ACG CTG AAT GGC TCT CAG ATG CTC CTG    48
Met Pro Gly Gln Glu Leu Arg Thr Leu Asn Gly Ser Gln Met Leu Leu
            60              65              70

GTG TTG CTG GTG CTC TCG TGG CTG CCG CAT GGG GGC GCC CTG TCT CTG    96
Val Leu Leu Val Leu Ser Trp Leu Pro His Gly Gly Ala Leu Ser Leu
            75              80              85

GCC GAG GCG AGC CGC GCA AGT TTC CCG GGA CCC TCA GAG TTG CAC ACC   144
Ala Glu Ala Ser Arg Ala Ser Phe Pro Gly Pro Ser Glu Leu His Thr
            90              95              100

GAA GAC TCC AGA TTC CGA GAG TTG CGG AAA CGC TAC GAG GAC CTG CTA   192
Glu Asp Ser Arg Phe Arg Glu Leu Arg Lys Arg Tyr Glu Asp Leu Leu
105                 110             115                 120

```
ACC AGG CTG CGG GCC AAC CAG AGC TGG GAA GAT TCG AAC ACC GAC CTC          240
Thr Arg Leu Arg Ala Asn Gln Ser Trp Glu Asp Ser Asn Thr Asp Leu
                125                 130                 135

GTC CCG GCC CCT GCA GTC CGG ATA CTC ACG CCA GAA GTG CGG CTG GGA          288
Val Pro Ala Pro Ala Val Arg Ile Leu Thr Pro Glu Val Arg Leu Gly
            140                 145                 150

TCC GGC GGC CAC CTG CAC CTG CGT ATC TCT CGG GCC GCC CTT CCC GAG          336
Ser Gly Gly His Leu His Leu Arg Ile Ser Arg Ala Ala Leu Pro Glu
            155                 160                 165

GGG CTC CCC GAG GCC TCC CGC CTT CAC CGG GCT CTG TTC CGG CTG TCC          384
Gly Leu Pro Glu Ala Ser Arg Leu His Arg Ala Leu Phe Arg Leu Ser
170                 175                 180

CCG ACG GCG TCA AGG TCG TGG GAC GTG ACA CGA CCT CTG CGG CGT CAG          432
Pro Thr Ala Ser Arg Ser Trp Asp Val Thr Arg Pro Leu Arg Arg Gln
185                 190                 195                 200

CTC AGC CTT GCA AGA CCC CAG GCG CCC GCG CTG CAC CTG CGA CTG TCG          480
Leu Ser Leu Ala Arg Pro Gln Ala Pro Ala Leu His Leu Arg Leu Ser
                205                 210                 215

CCG CCG CCG TCG CAG TCG GAC CAA CTG CTG GCA GAA TCT TCG TCC GCA          528
Pro Pro Pro Ser Gln Ser Asp Gln Leu Leu Ala Glu Ser Ser Ser Ala
            220                 225                 230

CGG CCC CAG CTG GAG TTG CAC TTG CGG CCG CAA GCC GCC AGG GGG CGC          576
Arg Pro Gln Leu Glu Leu His Leu Arg Pro Gln Ala Ala Arg Gly Arg
            235                 240                 245

CGC AGA GCG CGT GCG CGC AAC GGG GAC CAC TGT CCG CTC GGG CCC GGG          624
Arg Arg Ala Arg Ala Arg Asn Gly Asp His Cys Pro Leu Gly Pro Gly
250                 255                 260

CGT TGC TGC CGT CTG CAC ACG GTC CGC GCG TCG CTG GAA GAC CTG GGC          672
Arg Cys Cys Arg Leu His Thr Val Arg Ala Ser Leu Glu Asp Leu Gly
265                 270                 275                 280

TGG GCC GAT TGG GTG CTG TCG CCA CGG GAG GTG CAA GTG ACC ATG TGC          720
Trp Ala Asp Trp Val Leu Ser Pro Arg Glu Val Gln Val Thr Met Cys
                285                 290                 295

ATC GGC GCG TGC CCG AGC CAG TTC CGG GCG GCA AAC ATG CAC GCG CAG          768
Ile Gly Ala Cys Pro Ser Gln Phe Arg Ala Ala Asn Met His Ala Gln
            300                 305                 310

ATC AAG ACG AGC CTG CAC CGC CTG AAG CCC GAC ACG GTG CCA GCG CCC          816
Ile Lys Thr Ser Leu His Arg Leu Lys Pro Asp Thr Val Pro Ala Pro
            315                 320                 325

TGC TGC GTG CCC GCC AGC TAC AAT CCC ATG GTG CTC ATT CAA AAG ACC          864
Cys Cys Val Pro Ala Ser Tyr Asn Pro Met Val Leu Ile Gln Lys Thr
330                 335                 340

GAC ACC GGG GTG TCG CTC CAG ACC TAT GAT GAC TTG TTA GCC AAA GAC          912
Asp Thr Gly Val Ser Leu Gln Thr Tyr Asp Asp Leu Leu Ala Lys Asp
345                 350                 355                 360

TGC CAC TGC ATA                                                          924
Cys His Cys Ile (2) INFORMATION FOR SEQ ID NO:252:

(i) SEQUENCE CHARACTERISTICS:
        (A) LENGTH: 308 amino acids
        (B) TYPE: amino acid
        (D) TOPOLOGY: linear (ii) MOLECULE TYPE: protein (xi) SEQUENCE DESCRIPTION: SEQ ID NO:252:

Met Pro Gly Gln Glu Leu Arg Thr Leu Asn Gly Ser Gln Met Leu Leu
 1               5                  10                  15

Val Leu Leu Val Leu Ser Trp Leu Pro His Gly Gly Ala Leu Ser Leu
```

-continued

```
                    20                  25                  30
Ala Glu Ala Ser Arg Ala Ser Phe Pro Gly Pro Ser Glu Leu His Thr
            35                  40                  45
Glu Asp Ser Arg Phe Arg Glu Leu Arg Lys Arg Tyr Glu Asp Leu Leu
        50                  55                  60
Thr Arg Leu Arg Ala Asn Gln Ser Trp Glu Asp Ser Asn Thr Asp Leu
65                  70                  75                  80
Val Pro Ala Pro Ala Val Arg Ile Leu Thr Pro Glu Val Arg Leu Gly
                85                  90                  95
Ser Gly Gly His Leu His Leu Arg Ile Ser Arg Ala Ala Leu Pro Glu
                100                 105                 110
Gly Leu Pro Glu Ala Ser Arg Leu His Arg Ala Leu Phe Arg Leu Ser
            115                 120                 125
Pro Thr Ala Ser Arg Ser Trp Asp Val Thr Arg Pro Leu Arg Arg Gln
        130                 135                 140
Leu Ser Leu Ala Arg Pro Gln Ala Pro Ala Leu His Leu Arg Leu Ser
145                 150                 155                 160
Pro Pro Pro Ser Gln Ser Asp Gln Leu Leu Ala Glu Ser Ser Ser Ala
                165                 170                 175
Arg Pro Gln Leu Glu Leu His Leu Arg Pro Gln Ala Ala Arg Gly Arg
                180                 185                 190
Arg Arg Ala Arg Ala Arg Asn Gly Asp His Cys Pro Leu Gly Pro Gly
            195                 200                 205
Arg Cys Cys Arg Leu His Thr Val Arg Ala Ser Leu Glu Asp Leu Gly
        210                 215                 220
Trp Ala Asp Trp Val Leu Ser Pro Arg Glu Val Gln Val Thr Met Cys
225                 230                 235                 240
Ile Gly Ala Cys Pro Ser Gln Phe Arg Ala Ala Asn Met His Ala Gln
                245                 250                 255
Ile Lys Thr Ser Leu His Arg Leu Lys Pro Asp Thr Val Pro Ala Pro
                260                 265                 270
Cys Cys Val Pro Ala Ser Tyr Asn Pro Met Val Leu Ile Gln Lys Thr
            275                 280                 285
Asp Thr Gly Val Ser Leu Gln Thr Tyr Asp Asp Leu Leu Ala Lys Asp
        290                 295                 300
Cys His Cys Ile
305
```

(2) INFORMATION FOR SEQ ID NO:253:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:253:

```
Cys Xaa Xaa Cys Xaa Gly Xaa Gly
1               5
```

HUMAN CDNAS AND PROTEINS ENCODED THEREBY

CROSS REFERENCE TO RELATED APPLICATION

This application is a continuation-in-part application of Ser. No. 08/379,441 filed on Feb. 3, 1995, now abandoned, which was filed under 35 USC §371 as national stage application of PCT/JP 93/01095, filed Aug. 4, 1993.

TECHNICAL FIELD

The present invention relates to human cDNAs derived from mRNA expressed in human cells, proteins encoded thereby, and vectors containing the cDNAs. The human cDNAs of the present invention can be used as probes for gene diagnosis and as gene resources for mass production of proteins encoded thereby. The proteins of the present invention can be used as antigens for preparing the antibodies against the proteins. The cDNA vectors of the invention facilitate preparation of probes and expression of the protein.

BACKGROUND ART

Human cells are estimated to express 100,000 kinds of genes and produce the corresponding proteins encoded thereby. Recent progress in molecular biology has revealed that every human protein plays an important role in maintaining our lives, and that many diseases result from mutation in the amino acid sequence of the protein or abnormal expression of proteins in the cell. Therefore, acquisition of whole human genes and elucidation of the structure of proteins encoded thereby would lead to elucidate the cause of many diseases. These genes and proteins are expected to be useful for diagnosis and as therapeutics of the diseases.

Conventional study on human proteins starts with isolating and purifying a protein showing a target activity. The purified protein is used to prepare probes such as oligonucleotide or antibody, by which a cDNA encoding the target protein is screened from a human cDNA library. Purification of the protein and cloning of its cDNA, however, require much time and laborious works. In fact, it is usual to take several years for cloning a cDNA encoding one target protein.

So far about 2,000 kinds of human genes have been isolated and used for investigating their relationships with diseases or their application to medical use. These genes can be used directly as a probe per se in diagnosis or for expressing encoded proteins that can be used for preparing antibodies useful as diagnostic probes. For this purpose, it is desirable to prepare genes as many as possible and to use them as probes. However, human genes elucidated so far are less than several percent of whole human genes. Since each of the genes is kept by individual researchers, it is difficult to use them together as probes.

Recently, it has been reported that cDNA clones were selected from the cDNA library prepared from human brain, partially sequenced, and used for genome mapping [Adams et al., Science 252:1651–1656, 1992; Adams et al., Nature 355:632–634, 1992]. Since the cDNA library used was prepared by a random primer method, each clone contained only a fragment of cDNA. Thus, it is impossible to judge which part of mRNA the cDNA originated from, and even whether the cDNA encodes a protein.

In fact, the functions of proteins encoded by most of the reported cDNAs are unclear. Even if the cDNA possesses a part of coding region, it requires complicated steps such as screening a clone containing an intact coding region from a library and subcloning the coding region into an expression vector to produce the protein. Their cDNAs have another problem that some of the obtained sequences are not derived from a single species of mRNA, because it has been pointed out that they contain some artifact (Burglin et al., Nature 357:367, 1992).

DISCLOSURE OF INVENTION

It is therefore an object of the present invention to simultaneously provide a large number of human cDNAs satisfying the following requirements.

(1) The cDNA originates from a mRNA expressed in human cells.

(2) The cDNA contains a protein-coding region.

(3) The amino acid sequence of the protein encoded by the cDNA has similarity to that of the protein whose function is known.

The invention further provides vectors carrying the following characteristics.

(1) The encoded protein can be produced by in vitro and/or in vivo translation without transferring the cDNA insert into other vectors.

(2) A sense RNA probe or an antisense DNA probe against cDNA can be prepared without transferring the cDNA insert into other vectors.

BEST MODE FOR CARRYING OUT THE INVENTION

Figure 1:
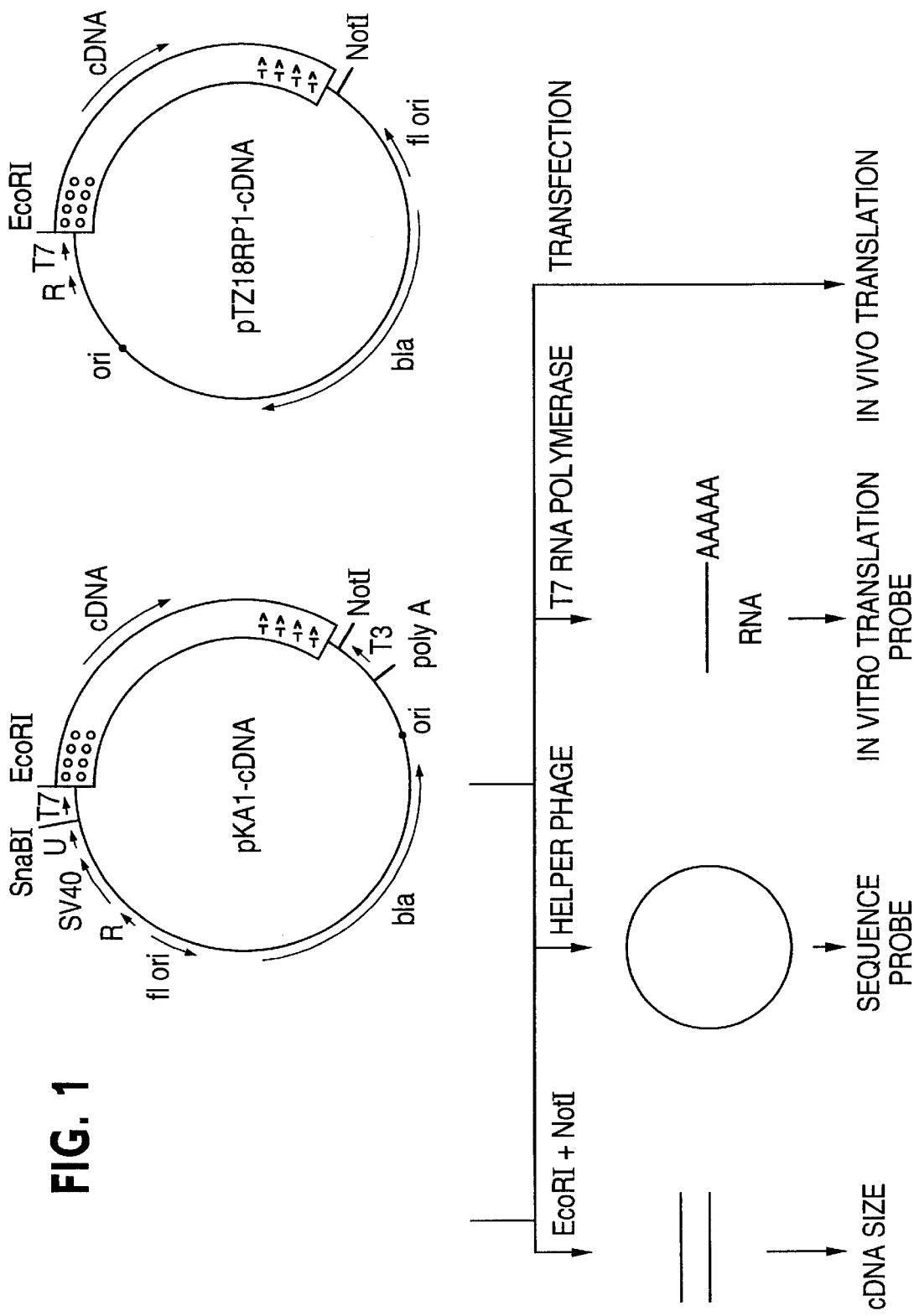
FIG. 1 shows the structure of a cDNA vector of this invention.

The present invention relates to human cDNAs, proteins encoded thereby, and vectors carrying these cDNAs. Human cDNAs and vectors containing them can be cloned from a cDNA library prepared using a multifunctional cloning vector. Any vector containing a replication origin derived from a single-stranded phage and a promoter for RNA polymerase upstream of the cDNA cloning site, e.g. pTZ18RP1 or pKA1 (EP-0426455-A2), can be used as a multifunctional cloning vector.

The cDNAs are synthesized using poly(A)$^+$RNA isolated from human cells, the cell being obtained from tissues isolated from human body by an operation or cultured cells. For example, poly(A)$^+$RNA isolated from human fibrosarcoma cell line HT-1080 and human lymphoma cell line U937 can be used. cDNAs can be synthesized according to any method, e.g. the Okayama-Berg method [Okayama, H. & Berg, P., Mol.Cell.Biol. 2:161–170, 1982] or the Gubler-Hoffman method [Gubler, U. & Hoffman, J., Gene 25:263–269, 1983]. To obtain full-length cDNAs effectively, the method using a vector primer as described in example is preferable.

Each of the cDNA is identified by (1) determining the length of the cDNA insert by restriction enzyme digestion, (2) determining a partial or entire sequence of the cDNA, (3) searching a known protein having similar amino acid sequence to the sequence deduced from the nucleotide sequence of the cDNA, (4) expressing a protein by in vitro translation.

Based on the above strategy, the inventors have discovered a large number of novel cDNAs encoding human proteins. Every cDNA contains the coding region, 3'-noncoding region, and poly(A) tail originated from the corresponding mRNA, and is not a fragment of cDNA. The cDNAs are found to be novel genes, because their nucleotide sequences are not identical to those of known genes. The amino acid sequence of the protein deduced from the cDNA, however, shows great similarity to that of known protein originated from human or the other species, so that the function of the protein can be estimated. Tables 1 to 7 show the names of the encoded proteins. Using the oligonucleotide probe synthesized based on the nucleotide sequence of the cDNAs of the invention, the cDNAs can be readily obtained by screening human cDNA library prepared from the cell lines used in this invention.

The proteins of the present invention can be produced in vitro by preparing RNAs via in vitro transcription using the cDNA vectors of the invention followed by in vitro translation. If the coding region of the cDNA is transferred into other adequate expression vector, a large amount of the encoded protein can be produced in E. coli, Bacillus subtilis, yeast, animal cells and the like. Another way to produce the corresponding peptides is chemical synthesis based on the amino acid sequences of the invention.

The cDNA vector of this invention can be constructed by transferring the cDNA of this invention into a multifunctional cloning vector carrying an f1 phage origin and an RNA polymerase promoter resided upstream of the cloning site. If the original cDNA library is prepared using the multifunctional cloning vector as described in examples below, the subcloning process can be omitted because the resulting cDNA vectors have already satisfied the requirement.

Because the cDNA vector of this invention contains an origin of an f1 phage and an RNA polymerase promoter as shown in FIG. 1, an antisense single-stranded DNA and a sense RNA can be readily prepared without subcloning the cDNA into other vectors. When E. coli cells (F' strain) carrying the cDNA vector of this invention are infected with helper phage, phage particles carrying an antisense single-stranded DNA are released into the culture medium. Thus an antisense DNA can be readily prepared by recovering the phage particles from the medium. The obtained single-stranded DNA is used for sequencing as shown in the examples. A sense strand RNA can be prepared by reacting RNA polymerase with the cDNA vector linearized by restriction enzyme digestion. If this reaction is carried out in the presence of a substrate labeled with a radioisotope or dye, a labeled-probe can be obtained.

When the plasmid pKA1 carrying a replication origin and the early promotor of SV40 is used as a vector primer, the cDNA vector of this invention can be expressed in vivo after transfection into mammalian cells.

EXAMPLE

The present invention will now be described by way of examples. The basic procedure of DNA recombination and the reaction conditions were in accordance with the literature ["Molecular Cloning. A Laboratory Manual", Cold Spring Harbor Laboratory, 1989]. The restriction enzymes and modified enzymes were purchased from Takara Shuzo except for mentioned otherwise. The buffer compositions and reaction conditions for each enzymatic reaction were as described in the attached protocols.

Preparation of poly(A)$^+$RNA

Human T cell lymphoma cell line HUT-78 (ATCC TIB 161), human fibrosarcoma cell line HT-1080 (ATCC CCL 121), and human histiocytic lymphoma cell line U937 (ATCC CRL 1593) were cultured according to the standard conditions. From these cells, total RNA was prepared using the guanidinium isothiocyanate method [Okayama et al., "Method in Enzymology" Vol. 164, Academic Press, 1987]. A poly(A)$^+$RNA was purified by oligo-dT cellulose column chromatography as described in the above literature.

Preparation of cDNA Library pTZ18RP1 or pKA1 (EP-0426455-A2) was digested with KpnI and a (dT) tail of c.a. 60 nucleotides was added using terminal deoxynucleotidyl transferase. After one end of (dT) tail was removed by EcoRV digestion, the resulting vector was used as a vector primer.

The reaction conditions of cDNA synthesis was the same as described in the literature (Okayama et al., described above). Six μg of poly(A)$^+$RNA was annealed with 2.2 μg of the vector primer prepared above and then incubated with 144 U of reverse transcriptase (Seikagaku Kogyo) at 37° C. for 1 hour to synthesize the first strand cDNA.

After phenol extraction and ethanol precipitation of the reaction mixture, the (dC) tail was added to the first strand cDNA by incubating it at 37° C. for 30 min with 2.5 μM dCTP and 15 units of terminal deoxynucleotidyl transferase. After phenol extraction and ethanol precipitation of the reaction mixture, the product was digested at 55° C. for 2 hours with BstXI (New England Biolabs). After phenol extraction and ethanol precipitation of the reaction mixture, the product was annealed and self-ligated at 12° C. overnight with 300 units of E. coli DNA ligase.

After adding dNTP (dATP, dCTP, dGTP, dTTP), 300 units of E. coli DNA ligase, 20 units of E. coli DNA polymerase I, 15 units of E. coli RNase H to the reaction solution, the resulting mixture was incubated at 12° C. for 1 hour and then at 22° C. for 1 hour to replace the RNA strand to a DNA strand. The reaction mixture of above cDNA synthesis was used to transform E. coli NM522 (Pharmacia). The transformation was done according to the Hanahan's method [D. Hanahan (1983) J.Mol.Biol. 166:557–580].

Acquisition of Human cDNA Clone

Part of above cDNA library was spread on a 2×YT agar plate containing 100 μg/ml ampicillin and incubated at 37° C. overnight. Colonies grew on the plate were selected at random, inoculated in 2 ml of a 2×YT medium containing 100 μg/ml ampicillin, and incubated at 37° C. for 2 hours. After infection of helper phage M13KO7, the incubation was continued at 37° C. overnight. The culture medium was centrifuged to separate a cell pellet and a supernatant. A double-stranded plasmid DNA was isolated from the cell pellet by the alkaline lysis method. A single-stranded phage DNA was isolated from the supernatant according to the conventional method.

The double-stranded plasmid DNA was double-digested with EcoRI and NotI, and analyzed on 0.8% agarose gel electrophoresis to determine the size of the cDNA insert. On the other hand, the single-stranded phage DNA was subjected to sequencing reaction and then used for determining the nucleotide sequence with an automated DNA sequencer (Applied Biosystems). The sequencing reaction was carried out using a fluorescent dye-labeled M13 sequencing primer and Taq polymerase (Applied Biosystems kit) in accordance with the reaction conditions described in the protocol attached to the kit. Tables 1 to 7 show the clone number and the insert size of the obtained cDNA. The sequence table shows a part or entire sequence of ach clone.

TABLE 1

| SEQ. ID NO: | HP No. | Cell | Vector | CDNA size (kbp) | Encoded protein |
|---|---|---|---|---|---|
| 1 and 2 | HP00005 | HT-1080 | pKA1 | 2 | Aconitase-like |
| 3 and 4 | HP00008 | HT-1080 | pKA1 | 2 | t-complex 1-like |
| 5 and 6 | HP00011 | HT-1080 | pKA1 | 2.8 | Myosin light chain kinase-like |
| 7 and 8 | HP00012 | HT-1080 | pKA1 | 6.5 | Cadhein-like |
| 9 and 10 | HP00013 | HT-1080 | pKA1 | 1.2 | Protein phosphatase-like |
| 11 and 12 | HP00014 | HT-1080 | pKA1 | 1 | Histone H3.3-like |
| 13 and 14 | HP00018 | HT-1080 | pKA1 | 1 | eIF4A-II-like |
| 15 and 16 | HP00020 | HT-1080 | pKA1 | 1.1 | ATP synthase gamma chain-like |
| 17 and 18 | HP00021 | HT-1080 | pKA1 | 1.8 | CYR61 protein-like |
| 19 and 20 | HP00027 | HT-1080 | pKA1 | 0.6 | Ribosomal protein YS24-like |
| 21 and 22 | HP00034 | HT-1080 | pKA1 | 1.5 | Ribosomal protein L1B-like |
| 23 and 24 | HP00035 | HT-1080 | pKA1 | 0.8 | Signal sequence reseptor beta subunit-like |
| 25 and 26 | HP00038 | HT-1080 | pKA1 | 0.6 | DEAD ATP helicase-like |
| 27 and 28 | HP00046 | HT-1080 | pKA1 | 2.7 | Enoyl-CoA hydratase-like |
| 29 and 30 | HP00050 | HT-1080 | pKA1 | 0.6 | Ribosomal protein L37-like |

TABLE 2

| SEQ. ID NO: | HP No. | Cell | Vector | CDNA size (kbp) | Encoded protein |
|---|---|---|---|---|---|
| 31 and 32 | HP00058 | HT-1080 | pKA1 | 1.6 | Ubiquitin-conjugating enzyme E2-16K-like |
| 33 and 34 | HP00060 | HT-1080 | pKA1 | 2.2 | Nucleoskeleton-like |
| 35 and 36 | HP00062 | HT-1080 | pKA1 | 1.6 | Zinc resitance protein-like |
| 37 and 38 | HP00063 | HT-1080 | pKA1 | 0.5 | Ribosomal protein L37A-like |
| 39 and 40 | HP00065 | HT-1080 | pKA1 | 2.5 | Cystein proteinase 1-like |
| 41 and 42 | HP00067 | HT-1080 | pKA1 | 1.5 | DnaJ protein-like |
| 43 and 44 | HP00069 | HT-1080 | pKA1 | 0.6 | Calcium-binding protein-like |
| 45 and 46 | HP00072 | HT-1080 | pKA1 | 0.7 | Ribosomal protein L11-like |
| 47 and 48 | HP00073 | HT-1080 | pKA1 | 0.54 | Ribosomal protein S20-like |
| 49 and 50 | HP00075 | HT-1080 | pKA1 | 1.6 | Nuclear protein SNF2-like |
| 51 and 52 | HP00076 | HT-1080 | pKA1 | 3.5 | Fatty acid synthase-like |
| 53 and 54 | HP00081 | HT-1080 | pKA1 | 0.8 | Serine hydroxymethyl-transferase-like |
| 55 and 56 | HP00084 | HT-1080 | pKA1 | 0.8 | U1 snRNP 70kDa-like |
| 57 and 58 | HP00093 | HT-1080 | pKA1 | 0.6 | Ubiquitin-like |
| 59 and 60 | HP00104 | U937 | pKA1 | 1.1 | Ribosomal protein L5-like |
| 61 and 62 | HP00108 | HT-1080 | pKA1 | 0.7 | tat-binding protein-like |
| 63 and 64 | HP00118 | HT-1080 | pKA1 | 0.7 | Porin 31HL-like |
| 65 and 66 | HP00119 | HT-1080 | pKA1 | 1.5 | Glycogenin-like |
| 67 and 68 | HP00127 | HT-1080 | pKA1 | 0.7 | Cyclophilin B-like |
| 69 and 70 | HP00128 | HT-1080 | pKA1 | 1.5 | Zn finger protein-like |
| 71 and 72 | HP00131 | HT-1080 | pKA1 | 1.8 | D-3-phosphoglycerate dehydrogenase like |

TABLE 3

| SEQ. ID NO: | HP No. | Cell | Vector | CDNA size (kbp) | Encoded protein |
|---|---|---|---|---|---|
| 73 and 74 | HP00137 | HT-1080 | pKA1 | 1.1 | Phenylethanolamine-N-methyltransferase-like |
| 75 and 76 | HP00150 | HUT-78 | pTZ18RP1 | 1.1 | Heat shock protein-like |
| 77 and 78 | HP00154 | HT-1080 | pKA1 | 2 | Desmoplakin-like |
| 79 and 80 | HP00157 | HUT-78 | pTZ18RP1 | 0.86 | Serine dehydratase-like |
| 81 and 82 | HP00160 | U937 | pTZ18RP1 | 2.1 | U2 snRNP A'-like |
| 83 and 84 | HP00161 | U937 | pTZ18RP1 | 1 | Ubiquitin-conjugating enzyme E2-20K-like |

TABLE 3-continued

| SEQ. ID NO: | HP No. | Cell | Vector | CDNA size (kbp) | Encoded protein |
|---|---|---|---|---|---|
| 85 and 86 | HP00170 | HT-1080 | pKA1 | 5.5 | Oxysterol-binding protein-like |
| 87 and 88 | HP00175 | U937 | pTZ18RP1 | 0.36 | NAD(+)ADP-rybosyltransferase-like |
| 89 and 90 | HP00177 | HT-1080 | pKA1 | 1.1 | DnaK protein-like |
| 91 and 92 | HP00180 | U937 | pTZ18RP1 | 1.6 | eIF4A-I-like |
| 93 and 94 | HP00188 | U937 | pTZ18RP1 | 1.6 | Zinc finger protein-like |
| 95 and 96 | HP00189 | U937 | pTZ18RP1 | 1.4 | Ribosomal protein BS2-like |
| 97 and 98 | HP00202 | U937 | pKA1 | 0.8 | Polyadenylate binding protein-like |
| 99 and 100 | HP00207 | HT-1080 | pTZ18RP1 | 0.45 | COP protein beta-like |
| 100 and 102 | HP00210 | HT-1080 | pKA1 | 1.5 | Smooth muscle protein 22 alpha-like |
| 103 and 104 | HP00211 | HUT-78 | pTZ18RP1 | 1.1 | NADH-ubiquinone oxidoreductase 30 kDa subunit-like |
| 105 and 106 | HP00212 | HT-1080 | pKA1 | 0.9 | Ribosomal protein L6-like |
| 107 and 108 | HP00225 | HT-1080 | pKA1 | 5.8 | Bone morphogenetic factor-like |

TABLE 4

| SEQ. ID NO: | HP No. | Cell | Vector | CDNA size (kbp) | Encoded protein |
|---|---|---|---|---|---|
| 109 and 110 | HP00231 | HUT-78 | pTZ18RP1 | 1.6 | Farnesyl 2-phosphate farnesyl-transferase-like |
| 111 and 112 | HP00235 | HT-1080 | pKA1 | 3.4 | MHC class II antigen-like |
| 113 and 114 | HP00239 | HT-1080 | pKA1 | 0.8 | NADH-ubiquinone oxidoreductase like |
| 115 and 116 | HP00241 | HT-1080 | pKA1 | 0.7 | 5-aminoimidazol-4-carboxyamide ribonucleotide transformilase/inosine monophosphate cyclohydrolase like |
| 117 and 118 | HP00252 | HT-1080 | pKA1 | 0.9 | Short-chain ADH/ribitol dehydrogenase-like |
| 119 and 120 | HP00255 | HT-1080 | pKA1 | 2.5 | Protein kinase-like |
| 121 and 122 | HP00257 | HT-1080 | pKA1 | 1.5 | Ca2+-transporting ATPase-like |
| 123 and 124 | HP00260 | HT-1080 | pKA1 | 2 | Myosin heavy chain-like |
| 125 and 126 | HP00261 | HT-1080 | pKA1 | 1.9 | DNA strand exchange protein-like |
| 127 and 128 | HP00263 | HT-1080 | pKA1 | 2.2 | t-complex protein 1-like |
| 129 and 130 | HP00265 | U937 | pKA1 | 2.5 | Ribosomal protein TS12-like |
| 131 and 132 | HP00267 | U937 | pKA1 | 0.9 | Growth-dependent protein-like |
| 133 and 134 | HP00269 | HT-1080 | pKA1 | 0.8 | Bone morphogenetic protein-like |
| 135 and 136 | HP00271 | HT-1080 | pKA1 | 1.4 | Complement factor-like |
| 137 and 138 | HP00278 | HT-1080 | pKA1 | 1 | Heat shock protein 90 kDa family-like |
| 139 and 140 | HP00280 | HT-1080 | pKA1 | 1.5 | MHC class I antigen-like |
| 141 and 142 | HP00285 | HT-1080 | pKA1 | 0.6 | Ribosomal protein S26-like |
| 143 and 144 | HP00294 | HT-1080 | pKA1 | 0.9 | t-complex protein 1-like |

TABLE 5

| SEQ. ID NO: | HP No. | Cell | Vector | CDNA size (kbp) | Encoded protein |
|---|---|---|---|---|---|
| 145 and 146 | HP00300 | U937 | pKA1 | 0.5 | Zinc finger protein-like |
| 147 and 148 | HP00301 | U937 | pKA1 | 0.8 | Ribosomal protein L9-like |
| 149 and 150 | HP00302 | U937 | pKA1 | 0.7 | Ribosomal protein YL30-like |
| 151 and 152 | HP00303 | U937 | pKA1 | 1.5 | hnRNP-like |
| 153 and 154 | HP00305 | U937 | pKA1 | 0.6 | Ribosomal protein L25-like |
| 155 and 156 | HP00306 | U937 | pKA1 | 0.7 | ATP synthase lipid-binding protein 2-like |
| 157 and 158 | HP00310 | U937 | pKA1 | 0.6 | Ribosomal protein L21-like |
| 159 and 160 | HP00313 | U937 | pKA1 | 0.9 | hnRNPA1-like |
| 161 and 162 | HP00321 | U937 | pKA1 | 0.8 | Ribosomal protein YL43-like |
| 163 and 164 | HP00322 | U937 | pKA1 | 2 | Transforming protein bmil-like |
| 165 and 166 | HP00324 | U937 | pKA1 | 0.7 | Ribosomal protein BS17-like |
| 167 and 168 | HP00325 | U937 | pKA1 | 0.6 | Ribosomal protein L6-like |
| 169 and 170 | HP00327 | U937 | pKA1 | 1.5 | Protein kinase-like |
| 171 and 172 | HP00228 | U937 | pKA1 | 2.5 | Isocitrate dehydrogenase-like |
| 173 and 174 | HP00332 | U937 | pKA1 | 0.5 | Ribosomal protein L36A-like |
| 175 and 176 | HP00334 | U937 | pKA1 | 1 | Proteasome-like |
| 177 and 178 | HP00343 | U937 | pKA1 | 1.1 | Clathrin heavy chain-like |
| 179 and 180 | HP00344 | U937 | pKA1 | 1.1 | RNA-binding protein-like |
| 181 and 182 | HP00346 | U937 | pKA1 | 0.7 | Ubiquitin-like |
| 183 and 184 | HP00347 | U937 | pKA1 | 0.5 | Ribosomal protein L34-like |

TABLE 6

| SEQ. ID NO: | HP No. | Cell | Vector | CDNA size (kbp) | Encoded protein |
|---|---|---|---|---|---|
| 185 and 186 | HP00348 | U937 | pKA1 | 0.9 | Ribosomal protein L8-like |
| 187 and 188 | HP00349 | U937 | pKA1 | 2.5 | Malate dehydrogenase-like |
| 189 and 190 | HP00352 | HT-1080 | pKA1 | 1.2 | Sc synaptonemal complex-like |
| 191 and 192 | HP00353 | HT-1080 | pKA1 | 1.5 | Protein disulfide-isomerase-like |
| 193 and 194 | HP00359 | U937 | pKA1 | 2.7 | Uridine monophosphokinase-like |
| 195 and 196 | HP00361 | U937 | pKA1 | 1.1 | Proteasome-like |
| 197 and 198 | HP00362 | U937 | pKA1 | 1 | RNA-binding protein-like |
| 199 and 200 | HP00367 | U937 | pKA1 | 1.9 | Glutamine phosphoribosyl-phosphate amidotransferase-like |
| 201 and 202 | HP00374 | U937 | pKA1 | 0.7 | ATP synthase lipid-binding protein 2-like |
| 203 and 204 | HP00375 | U937 | pKA1 | 0.7 | ATP synthase oligomycin sensitivity conferral protein-like |
| 205 and 206 | HP00379 | U937 | pKA1 | 0.5 | Ribosomal protein L38-like |
| 207 and 208 | HP00391 | U937 | pTZ18RP1 | 1 | Annexin XI-like |
| 209 and 210 | HP00395 | U937 | pKA1 | 3.4 | Phosphatidylinositol 3-kinase 110 kDa subunit-like |
| 211 and 212 | HP00403 | U937 | pKA1 | 1.5 | DnaJ protein-like |
| 213 and 214 | HP00405 | U937 | pKA1 | 1.2 | NADH-ubiquinone oxidoreductase 51 kDa subunit-like |
| 215 and 216 | HP00411 | U937 | pKA1 | 1.6 | eIF-2-like |

TABLE 7

| SEQ. ID NO: | HP No. | Cell | Vector | cDNA size (kbp) | Encoded protein |
|---|---|---|---|---|---|
| 217 and 218 | HP00417 | U937 | pKA1 | 1 | Zinc finger protein-like |
| 219 and 220 | HP00419 | HT-1080 | pKA1 | 1 | Ribosomal protein S9-like |
| 221 and 222 | HP00425 | U937 | pKA1 | 2.8 | Beta coat protein-like |
| 223 and 224 | HP00434 | HT-1080 | pKA1 | 1.5 | Membrane glycoprotein gp25L-like |
| 225 and 226 | HP00441 | HT-1080 | pKA1 | 0.8 | NADH-ubiquinone oxidoreductase PSST-like |
| 227 and 228 | HP00442 | HT-1080 | pKA1 | 1.2 | H+-ATPase proteolipid protein-like |
| 229 and 230 | HP00444 | HT-1080 | pKA1 | 0.4 | snRNP-E-related protein C29-like |
| 231 and 232 | HP00448 | HT-1080 | pKA1 | 0.6 | Ribosomal protein L35-like |
| 233 and 234 | HP00451 | HT-1080 | pKA1 | 0.6 | Ribosomal protein YL25-like |
| 235 and 236 | HP00456 | HT-1080 | pKA1 | 1 | Acyl-CoA oxidase I-like |
| 237 and 238 | HP00465 | HT-1080 | pKA1 | 1.5 | F-actin capping protein-like |
| 239 and 240 | HP00466 | HT-1080 | pKA1 | 1.1 | DNA-binding protein Id-like |
| 241 and 242 | HP00471 | HT-1080 | pKA1 | 1.9 | Clathrin coat assembly protein-like |
| 243 and 244 | HP00476 | HT-1080 | pKA1 | 1.8 | Citrate synthase-like |
| 245 and 246 | HP00495 | HT-1080 | pKA1 | 1.2 | Glutamyl-tRNA synthase-like |
| 247 and 248 | HP00500 | HT-1080 | pKA1 | 1.3 | Mitochondrial proteolipid 6.8 kDa protein-like |
| 249 and 250 | HP00502 | HT-1080 | pKA1 | 0.4 | Ribosomal protein BS14-like |

Identification of a Protein Encoded by the cDNA

Three frames of the amino acid sequence deduced from the obtained nucleotide sequence were used for searching the protein database (SWISS-PROT, NBRF-PDB) by means of a sequence analysis software GENETYX-MAC (Software Development). The amino acid sequence of a protein encoded by every cDNA showed great similarity to that of known protein. The name of the protein encoded by each clone is listed in Tables 1 to 7, and their amino acid sequences are shown in the sequence table.

Protein Synthesis by in Vitro Translation

The plasmid DNA carrying a cDNA was linearized by NotI digestion and then used for synthesizing an RNA corresponding to the cDNA in a solution containing a cap (m7G(ppp(5')G) by means of T7 RNA polymerase. The reaction was carried out using in vitro transcription kit (Boehringer Mannheim). Then, the resulting RNA was used as a template for in vitro translation by means of rabbit reticulocyte lysate (Promega). Alternatively, the plasmid carrying a cDNA was used as a template for in vitro translation by means of in vitro translation kit (Promega). In these procedures, [$^{35}$S]methionine was added to the reaction solution to obtain a radioisotope-labeled product. Either reaction was carried out according to the protocols attached to the kits. The molecular weight of translation product was determined on SDS-polyacrylamide gel electrophoresis followed by autoradiography. Some examples were listed in Tables 8 and 9.

TABLE 8

| SEQ. ID NO: | HP No. | MW of translation product |
|---|---|---|
| 3 | HP00008 | 60,000 |
| 15 | HP00020 | 38,000 |

TABLE 8-continued

| SEQ. ID NO: | HP No. | MW of translation product |
|---|---|---|
| 21 | HP00034 | 46,500 |
| 31 | HP00058 | 19,800 |
| 37 | HP00063 | 14,600 |
| 39 | HP00065 | 17,500 |
| 41 | HP00067 | 45,000 |
| 43 | HP00069 | 15,200 |

TABLE 9

| SEQ. ID NO: | HP No. | MW of translation product |
|---|---|---|
| 45 | HP00072 | 24,900 |
| 47 | HP00073 | 18,100 |
| 73 | HP00137 | 29,000 |
| 83 | HP00161 | 21,500 |
| 91 | HP00180 | 46,000 |
| 97 | HP00202 | 41,000 |
| 105 | HP00212 | 33,300 |
| 119 | HP00255 | 44,300 |
| 141 | HP00285 | 13,000 |
| 147 | HP00301 | 22,000 |
| 157 | HP00310 | 19,000 |
| 161 | HP00321 | 26,800 |
| 169 | HP00327 | 39,700 |
| 185 | HP00348 | 31,900 |
| 195 | HP00361 | 30,900 |
| 197 | HP00362 | 26,300 |
| 199 | HP00367 | 59,700 |
| 201 | HP00374 | 15,600 |
| 203 | HP00375 | 28,100 |
| 205 | HP00379 | 10,800 |
| 211 | HP00403 | 35,100 |
| 225 | HP00441 | 26,000 |
| 227 | HP00442 | 25,500 |
| 241 | HP00471 | 51,000 |

Determination of the Entire Nucleotide Sequence

The SEQ ID NOS 41 and 42, 73 and 74, show the examples of the entire nucleotide sequence determined on each cDNA insert.

The clone represented by SEQ ID NOS 41 and 42 contained the cDNA insert of c.a. 1.5 kbp. Determination of its ence showed that this cDNA contains a 5'-noncoding region of 118 bp, an open reading frame of 1194 bp, a 3'-noncoding region of 124 bp, and a poly(A) tail of 69 bp. The open reading frame encodes a protein of 397 amino acid residues. The search of protein database revealed that the N terminal amino acid sequence of 309 residues of this protein shows a similarity of 38.2% to E. coli DnaJ protein. Furthermore, this sequence contains four motif sequences conserved in a DnaJ protein, Cys-X-X-Cys-X-Gly-X-Gly. (SEQ ID NO:258). These results suggest that this clone encodes human DnaJ protein. The molecular weight calculated from the amino acid sequence, 44,877, virtually agreed with one determined experimentally from the in vitro translation product of this clone, 45,000.

The clone represented by SEQ ID NO:73contained the cDNA insert of c.a. 1.1 kbp. Determination of its entire sequence showed that this cDNA contains a 5'-noncoding region of 92 bp, an open reading frame of 795 bp, a 3'-noncoding region of 94 bp, and a poly(A) tail of 56 bp. The open reading frame encodes a protein of 264 amino acid residues (SEQ ID NO:74). The search of protein database revealed that the N terminal amino acid sequence of 222 residues of this protein shows a similarity of 41.9% to human phenylethanolamine N-methyltransferase. These results suggest that this clone encodes a novel N-methyltransferase. The molecular weight calculated from the amino acid sequence, 29,586, virtually agreed with one determined experimentally from the in vitro translation product of this clone, 29,000.

The clone represented by SEQ ID NO:91 contained the cDNA insert of c.a. 1.6 kbp. Determination of its entire sequence showed that this cDNA contains a 5'-noncoding region of 16 bp, an open reading frame of 1221 bp, a 3'-noncoding region of 147 bp, and a poly(A) tail of 92 bp. The open reading frame encodes a protein of 406 amino acid residues (SEQ ID NO:92). The search of protein database revealed that the amino acid sequence of this protein agreed with that of mouse eukaryotic initiation factor 4A-I. Thus this clone is judged to encode human eukaryotic initiation factor 4A-I. The molecular weight calculated from the amino acid sequence, 46,153, virtually agreed with one determined experimentally from the in vitro translation product of this clone, 46,000.

The clone represented by SEQ ID NO:251 contained the cDNA insert of 1.3 kbp. Determination of its entire sequence showed that this cDNA contains a 5'-noncoding region of 32 bp, an open reading frame of 927 bp, a 3'-noncoding region of 242 bp, and a poly(A) tail of 40 bp. The open reading frame encodes a protein of 308 amino acid residues. (SEQ ID NO:252). The sequence overlapped with that of SEQ ID NO:133and 134. The search of protein database revealed that the C terminal amino acid sequence of 98 residues of this protein shows a similarity to TGF-beta super-family proteins. The percent identity was 35.7% with human bone morphogenetic factor 6, 34.7% with GDF-1, 21.4% with inhibin beta, and 25.5% with TGF-beta2. Especially, the positions of seven Cys residues were completely conserved. These results suggest that this clone encodes a novel protein belonging to a TGF-beta super-family.

Expression in Mammalian Cells

The plasmid carrying the cDNA represented by SEQ ID NO:251 was introduced into monkey COS-7 cells using a DEAE-dextran method. The culture medium of the transfected cells was added to the 1 ml culture of mouse preosteoblastoma MC3T3-E1 cells. The alkaline phosphatase activity in the culture medium of the MC3T3-E1 was determined using a kit (Wako Pure Chemical Industry). Table 10 shows that the expression product (SEQ ID NO:127) of this cDNA can enhance the alkaline phosphatase activity of mouse preosteoblastoma cells.

TABLE 10

|  | Amount ($\mu l$) | Alkaline phosphatase activity (IU/l) |
|---|---|---|
| Sample | 25 | 210 ± 10 |
| SEQ ID NOS 251 and 252 | 100 | 280 ± 10 |
| Control | 25 | 50 ± 2 |
| (pKA1) | 100 | 60 ± 2 |

Above examples show that the cDNA clone of this invention contains the same primary structure as poly(A)$^+$ RNA used as a starting material. Furthermore, the examples confirm that the cDNA clones of the invention encode the proteins whose amino acid sequence are described in the sequence table, because the protein encoded by the cDNAs could be produced by in vitro translation and the molecular weights of the translated products agreed with those calculated from the amino acid sequences deduced from the nucleotide sequences of the open reading frames.

Furthermore, the present invention relates to a novel protein and a cDNA encoding the protein, which is created by deletion of one or above, e.g., 1 to 20 amino acid residues in the amino acid sequence described by SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248 and 250, addition of the same, and/or replacement of the same by the other amino acid residue. These changes are carried out according to the conventional method such as site-specific mutagenesis, digestion with restriction enzymes, deletion with exonuclease, and ligation with ligase.

Furthermore the present invention relates to a cDNA or an RNA containing the nucleotide sequence capable of hybridizing the nucleotide sequence described in SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247 and 249, and a novel protein or peptide encoded thereby.

The cDNA of this invention or an antibody prepared against the protein of present invention is used as a probe for diagnosis. A group of cDNAs of present invention encodes proteins localized at various sites in the cell as shown in Tables 1 to 7, including cytoplasmic proteins (myosin light chain kinase, ribosomal protein etc.), membrane proteins (porin, cadherin etc.), secretory proteins (bone morphogenetic factor, CYR61 etc.), mitochondrial proteins (aconitase, ATP synthetase etc.) and so on. Thus, if a group of these cDNAs or a group of antibodies against the proteins encoded by the cDNAs is used together as probes, simultaneous monitoring of the expression level of these genes in the cell or tissue is possible. Because the expression level of various genes and proteins in the cell has been known to vary drastically in the case of various disease including cancer, a new type of diagnosis using a group of these probes is expected to be developed.

The cDNAs of this invention can be used not only as a group but also individually for the separate purpose. For example, the cDNA can be used as a probe for detecting mutation in the nucleotide sequence, a probe for cloning a genomic sequence, a marker for genomic mapping, an antisense cDNA for regulating the translation of mRNA and so on. Because the function of the protein encoded by each cDNA has already been estimated, an expressed product of the cDNA can be used as a medicine. The cDNAs can be used as resources of genes for gene therapy.

The cDNA vector of this invention facilitates preparation of above probes or expression of the proteins.

We claim:

1. An isolated human cDNA selected from the group consisting of SEQ ID NOS:73, 181, and 211.

2. An isolated human cDNA consisting of the sequence of SEQ ID NO:227.

3. An isolated DNA or RNA comprising a sequence selected from the group consisting of SEQ ID NOS:73, 181, 211.

4. An isolated DNA or RNA comprising the sequence of SEQ ID NO:227.

5. A vector comprising a human cDNA according to claim 1.

6. The vector of claim 5, further comprising an f1 phage origin and an RNA polymerase promoter upstream of a cloning site.

7. A vector comprising a human cDNA according to claim 2.

8. The vector of claim 7, further comprising an f1 phage origin and an RNA polymerase promoter upstream of a cloning site.

* * * * *